(12) United States Patent
Cole et al.

(10) Patent No.: US 11,566,002 B2
(45) Date of Patent: Jan. 31, 2023

(54) SUBSTITUTED TETRAHYDROCYCLOPENTA[C]PYRROLES, SUBSTITUTED DIHYDROPYRROLIZINES, ANALOGUES THEREOF, AND METHODS USING SAME

(71) Applicant: Arbutus Biopharma Corporation, Burnaby (CA)

(72) Inventors: Andrew G. Cole, Cranbury, NJ (US); Steven Kultgen, Warminster, PA (US)

(73) Assignee: Arbutus Biopharma Corporation, Burnaby (CA)

( * ) Notice: Subject to any disclaimer, the term of this patent is extended or adjusted under 35 U.S.C. 154(b) by 8 days.

(21) Appl. No.: 17/259,751

(22) PCT Filed: Jul. 25, 2019

(86) PCT No.: PCT/US2019/043373
§ 371 (c)(1),
(2) Date: Jan. 12, 2021

(87) PCT Pub. No.: WO2020/023710
PCT Pub. Date: Jan. 30, 2020

(65) Prior Publication Data
US 2021/0179557 A1    Jun. 17, 2021

Related U.S. Application Data

(60) Provisional application No. 62/711,303, filed on Jul. 27, 2018.

(51) Int. Cl.
*C07D 209/44* (2006.01)

(52) U.S. Cl.
CPC .................... *C07D 209/44* (2013.01)

(58) Field of Classification Search
CPC ..................................................... C07D 209/44
See application file for complete search history.

(56) References Cited

U.S. PATENT DOCUMENTS

2014/0275033 A1    9/2014  Li et al.

FOREIGN PATENT DOCUMENTS

WO    2018039531 A1    3/2018

OTHER PUBLICATIONS

Bezencon, et al., "Discovery and evaluation of Cav3.2-selective T-type calcium channel blockers", Bioorganic & Medicinal Chemistry Letters, vol. 27, 2017, pp. 5326-5331.
International Search Report & Written Opinion dated Nov. 15, 2019 for PCT International Application No. PCT/US2019/043373.

*Primary Examiner* — Shawquia Jackson
(74) *Attorney, Agent, or Firm* — Saul Ewing LLP; Domingos J. Silva; Kevin T. O'Brien

(57) ABSTRACT

The present invention includes novel substituted bicyclic compounds, and compositions comprising the same, that can be used to treat or prevent hepatitis B virus (HBV) infection and/or hepatitis D virus (HDV) infection in a patient.

50 Claims, No Drawings

SUBSTITUTED TETRAHYDROCYCLOPENTA[C]PYRROLES, SUBSTITUTED DIHYDROPYRROLIZINES, ANALOGUES THEREOF, AND METHODS USING SAME

CROSS-REFERENCE TO RELATED APPLICATIONS

The present application is a 35 U.S.C. § 371 national phase application from, and claims priority to, PCT International Patent Application No. PCT/US2019/043373, filed Jul. 25, 2019, which claims priority under 35 U.S.C. § 119(e) to U.S. Provisional Application 62/711,303, filed Jul. 27, 2018, all of which are hereby incorporated by reference herein in their entireties.

BACKGROUND OF THE INVENTION

Hepatitis B is one of the world's most prevalent diseases, being listed by National Institute of Allergy and Infectious Diseases (NIAID) as a High Priority Area of Interest. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis and/or other complications.

Hepatitis B is caused by infection with Hepatitis B virus (HBV), which is a noncytopathic, liver tropic DNA virus belonging to Hepadnaviridae family. Pregenomic (pg) RNA is the template for reverse transcriptional replication of HBV DNA. The encapsidation of pg RNA, together with viral DNA polymerase, into a nucleocapsid is essential for the subsequent viral DNA synthesis. Inhibition of pg RNA encapsidation may block HBV replication and provide a new therapeutic approach to HBV treatment. A capsid inhibitor acts by inhibiting the expression and/or function of a capsid protein either directly or indirectly: for example, it may inhibit capsid assembly, induce formation of non-capsid polymers, promote excess capsid assembly or misdirected capsid assembly, affect capsid stabilization, and/or inhibit RNA encapsidation. A capsid inhibitor may also act by inhibiting capsid function in one or more downstream events within the replication process, such as, but not limited to, viral DNA synthesis, transport of relaxed circular DNA (rcDNA) into the nucleus, covalently closed circular DNA (cccDNA) formation, virus maturation, budding and/or release.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit HBV DNA polymerase. At present, the first-line treatment choices are entecavir, tenofovir and/or peg-interferon alfa-2a. However, peg-interferon alfa-2a achieves desirable serological milestones in only one third of treated patients, and is frequently associated with severe side effects. Entecavir and tenofovir are potent HBV inhibitors, but require long-term or possibly lifetime administration to continuously suppress HBV replication, and may eventually fail due to emergence of drug-resistant viruses. There is thus a pressing need for the introduction of novel, safe, and effective therapies for chronic hepatitis B.

Hepatitis D virus (HDV) is a small circular enveloped RNA virus that can propagate only in the presence of HBV. In particular, HDV requires the HBV surface antigen protein to propagate itself. Infection with both HBV and HDV results in more severe complications compared to infection with HBV alone. These complications include a greater likelihood of experiencing liver failure in acute infections and a rapid progression to liver cirrhosis, with an increased chance of developing liver cancer in chronic infections. In combination with hepatitis B, hepatitis D has the highest mortality rate of all the hepatitis infections. The routes of transmission of HDV are similar to those for HBV. Infection is largely restricted to persons at high risk of HBV infection, particularly injecting drug users and persons receiving dotting factor concentrates.

Currently, there is no effective antiviral therapy available for the treatment of acute or chronic type D hepatitis. Interferon-alfa given weekly for 12 to 18 months is the only licensed treatment for hepatitis D. Response to this therapy is limited, as only about one-quarter of patients is serum HDV RNA undetectable 6 months post therapy.

Clinically, inhibition of pg RNA encapsidation, or more generally inhibition of nucleocapsid assembly, may offer certain therapeutic advantages for treatment of hepatitis B and/or hepatitis D. In one aspect, inhibition of pg RNA encapsidation may complement the current medications by providing an option for a subpopulation of patients that do not tolerate or benefit from the current medications. In another aspect, based on their distinct antiviral mechanism, inhibition of pg RNA encapsidation may be effective against HBV and/or HDV variants resistant to the currently available DNA polymerase inhibitors. In yet another aspect, combination therapy of the pg RNA encapsidation inhibitors with DNA polymerase inhibitors may synergistically suppress HBV and/or HDV replication and prevent drug resistance emergence, thus offering a more effective treatment for chronic hepatitis B and/or hepatitis D infection.

There is thus a need in the art for the identification of novel compounds that can be used to treat and/or prevent HBV and/or HDV infection in a subject. In certain embodiments, the novel compounds inhibit HBV and/or HDV nucleocapsid assembly. In other embodiments, the novel compounds can be used in patients that are HBV and/or HBV-HDV infected, patients who are at risk of becoming HBV and/or HBV-HDV infected, and/or patients that are infected with drug-resistant HBV and/or HDV. The present invention addresses this need.

BRIEF SUMMARY OF THE INVENTION

The disclosure provides a compound of formula (I) or (II), or a salt, solvate, prodrug, stereoisomer, tautomer, or isotopically labeled derivative thereof, or any mixtures thereof:

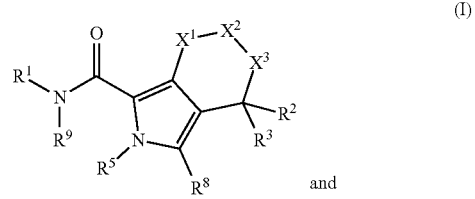

and

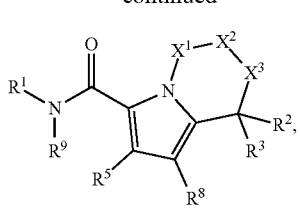

(II)

wherein $X^1$, $X^2$, $X^3$, $R^1$, $R^2$, $R^3$, $R^5$, $R^8$, and $R^9$ are as defined elsewhere herein.

The disclosure further provides a pharmaceutical composition comprising at least one compound of the disclosure and a pharmaceutically acceptable carrier.

The disclosure further provides a method of treating or preventing hepatitis B virus (HBV) infection and/or hepatitis D virus (HDV) infection in a subject.

The disclosure further provides a method of inhibiting expression and/or function of a viral capsid protein directly or indirectly in a HBV-infected and/or HDV-infected subject.

In certain embodiments, the method of the disclosure comprises administering to the subject in need thereof a therapeutically effective amount of at least one compound of the disclosure.

DETAILED DESCRIPTION OF THE INVENTION

The invention relates, in certain aspects, to the discovery of certain substituted bicyclic compounds that are useful to treat and/or prevent hepatitis B virus (HBV) infection and/or HBV-hepatitis D virus (HDV) infection and related conditions in a subject. In certain embodiments, the compounds of the invention are viral capsid inhibitors.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or iso-propoxy) and the higher homologs and isomers. A specific example is (C$_1$-C$_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A specific embodiment is (C$_1$-C$_6$)alkyl, such as, but not limited to, ethyl, methyl, isopropyl, isobutyl, n-pentyl, n-hexyl, and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH.

As used herein, the term "aromatic" refers to a carbocycle or heterocycle with one or more polyunsaturated rings and having aromatic character, i.e., having (4n+2) delocalized π (pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-($C_1$-$C_6$)alkyl" refers to a functional group wherein a one-to-six carbon alkylene chain is attached to an aryl group, e.g., —$CH_2CH_2$-phenyl or —$CH_2$— phenyl (or benzyl). Specific examples are aryl-$CH_2$— and aryl-$CH(CH_3)$—. The term "substituted aryl-($C_1$-$C_6$)alkyl" refers to an aryl-($C_1$-$C_6$)alkyl functional group in which the aryl group is substituted. A specific example is substituted aryl($CH_2$)—. Similarly, the term "heteroaryl-($C_1$-$C_6$)alkyl" refers to a functional group wherein a one-to-three carbon alkylene chain is attached to a heteroaryl group, e.g., —$CH_2CH_2$-pyridyl. A specific example is heteroaryl-($CH_2$)—. The term "substituted heteroaryl-($C_1$-$C_6$)alkyl" refers to a heteroaryl-($C_1$-$C_6$)alkyl functional group in which the heteroaryl group is substituted. A specific example is substituted heteroaryl-($CH_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples of ($C_3$-$C_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes bicyclic hydrocarbon rings, non-limiting examples of which include, bicyclo[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —$OCH_2CH_2CH_3$, —$CH_2CH_2CH_2OH$, —$CH_2CH_2NHCH_3$, —$CH_2SCH_2CH_3$, and —$CH_2CH_2S(=O)CH_3$. Up to two heteroatoms may be consecutive, such as, for example, —$CH_2NH$—$OCH_3$, or —$CH_2CH_2SSCH_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4- triazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface-active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, inorganic bases, solvates (including hydrates) and clathrates thereof.

As used herein, a "pharmaceutically effective amount," "therapeutically effective amount," or "effective amount" of a compound is that amount of compound that is sufficient to provide a beneficial effect to the subject to which the compound is administered.

The term "prevent," "preventing," or "prevention" as used herein means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl," or "substituted alkynyl" refers to alkyl, cycloalkyl, alkenyl, or alkynyl, as defined elsewhere herein, substituted by one, two or three substituents independently selected from the group consisting of halogen, —OH, alkoxy, tetrahydro-2-H-pyranyl, —NH$_2$, —NH(C$_1$-C$_6$ alkyl), —N(C$_1$-C$_6$ alkyl)$_2$, 1-methyl-imidazol-2-yl, pyridin-2-yl, pyridin-3-yl, pyridin-4-yl, —C(=O)OH, —C(=O)O(C$_1$-C$_6$)alkyl, trifluoromethyl, —C(=O)NH$_2$, —C(=O)NH(C$_1$-C$_6$)alkyl, —C(=O)N((C$_1$-C$_6$)alkyl)$_2$, —SO$_2$NH$_2$, —SO$_2$NH(C$_1$-C$_6$ alkyl), —SO$_2$N(C$_1$-C$_6$ alkyl)$_2$, —C(=NH)NH$_2$, and —NO$_2$, in certain embodiments containing one or two substituents independently selected from halogen, —OH, alkoxy, —NH$_2$, trifluoromethyl, —N(CH$_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, cyano, amino, acetamido, and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Certain abbreviations used herein follow: cccDNA, covalently closed circular DNA; DMSO, dimethylsulfoxide; HBsAg, HBV surface antigen; HBV, hepatitis B virus; HDV, hepatitis D virus; HPLC, high performance liquid chromatography; LCMS, liquid chromatography mass spectrometry; NARTI or NRTI, reverse-transcriptase inhibitor; NMR, Nuclear Magnetic Resonance; NtARTI or NtRTI, nucleotide analog reverse-transcriptase inhibitor; pg RNA, pregenomic RNA; rcDNA, relaxed circular DNA; sAg, surface antigen; TLC, thin layer chromatography.

Ranges: throughout this disclosure, various aspects of the present invention can be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise. This applies regardless of the breadth of the range.

Compounds

The invention includes a compound of formula (I) or (II), or a salt, solvate, prodrug, isotopically labeled derivative, stereoisomer (such as, in a non-limiting example, an enantiomer or diastereoisomer, and/or any mixtures thereof, such as, in a non-limiting example, mixtures in any proportions of enantiomers and/or diastereoisomers thereof), tautomer and any mixtures thereof, and/or geometric isomer and any mixtures thereof:

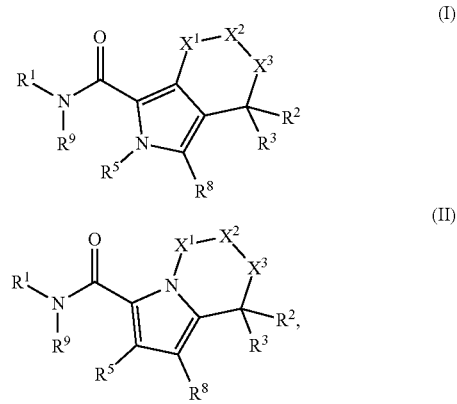

wherein independently in (I) or (II):

—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH(CH_3)CH(CH_3)$—*, —$C(CH_3)_2CH(CH_3)$—*, and —$CH(CH_3)C(CH_3)_2$—*, wherein the single bond marked as "*" is formed with $X^3$;

—$X^3$— is selected from the group consisting of a bond (i.e., absent), —$CH_2$—, —$CH(CH_3)$—, —$C(CH_3)_2$—, —$CH_2CH_2$—, *—$CH_2CH(CH_3)$—, *—$CH_2C(CH_3)_2$—, *—$CH(CH_3)CH_2$—, *—$C(CH_3)_2CH_2$—, —$CH(CH_3)CH(CH_3)$—, *—$C(CH_3)_2CH(CH_3)$—*, and *—$CH(CH_3)C(CH_3)_2$—, wherein the single bond marked as "*" is formed with $X^1$—$X^2$—;

$R^1$ is selected from the group consisting of optionally substituted phenyl, optionally substituted benzyl, optionally substituted heteroaryl, and —$(CH_2)$(optionally substituted heteroaryl);

$R^2$ is selected from the group consisting of H, —OH, —$OR^6$, —$NH_2$, —$NHR^6$, —$NR^6R^{6a}$, —$OC(=O)OR^6$, —$OC(=O)N(R^4)R^6$, —$N(R^3)C(=O)OR^6$ [such as but not limited to $N(R^4)C(=O)O$ (optionally substituted $C_1$-$C_6$ alkyl), such as, for example, —$N(R^4)C(=O)O(CH_2)_{1-3}$ (optionally substituted cycloalkyl), —$N(R^4)C(=O)O$-(optionally substituted benzyl), —$N(R^4)C(=O)O(CH_2)_{1-3}$ (optionally substituted pyridinyl), —$N(R^4)C(=O)O(CH_2)_{1-3}$ (optionally substituted azolyl, such as but not limited to optionally substituted isoxazolyl or optionally substituted oxazolyl], —$NR^7C(=O)N(R^6)(R^7)$, —$N(R^4)C(=O)R^6$, and —$NR^4S(=O)_{1-2}R^6$;

$R^3$ is H or $C_1$-$C_6$ alkyl;

or $R^2$ and $R^3$ combine to form =O;

each occurrence of $R^4$ is independently selected from the group consisting of H and $C_1$-$C_6$ alkyl;

$R^5$ is selected from the group consisting of H and $C_1$-$C_6$ alkyl;

each occurrence of $R^6$ is independently selected from the group consisting of optionally substituted $C_1$-$C_6$ alkyl, optionally substituted $C_1$-$C_6$ alkenyl, optionally substituted $C_1$-$C_6$ alkynyl, optionally substituted $C_3$-$C_8$ cycloalkyl, optionally substituted phenyl, and optionally substituted hetereoaryl;

each occurrence of $R^ha$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl;

each occurrence of $R^7$ is independently selected from the group consisting of H and optionally substituted $C_1$-$C_6$ alkyl;

or, if $R^6$ and $R^7$ are bound to the same N atom, $R^6$ and $R^7$ optionally combine with the N atom to which both are bound to form an optionally substituted 3-7 membered heterocycle;

$R^8$ is selected from the group consisting of H, halo, $C_1$-$C_6$ alkyl, $C_1$-$C_6$ haloalkyl (such as, but not limited to, trifluoromethyl), $C_3$-$C_8$ cycloalkyl, and optionally substituted phenyl; and $R^9$ is selected from the group consisting of H and $C_1$-$C_6$ alkyl.

In certain embodiments, the configuration is (R) at the $C(R^2)(R^3)$ center.

In certain embodiments, the configuration is (S) at the $C(R^2)(R^3)$ center.

In certain embodiments, the compound of formula (I) is a compound of formula (I-1):

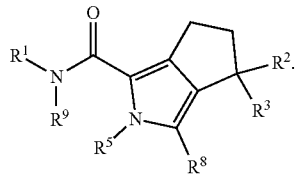

(I-1)

In certain embodiments, the compound of formula (I) is a compound of formula (I-2):

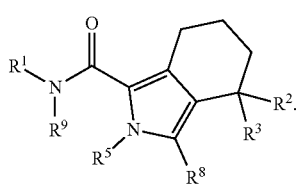

(I-2)

In certain embodiments, the compound of formula (I) is a compound of formula (I-3):

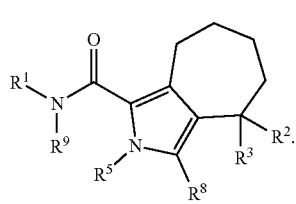

(I-3)

In certain embodiments, the compound of formula (I) is selected from the group consisting of:

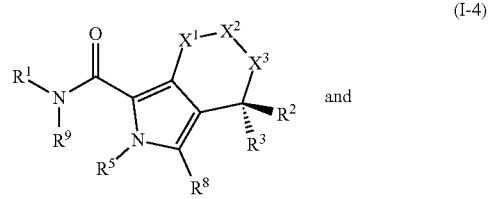

(I-4)

and

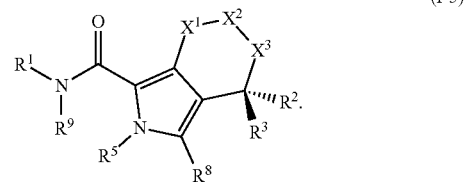

(I-5)

In certain embodiments, the compound of formula (I) is selected from the group consisting of:

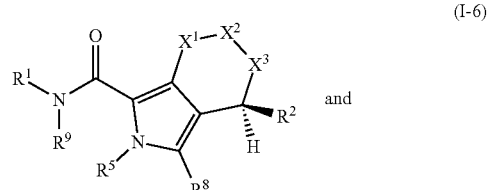

(I-6)

and

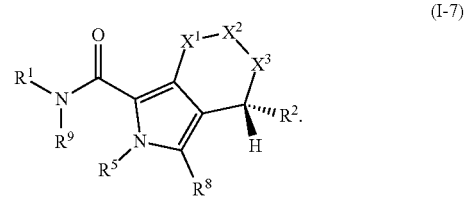

(I-7)

In certain embodiments, the compound of formula (I) is selected from the group consisting of:

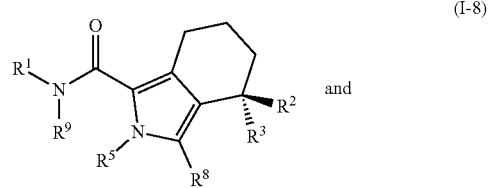

(I-8)

and

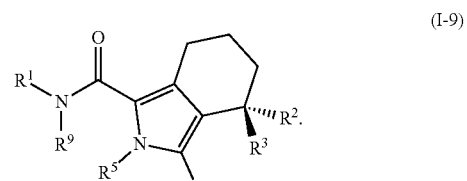

(I-9)

In certain embodiments, the compound of formula (I) is selected from the group consisting of:

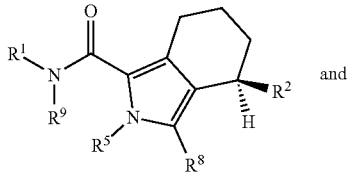
(I-10)

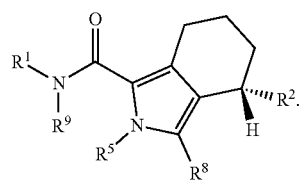
(I-11)

In certain embodiments, the compound of formula (I) is selected from the group consisting of:

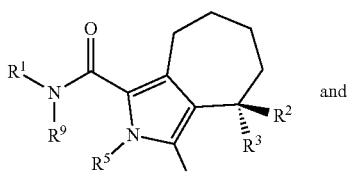
(I-12)

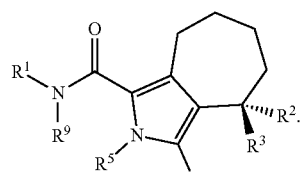
(I-13)

In certain embodiments, the compound of formula (I) is selected from the group consisting of:

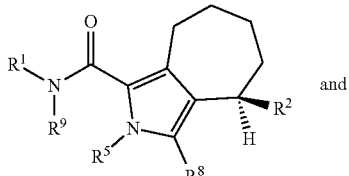
(I-14)

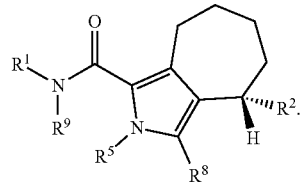
(I-15)

In certain embodiments, the compound of formula (I) is selected from the group consisting of:

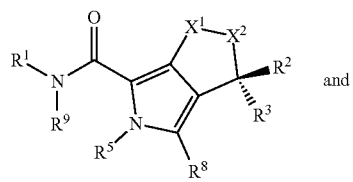
(I-16)

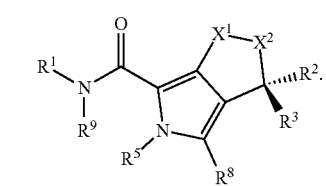
(I-17)

In certain embodiments, the compound of formula (I) is selected from the group consisting of:

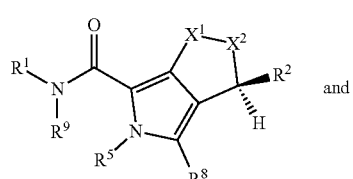
(I-18)

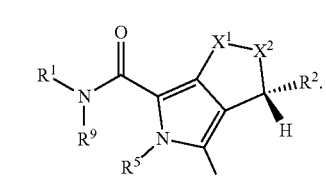
(I-19)

In certain embodiments, the compound of formula (I) is selected from the group consisting of:

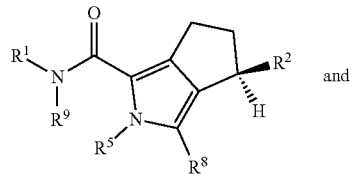
(I-20)

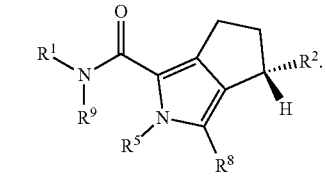
(I-21)

In certain embodiments, the compound of formula (I) is selected from the group consisting of:

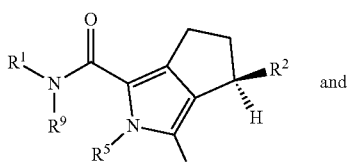
(I-22)

and

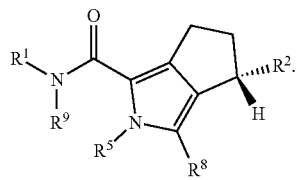
(I-23)

In certain embodiments, the compound of formula (II) is a compound of formula (II-1):

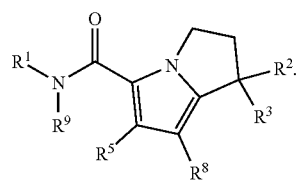
(II-1)

In certain embodiments, the compound of formula (II) is a compound of formula (II-2):

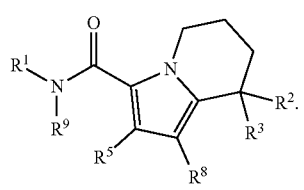
(II-2)

In certain embodiments, the compound of formula (II) is a compound of formula (II-3):

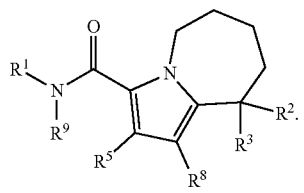
(II-3)

In certain embodiments, the compound of formula (II) is selected from the group consisting of:

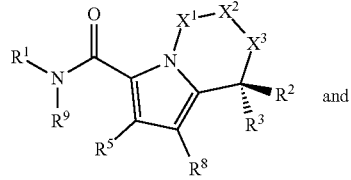
(II-4)

and

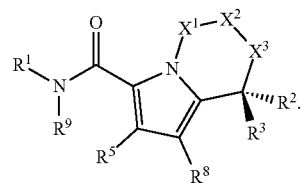
(II-5)

In certain embodiments, the compound of formula (II) is selected from the group consisting of:

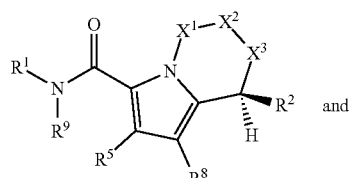
(II-6)

and

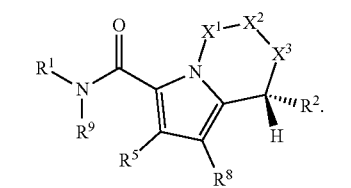
(II-7)

In certain embodiments, the compound of formula (II) is selected from the group consisting of:

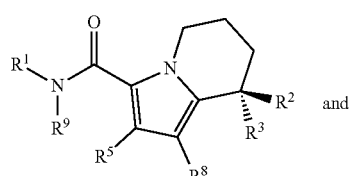
(II-8)

and

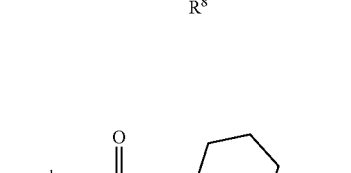
(II-9)

In certain embodiments, the compound of formula (II) is selected from the group consisting of:

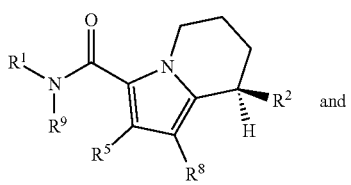
(II-10)

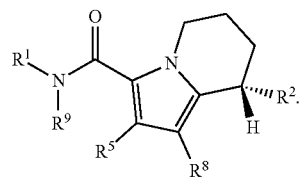
(II-11)

In certain embodiments, the compound of formula (II) is selected from the group consisting of:

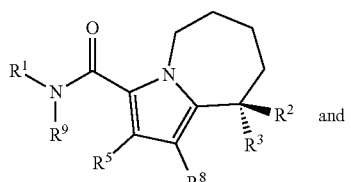
(II-12)

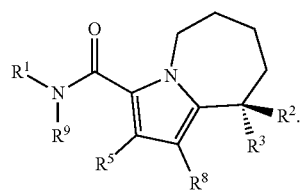
(II-13)

In certain embodiments, the compound of formula (II) is selected from the group consisting of:

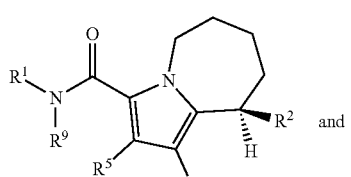
(II-14)

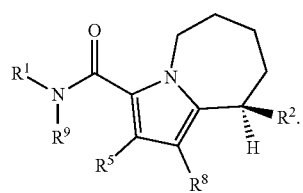
(II-15)

In certain embodiments, the compound of formula (II) is selected from the group consisting of:

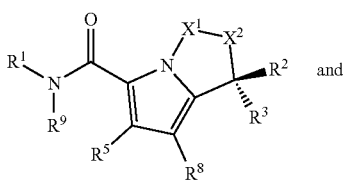
(II-16)

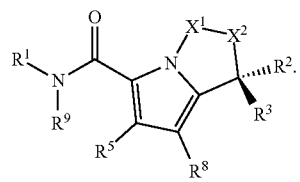
(II-17)

In certain embodiments, the compound of formula (II) is selected from the group consisting of:

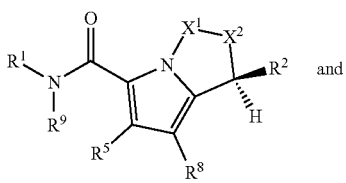
(II-18)

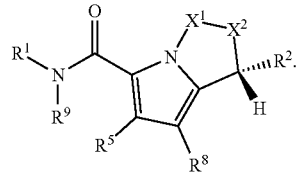
(II-19)

In certain embodiments, the compound of formula (II) is selected from the group consisting of:

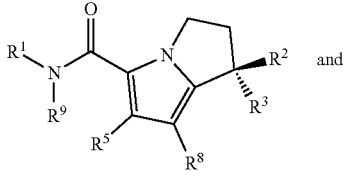
(II-20)

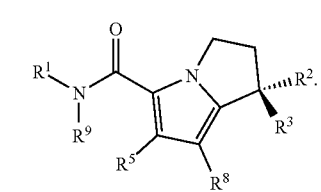
(II-21)

In certain embodiments, the compound of formula (II) is selected from the group consisting of:

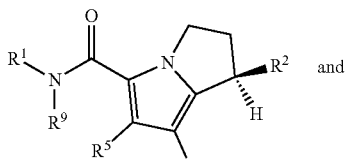 (II-22)

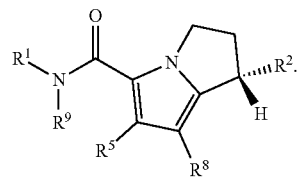 (II-23)

In certain embodiments, each occurrence of alkyl, alkenyl, alkynyl, or cycloalkyl is independently optionally substituted with at least one substituent selected from the group consisting of $C_1$-$C_6$ alkyl, $C_2$-$C_8$ alkenyl, $C_2$-$C_8$ alkynyl, $C_3$-$C_8$ cycloalkyl, halo, cyano, —$OR^a$, optionally substituted phenyl (thus yielding, in non-limiting examples, optionally substituted phenyl-($C_1$-$C_3$ alkyl), such as, but not limited to, benzyl or substituted benzyl), optionally substituted heteroaryl, optionally substituted heterocyclyl, —N($R^a$)C(=O)$R^a$, —C(=O)OH, —C(=O)$OR^a$, —C(=O)N$R^a R^a$, and —N($R^a$)($R^a$), wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, heterocyclyl, halo, —CN, —$OR^b$, —N($R^b$)($R^b$), —$NO_2$, —S(=O)$_2$N($R^b$)($R^b$), acyl, and $C_1$-$C_6$ alkoxycarbonyl, wherein each occurrence of $R^b$ is independently H, $C_1$-$C_6$ alkyl or $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, heterocyclyl, halo, —CN, —N($R^c$)($R^c$), and $C_1$-$C_6$ alkoxycarbonyl, wherein each occurrence of $R^c$ is independently H, $C_1$-$C_6$ alkyl or $C_3$-$C_8$ cycloalkyl.

In certain embodiments, the alkyl, cycloalkyl, heteroaryl, heterocyclyl, aryl, or benzyl group is optionally independently substituted with at least one group selected from the group consisting of $C_1$-$C_6$ alkyl, $C_1$-$C_6$ alkoxy, $C_1$-$C_6$ haloalkyl, $C_1$-$C_6$ haloalkoxy, —$NH_2$, —NH($C_1$-$C_6$ alkyl), —N($C_1$-$C_6$ alkyl)($C_1$-$C_6$ alkyl), halogen, —OH, —CN, phenoxy, —NHC(=O)H, —NHC(=O)$C_1$-$C_6$ alkyl, —C(=O)$NH_2$, —C(=O)NH$C_1$-$C_6$ alkyl, —C(=O)N($C_1$-$C_6$ alkyl)($C_1$-$C_6$ alkyl), tetrahydropyranyl, morpholinyl, —C(=O)$CH_3$, —C(=O)$CH_2$OH, —C(=O)$NHCH_3$, —C(=O)$CH_2$OMe, or an N-oxide thereof.

In certain embodiments, each occurrence of the heteroaryl is independently selected from the group consisting of quinolinyl, imidazo[1,2-a]pyridyl, pyridyl, pyrimidyl, pyrazinyl, imidazolyl, thiazolyl, pyrazolyl, isoxazolyl, oxadiazolyl (including 1,2,3-, 1,2,4-, 1,2,5-, and 1,3,4-oxadiazolyl), tetrazolyl, and triazolyl (such as, but not limited to, 1,2,4-triazolyl or 1,2,3-triazolyl). In certain embodiments, the heteroaryl is quinolinyl. In certain embodiments, the heteroaryl is imidazo[1,2-a]pyridyl. In certain embodiments, the heteroaryl is pyridyl. In certain embodiments, the heteroaryl is pyrimidyl. In certain embodiments, the heteroaryl is pyrazinyl. In certain embodiments, the heteroaryl is imidazolyl. In certain embodiments, the heteroaryl is thiazolyl. In certain embodiments, the heteroaryl is pyrazolyl. In certain embodiments, the heteroaryl is isoxazolyl. In certain embodiments, the heteroaryl is oxadiazolyl. In certain embodiments, the heteroaryl is 1,2,3-oxadiazolyl. In certain embodiments, the heteroaryl is 1,2,4-oxadiazolyl. In certain embodiments, the heteroaryl is 1,2,5-oxadiazolyl. In certain embodiments, the heteroaryl is 1,3,4-oxadiazolyl. In certain embodiments, the heteroaryl is tetrazolyl. In certain embodiments, the heteroaryl is triazolyl. In certain embodiments, the heteroaryl is 1,2,4-triazolyl. In certain embodiments, the heteroaryl is 1,2,3-triazolyl.

In certain embodiments, each occurrence of the heterocyclyl group is independently selected from the group consisting of tetrahydrofuranyl, tetrahydropyranyl, piperidinyl, piperazinyl, pyrrolidinyl, morpholinyl, thiomorpholinyl, 1-oxido-thiomorpholinyl, 1,1-dioxido-thiomorpholinyl, oxazolidinyl, azetidinyl, and the corresponding oxo analogues (where a methylene ring group is replaced with a carbonyl) thereof, such as but not limited to pyrrolidinonyl, piperidinonyl, piperazinonyl, and/or morpholinonyl. In certain embodiments, the heterocyclyl group is tetrahydrofuranyl. In certain embodiments, the heterocyclyl group is tetrahydropyranyl. In certain embodiments, the heterocyclyl group is piperidinyl. In certain embodiments, the heterocyclyl group is piperazinyl. In certain embodiments, the heterocyclyl group is pyrrolidinyl. In certain embodiments, the heterocyclyl group is morpholinyl. In certain embodiments, the heterocyclyl group is thiomorpholinyl. In certain embodiments, the heterocyclyl group is 1-oxido-thiomorpholinyl. In certain embodiments, the heterocyclyl group is 1,1-dioxido-thiomorpholinyl. In certain embodiments, the heterocyclyl group is oxazolidinyl. In certain embodiments, the heterocyclyl group is azetidinyl. In certain embodiments, the heterocyclyl group is pyrrolidinonyl. In certain embodiments, the heterocyclyl group is piperidinonyl. In certain embodiments, the heterocyclyl group is piperazinonyl. In certain embodiments, the heterocyclyl group is morpholinonyl.

In certain embodiments, $R^1$ is optionally substituted phenyl. In certain embodiments, $R^1$ is optionally substituted benzyl. In certain embodiments, $R^1$ is optionally substituted heteroaryl. In certain embodiments, $R^1$ is —($CH_2$)(optionally substituted heteroaryl). In certain embodiments, $R^1$ is selected from the group consisting of optionally substituted phenyl, optionally substituted benzyl, and —($CH_2$)(optionally substituted heteroaryl), wherein the phenyl, benzyl, or heteroaryl is optionally substituted with at least one selected from the group consisting of $C_1$-$C_6$ alkyl (such as, for example, methyl, ethyl, and isopropyl), halo (such as, for example, F, Cl, Br, and I), $C_1$-$C_3$ haloalkyl (such as, for example, monofluoromethyl, difluoromethyl, and trifluoromethyl), and —CN.

In certain embodiments, $R^1$ is selected from the group consisting of: phenyl, 3-chlorophenyl, 4-chlorophenyl, 3-fluorophenyl, 4-fluorophenyl, 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, 2-chloro-4-pyridyl, 2-fluoro-4-pyridyl, 2-fluoromethyl-4-pyridyl, 2-difluoromethyl-4-pyridyl, 2-trifluoromethyl-4-pyridyl, and 6-methyl-4-pyridyl. In other embodiments, $R^1$ is 3,4-difluorophenyl. In yet other embodiments, $R^1$ is 3-chloro-4-fluorophenyl. In yet other embodiments, $R^1$ is 4-chloro-3-fluorophenyl. In yet other embodiments, $R^1$ is 3-fluoro-4-methylphenyl. In yet other embodiments, $R^1$ is 4-fluoro-3-methylphenyl. In yet other embodiments, $R^1$ is 3-cyano-4-fluorophenyl. In yet other embodiments, $R^1$ is 3-difluoromethyl-4-fluorophenyl.

In certain embodiments, $R^2$ is H. In certain embodiments, $R^2$ is —OH. In certain embodiments, $R^2$ is —$OR^6$. In certain embodiments, $R^2$ is —$NH_2$. In certain embodiments, $R^2$ is —$NHR^6$. In certain embodiments, $R^2$ is —$NR^6R^{6a}$. In certain embodiments, $R^2$ is —OC(=O)$OR^6$. In certain embodiments, $R^2$ is —OC(=O)N($R^4$)$R^6$. In certain embodiments, $R^2$ is —N($R^3$)C(=O)$OR^6$. In certain embodiments, $R^2$ is N($R^4$)C(=O)O (optionally substituted $C_1$-$C_6$ alkyl). In certain embodiments, $R^2$ is —N($R^4$)C(=O)O($CH_2$)$_{1-3}$ (optionally substituted cycloalkyl). In certain embodiments, $R^2$ is —N($R^4$)C(=O)O-(optionally substituted benzyl). In certain embodiments, $R^2$ is —N($R^4$)C(=O)O($CH_2$)$_{1-3}$ (optionally substituted pyridinyl). In certain embodiments, $R^2$ is —N($R^4$)C(=O)O($CH_2$)$_{1-3}$ (optionally substituted azolyl). In certain embodiments, $R^2$ is —N($R^4$)C(=O)O($CH_2$)$_{1-3}$ (optionally substituted isoxazolyl). In certain embodiments, $R^2$ is —N($R^4$)C(=O)O($CH_2$)$_{1-3}$ (optionally substituted oxazolyl). In certain embodiments, $R^2$ is —$NR^7$C(=O)N($R^6$)($R^7$). In certain embodiments, $R^2$ is —N($R^4$)C(=O)$R^6$. In certain embodiments, $R^2$ is —$NR^4$S(=O)$_{1-2}R^6$.

In certain embodiments, $R^2$ is selected from the group consisting of —NHS(=O)$_2$($C_1$-$C_6$ alkyl) and —NHS(=O)$_2$($C_3$-$C_6$ cycloalkyl).

In certain embodiments, $R^2$ is selected from the group consisting of —NHC(=O)($C_1$-$C_6$ alkyl) and —NHC(=O) ($C_3$-$C_8$ cycloalkyl).

In certain embodiments, $R^2$ is selected from the group consisting of —NHC(=O)O($C_1$-$C_6$ alkyl); —NHC(=O)O ($C_3$-$C_8$ cycloalkyl); —NHC(=O)O($C_1$-$C_6$haloalkyl); —NHC(=O)O($CH_2$)$_{1-3}$ ($C_3$-$C_8$ cycloalkyl); —NHC(=O)O ($CH_2$)$_{1-3}$ (pyridinyl); —NHC(=O)O($CH_2$)$_{1-3}$ (pyrazinyl); —NHC(=O)O($CH_2$)$_{1-3}$ (pyrimidinyl); —NHC(=O)O ($CH_2$)$_{1-3}$ (isoxazolyl); —NHC(=O)O($CH_2$)$_{1-3}$ (oxazolyl); —NHC(=O)O($CH_2$)$_{1-3}$ (oxadiazolyl); —NHC(=O)O ($CH_2$)$_{1-3}$ (triazolyl); —NHC(=O)O($CH_2$)$_{1-3}$ (thiazolyl); —NHC(=O)O($CH_2$)$_{1-3}$ (imidazolyl); —NHC(=O) O($CH_2$)$_{1-3}$ (1,2,3-pyrazolyl); —NHC(=O)O($CH_2$)$_{1-3}$ (1,2,4-pyrazolyl); —NHC(=O)O($CH_2$)$_{1-3}$ (pyrrolidinonyl); and —NHC(=O)O($CH_2$)$_{1-3}$ (tetrazolyl); wherein each substituent in $R^2$ is optionally substituted as contemplated elsewhere herein.

In certain embodiments, $R^2$ is selected from the group consisting of —NHC(=O)NH($C_1$-$C_6$ alkyl); —NHC(=O) NH($C_3$-$C_8$ cycloalkyl); —NHC(=O)NH($C_1$-$C_6$ haloalkyl); —NHC(=O)NH($CH_2$)$_{1-3}$ (pyridinyl); —NHC(=O)NH ($CH_2$)$_{1-3}$ (pyrazinyl); —NHC(=O)NH($CH_2$)$_{1-3}$ (pyrimidinyl); —NHC(=O)NH($CH_2$)$_{1-3}$ (isoxazolyl); —NHC(=O) NH($CH_2$)$_{1-3}$ (oxazolyl); —NHC(=O)NH($CH_2$)$_{1-3}$ (oxadiazolyl); —NHC(=O)NH($CH_2$)$_{1-3}$(triazolyl); —NHC (=O)NH($CH_2$)$_{1-3}$ (thiazolyl); —NHC(=O)NH($CH_2$)$_{1-3}$ (imidazolyl); —NHC(=O)NH($CH_2$)$_{1-3}$ (1,2-pyrazolyl); —NHC(=O)NH($CH_2$)$_{1-3}$ (1,2,3-pyrazolyl); —NHC(=O)NH ($CH_2$)$_{1-3}$ (1,2,4-pyrazolyl); —NHC(=O)NH($CH_2$)$_{1-3}$ (pyrrolidinonyl); and —NHC(=O)NH($CH_2$)$_{1-3}$ (tetrazolyl); wherein each of the urea nitrogen atoms is independently optionally substituted with $C_1$-$C_6$ alkyl.

In certain embodiments, $R^3$ is H. In certain embodiments, $R^3$ is $C_1$-$C_6$ alkyl. In certain embodiments, $R^3$ is H or methyl. In certain embodiments, $R^3$ is methyl.

In certain embodiments, $R^2$ and $R^3$ combine to form =O.

In certain embodiments, $R^4$ is H. In certain embodiments, $R^4$ is $C_1$-$C_6$ alkyl. In certain embodiments, each occurrence of $R^4$ is independently selected from the group consisting of H and methyl. In certain embodiments, $R^4$ is methyl.

In certain embodiments, $R^5$ is H. In certain embodiments, $R^5$ is $C_1$-$C_6$ alkyl. In certain embodiments, $R^5$ is H or methyl. In certain embodiments, $R^5$ is methyl.

In certain embodiments, $R^6$ is optionally substituted $C_1$-$C_6$ alkyl. In certain embodiments, $R^6$ is optionally substituted $C_1$-$C_6$ alkenyl. In certain embodiments, $R^6$ is optionally substituted $C_1$-$C_6$ alkynyl. In certain embodiments, $R^6$ is optionally substituted $C_3$-$C_8$ cycloalkyl. In certain embodiments, $R^6$ is optionally substituted phenyl. In certain embodiments, $R^6$ is optionally substituted hetereoaryl. In certain embodiments, $R^6$ is $C_1$-$C_6$ alkyl. In certain embodiments, $R^6$ is $C_1$-$C_6$ alkenyl. In certain embodiments, $R^6$ is $C_1$-$C_6$ alkynyl. In certain embodiments, $R^6$ is $C_3$-$C_8$ cycloalkyl. In certain embodiments, $R^6$ is phenyl. In certain embodiments, $R^6$ is heteroaryl. In certain embodiments, each occurrence of $R^6$ is independently selected from the group consisting of $C_1$-$C_6$ alkyl optionally substituted with at least one selected from the group consisting of halogen, OH, $C_1$-$C_3$ alkoxy, and cyano; —($CH_2$)$_{0-3}$ (optionally substituted heterocyclyl); —($CH_2$)$_{0-3}$ (optionally substituted heteroaryl); and —($CH_2$)$_{0-3}$ (optionally substituted heteroaryl).

In certain embodiments, $R^{6a}$ is H. In certain embodiments, $R^{6a}$ is optionally substituted $C_1$-$C_6$ alkyl. In certain embodiments, $R^{6a}$ is optionally substituted $C_3$-$C_8$ cycloalkyl. In certain embodiments, $R^{6a}$ is optionally substituted phenyl. In certain embodiments, $R^{6a}$ is optionally substituted hetereoaryl. In certain embodiments, $R^{6a}$ is $C_1$-$C_6$ alkyl. In certain embodiments, $R^{6a}$ is $C_3$-$C_8$ cycloalkyl. In certain embodiments, $R^{6a}$ is phenyl. In certain embodiments, $R^{6a}$ is hetereoaryl. In certain embodiments, each occurrence of $R^{6a}$ is independently selected from the group consisting of $C_1$-$C_6$ alkyl optionally substituted with at least one selected from the group consisting of halogen, OH, $C_1$-$C_3$ alkoxy, and cyano; —($CH_2$)$_{0-3}$ (optionally substituted heterocyclyl); —($CH_2$)$_{0-3}$ (optionally substituted heteroaryl); and —($CH_2$)$_{0-3}$ (optionally substituted heteroaryl).

In certain embodiments, $R^7$ is H. In certain embodiments, $R^7$ is optionally substituted $C_1$-$C_6$ alkyl. In certain embodiments, $R^7$ is $C_1$-$C_6$ alkyl. In certain embodiments, $R^7$ is H or methyl. In certain embodiments, $R^7$ is H. In certain embodiments, $R^7$ is methyl.

In certain embodiments, $R^6$ and $R^7$ are bound to the same N atom and optionally combine with the N atom to which both are bound to form an optionally substituted 3-7 membered heterocycle.

In certain embodiments, $R^8$ is H. In certain embodiments, $R^8$ is halo. In certain embodiments, $R^8$ is $C_1$-$C_6$ alkyl. In certain embodiments, $R^8$ is $C_1$-$C_6$ haloalkyl. In certain embodiments, $R^8$ is trifluoromethyl. In certain embodiments, $R^8$ is $C_3$-$C_8$ cycloalkyl. In certain embodiments, $R^8$ is optionally substituted phenyl. In certain embodiments, $R^8$ is phenyl. In certain embodiments, $R^8$ is selected from the group consisting of H, halo, and methyl. In certain embodiments, $R^8$ is H. In certain embodiments, $R^8$ is methyl. In certain embodiments, $R^8$ is fluoro. In certain embodiments, $R^8$ is chloro. In certain embodiments, $R^8$ is bromo. In certain embodiments, $R^8$ is iodo.

In certain embodiments, $R^9$ is H. In certain embodiments, $R^9$ is $C_1$-$C_6$ alkyl. In certain embodiments, $R^9$ is selected from the group consisting of H and methyl. In certain embodiments, $R^9$ is H. In certain embodiments, $R^9$ is methyl.

In certain embodiments, —$X^1$—$X^2$— is —$CH_2CH_2$—*. In certain embodiments, —$X^1$—$X^2$— is —$CH_2CH(CH_3)$—*. In certain embodiments, —$X^1$—$X^2$— is —$CH_2C(CH_3)_2$—*. In certain embodiments, —$X^1$—$X^2$— is —$CH(CH_3)CH_2$—*. In certain embodiments, —$X^1$—$X^2$— is —$C(CH_3)_2CH_2$—*. In certain embodiments, —$X^1$—$X^2$— is —$CH(CH_3)CH(CH_3)$—*. In certain embodiments, —$X^1$—$X^2$— is —$C(CH_3)_2CH(CH_3)$—*. In certain embodiments, —$X^1$—$X^2$— is —$CH(CH_3)C(CH_3)_2$—*. As defined elsewhere herein, the single bond marked as "*" is formed with $X^3$.

In certain embodiments, —$X^3$— is a bond (i.e., absent). In certain embodiments, —$X^3$— is —$CH_2$—. In certain embodiments, —$X^3$— is —$CH(CH_3)$—. In certain embodiments, —$X^3$— is —$C(CH_3)_2$—. In certain embodiments, —$X^3$— is —$CH_2CH_2$—. In certain embodiments, —$X^3$— is *—$CH_2CH(CH_3)$—.

In certain embodiments, —$X^3$— is *—$CH_2C(CH_3)_2$—. In certain embodiments, —$X^3$— is *—$CH(CH_3)CH_2$—. In certain embodiments, —$X^3$— is *—$C(CH_3)_2CH_2$—. In certain embodiments, —$X^3$— is —$CH(CH_3)CH(CH_3)$—. In certain embodiments, —$X^3$— is *—$C(CH_3)_2CH(CH_3)$—*. In certain embodiments, —$X^3$— is *—$CH(CH_3)C(CH_3)_2$—. As defined elsewhere herein, the single bond marked as "*" is formed with $X^1$—$X^2$—;

In certain embodiments, the compound of the invention is any compound disclosed herein, or a salt, solvate, prodrug, isotopically labeled (such as for example at least partially deuterated), stereoisomer, any mixture of stereoisomers, tautomer, and/or any mixture of tautomers thereof.

In certain embodiments, the compound is at least one selected from Table 1, or a salt, solvate, prodrug, isotopically labeled, stereoisomer, any mixture of stereoisomers, tautomer, and/or any mixture of tautomers thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including, by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or any mixtures thereof, or in the case where two or more chiral centers are present, all diastereomers or any mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV and/or HDV infections. These additional agents may comprise compounds or compositions identified herein, or compounds (e.g., commercially available compounds) known to treat, prevent, or reduce the symptoms of HBV and/or HDV infections.

Non-limiting examples of one or more additional agents useful for treating HBV infections include: (a) reverse transcriptase inhibitors; (b) capsid inhibitors; (c) cccDNA formation inhibitors; (d) RNA destabilizers; (e) oligomeric nucleotides targeted against the HBV genome; (f) immunostimulators, such as checkpoint inhibitors (e.g., PD-L1 inhibitors); and (g) GalNAc-siRNA conjugates targeted against an HBV gene transcript.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl (4(1R,3R,4R,5R)-3-(6-amino-9H-purin-9-yl)-4-fluoro-5-hydroxy-2-methylenecyclopentyl) methoxy)(phenoxy) phosphoryl)-(D or L)-alaninate and methyl ((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394; and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) RNA Destabilizer

As used herein, the term "RNA destabilizer" refers to a molecule, or a salt or solvate thereof, that reduces the total amount of HBV RNA in mammalian cell culture or in a live human subject. In a non-limiting example, an RNA destabilizer reduces the amount of the RNA transcript(s) encoding one or more of the following HBV proteins: surface antigen, core protein, RNA polymerase, and e antigen. In certain embodiments, the RNA destabilizer reduces the total amount of HBV RNA in mammalian cell culture or in a live human subject by at least 5%, at least 10%, at least 20%, at least 50%, at least 75%, or at least 90%.

Reported RNA destabilizers include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported RNA destabilizers include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821, WO 2018085619, and are incorporated herein in their entirety by reference.

(e) Oligomeric Nucleotides Targeted Against the HBV Genome

Reported oligomeric nucleotides targeted against the HBV genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the HBV genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

(f) Immunostimulators

Checkpoint Inhibitors

As described herein, the term "checkpoint inhibitor" includes any compound that is capable of inhibiting immune checkpoint molecules that are regulators of the immune system (e.g., stimulate or inhibit immune system activity). For example, some checkpoint inhibitors block inhibitory checkpoint molecules, thereby stimulating immune system function, such as stimulation of T cell activity against cancer cells. A non-limiting example of a checkpoint inhibitor is a PD-L1 inhibitor.

As described herein, the term "PD-L1 inhibitor" includes any compound that is capable of inhibiting the expression and/or function of the protein Programmed Death-Ligand 1 (PD-L1) either directly or indirectly. PD-L1, also known as cluster of differentiation 274 (CD274) or B7 homolog 1 (B7-H1), is a type 1 transmembrane protein that plays a major role in suppressing the adaptive arm of immune system during pregnancy, tissue allograft transplants, autoimmune disease, and hepatitis. PD-L1 binds to its receptor, the inhibitory checkpoint molecule PD-1 (which is found on activated T cells, B cells, and myeloid cells) so as to modulate activation or inhibition of the adaptive arm of immune system. In certain embodiments, the PD-L1 inhibitor inhibits the expression and/or function of PD-L1 by at least 5%, at least 10%, at least 20%, at least 50%, at least 75%, or at least 90%.

Reported PD-L1 Inhibitors include, but are not limited to, compounds recited in one of the following patent application publications: US 2018/0057455; US 2018/0057486; WO 2017/106634; WO 2018/026971; WO 2018/045142; WO 2018/118848; WO 2018/119221; WO 2018/119236; WO 2018/119266; WO 2018/119286; WO 2018/121560; WO 2019/076343; WO 2019/087214; and are incorporated herein in their entirety by reference.

(g) GalNAc-siRNA Conjugates Targeted Against an HBV Gene Transcript

"GalNAc" is the abbreviation for N-acetylgalactosamine, and "siRNA" is the abbreviation for small interfering RNA. An siRNA that targets an HBV gene transcript is covalently bonded to GalNAc in a GalNAc-siRNA conjugate useful in the practice of the present invention. While not wishing to be bound by theory, it is believed that GalNAc binds to asialoglycoprotein receptors on hepatocytes thereby facilitating the targeting of the siRNA to the hepatocytes that are infected with HBV. The siRNA enter the infected hepatocytes and stimulate destruction of HBV gene transcripts by the phenomenon of RNA interference.

Examples of GalNAc-siRNA conjugates useful in the practice of this aspect of the present invention are set forth in published international application PCT/CA2017/050447 (PCT Application Publication number WO/2017/177326, published on Oct. 19, 2017) which is hereby incorporated by reference in its entirety.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high-performance liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

A compound of formula (I) can be prepared, for example, according to the synthetic methods outlined in Scheme 1:

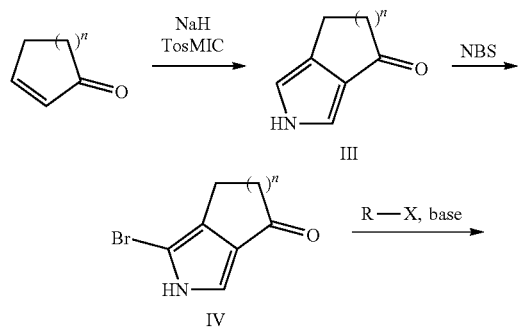

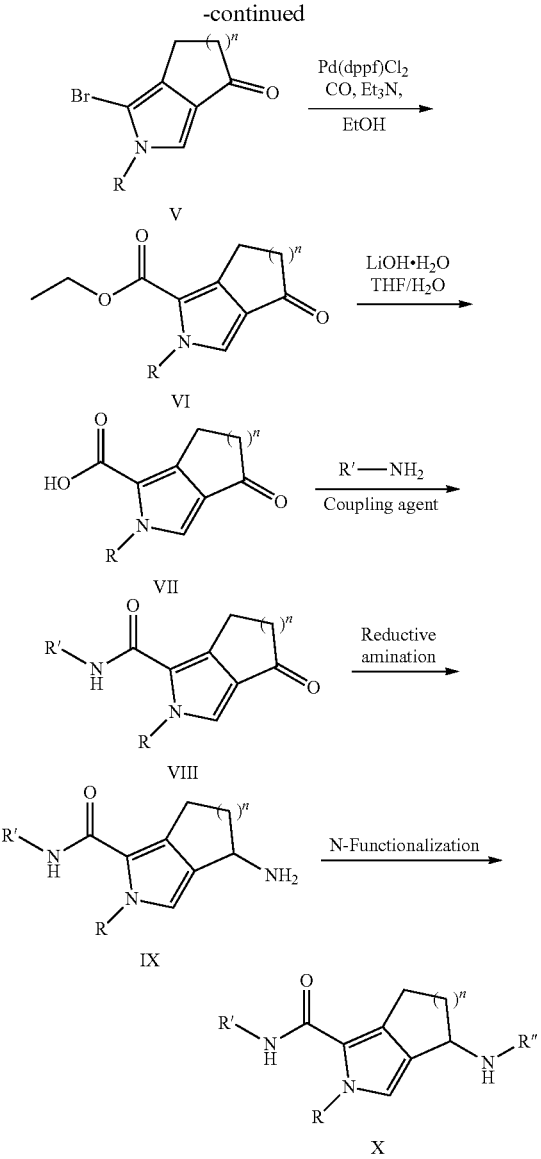

Conversion of a cyclic α,β-unsaturated ketone to bicyclic pyrrole derivative III can be achieved by reaction with tosylmethyl isocyanide (TosMIC) (exemplified in *Tetrahedron Lett.*, 2012, 53, 819). Bromination of III with N-bromosuccinimide to provide IV can be followed by N-functionalization to generate V. Palladium (II) catalyzed carbonylation in the presence of carbon monoxide and ethanol provides ester VI, which can be hydrolyzed and converted to carboxamide VIII. Reductive amination, either by chiral or racemic methods, utilizing ketone VIII can be performed to provide IX, which can be further functionalized to provide X.

Methods

The invention provides a method of treating or preventing hepatitis virus infection in a subject. In certain embodiments, the infection comprises hepatitis B virus (HBV) infection. In other embodiments, the infection comprises hepatitis D virus (HDV) infection. In yet other embodiments, the infection comprises HBV-HDV infection. In yet other embodiments, the method comprises administering to the subject in need thereof a therapeutically effective amount of at least one compound of the invention. In yet other embodiments, the at least one compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis infection. In yet other embodiments, the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript. In yet other embodiments, the subject is co-administered the at least one compound and the at least one additional agent. In yet other embodiments, the at least one compound and the at least one additional agent are coformulated.

The invention further provides a method of inhibiting expression and/or function of a viral capsid protein either directly or indirectly in a subject. In certain embodiments, the method comprises administering to the subject in need thereof a therapeutically effective amount of at least one compound of the invention. In other embodiments, the at least one compound is administered to the subject in a pharmaceutically acceptable composition. In yet other embodiments, the at least one compound of the invention is the only antiviral agent administered to the subject. In yet other embodiments, the subject is further administered at least one additional agent useful for treating HBV and/or HDV infection. In yet other embodiments, the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript. In yet other embodiments, the subject is co-administered the at least one compound and the at least one additional agent. In yet other embodiments, the at least one compound and the at least one additional agent are coformulated. In yet other embodiments, the subject is a mammal. In yet other embodiments, the mammal is a human.

The invention further provides methods of preparing compounds of the invention, using for examples synthetic transformations illustrated in Schemes 1-4, or any experimental examples recited herein.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or any combinations of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous, or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring, and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and any combinations thereof. One such preservative is a combination of about 0.5% to 2.0% benzyl alcohol and 0.05-0.5% sorbic acid.

The composition may include an antioxidant and a chelating agent that inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e. g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non-ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

The following procedures can be utilized in evaluating and selecting compounds that inhibit hepatitis B virus infection.

HepDE19 Assay with bDNA Quantitation of HBV rcDNA:

HepDE19 cell culture system is a HepG2 (human hepatocarcinoma) derived cell line that supports HBV DNA replication and cccDNA formation in a tetracycline (Tet)-regulated manner and produces HBV rcDNA and a detectable reporter molecule dependent on the production and maintenance of cccDNA (Guo, et al., 2007, J. Virol. 81:12472-12484).

HepDE19 (50,000 cells/well) were plated in 96-well collagen-coated tissue-culture treated microtiter plates in DMEM/F12 medium supplemented with 10% fetal bovine serum, 1% penicillin-streptomycin and 1 μg/mL tetracycline and incubated in a humidified incubator at 37° C. and 5% $CO_2$ overnight. Next day, the cells were switched to fresh medium without tetracycline and incubated for 4 hours at 37° C. and 5% $CO_2$. The cells were treated with fresh Tet-free medium with compounds at concentrations starting at 25 μM and a serial, ½ log, 8-point, titration series in duplicate. The final DMSO concentration in the assay was 0.5%. The plates were incubated for 7 days in a humidified incubator at 37° C. and 5% $CO_2$. Following a 7 day-incubation, the level of rcDNA present in the inhibitor-treated wells was measured using a Quantigene 2.0 bDNA assay kit (Affymetrix, Santa Clara, Calif.) with HBV specific custom probe set and manufacturers instructions. Concurrently, the effect of compounds on cell viability was assessed using replicate plates, plated at a density of 5,000 cells/well and incubated for 4 days, to determine the ATP content as a measure of cell viability using the cell-titer glo reagent (CTG; Promega Corporation, Madison, Wis.) as per manufacturer's instructions. The plates were read using a Victor luminescence plate reader (PerkinElmer Model 1420 Multilabel counter) and the relative luminescence units (RLU) data generated from each well was calculated as % inhibition of the untreated control wells and analyzed using XL-Fit module in Microsoft Excel to determine $EC_{50}$ and $EC_{90}$ (bDNA) and $CC_{50}$ (CTG) values using a 4-parameter curve fitting algorithm.

LCMS Methods:

LCMS Method A: Waters Acquity UPLC system employing a Waters Acquity UPLC BEH C18, 1.7 μm, 50×2.1 mm column with an aqueous component of 0.05% trifluoroacetic acid in water and an organic component of 0.05% trifluoroacetic acid in acetonitrile. Solvent events: 0-9.5 min, linear gradient of 0-98% of (0.05% trifluoroacetic acid in acetonitrile); 9.5-10.5 min, linear gradient of 98-0% of (0.05% trifluoroacetic acid in acetonitrile). Flow rate=0.8 mL/min. Column temperature 25° C.

HPLC Methods:

HPLC Method B: Waters 2695/2998 system employing a Xbridge C18, 5μ, 150×4.6 mm column with an aqueous component of 0.05% trifluoroacetic acid in water and an organic component of 0.05% trifluoroacetic acid in acetonitrile. Solvent events: 0-1 min, isocratic 5% (0.05% trifluoroacetic acid in acetonitrile); 1-8 min, linear gradient of 5-95% of (0.05% trifluoroacetic acid in acetonitrile); 8-9 min, isocratic 95% (0.05% trifluoroacetic acid in acetonitrile); 9-10 min, linear gradient of 95-5% of (0.05% trifluoroacetic acid in acetonitrile). Flow rate=1.2 mL/min. Column temperature 25° C.

"Enantiomer I" or "Diastereomer I" refers to the first enantiomer or diastereomer eluded from the chiral column under the specific chiral analytical conditions detailed for examples provided elsewhere herein; and "Enantiomer II" or "Diastereomer II" refers to the second enantiomer or diastereomer eluded from the chiral column under the specific chiral analytical conditions detailed for examples provided elsewhere herein. Such nomenclature does not imply or impart any particular relative and/or absolute configuration for these compounds.

Example 1: N-(3-Chloro-4-fluorophenyl)-2-methyl-4-oxo-2,4,5,6-tetrahydrocyclopenta[c]pyrrole-1-carboxamide (44, VIIIa)

5,6-Dihydrocyclopenta[c]pyrrol-4(2H)-one (IIIa)

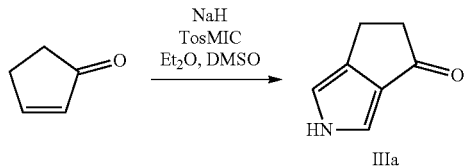

To 3.9 g (97.5 mmol, 1.6 eq.) of a 60% dispersion of sodium hydride in mineral oil in 80 mL of 1:1 (v/v) diethyl ether:dimethyl sulfoxide at 0° C. was added drop-wise a solution of 5.0 g (60.9 mmol, 1.0 eq.) of cyclopent-2-en-1-one and 13.0 g (67.1 mmol, 1.1 eq.) of tosylmethyl isocyanide (TosMIC) in 80 mL of 1:1 (v/v) diethyl ether:dimethyl sulfoxide. The reaction mixture was stirred at room temperature for 16 h and then quenched by the addition of 100 mL of sat. ammonium chloride solution. The mixture was extracted with 3×100 mL of ethyl acetate and the combined organic extracts were washed with 100 mL of water, 100 mL of brine, dried ($Na_2SO_4$) and the solvent was removed in vacuo. The residue was purified by flash chromatography ($SiO_2$, eluting with a linear gradient of 30-50% ethyl acetate/petroleum ether) to provide 2.5 g (20.6 mmol, 34%) of 5,6-dihydrocyclopenta[c]pyrrol-4(2H)-one (IIIa). LCMS: m/z found 122.2, $[M+H]^+$; $^1$H NMR (500 MHz, DMSO-$d_6$): δ 11.67 (bs, 1H), 7.14-7.16 (m, 1H), 6.63-6.64 (m, 1H), 2.76-2.81 (m, 2H), 2.70-2.73 (m, 2H). The above reaction was carried out on multiple batches with consistent results to provide 40 g of 5,6-dihydrocyclopenta[c]pyrrol-4(2H)-one (IIIa).

1-Bromo-5,6-dihydrocyclopenta[c]pyrrol-4(2H)-one (IVa)

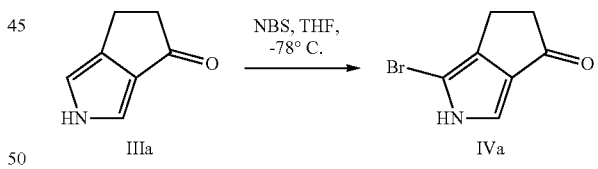

To a solution of 2.0 g (16.4 mmol, 1.0 eq.) of 5,6-dihydrocyclopenta[c]pyrrol-4(2H)-one (IIIa) in 70 mL of THF at −78° C. under a nitrogen atmosphere was added drop-wise a solution of 2.9 g (16.4 mmol, 1.0 eq.) of N-bromosuccinimide in 10 mL of THF and the mixture was stirred at −78° C. for 2 h. The mixture was allowed to warm to room temperature and diluted with 70 mL of water. The mixture was then and extracted with 3×50 mL of ethyl acetate and the combined organic extracts were washed with 50 mL of water, 50 mL of brine, dried ($Na_2SO_4$) and the solvent was removed in vacuo. The residue was purified by flash chromatography ($SiO_2$, eluting with a linear gradient of 5-20% ethyl acetate/petroleum ether) to provide 1.5 g (7.5 mmol, 45%) of 1-bromo-5,6-dihydrocyclopenta[c]pyrrol-4(2H)-one (IVa) as an off-white solid. $^1$H NMR (400 MHz, $CDCl_3$): δ 9.00 (br s, 1H), 7.14-7.15 (m, 1H), 2.88-2.92 (m, 2H), 2.80-2.84 (m, 2H). The above reaction was carried out on multiple batches with consistent results to provide 30 g of 1-bromo-5,6-dihydrocyclopenta[c]pyrrol-4(2H)-one (IVa).

1-Bromo-2-methyl-5,6-dihydrocyclopenta[c]pyrrol-4(2H)-one (Va)

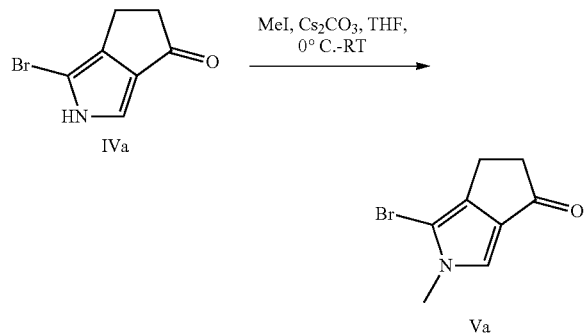

To a solution of 10.0 g (50.3 mmol, 1.0 eq.) of 1-bromo-5,6-dihydrocyclopenta[c]pyrrol-4(2H)-one (IVa) in 150 mL of THF at 0° C. was added 32.7 g (100.5 mmol, 2.0 eq.) of caesium carbonate and 10.6 g (75.4 mmol, 1.5 eq.) of methyl iodide. The mixture was then allowed to warm to room temperature and stirred for 16 h. The mixture was diluted with 200 mL of water and extracted with 3×300 mL of ethyl acetate. The combined organic extracts were washed with 200 mL of water, 200 mL of brine, dried (Na$_2$SO$_4$) and the solvent was removed in vacuo. The residue was purified by trituration with 100 mL of 1:1 (v/v) diethyl ether:n-pentane mixture and dried under high vacuum to provide 8.1 g (37.9 mmol, 75%) of 1-bromo-2-methyl-5,6-dihydrocyclopenta[c]pyrrol-4(2H)-one (Va). LCMS: m/z found 214.3/216.3 [M+H]$^+$; $^1$H NMR (400 MHz, CDCl$_3$): δ 7.09 (s, 1H), 3.67 (s, 3H), 2.76-2.85 (m, 4H). The above reaction was carried out on multiple batches with consistent results to provide 24 g of 1-bromo-2-methyl-5,6-dihydrocyclopenta[c]pyrrol-4(2H)-one (Va).

Ethyl 2-methyl-4-oxo-2,4,5,6-tetrahydrocyclopenta[c]pyrrole-1-carboxylate (VIa)

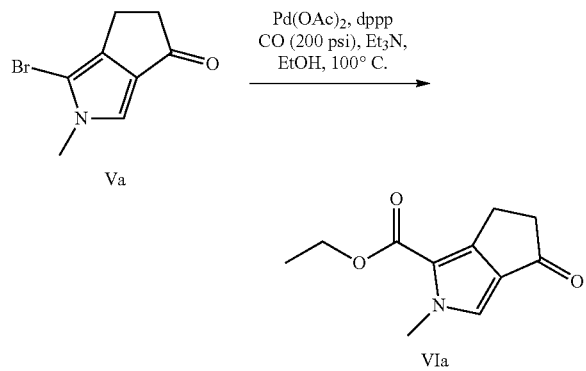

To a solution of 3.0 g (13.2 mmol, 1.0 eq.) of 1-bromo-2-methyl-5,6-dihydrocyclopenta[c] pyrrol-4(2H)-one (Va) in 30 mL of ethanol was added 9.2 mL (65.8 mmol, 5.0 eq.) of triethylamine. The mixture was degassed with argon for 15 min and 0.3 g (1.32 mmol, 0.1 eq.) of palladium(II) acetate was added followed by and 0.81 g (1.97 mmol, 0.15 eq.) of 1,3-bis(diphenylphosphino)propane (dppp). The mixture was then stirred at 100° C. under 200 psi of carbon monoxide gas for 16 h. The mixture was allowed to cool to room temperature, filtered through CELITE® and the pad was washed with 20 mL of ethanol. The solvent was removed in vacuo and the residue was resuspended in 100 mL of water. The mixture was extracted with 3×80 mL of ethyl acetate and the combined organic extracts were washed with 50 mL of water, 50 mL of brine, dried (Na$_2$SO$_4$), filtered and the solvent was removed in vacuo. The residue was purified by flash chromatography (SiO$_2$, eluting with a linear gradient of 10-25% ethyl acetate/petroleum ether) to provide 2.1 g (10.1 mmol, 77%) of ethyl 2-methyl-4-oxo-2,4,5,6-tetrahydrocyclopenta[c]pyrrole-1-carboxylate (VIa). $^1$H NMR (300 MHz, CDCl$_3$): δ 7.10 (s, 1H), 4.31 (q, 2H), 4.00 (s, 3H), 3.06-3.10 (m, 2H), 2.82-2.85 (m, 2H), 1.37 (t, 3H). The above reaction was carried out on multiple batches with consistent results to provide 15 g of ethyl 2-methyl-4-oxo-2,4,5,6-tetrahydrocyclopenta[c]pyrrole-1-carboxylate (VIa).

2-Methyl-4-oxo-2,4,5,6-tetrahydrocyclopenta[c]pyrrole-1-carboxylic acid (VIIa)

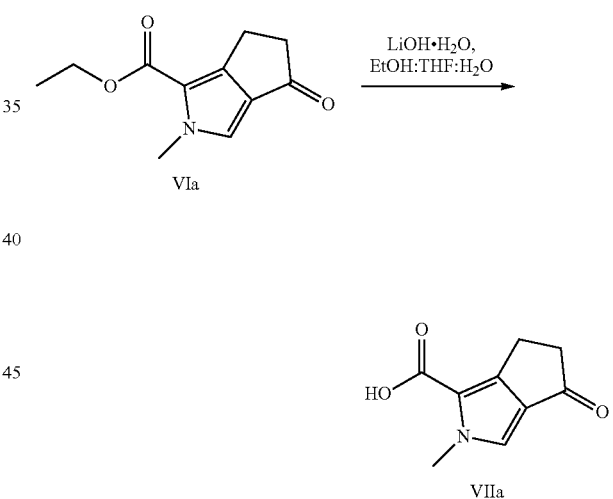

To a solution of 5.5 g (26.6 mmol, 1.0 eq.) of ethyl 2-methyl-4-oxo-2,4,5,6-tetrahydrocyclopenta[c]pyrrole-1-carboxylate (VIa) in 100 mL of 2:2:1 (v/v/v) ethanol:THF:water was added 2.5 g (59.5 mmol, 2.3 eq.) of lithium hydroxide monohydrate and the mixture was stirred at room temperature for 16 h. The organics were removed in vacuo and the residue was acidified using 5 M aq. HCl to pH 3. The precipitated solid was isolated by vacuum filtration, washed with 30 mL of n-pentane and then dried under high vacuum to provide 4.5 g (25.1 mmol, 89%) of 2-methyl-4-oxo-2,4,5,6-tetrahydro cyclopenta[c]pyrrole-1-carboxylic acid (VIIa). LCMS: m/z found 180.39 [M+H]$^+$. The above reaction was carried out on multiple batches with consistent results to provide 9 g of 2-methyl-4-oxo-2,4,5,6-tetrahydrocyclopenta[c]pyrrole-1-carboxylic acid (VIIa).

N-(3-Chloro-4-fluorophenyl)-2-methyl-4-oxo-2,4,5, 6-tetrahydrocyclopenta[c]pyrrole-1-carboxamide (44, VIIIa)

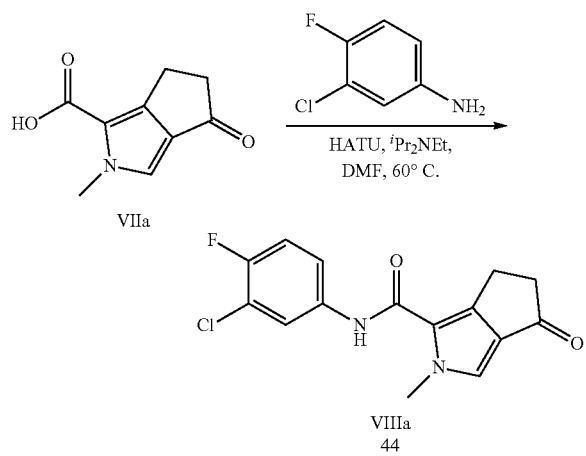

VIIIa
44

To a solution of 4.5 g (25.1 mmol, 1.0 eq.) of 2-methyl-4-oxo-2,4,5,6-tetrahydro cyclopenta[c]pyrrole-1-carboxylic acid (VIIa) in 35 mL of DMF at 0° C. was added 9.7 g (75.4 mmol, 3.0 eq.) of N,N-diisopropylethylamine followed by 14.3 g (37.6 mmol, 1.5 eq.) of hexafluorophosphate azabenzotriazole tetramethyl uronium (HATU) and 5.4 g (37.2 mmol, 1.5 eq.) of 3-chloro-4-fluoro aniline, and the mixture was heated at 60° C. for 16 h. The mixture was allowed to cool to room temperature and diluted with 100 mL of ice-cold water. The resulting precipitate was isolated by vacuum filtration, dried under vacuum and purified by trituration with pentane and with diethyl ether to provide 5.6 g (18.3 mmol, 72%) of N-(3-chloro-4-fluorophenyl)-2-methyl-4-oxo-2,4,5,6-tetrahydrocyclopenta[c]pyrrole-1-carboxamide (VIIIa, 44). LCMS: m/z found 307.2/309.2 [M+H]+, RT=5.85 min (Method A); HPLC: 7.50 min (Method B); $^1$H NMR (400 MHz, CDCl$_3$): δ 7.76-7.73 (m, 1H), 7.36-7.32 (m, 1H), 7.22 (br s, 1H), 7.16 (s, 1H), 7.13 (t, 1H), 4.06 (s, 3H), 3.17 (t, 2H), 2.98-2.95 (m, 2H). The above reaction was carried out on multiple batches with consistent results to provide N-(3-Chloro-4-fluorophenyl)-2-methyl-4-oxo-2,4,5,6-tetrahydrocyclopenta[c]pyrrole-1-carboxamide (VIIIa).

Example 2: Methyl 1-(3-chloro-4-fluorophenylcarbamoyl)-2-methyl-2,4,5,6-tetrahydrocyclopenta[c]pyrrol-4-ylcarbamate (1, 4, 5)

4-Amino-N-(3-chloro-4-fluorophenyl)-2-methyl-2,4, 5,6-tetrahydrocyclopenta[c]pyrrole-1-carboxamide (IXa, 100) Procedure A

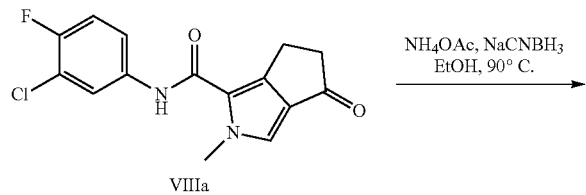

VIIIa

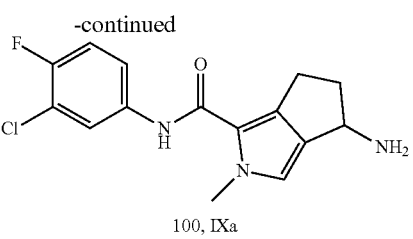

100, IXa

To a solution of 0.25 g (0.82 mmol, 1.0 eq.) of N-(3-chloro-4-fluorophenyl)-2-methyl-4-oxo-2,4,5,6-tetrahydrocyclopenta[c]pyrrole-1-carboxamide (VIIIa) in 10 mL of ethanol was added 1.03 g (16.33 mmol, 20.0 eq.) of ammonium acetate and 0.13 g (1.63 mmol, 2.0 eq.) of sodium cyanoborohydride and the mixture was subjected to microwave irradiation maintaining a reaction temperature of 90° C. for 2 h. The solvent was removed in vacuo and the residue was resuspended in 30 mL of ethyl acetate. The mixture was washed 20 mL of water, 20 mL of brine, dried (Na$_2$SO$_4$), filtered and the solvent was removed in vacuo. The residue was purified by flash chromatography (SiO$_2$, eluting with a linear gradient of 15-20% ethyl acetate/hexanes to provide 0.20 g (0.65 mmol, 79%) of 4-amino-N-(3-chloro-4-fluorophenyl)-2-methyl-2,4,5,6-tetrahydrocyclopenta[c]pyrrole-1-carboxamide (IXa). LCMS (ES−): m/z found 306.2/308.2 [M−H]. $^1$H NMR (400 MHz, DMSO-d$_6$): δ 9.30 (bs, 1H), 7.91-7.94 (m, 1H), 7.55-7.60 (m, 1H), 7.36 (t, 1H), 6.75 (s, 1H), 4.14-4.19 (m, 1H), 3.77 (s, 3H), 2.90-2.98 (m, 1H), 2.71-2.79 (m, 1H), 2.49-2.56 (m, 1H), 1.85-1.91 (m, 1H). The above reaction was performed on multiple batches with consistent results.

4-Amino-N-(3-chloro-4-fluorophenyl)-2-methyl-2,4, 5,6-tetrahydrocyclopenta[c]pyrrole-1-carboxamide (IXa) Procedure B

4-((tert-Butylsulfinyl)amino)-N-(3-chloro-4-fluorophenyl)-2-methyl-2,4,5,6-tetrahydrocyclopenta[c] pyrrole-1-carboxamide (XIa)

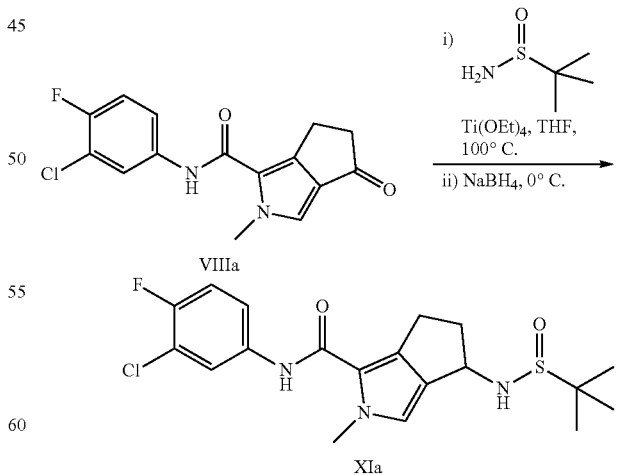

To a solution of 5.0 g (15.6 mmol, 1.0 eq.) of N-(3-chloro-4-fluorophenyl)-2-methyl-4-oxo-2,4,5,6-tetrahydrocyclopenta[c]pyrrole-1-carboxamide (VIIIa) in 50 mL of THF was added 3.7 g (30.7 mmol, 2.0 eq.) of racemic 2-methylpropane-2-sulfinamide and 24.9 g 109 mmol, 7.0 eq.) of titanium tetraethoxide and the mixture was stirred at 100° C. in a sealed tube for 16 h. The mixture was then cooled to 0° C. and 1.39 g (36.7 mmol, 2.3 eq.) of sodium borohydride was added and stirring was continued for an additional 6 h. The reaction was quenched with 250 mL of ice-cold water and the resultant heterogeneous mixture was filtered. The filtrate was then extracted with 3×100 mL of ethyl acetate and the combined organic extracts were washed with 200 mL of brine, dried (Na$_2$SO$_4$), filtered and the solvent was removed in vacuo. The residue was purified by flash chromatography (SiO$_2$, eluting with a linear gradient of 20-60% ethyl acetate/petroleum ether) to provide 4.9 g (11.9 mmol, 76%) of 4-((tert-butylsulfinyl)amino)-N-(3-chloro-4-fluorophenyl)-2-methyl-2,4,5,6-tetrahydrocyclopenta[c]pyrrole-1-carboxamide (XIa) as a mixture of diastereomers, which was taken forward without separation. LCMS: m/z found 412.4/414.4 [M+H]$^+$, 2.47, 2.52 min.

4-Amino-N-(3-chloro-4-fluorophenyl)-2-methyl-2,4,5,6-tetrahydrocyclopenta[c]pyrrole-1-carboxamide (IXa)

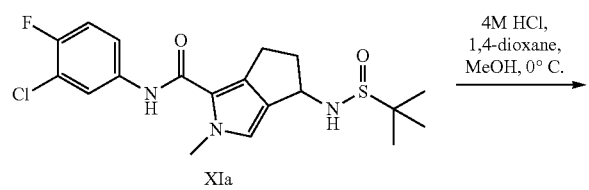

To a solution of 1.0 g (2.4 mmol, 1.0 eq.) of 4-((tert-butylsulfinyl)amino)-N-(3-chloro-4-fluorophenyl)-2-methyl-2,4,5,6-tetrahydrocyclopenta[c]pyrrole-1-carboxamide (XIa) in 10 mL of methanol at 0° C. was added 1 mL of a 4 M solution of HCl in 1,4-dioxane and the mixture was stirred at 0° C. for 1 h. The solvent was removed in vacuo and the residue was triturated with 8 mL of 1:4 (v/v) ethyl acetate:diethyl ether. The resulting solid was dissolved in 50 mL of 1:4 (v/v) methanol:methylene chloride and washed with 2×50 mL of saturated sodium bicarbonate solution, dried (Na$_2$SO$_4$), filtered and the solvent removed in vacuo to provide 0.7 g (2.27 mmol, 93%) of racemic 4-amino-N-(3-chloro-4-fluorophenyl)-2-methyl-2,4,5,6-tetrahydrocyclopenta[c]pyrrole-1-carboxamide (IXa). LCMS (ES-): m/z found 306.4/308.4 [M−H], RT=1.85 min. The above reaction was performed on multiple batches with consistent results.

Example 3: Methyl 1-(3-chloro-4-fluorophenylcarbamoyl)-2-methyl-2,4,5,6-tetrahydrocyclopenta[c]pyrrol-4-ylcarbamate (1, 4, 5)

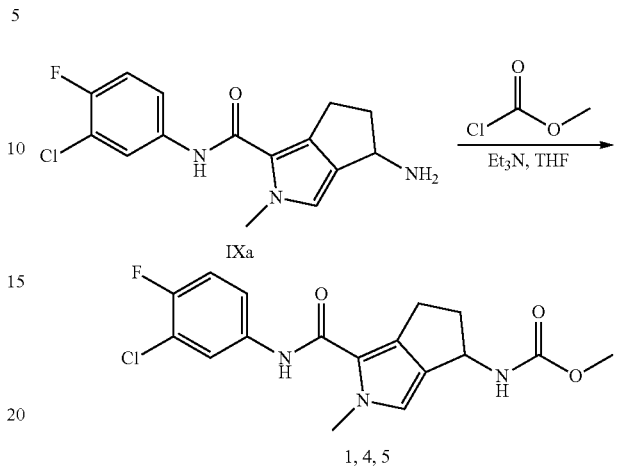

To a solution of 0.20 g (0.65 mmol, 1.0 eq.) of 4-amino-N-(3-chloro-4-fluorophenyl)-2-methyl-2,4,5,6-tetrahydrocyclopenta[c]pyrrole-1-carboxamide (IXa) in 10 mL of THF was added 0.25 mL (1.95 mmol, 3.0 eq.) of triethylamine followed by 0.09 g (0.98 mmol, 1.5 eq.) of methyl chloroformate and the mixture was stirred at room temperature for 30 min. The solvent was removed in vacuo and the residue was redissolved in 25 mL of ethyl acetate. The organic solution was washed with 15 mL of water, 15 mL of brine, dried (Na$_2$SO$_4$), filtered and the solvent was removed in vacuo. The residue was purified by semi-preparative HPLC to provide 0.080 g (0.22 mmol, 34%) of racemic methyl 1-(3-chloro-4-fluorophenylcarbamoyl)-2-methyl-2,4,5,6-tetrahydrocyclopenta[c]pyrrol-4-ylcarbamate (1); LCMS: m/z found 366.2/366.4 [M+H]$^+$, RT=6.65 min (Method A); $^1$H NMR (400 MHz, DMSO-d$_6$): δ 9.35 (s, 1H), 7.93 (dd, 1H), 7.56-7.58 (m, 1H), 7.34-7.43 (m, 2H), 6.80 (s, 1H), 4.79-4.80 (m, 1H), 3.77 (s, 3H), 3.53 (s, 3H), 2.91-2.96 (m, 1H), 2.78-2.83 (m, 1H), 2.56-2.62 (m, 1H), 2.06-2.13 (m, 1H). The enantiomers were subsequently separated by SFC (Waters SFC investigator. Method isocratic, Mobile phase MeOH:CO$_2$—50:50. Column: Chiralpak AD-H (30×250 mm), 5 μm, flow rate: 60 g/min.

Methyl 1-(3-chloro-4-fluorophenylcarbamoyl)-2-methyl-2,4,5,6-tetrahydrocyclopenta[c] pyrrol-4-ylcarbamate—Enantiomer I (4) LCMS: m/z found 366.2/366.4 [M+H]$^+$, RT=6.64 min (Method A); HPLC: 8.13 min (Method B); Chiral HPLC: RT=2.36 min; $^1$H NMR (400 MHz, DMSO-d$_6$): δ 9.33 (s, 1H), 7.93 (dd, 1H), 7.55-7.59 (m, 1H), 7.34-7.41 (m, 2H), 6.79 (s, 1H), 4.79-4.80 (m, 1H), 3.76 (s, 3H), 3.53 (s, 3H), 2.90-2.96 (m, 1H), 2.77-2.83 (m, 1H), 2.56-2.62 (m, 1H), 2.06-2.33 (m, 1H).

Methyl 1-(3-chloro-4-fluorophenylcarbamoyl)-2-methyl-2,4,5,6-tetrahydrocyclopenta[c] pyrrol-4-ylcarbamate—Enantiomer II (5) LCMS: m/z found 366.2/366.4 [M+H]$^+$, RT=6.63 min (Method A); HPLC: 8.11 min (Method B); Chiral HPLC: RT=3.08 min; $^1$H NMR (400 MHz, DMSO-d$_6$): δ 9.34 (s, 1H), 7.93 (dd, 1H), 7.55-7.59 (m, 1H), 7.34-7.41 (m, 2H), 6.79 (s, 1H), 4.79-4.80 (m, 1H), 3.77 (s, 3H), 3.53 (s, 3H), 2.91-2.96 (m, 1H), 2.78-2.83 (m, 1H), 2.56-2.62 (m, 1H), 2.06-2.33 (m, 1H).

Example 4: N-(3-Chloro-4-fluorophenyl)-2-methyl-4-(3-methylureido)-2,4,5,6-tetrahydrocyclopenta[c]pyrrole-1-carboxamide (3)

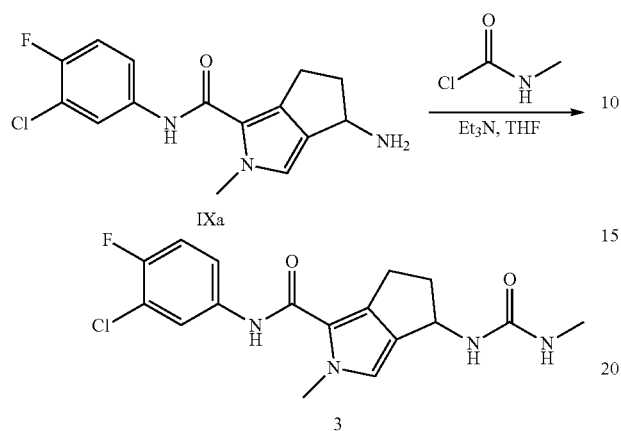

To a solution of 0.20 g (0.65 mmol, 1.0 eq.) of 4-amino-N-(3-chloro-4-fluorophenyl)-2-methyl-2,4,5,6-tetrahydrocyclopenta[c]pyrrole-1-carboxamide (IXa) in 5 mL of THF was added 0.18 mL (1.30 mmol, 1.5 eq.) of triethylamine followed by 0.09 g (0.98 mmol, 1.5 eq.) of N-methyl carbamoyl chloride and the mixture was stirred at room temperature for 4 h. The solvent was removed in vacuo and the residue was crystallized with ethanol and dried under vacuum to provide 0.015 g (0.041 mmol, 6.0%) of racemic N-(3-chloro-4-fluorophenyl)-2-methyl-4-(3-methylureido)-2,4,5,6-tetrahydrocyclopenta[c]pyrrole-1-carboxamide (3). $^1$H NMR (400 MHz, DMSO-$d_6$): δ 9.34 (s, 1H), 7.93 (dd, 1H), 7.55-7.59 (m, 1H), 7.36 (dd, 1H), 6.79 (s, 1H), 6.02 (d, 1H), 5.57-5.59 (m, 1H), 4.83-4.88 (m, 1H), 3.77 (s, 3H), 2.93-2.97 (m, 2H), 2.56 (d, 1H), 2.51 (s, 3H), 1.94-2.04 (m, 1H).

Non-Limiting Illustrative Procedure for Formation of Imidazole Carboxylates

Scheme 2.

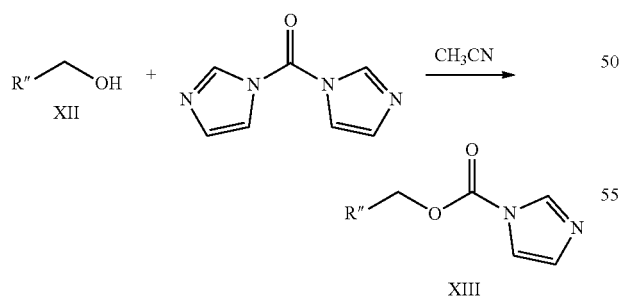

A solution of 1.25 mmol (1.0 eq.) of the alcohol (XII) in 0.5 mL of anhydrous acetonitrile was added to a rapidly stirred mixture of 1.87 mmol (1.5 eq.) of 1,1'-carbonyldiimidazole in 1.5 mL of anhydrous acetonitrile. The reaction mixture was stirred for 40 minutes, and the volatiles were then removed in vacuo. The resulting residue was resuspended in 15 mL of water and extracted with 3 volumes of organic solvent. The combined organic extracts were washed with sat. sodium carbonate solution, followed by brine, dried ($Na_2SO_4$), filtered and evaporated to dryness. The residue was dried under high vacuum to provide the product (XIII), which was used without further purification.

Non-Limiting Illustrative Procedure for Formation of Carbamates Using Imidazole Carboxylates Scheme 3.

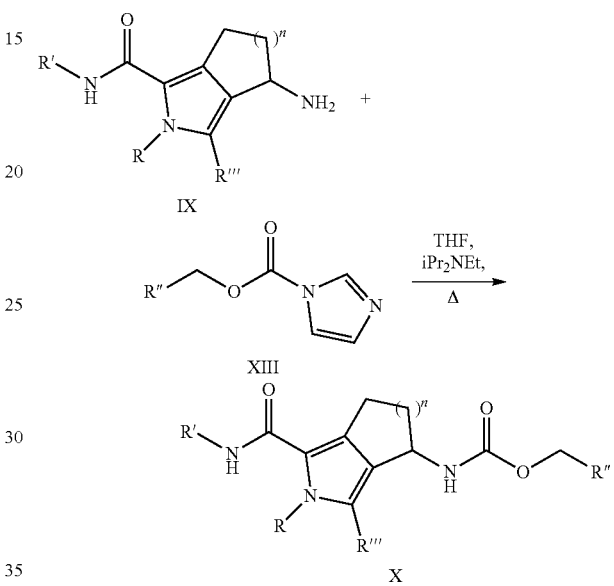

To a solution of 1.0 eq. of IX, 1.3 eq. of XIII and 0.2 eq. of N,N-dimethylaminopyridine in THF was added 1.3 eq. of N,N-diisopropylethylamine, and the mixture was stirred until a solution was formed. The mixture was then heated at 65° C. for 16 hours and diluted with ethyl acetate. The mixture was washed with water, followed by two volumes of sat. $NaHCO_3$ and then brine. The organic phase was dried ($Na_2SO_4$), filtered and the solvent was removed in vacuo. The residue was purified by flash chromatography to provide X.

Example 5: (1-Methyl-1H-1,2,4-triazol-3-yl)methyl (1-((3-chloro-4-fluorophenyl) carbamoyl)-2-methyl-2,4,5,6-tetrahydrocyclopenta[c]pyrrol-4-yl)carbamate (25, 26)

(1-Methyl-1H-1,2,4-triazol-3-yl)methyl 1H-imidazole-1-carboxylate (XIIIa)

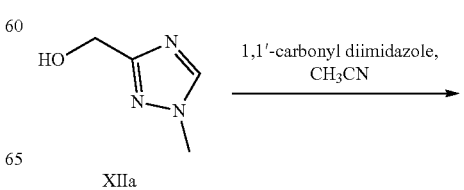

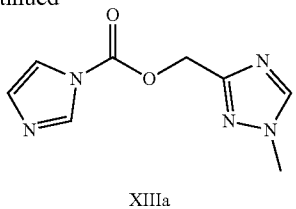

XIIIa

To a solution of 0.5 g (4.42 mmol, 1.0 eq.) of (1-methyl-1H-1,2,4-triazol-3-yl)methanol (XIIa) in 20 mL of acetonitrile was added 1.07 g (6.63 mmol, 1.5 eq.) of 1,1′-carbonyl and the mixture was stirred at room temperature for 2 h. Volatiles were removed in vacuo and the residue was resuspend in 20 mL of water. The mixture was extracted with 3×50 mL of 5% methanol in methylene chloride. The combined organic extracts were washed with 50 mL of sat. sodium carbonate solution, followed by 50 mL of brine, dried ($Na_2SO_4$), filtered and the solvent was removed in vacuo to provide 0.77 g of (1-methyl-1H-1,2,4-triazol-3-yl)methyl 1H-imidazole-1-carboxylate (XIIIa).

(1-Methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate (25, 26)

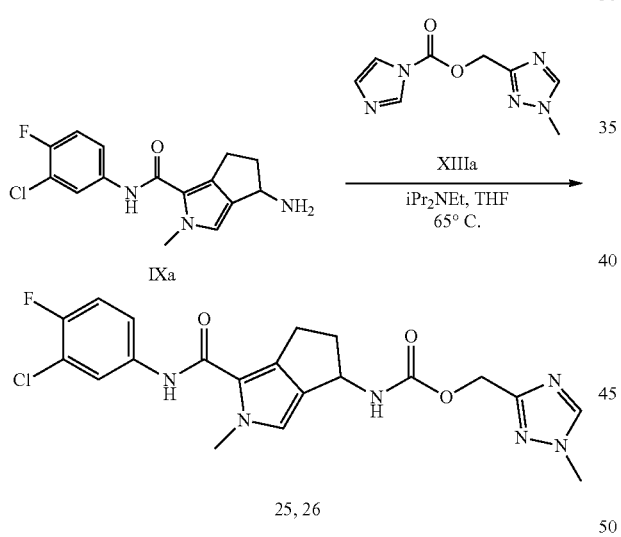

To a solution of 0.55 g (1.79 mmol, 1.0 eq.) of 4-amino-N-(3-chloro-4-fluorophenyl)-2-methyl-2,4,5,6-tetrahydrocyclopenta[c]pyrrole-1-carboxamide (IXa) in 6 mL of THF at 0° C. under a nitrogen atmosphere was added 0.67 g (5.37 mmol, 3.0 eq.) of N,N-diisopropylethyl amine followed by 0.56 g (2.68 mmol, 1.5 eq.) of (1-methyl-1H-1,2,4-triazol-3-yl)methyl 1H-imidazole-1-carboxylate (XIIIa). The reaction mixture was then stirred at 65° C. for 16 h. The mixture was allowed to cool to room temperature and diluted with 100 mL of water. The mixture was extracted with 3×100 mL of ethyl acetate and the combined organic extracts were washed with 80 mL of water, 80 mL of brine, dried ($Na_2SO_4$), filtered and the solvent was removed in vacuo. The residue was purified by flash chromatography ($SiO_2$, eluted with a linear gradient of 0-4% methanol in methylene chloride) to provide 0.55 g (1.23 mmol, 68%) of racemic (1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate. The enantiomers were subsequently separated by SFC (Waters SFC investigator. Method isocratic, Mobile phase MeOH:$CO_2$—40:60. Column: Chiralcel OJ-H (30×250 mm), 5 µm, flow rate: 70 g/min.

(1-Methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate—Enantiomer I (25) LCMS: m/z found 447.3/449.2 [M+H]$^+$, RT=3.94 min, (Method A); $^1$H NMR (400 MHz, DMSO-d$_6$): δ 9.36 (s, 1H), 8.43 (s, 1H), 7.93 (dd, 1H), 7.56-7.59 (m, 2H), 7.36 (dd, 1H), 6.81 (s, 1H), 4.99 (s, 2H), 4.79-4.83 (m, 1H), 3.84 (s, 3H), 3.77 (s, 3H), 2.78-2.98 (m, 2H), 2.55-2.59 (m, 1H), 2.07-2.12 (m, 1H); Chiral SFC: RT=2.13 min (Column: Chiralcel OJ-H (250 mm×4.6 mm, 5 µm).

(1-Methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate—Enantiomer II (26) LCMS: m/z found 447.3/449.2 [M+H]$^+$, RT=3.93 min, (Method A); $^1$H NMR (400 MHz, DMSO-d$_6$): δ 9.36 (s, 1H), 8.43 (s, 1H), 7.93 (dd, 1H), 7.56-7.59 (m, 2H), 7.36 (dd, 1H), 6.81 (s, 1H), 4.99 (s, 2H), 4.79-4.83 (m, 1H), 3.84 (s, 3H), 3.77 (s, 3H), 2.78-2.98 (m, 2H), 2.55-2.59 (m, 1H), 2.07-2.12 (m, 1H); Chiral SFC: RT=5.23 min (Column: Chiralcel OJ-H (250 mm×4.6 mm, 5 µm).

Example 6: 1-(3-Chloro-4-fluorophenylcarbamoyl)-2-methyl-2,4,5,6-tetrahydrocyclopenta[c]pyrrol-4-ylcarbamate (2, 6, 7)

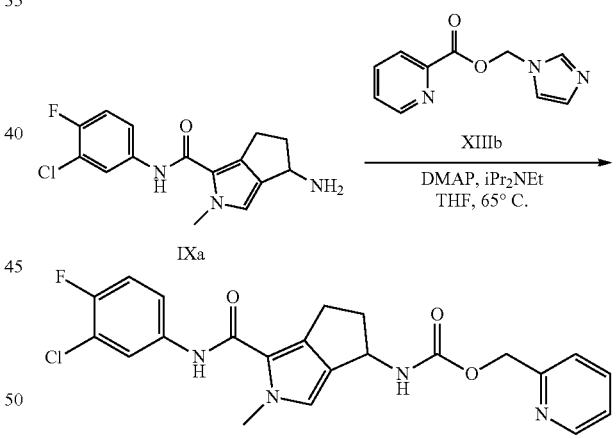

1-(3-Chloro-4-fluorophenylcarbamoyl)-2-methyl-2,4,5,6-tetrahydrocyclopenta[c]pyrrol-4-ylcarbamate (2) was synthesized in a similar manner as described above from 4-amino-N-(3-chloro-4-fluorophenyl)-2-methyl-2,4,5,6-tetrahydrocyclopenta[c]pyrrole-1-carboxamide (IXa) and pyridin-2-ylmethyl-1H-imidazole-1-carboxylate (XIIIb) LCMS: m/z found 443.25 [M+H]$^+$; $^1$H NMR (400 MHz, DMSO-d$_6$): δ 9.36 (s, 1H), 8.54 (d, 1H), 7.93 (dd, 1H), 7.82 (m, 1H), 7.69 (d, 1H), 7.56-7.59 (m, 1H), 7.31-7.39 (m, 3H), 6.81 (s, 1H), 5.09 (s, 2H), 4.81-4.84 (m, 1H), 3.79 (s, 3H), 2.92-2.99 (m, 1H), 2.79-2.86 (m, 1H), 2.61-2.67 (m, 1H), 2.09-2.15 (m, 1H). The enantiomers were subsequently separated by SFC (Waters SFC investigator. Method: isocratic, Mobile phase methanol:$CO_2$—40:60. Column: Chiralpak AD-H (30×250 mm, 5 μm), flow rate: 70 g/min.

1-(3-Chloro-4-fluorophenylcarbamoyl)-2-methyl-2,4,5,6-tetrahydrocyclopenta[c]pyrrol-4-ylcarbamate—Enantiomer I (6) LCMS: m/z found 443.3/445.3 $[M+H]^+$, RT=6.09 min (Method A); HPLC: RT=7.07 min (Method B); Chiral HPLC: RT: 2.13 min; $^1$H NMR (400 MHz, DMSO-$d_6$): δ 9.35 (s, 1H), 8.54 (d, 1H), 7.93 (dd, 1H), 7.82 (m, 1H), 7.69 (d, 1H), 7.56-7.59 (m, 1H), 7.32-7.38 (m, 3H), 6.81 (s, 1H), 5.09 (s, 2H), 4.81-4.84 (m, 1H), 3.78 (s, 3H), 2.94-2.99 (m, 1H), 2.79-2.86 (m, 1H), 2.61-2.67 (m, 1H), 2.07-2.15 (m, 1H). 1-(3-Chloro-4-fluorophenylcarbamoyl)-2-methyl-2,4,5,6-tetrahydrocyclopenta[c]pyrrol-4-ylcarbamate—Enantiomer II (7) LCMS: m/z found 443.3/445.3 $[M+H]^+$, RT=6.09 min (Method A); HPLC: RT=7.07 min (Method B); Chiral HPLC: RT: 5.77 min; $^1$H NMR (400 MHz, DMSO-$d_6$): δ 9.35 (s, 1H), 8.54 (d, 1H), 7.93 (dd, 1H), 7.82 (m, 1H), 7.69 (d, 1H), 7.56-7.59 (m, 1H), 7.32-7.38 (m, 3H), 6.81 (s, 1H), 5.09 (s, 2H), 4.81-4.84 (m, 1H), 3.78 (s, 3H), 2.94-2.99 (m, 1H), 2.79-2.86 (m, 1H), 2.61-2.67 (m, 1H), 2.07-2.15 (m, 1H).

Example 7: (1-Methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate (21, 22)

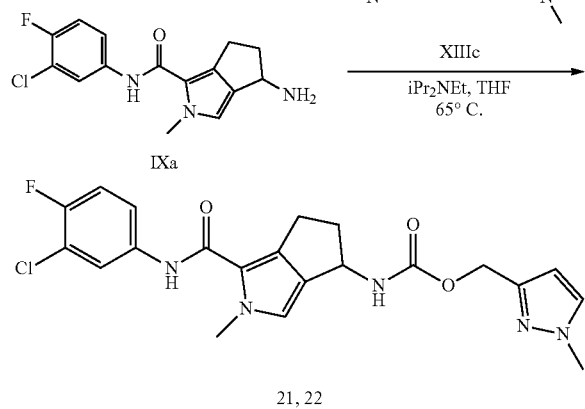

21, 22

(1-Methyl-1H-pyrazol-3-yl)methyl(1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (1-methyl-1H-pyrazol-3-yl)methyl 1H-imidazole-1-carboxylate (XIIIc). The enantiomers were subsequently separated by SFC (Waters SFC investigator). Method isocratic, Mobile phase MeOH:$CO_2$—30:70. Column: Chiralcel OJ-H (30×250 mm, 5 μm), flow rate: 60 g/min.

(1-Methyl-1H-pyrazol-3-yl)methyl(1-((3-chloro-4-fluorophenyl)carbamoyl)-2-methyl-2,4,5,6-tetrahydrocyclopenta[c]pyrrol-4-yl)carbamate—Enantiomer I (21) LCMS: m/z found 446.2/448.2 $[M+H]^+$, RT=4.43 min (Method A); Chiral-SFC: RT=2.96 min (Chiralpak AD-H (150 mm×4.6 mm, 3 μm); $^1$H NMR (300 MHz, DMSO-$d_6$): δ 9.36 (s, 1H), 7.93 (dd, 1H), 7.63 (s, 1H), 7.55-7.60 (m, 1H), 7.48 (d, 1H), 7.37 (t, 1H), 6.80 (s, 1H), 6.22 (s, 1H), 4.93 (s, 2H), 4.78-4.83 (m, 1H), 3.80 (s, 3H), 3.77 (s, 3H), 2.78-2.93 (m, 2H), 2.55-2.61 (m, 1H), 2.06-2.13 (m, 1H).

(1-Methyl-1H-pyrazol-3-yl)methyl(1-((3-chloro-4-fluorophenyl)carbamoyl)-2-methyl-2,4,5,6-tetrahydrocyclopenta[c]pyrrol-4-yl)carbamate—Enantiomer II (22) LCMS: m/z found 446.2/448.2 $[M+H]^+$, RT=4.43 min (Method A); Chiral-SFC: RT=4.16 min (Chiralpak AD-H (150 mm×4.6 mm, 3 μm); $^1$H NMR (300 MHz, DMSO-$d_6$): δ 9.36 (s, 1H), 7.93 (dd, 1H), 7.63 (s, 1H), 7.55-7.60 (m, 1H), 7.48 (d, 1H), 7.37 (dd, 1H), 6.80 (s, 1H), 6.22 (s, 1H), 4.93 (s, 2H), 4.78-4.83 (m, 1H), 3.80 (s, 3H), 3.77 (s, 3H), 2.78-2.93 (m, 2H), 2.55-2.61 (m, 1H), 2.06-2.13 (m, 1H).

Example 8: (1-Methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (116, 117)

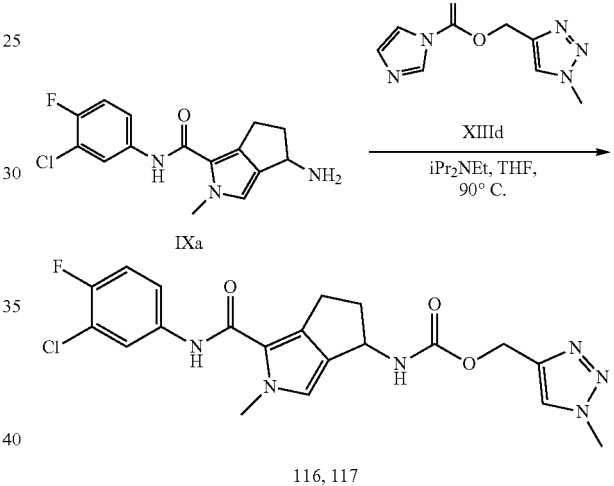

116, 117

(1-Methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (1-methyl-1H-1,2,3-triazol-4-yl)methyl 1H-imidazole-1-carboxylate (XIIId) The enantiomers were subsequently separated by SFC (Waters SFC investigator). Method: isocratic, Mobile phase MeOH:$CO_2$—45:55. Column: Chiralpak IA (30×250 mm), 5 μm, flow rate: 100 g/min.

(1-Methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer I (116) LCMS: m/z found 447.3/449.2 $[M+H]^+$, RT=7.50 min; (Method A); Chiral SFC: RT: 3.83 min, Column: Chiralpak IA (4.6×250 mm, 5 μm). $^1$H NMR (400 MHz, DMSO-$d_6$): δ 9.38 (s, 1H), 8.06 (s, 1H), 7.91-7.94 (m, 1H), 7.55-7.60 (m, 1H), 7.53 (bd, 1H), 7.36 (t, 1H), 6.80 (s, 1H), 5.05 (s, 2H), 4.79-4.83 (m, 1H), 4.04 (s, 3H), 3.77 (s, 3H), 2.89-2.98 (m, 1H), 2.77-2.85 (m, 1H), 2.53-2.61 (m, 1H), 2.16-2.23 (m, 1H).

(1-Methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer II (117) LCMS: m/z found 447.3/449.2 [M+H]⁺, RT=7.50 min; (Method A); Chiral SFC: RT: 5.57 min, Column: Chiralpak IA (4.6×250 mm, 5 μm). ¹H NMR (400 MHz, DMSO-d₆): δ 9.38 (s, 1H), 8.06 (s, 1H), 7.91-7.94 (m, 1H), 7.55-7.60 (m, 1H), 7.53 (bd, 1H), 7.36 (t, 1H), 6.80 (s, 1H), 5.05 (s, 2H), 4.79-4.83 (m, 1H), 4.04 (s, 3H), 3.77 (s, 3H), 2.89-2.98 (m, 1H), 2.77-2.85 (m, 1H), 2.53-2.61 (m, 1H), 2.16-2.23 (m, 1H).

Example 9: Oxazol-2-ylmethyl (1-((3-chloro-4-fluorophenyl)carbamoyl)-2-methyl-2,4,5,6-tetrahydro cyclopenta[c]pyrrol-4-yl)carbamate (34, 35)

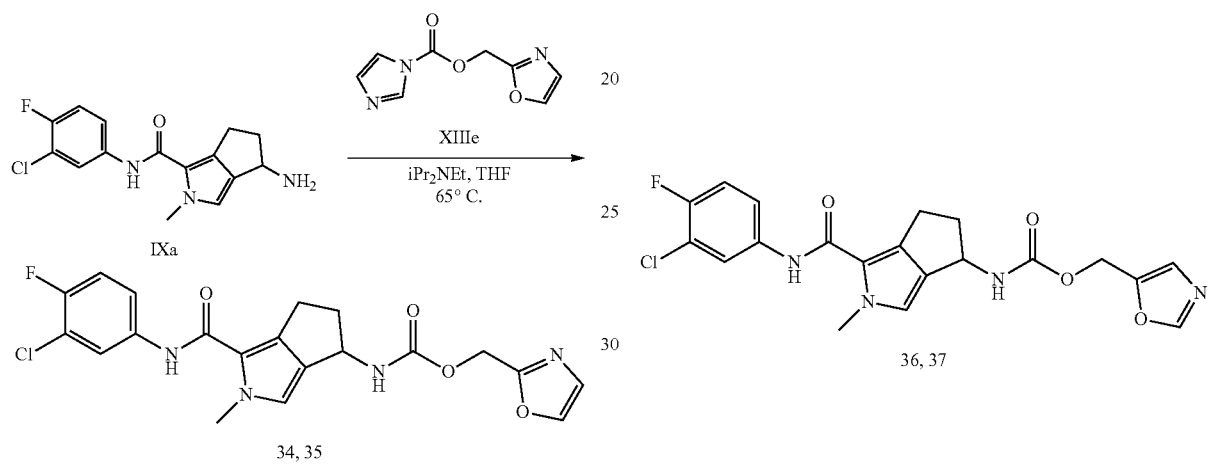

34, 35

Oxazol-2-ylmethyl (1-((3-chloro-4-fluorophenyl)carbamoyl)-2-methyl-2,4,5,6-tetrahydro cyclopenta[c]pyrrol-4-yl) carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and oxazol-2-ylmethyl 1H-imidazole-1-carboxylate (XIIIe). The enantiomers were subsequently separated by SFC (Waters SFC investigator). Method isocratic, Mobile phase MeOH:CO₂—40:60. Column: Chiralpak IA (30×250 mm), 5 μm, flow rate: 90 g/min.

Oxazol-2-ylmethyl (1-((3-chloro-4-fluorophenyl)carbamoyl)-2-methyl-2,4,5,6-tetrahydro cyclopenta[c]pyrrol-4-yl)carbamate—Enantiomer I (34) LCMS: m/z found 433.3/435.3 [M+H]⁺, RT=6.13 min (Method A); ¹H NMR (400 MHz, DMSO-d₆): δ 9.39 (s, 1H), 8.14 (s, 1H), 7.91-7.94 (m, 1H), 7.75-7.77 (m, 1H), 7.55-7.59 (m, 1H), 7.37 (dd, 1H), 7.24 (s, 1H), 6.81 (s, 1H), 5.11 (s, 2H), 4.79-4.83 (m, 1H), 3.77 (s, 3H), 2.91-2.97 (m, 1H), 2.80-2.85 (m, 1H), 2.55-2.61 (m, 1H), 2.08-2.14 (m, 1H); Chiral SFC: RT: 3.09 min (Chiralpak IA 4.6×150 mm, 5 μm).

Oxazol-2-ylmethyl (1-((3-chloro-4-fluorophenyl)carbamoyl)-2-methyl-2,4,5,6-tetrahydro cyclopenta[c]pyrrol-4-yl)carbamate—Enantiomer II (35) LCMS: m/z found 433.3/435.3 [M+H]⁺, RT=6.13 min (Method A); ¹H NMR (400 MHz, DMSO-d₆): δ 9.39 (s, 1H), 8.14 (s, 1H), 7.91-7.94 (m, 1H), 7.75-7.77 (m, 1H), 7.55-7.59 (m, 1H), 7.37 (dd, 1H), 7.24 (s, 1H), 6.81 (s, 1H), 5.11 (s, 2H), 4.79-4.83 (m, 1H), 3.77 (s, 3H), 2.91-2.97 (m, 1H), 2.80-2.85 (m, 1H), 2.55-2.61 (m, 1H), 2.08-2.14 (m, 1H); Chiral SFC: RT: 5.61 min (Chiralpak IA 4.6×150 mm, 5 μm)

Example 10: Oxazol-5-ylmethyl (1-((3-chloro-4-fluorophenyl)carbamoyl)-2-methyl-2,4,5,6-tetrahydro cyclopenta[c]pyrrol-4-yl)carbamate (36, 37)

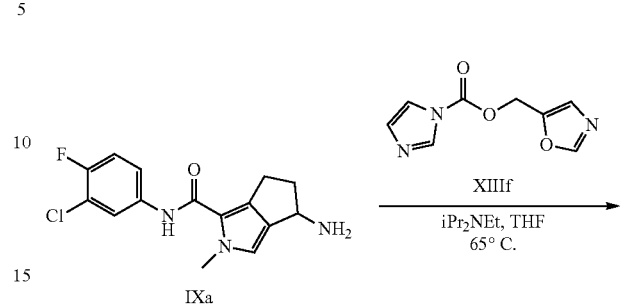

36, 37

Oxazol-5-ylmethyl (1-((3-chloro-4-fluorophenyl)carbamoyl)-2-methyl-2,4,5,6-tetrahydro cyclopenta[c]pyrrol-4-yl) carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and oxazol-5-ylmethyl 1H-imidazole-1-carboxylate (XIIIf). The enantiomers were subsequently separated by SFC (Waters SFC investigator. Method isocratic, Mobile phase MeOH:CO₂—50:50. Column: Chiralpak ID-H (30×250 mm), 5 μm, flow rate: 90 g/min.

Oxazol-5-ylmethyl (1-((3-chloro-4-fluorophenyl)carbamoyl)-2-methyl-2,4,5,6-tetrahydro cyclopenta[c]pyrrol-4-yl)carbamate—Enantiomer I (36) LCMS: m/z found 433.3/435.3 [M+H]⁺, RT=5.84 (Method A); Chiral SFC: RT=3.38 min; (Chiralpak AD-3 4.6×150 mm, 3 μm; ¹H NMR (400 MHz, DMSO-d₆): δ 9.37 (br s, 1H), 8.39 (s, 1H), 7.91-7.94 (m, 1H), 7.63-7.66 (m, 1H), 7.55-7.59 (m, 1H), 7.37 (dd, 1H), 7.24 (s, 1H), 6.80 (s, 1H), 5.09 (s, 2H), 4.78-4.83 (m, 1H), 3.76 (s, 3H), 2.89-2.97 (m, 1H), 2.79-2.85 (m, 1H), 2.56-2.61 (m, 1H), 2.06-2.12 (m, 1H).

Oxazol-5-ylmethyl (1-((3-chloro-4-fluorophenyl)carbamoyl)-2-methyl-2,4,5,6-tetrahydro cyclopenta[c]pyrrol-4-yl)carbamate—Enantiomer II (37) LCMS: m/z found 433.3/435.3 [M+H]⁺, RT=5.84 min (Method A); Chiral SFC: RT=5.91 min; (Chiralpak AD-3 4.6×150 mm, 3 μm; ¹H NMR (400 MHz, DMSO-d₆): δ 9.37 (br s, 1H), 8.39 (s, 1H), 7.91-7.94 (m, 1H), 7.63-7.66 (m, 1H), 7.55-7.59 (m, 1H), 7.37 (dd, 1H), 7.24 (s, 1H), 6.80 (s, 1H), 5.09 (s, 2H), 4.78-4.83 (m, 1H), 3.76 (s, 3H), 2.89-2.97 (m, 1H), 2.79-2.85 (m, 1H), 2.56-2.61 (m, 1H), 2.06-2.12 (m, 1H).

Example 11: 2-Cyanoethyl (1-((3-chloro-4-fluorophenyl)carbamoyl)-2-methyl-2,4,5,6-tetrahydro cyclopenta[c]pyrrol-4-yl)carbamate (49, 50)

Example 12: Prop-2-yn-1-yl (1-((3-chloro-4-fluorophenyl)carbamoyl)-2-methyl-2,4,5,6-tetrahydro cyclopenta[c]pyrrol-4-yl)carbamate (101, 102)

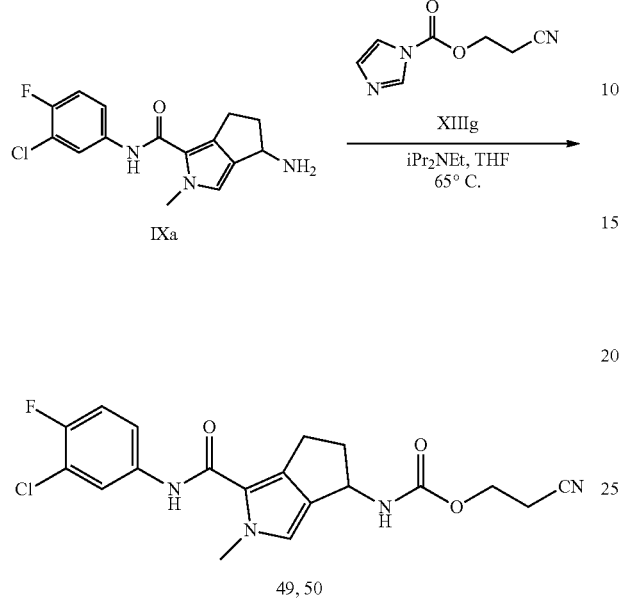

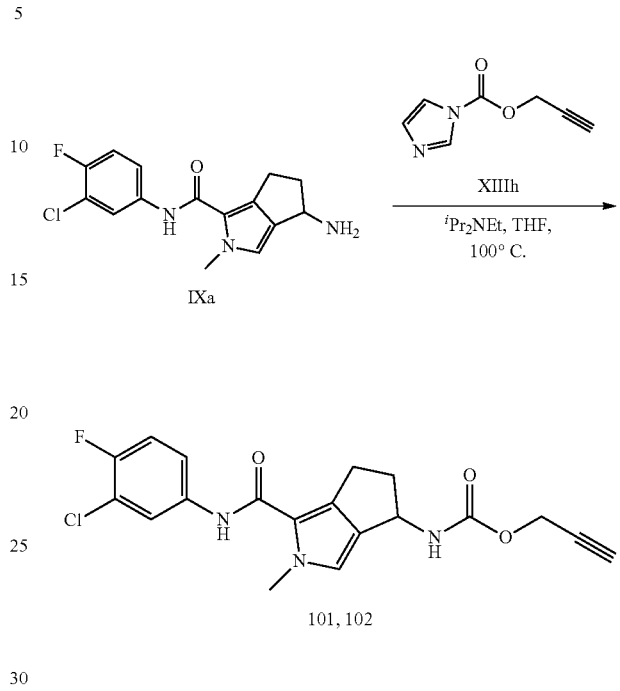

2-Cyanoethyl (1-((3-chloro-4-fluorophenyl)carbamoyl)-2-methyl-2,4,5,6-tetrahydrocyclopenta [c]pyrrol-4-yl)carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and 2-cyanoethyl 1H-imidazole-1-carboxylate (XIIIg). The enantiomers were subsequently separated by SFC (Waters SFC investigator. Method isocratic, Mobile phase MeOH:CO$_2$—30:70. Column: Chiralpak AD-H (30× 250 mm), 5 μm, flow rate: 70 g/min.

2-Cyanoethyl (1-((3-chloro-4-fluorophenyl)carbamoyl)-2-methyl-2,4,5,6-tetrahydrocyclopenta[c]pyrrol-4-yl)carbamate—Enantiomer I (49) LCMS: m/z found 405.2/407.2 [M+H]$^+$, RT=6.38 min (Method A); Chiral SFC: RT: 2.44 min (Chiralpak AD-3 4.6×150 mm, 3 μm); $^1$H NMR (400 MHz, DMSO-d$_6$): δ 9.37 (s, 1H), 7.92-7.94 (m, 1H), 7.68 (d, 1H), 7.55-7.60 (m, 1H), 7.37 (dd, 1H), 6.81 (s, 1H), 4.77-4.83 (m, 1H), 4.14 (t, 2H), 3.77 (s, 3H), 2.91-2.99 (m, 1H), 2.79-2.87 (m, 3H), 2.55-2.61 (m, 1H), 2.09-2.16 (m, 1H).

2-Cyanoethyl (1-((3-chloro-4-fluorophenyl)carbamoyl)-2-methyl-2,4,5,6-tetrahydrocyclopenta[c]pyrrol-4-yl)carbamate—Enantiomer II (50) LCMS: m/z found 405.2/407.2 [M+H]$^+$, RT=6.38 min (Method A); Chiral SFC: RT: 3.37 min (Chiralpak AD-3 4.6×150 mm, 3 μm); $^1$H NMR (400 MHz, DMSO-d$_6$): δ 9.37 (s, 1H), 7.92-7.94 (m, 1H), 7.68 (d, 1H), 7.55-7.60 (m, 1H), 7.37 (dd, 1H), 6.81 (s, 1H), 4.77-4.83 (m, 1H), 4.14 (t, 2H), 3.77 (s, 3H), 2.91-2.99 (m, 1H), 2.79-2.87 (m, 3H), 2.55-2.61 (m, 1H), 2.09-2.16 (m, 1H).

(Prop-2-yn-1-yl (1-((3-chloro-4-fluorophenyl)carbamoyl)-2-methyl-2,4,5,6-tetrahydro cyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and prop-2-yn-1-yl 1H-imidazole-1-carboxylate (XIIIh). The enantiomers were subsequently separated by SFC (Waters SFC investigator). Method isocratic, Mobile phase MeOH:CO$_2$—40:60. Column: Chiralcel OJ-H (30× 250 mm, 5 μm), flow rate: 90 g/min.

(Prop-2-yn-1-yl (1-((3-chloro-4-fluorophenyl)carbamoyl)-2-methyl-2,4,5,6-tetrahydro cyclopenta[c]pyrrol-4-yl)carbamate—Enantiomer I (101) LCMS: m/z found 390.3/392.3 [M+H]$^+$, RT=7.81 min (Method A); Chiral-SFC: RT=2.57 min (Chiralpak OJ-H (150 mm×4.6 mm, 3 μm); $^1$H NMR (400 MHz, DMSO-d$_6$): δ 9.36 (s, 1H), 7.91-7.95 (m, 1H), 7.66 (bd, 1H), 7.55-7.61 (m, 1H), 7.37 (t, 1H), 6.81 (s, 1H), 4.77-4.82 (m, 1H), 4.64 (s, 2H), 3.77 (s, 3H), 3.48 (s, 1H), 2.90-2.99 (m, 1H), 2.78-2.87 (m, 1H), 2.54-2.63 (m, 1H), 2.04-2.13 (m, 1H).

(Prop-2-yn-1-yl (1-((3-chloro-4-fluorophenyl)carbamoyl)-2-methyl-2,4,5,6-tetrahydro cyclopenta[c]pyrrol-4-yl)carbamate—Enantiomer II (102) LCMS: m/z found 390.3/392.3 [M+H]$^+$, RT=7.81 min (Method A); Chiral-SFC: RT=4.55 min (Chiralpak OJ-H (150 mm×4.6 mm, 3 μm); $^1$H NMR (400 MHz, DMSO-d$_6$): δ 9.36 (s, 1H), 7.91-7.95 (m, 1H), 7.66 (bd, 1H), 7.55-7.61 (m, 1H), 7.37 (t, 1H), 6.81 (s, 1H), 4.77-4.82 (m, 1H), 4.64 (s, 2H), 3.77 (s, 3H), 3.48 (s, 1H), 2.90-2.99 (m, 1H), 2.78-2.87 (m, 1H), 2.54-2.63 (m, 1H), 2.04-2.13 (m, 1H).

Example 13: But-2-yn-1-yl (1-((3-chloro-4-fluorophenyl)carbamoyl)-2-methyl-2,4,5,6-tetrahydrocyclopenta[c]pyrrol-4-yl)carbamate (110, 111)

Example 14: Pent-2-yn-1-yl (1-((3-chloro-4-fluorophenyl)carbamoyl)-2-methyl-2,4,5,6-tetrahydrocyclopenta[c]pyrrol-4-yl)carbamate (112, 113)

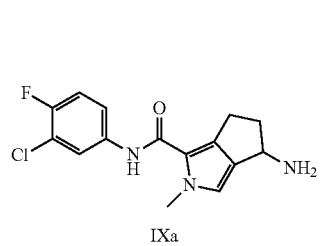
IXa

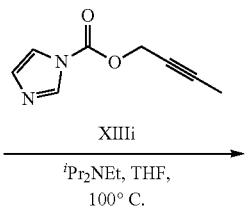
XIIIi
$^i$Pr$_2$NEt, THF, 100° C.

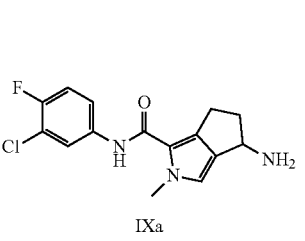
IXa

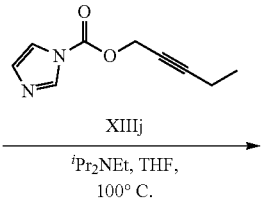
XIIIj
$^i$Pr$_2$NEt, THF, 100° C.

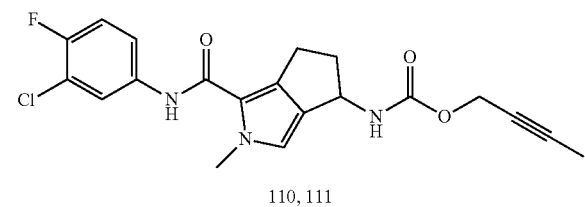
110, 111

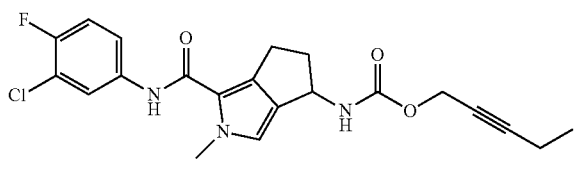
112, 113

But-2-yn-1-yl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and but-2-yn-1-yl 1H-imidazole-1-carboxylate (XIIIi). The enantiomers were subsequently separated by SFC (Waters SFC investigator). Method isocratic, Mobile phase MeOH:CO$_2$—30:70. Column: Chiralcel OJ-H (30× 250 mm), 5 μm, flow rate: 90 g/min.

But-2-yn-1-yl (1-((3-chloro-4-fluorophenyl)carbamoyl)-2-methyl-2,4,5,6-tetrahydrocyclopenta[c]pyrrol-4-yl)carbamate—Enantiomer I (110) LCMS: m/z found 404.2/406.2 [M+H]$^+$, RT=8.26 min (Method A); Chiral-SFC: RT=1.83 min (Chiralpak OJ-H (150 mm×4.6 mm, 3 μm); $^1$H NMR (400 MHz, DMSO-d$_6$): δ 9.36 (s, 1H), 7.91-7.95 (m, 1H), 7.55-7.60 (m, 2H), 7.37 (t, 1H), 6.80 (s, 1H), 4.77-4.82 (m, 1H), 4.59 (s, 2H), 3.77 (s, 3H), 2.90-2.99 (m, 1H), 2.78-2.87 (m, 1H), 2.54-2.64 (m, 1H), 2.05-2.13 (m, 1H), 1.82 (s, 3H).

But-2-yn-1-yl (1-((3-chloro-4-fluorophenyl)carbamoyl)-2-methyl-2,4,5,6-tetrahydrocyclopenta[c]pyrrol-4-yl)carbamate—Enantiomer II (111) LCMS: m/z found 404.2/406.2 [M+H]$^+$, RT=8.26 min (Method A); Chiral-SFC: RT=3.88 min (Chiralpak OJ-H (150 mm×4.6 mm, 3 μm); $^1$H NMR (400 MHz, DMSO-d$_6$): δ 9.36 (s, 1H), 7.91-7.95 (m, 1H), 7.55-7.60 (m, 2H), 7.37 (t, 1H), 6.80 (s, 1H), 4.77-4.82 (m, 1H), 4.59 (s, 2H), 3.77 (s, 3H), 2.90-2.99 (m, 1H), 2.78-2.87 (m, 1H), 2.54-2.64 (m, 1H), 2.05-2.13 (m, 1H), 1.82 (s, 3H).

Pent-2-yn-1-yl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and pent-2-yn-1-yl 1H-imidazole-1-carboxylate (XIIIj). The enantiomers were subsequently separated by SFC (Waters SFC investigator). Method isocratic, Mobile phase MeOH:CO$_2$—30:70. Column: Chiralcel OJ-H (30× 250 mm, 5 μm), flow rate: 70 g/min.

Pent-2-yn-1-yl(1-((3-chloro-4-fluorophenyl)carbamoyl)-2-methyl-2,4,5,6-tetrahydrocyclopenta[c]pyrrol-4-yl)carbamate—Enantiomer I (112) LCMS: m/z found 418.2/420.2 [M+H]$^+$, RT=8.31 min (Method A); Chiral SFC: RT=1.77 min (Chiralpak OJ-H (150 mm×4.6 mm, 3 μm); $^1$H NMR (400 MHz, DMSO-d$_6$): δ 9.38 (s, 1H), 7.91-7.95 (m, 1H), 7.55-7.63 (m, 2H), 7.37 (t, 1H), 6.80 (s, 1H), 4.77-4.83 (m, 1H), 4.61 (s, 2H), 3.77 (s, 3H), 2.90-2.98 (m, 1H), 2.77-2.86 (m, 1H), 2.53-2.63 (m, 1H), 2.19-2.24 (m, 2H), 2.07-2.13 (m, 1H), 1.06 (t, 3H).

Pent-2-yn-1-yl(1-((3-chloro-4-fluorophenyl)carbamoyl)-2-methyl-2,4,5,6-tetrahydrocyclopenta[c]pyrrol-4-yl)carbamate—Enantiomer II (113) LCMS: m/z found 418.2/420.2 [M+H]$^+$, RT=8.31 min (Method A); Chiral SFC: RT=4.11 min (Chiralpak OJ-H (150 mm×4.6 mm, 3 μm); $^1$H NMR (400 MHz, DMSO-d$_6$): δ 9.38 (s, 1H), 7.91-7.95 (m, 1H), 7.55-7.63 (m, 2H), 7.37 (t, 1H), 6.80 (s, 1H), 4.77-4.83 (m, 1H), 4.61 (s, 2H), 3.77 (s, 3H), 2.90-2.98 (m, 1H), 2.77-2.86 (m, 1H), 2.53-2.63 (m, 1H), 2.19-2.24 (m, 2H), 2.07-2.13 (m, 1H), 1.06 (t, 3H).

Example 15: 3-Cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate (114, 115)

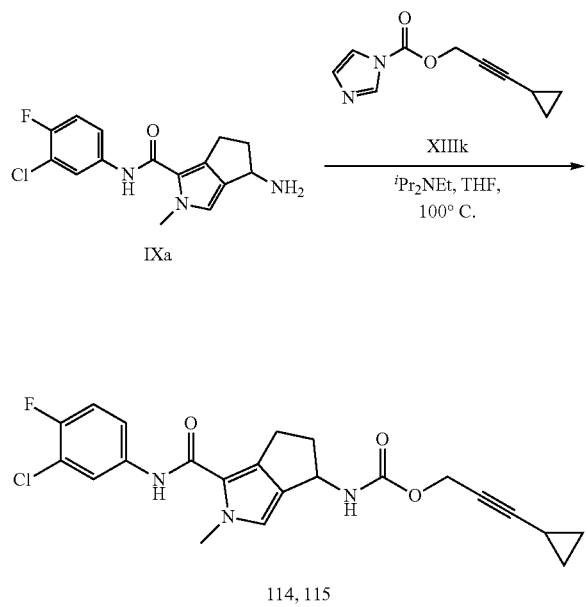

3-Cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and 3-cyclopropylprop-2-yn-1-yl 1H-imidazole-1-carboxylate (XIIIk). The enantiomers were subsequently separated by SFC (Waters SFC investigator). Method isocratic, Mobile phase MeOH:CO$_2$—40:60. Column: Chiralpak AD-H (30×250 mm), 5 μm, flow rate: 60 g/min.

3-Cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate—Enantiomer I (114) LCMS: m/z found 430.3/432.3 [M+H]$^+$, RT=8.31 min (Method A); Chiral-SFC: RT=2.81 min, Chiralpak AD-3 (150 mm×4.6 mm, 3 μm); $^1$H NMR (400 MHz, DMSO-d$_6$): δ 9.38 (s, 1H), 7.92-7.95 (m, 1H), 7.55-7.63 (m, 2H), 7.37 (t, 1H), 6.80 (s, 1H), 4.76-4.82 (m, 1H), 4.58 (s, 2H), 3.77 (s, 3H), 2.90-2.98 (m, 1H), 2.77-2.86 (m, 1H), 2.53-2.62 (m, 1H), 2.06-2.13 (m, 1H), 1.31-1.37 (m, 1H), 0.76-0.81 (m, 2H), 0.58-0.62 (m, 2H).

3-Cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate—Enantiomer II (115) LCMS: m/z found 430.3/432.3 [M+H]$^+$, RT=8.34 min (Method A); Chiral-SFC: RT=4.70 min, Chiralpak AD-3 (150 mm×4.6 mm, 3 μm); $^1$H NMR (400 MHz, DMSO-d$_6$): δ 9.38 (s, 1H), 7.92-7.95 (m, 1H), 7.55-7.63 (m, 2H), 7.37 (t, 1H), 6.80 (s, 1H), 4.76-4.82 (m, 1H), 4.58 (s, 2H), 3.77 (s, 3H), 2.90-2.98 (m, 1H), 2.77-2.86 (m, 1H), 2.53-2.62 (m, 1H), 2.06-2.13 (m, 1H), 1.31-1.37 (m, 1H), 0.76-0.81 (m, 2H), 0.58-0.62 (m, 2H).

Example 16: Isopropyl 1-((((1-((3-chloro-4-fluorophenyl)carbamoyl)-2-methyl-2,4,5,6-tetrahydrocyclopenta [c]pyrrol-4-yl)carbamoyl)oxy)methyl)-3,3-difluorocyclobutane-1-carboxylate (46)

3,3-Difluoro-1-(isopropoxycarbonyl)cyclobutyl) methyl 1H-imidazole-1-carboxylate

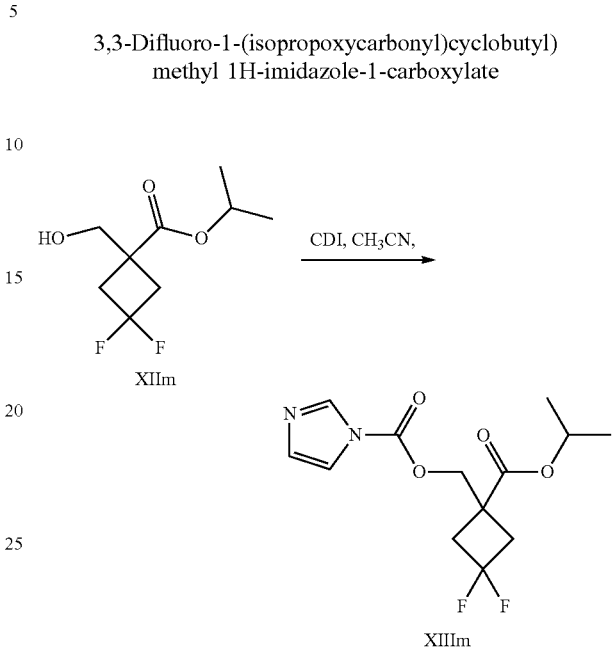

To a solution of 0.9 g (4.33 mmol, 1.0 eq.) of isopropyl 3,3-difluoro-1-(hydroxymethyl) cyclobutane-1-carboxylate (XIIm, synthesized according to Int'l Patent Publication No. WO201505901) in 15 mL of acetonitrile was added 1.05 g (6.49 mmol, 1.5 eq.) of 1,1'-carbonyl diimidazole and the mixture was stirred at room temperature for 2 h. The volatiles were removed in vacuo and the residue was dissolved in 50 mL of ethyl acetate. The organic solution was washed with 40 mL of brine, dried (Na$_2$SO$_4$), filtered and the solvent was removed in vacuo to provide 0.95 g of (3,3-difluoro-1-(isopropoxycarbonyl)cyclobutyl)methyl 1H-imidazole-1-carboxylate (XIIIm). $^1$H NMR (400 MHz, CDCl$_3$): δ 8.10 (s, 1H), 7.38 (s, 1H), 7.08 (s, 1H), 5.06-5.11 (m, 1H), 4.71 (s, 2H), 3.10-3.14 (m, 2H), 2.70-2.73 (m, 2H), 1.25 (d, 6H).

Isopropyl 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate (46)

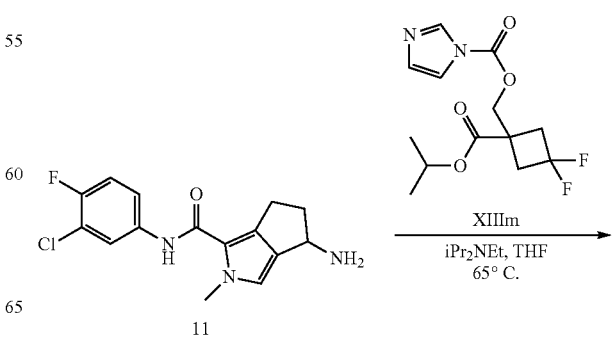

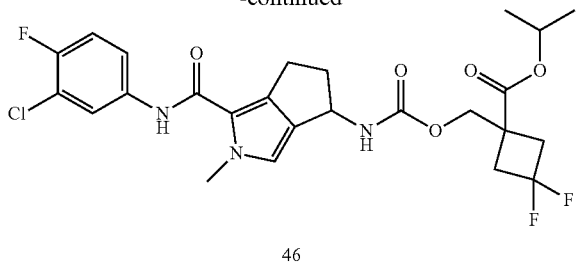

46

Racemic isopropyl 1-(((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate (46) was synthesized in a similar manner as described above from 4-amino-N-(3-chloro-4-fluorophenyl)-2-methyl-2,4,5,6-tetrahydrocyclopenta [c]pyrrole-1-carboxamide (IXa) and (3,3-difluoro-1-(isopropoxycarbonyl)cyclobutyl)methyl 1H-imidazole-1-carboxylate (XIIIm). LCMS: m/z found 542.4/544.4 [M+H]$^+$, RT=7.75 min (Method A); Chiral SFC: RT=1.67 and 2.01 min respectively (Column: Chiralcel OZ-3 4.6×150 mm, 3 μm); $^1$H NMR (400 MHz, DMSO-d$_6$): δ 9.36 (br s, 1H), 7.91-7.94 (m, 1H), 7.55-7.59 (m, 2H), 7.37 (dd, 1H), 6.77 (s, 1H), 4.91-4.96 (m, 1H), 4.75-4.79 (m, 1H), 4.26-4.31 (m, 2H), 3.76 (s, 3H), 2.88-2.98 (m, 3H), 2.72-2.83 (m, 3H), 2.51-2.57 (m, 1H), 2.07-2.13 (m, 1H), 1.18-1.21 (m, 6H);

Example 17: 1-(((((1-((3-Chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid (53)

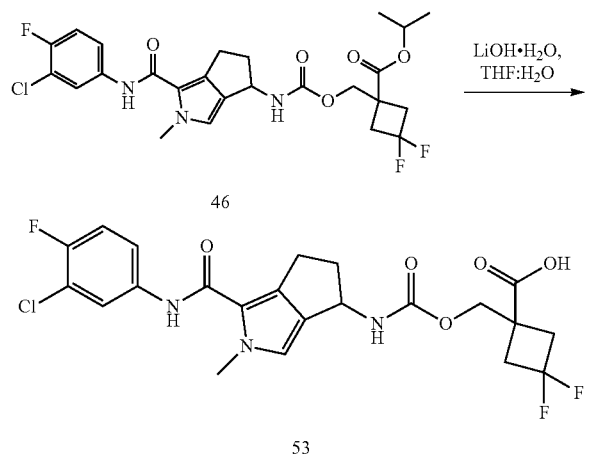

To a solution of 0.3 g (0.55 mmol, 1.0 eq) of isopropyl 1-(((((1-((3-chloro-4-fluorophenyl) carbamoyl)-2-methyl-2,4,5,6-tetrahydrocyclopenta [c]pyrrol-4-yl)carbamoyl)oxy)methyl)-3,3-difluorocyclobutane-1-carboxylate (46) in 6 mL of 1:1 (v/v) THF:H$_2$O was added 0.2 g (4.7 mmol, 8.6 eq) of lithium hydroxide monohydrate and the mixture was stirred at room temperature for 16 h. The organics were removed in vacuo and the residue was acidified to pH 3 using 1 M aq. HCl. The resulting mixture was extracted with 3×40 mL of ethyl acetate and the combined organic extracts were washed with 50 mL of brine, dried (Na$_2$SO$_4$), filtered and the solvent was removed in vacuo to provide 0.25 g (0.50 mmol, 91%) of racemic 1-(((((1-((3-chloro-4-fluorophenyl)carbamoyl)-2-methyl-2,4,5,6-tetrahydrocyclopenta [c]pyrrol-4-yl)carbamoyl) oxy)methyl)-3,3-difluorocyclobutane-1-carboxylic acid (53). LCMS: m/z found 500.1/502.1 [M+H]$^+$; Chiral SFC: RT=3.54 and 4.02 min, (Column: Chiralcel OX-3 4.6×150 mm, 3 μm); $^1$H NMR (400 MHz, DMSO-d$_6$): δ 13.02 (bs, 1H), 9.35 (bs, 1H), 7.91-7.94 (m, 1H), 7.55-7.59 (m, 2H), 7.36 (dd, 1H), 6.79 (s, 1H), 4.75-4.80 (m, 1H), 4.26 (s, 2H), 3.76 (s, 3H), 2.87-2.97 (m, 3H), 2.63-2.84 (m, 3H), 2.51-2.57 (m, 1H), 2.07-2.14 (m, 1H).

Example 18: (1-Carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl) carbamate (55, 56)

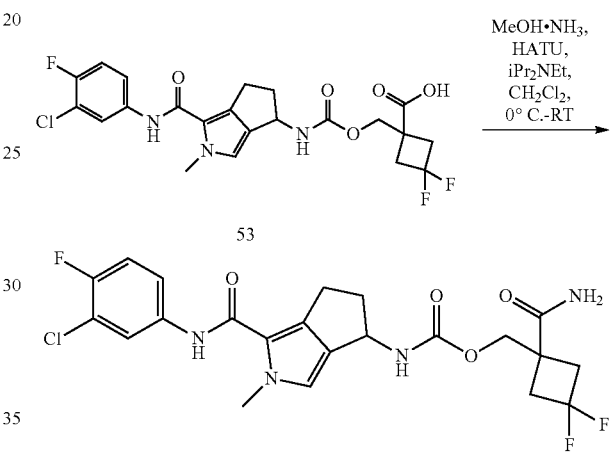

To a solution of 250 mg (0.50 mmol, 1.0 eq.) of racemic 1-(((((1-((3-chloro-4-fluorophenyl) carbamoyl)-2-methyl-2,4,5,6-tetrahydrocyclopenta[c]pyrrol-4-yl)carbamoyl) oxy)methyl)-3,3-difluorocyclobutane-1-carboxylic acid (53) in 10 mL of methylene chloride under a nitrogen atmosphere at 0° C. was added 0.32 g (2.51 mmol, 5.0 eq.) of N,N-diisopropylethylamine and 0.38 g (1.00 mmol, 2.0 eq.) of HATU. The mixture was stirred at 0° C. for 20 min and 5 mL of a saturated methanolic ammonia solution was added. The mixture was then allowed to warm to room temperature and stirred for an additional 16 h. The volatiles were removed in vacuo and the residue was partitioned between 50 mL of ethyl acetate and 30 mL of 0.5 M sodium hydroxide solution. The layers were separated and the organic phase was washed with 30 mL of brine, dried (Na$_2$SO$_4$), filtered and the solvent was removed in vacuo. The residue was purified by flash chromatography (SiO$_2$, eluting with a linear gradient of 0-2% methanol in methylene chloride) to provide 160 mg (0.32 mmol, 64%) of racemic (1-carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate. The enantiomers were subsequently separated by SFC (Waters SFC investigator. Method isocratic, Mobile phase MeOH:CO$_2$—20:80. Column: Chiralcel OD-H (30× 250 mm, 5 μm), flow rate: 70 g/min.

(1-Carbamoyl-3,3-difluorocyclobutyl)methyl(1-((3-chloro-4-fluorophenyl)carbamoyl)-2-methyl-2,4,5,6-tetrahydrocyclopenta[c]pyrrol-4-yl)carbamate—Enantiomer I

(55) LCMS: m/z found 499.3/501.3 [M+H]⁺, RT=6.29 min, (Method A); Chiral SFC: RT=4.17 min (Column: Chiralcel OD-3 4.6×150 mm, 3 μm); ¹H NMR (400 MHz, DMSO-d₆): δ 9.37 (s, 1H), 7.91-7.94 (m, 1H), 7.55-7.59 (m, 2H), 7.42 (s, 1H), 7.36 (dd, 1H), 7.21 (s, 1H), 6.79 (s, 1H), 4.75-4.80 (m, 1H), 4.25 (s, 2H), 3.77 (s, 3H), 2.80-2.96 (m, 4H), 2.50-2.58 (m, 3H), 2.09-2.14 (m, 1H).

(1-Carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate—Enantiomer II (56) LCMS: m/z found 499.3/501.3 [M+H]⁺, RT=6.29 min, (Method A); Chiral SFC: RT=5.37 min (Column: Chiralcel OD-3 4.6×150 mm, 3 μm); ¹H NMR (400 MHz, DMSO-d₆): δ 9.37 (s, 1H), 7.91-7.94 (m, 1H), 7.55-7.59 (m, 2H), 7.42 (s, 1H), 7.36 (dd, 1H), 7.21 (s, 1H), 6.79 (s, 1H), 4.75-4.80 (m, 1H), 4.25 (s, 2H), 3.77 (s, 3H), 2.80-2.96 (m, 4H), 2.50-2.58 (m, 3H), 2.09-2.14 (m, 1H).

Example 19: (1H-1,2,4-Triazol-3-yl)methyl (1-((3-chloro-4-fluorophenyl)carbamoyl)-2-methyl-2,4,5,6-tetrahydrocyclopenta[c]pyrrol-4-yl)carbamate (54, 57, 58)

Methyl 1-trityl-1H-1,2,4-triazole-3-carboxylate

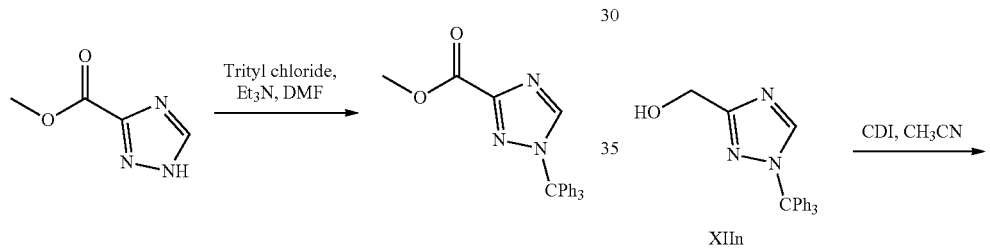

To a solution of 2.0 g (15.7 mmol, 1.0 eq.) of methyl 1H-1,2,4-triazole-3-carboxylate in 10 mL of DMF at 0° C. under inert atmosphere was added 6.5 mL (47.2 mmol 3.0 eq.) of triethylamine followed by 6.58 g (23.6 mmol, 1.5 eq.) of trityl chloride. The mixture was allowed to warm to room temperature and stirred for 16 h. The mixture was then diluted with 50 mL of ice-cold water and stirred for a further 30 min. The precipitated solid was collected by filtration, washed with 50 mL of water, 50 mL of diethyl ether and dried under vacuum to provide 4.0 g (10.8 mmol, 69%) of methyl 1-trityl-1H-1,2,4-triazole-3-carboxylate. ¹H NMR (400 MHz, CDCl₃): δ 8.03 (s, 1H), 7.29-7.38 (m, 9H), 7.10-7.14 (m, 6H), 3.96 (s, 3H).

(1-Trityl-1H-1,2,4-triazol-3-yl)methanol (XIIn)

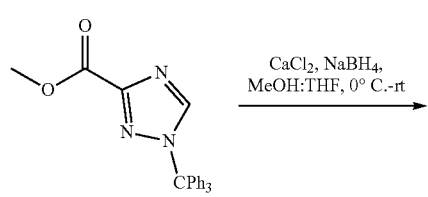

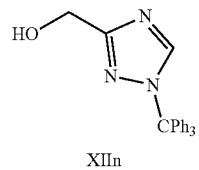

To a solution of 4.0 g (10.8 mmol, 1.0 eq.) of methyl 1-trityl-1H-1,2,4-triazole-3-carboxylate in 45 mL of THF at 0° C. under a nitrogen atmosphere was added 2.6 g (23.6 mmol, 2.0 eq.) of calcium(II) chloride followed by 1.8 g (47.61 mmol, 4.0 eq.) of sodium borohydride and the dropwise addition of 9 mL of methanol. The mixture was allowed to warm to room temperature and stirred for 3 h. The mixture was diluted with 50 mL of ice-cold water and extracted with 3×75 mL of ethyl acetate. The combined organic extracts were washed with 80 mL of brine, dried (Na₂SO₄), filtered and the solvent was removed in vacuo to provide 3.6 g (10.54 mmol, 97%) of (1-trityl-1H-1,2,4-triazol-3-yl)methanol (XIIn). ¹H NMR (400 MHz, DMSO-d₆): δ 8.03 (s, 1H), 7.38-7.43 (m, 9H), 7.03-7.09 (m, 6H), 5.31 (t, 1H), 4.44 (d, 2H).

(1-Trityl-1H-1,2,4-triazol-3-yl)methyl 1H-imidazole-1-carboxylate (XIIIn)

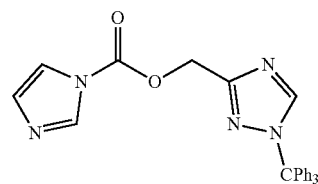

To a solution of 1.0 g (2.93 mmol, 1.0 eq.) of (1-trityl-1H-1,2,4-triazol-3-yl)methanol in 10 mL of acetonitrile was added 0.71 g (4.39 mmol, 1.5 eq.) of 1,1'-carbonyldiimidazole and the mixture was stirred at room temperature for 2 h. The solvent was removed in vacuo and the residue was redissolved in 20 mL of ethyl acetate. The organic solution was washed with 40 mL of brine, dried (Na₂SO₄), filtered and the solvent was removed in vacuo to provide 1.1 g of (1-trityl-1H-1,2,4-triazol-3-yl)methyl 1H-imidazole-1-carboxylate (XIIIn). LCMS: m/z found 436.4/438.4 [M+H]⁺.

(1-Trityl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate

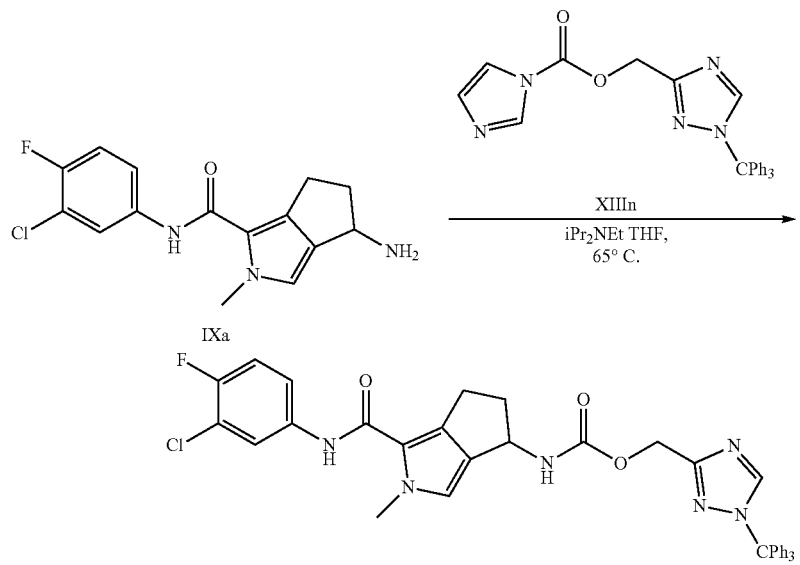

(1-Trityl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (1-trityl-1H-1,2,4-triazol-3-yl)methyl 1H-imidazole-1-carboxylate (XIIIn). LCMS: m/z found 675.4/677.4 [M+H]$^+$.

(1H-1,2,4-Triazol-3-yl)methyl (1-((3-chloro-4-fluorophenyl)carbamoyl)-2-methyl-2,4,5,6-tetrahydrocyclopenta[c]pyrrol-4-yl)carbamate (54, 57, 58)

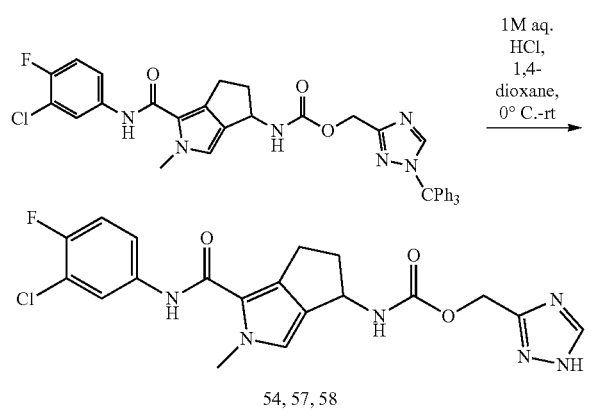

54, 57, 58

To a solution of 0.6 g of (1-trityl-1H-1,2,4-triazol-3-yl)methyl (1-((3-chloro-4-fluorophenyl) carbamoyl)-2-methyl-2,4,5,6-tetrahydrocyclopenta[c]pyrrol-4-yl)carbamate in 6 mL of 1,4-dioxane at 0° C. was added 1 mL of 1 M aqueous HCl solution drop-wise. The mixture was allowed to warm to room temperature and stirred for 3 h. The mixture was then basified with saturated sodium bicarbonate solution and extracted with 3×40 mL of ethyl acetate. The combined organic extracts were washed with 40 mL of brine, dried (Na$_2$SO$_4$), filtered and the solvent was removed in vacuo. The residue was purified by flash chromatography (SiO$_2$, eluting with linear gradient of 0-5% methanol in methylene chloride) to provide 0.17 g (0.38 mmol) of racemic (1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate (54). The enantiomers were subsequently separated by SFC (Waters SFC investigator). Method: isocratic, Mobile phase MeOH:CO$_2$—30:70. Column: CHIRALPAK IA (30×250 mm), 5 µm, flow rate: 90 g/min. (1H-1,2,4-Triazol-3-yl)methyl (1-((3-chloro-4-fluorophenyl)carbamoyl)-2-methyl-2,4,5,6-tetrahydrocyclopenta[c]pyrrol-4-yl)carbamate—Enantiomer I (57) LCMS: m/z found 433.4/435.4 [M+H]$^+$, RT=5.82 min (Method A); HPLC: 98.09%, RT=7.10 min (Method B); Chiral SFC: RT=3.06 min (Column: Chiralpak IA (4.6×250 mm, 5 µm). $^1$H NMR (400 MHz, DMSO-d$_6$): δ 12.46 (bs, 1H), 9.36 (s, 1H), 8.33 (s, 1H), 7.91-7.94 (m, 1H), 7.54-7.61 (m, 2H), 7.36 (dd, 1H), 6.81 (s, 1H), 5.04 (s, 2H), 4.80-4.83 (m, 1H), 3.77 (s, 3H), 2.91-2.96 (m, 1H), 2.78-2.84 (m, 1H), 2.54-2.61 (m, 1H), 2.09-2.13 (m, 1H).

(1H-1,2,4-Triazol-3-yl)methyl (1-((3-chloro-4-fluorophenyl)carbamoyl)-2-methyl-2,4,5,6-tetrahydrocyclopenta[c]pyrrol-4-yl)carbamate—Enantiomer II (58) LCMS: m/z found 433.4/435.4 [M+H]$^+$, RT=5.82 min (Method A); HPLC: 98.09%, RT=7.10 min, (Method B); Chiral SFC: RT=3.71 min, Column: Chiralpak IA (4.6×250 mm, 5 µm). $^1$H NMR (400 MHz, DMSO-d$_6$): δ 12.46 (bs, 1H), 9.36 (s, 1H), 8.33 (s, 1H), 7.91-7.94 (m, 1H), 7.54-7.61 (m, 2H), 7.36 (dd, 1H), 6.81 (s, 1H), 5.04 (s, 2H), 4.80-4.83 (m, 1H), 3.77 (s, 3H), 2.91-2.96 (m, 1H), 2.78-2.84 (m, 1H), 2.54-2.61 (m, 1H), 2.09-2.13 (m, 1H).

Example 20: (1H-1,2,3-Triazol-4-yl)methyl (1-((3-chloro-4-fluorophenyl)carbamoyl)-2-methyl-2,4,5,6-tetrahydrocyclopenta[c]pyrrol-4-yl)carbamate (59, 60)

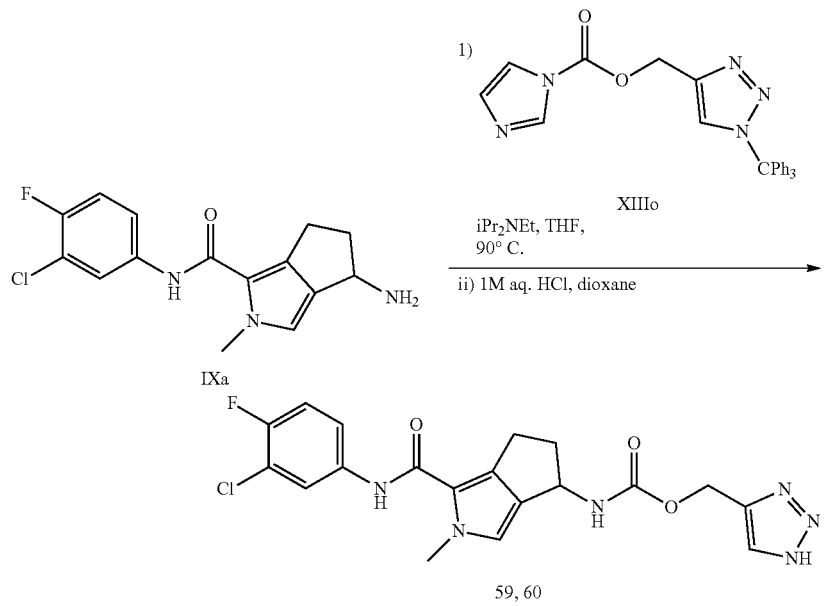

(1H-1,2,3-Triazol-4-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta [c]pyrrole-1-carboxamide (IXa) and (1-trityl-1H-1,2,3-triazol-4-yl)methyl 1H-imidazole-1-carboxylate (XIIIo) followed by acid mediated detritylation. The enantiomers were subsequently separated by SFC (Waters SFC investigator). Method: isocratic, Mobile phase MeOH:$CO_2$—30:70. Column: Chiralcel OJ-H (30×250 mm, 5 μm), flow rate: 70 g/min.

(1H-1,2,3-Triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer I (59) LCMS: m/z found 433.4/435.4 [M+H]$^+$, RT=6.05 min; (Method A); HPLC: 98.09%, RT=7.47 min (Method B); Chiral SFC: RT: 1.59 min, Column: Chiralpak OJ-3 (4.6×250 mm, 5 μm). $^1$H NMR (400 MHz, DMSO-$d_6$): δ 14.90 (br s, 1H), 9.35 (s, 1H), 7.91-7.94 (m, 1H), 7.75 (bs, 1H), 7.54-7.59 (m, 2H), 7.36 (dd, 1H), 6.80 (s, 1H), 5.09 (s, 2H), 4.80-4.83 (m, 1H), 3.76 (s, 3H), 2.91-2.97 (m, 1H), 2.78-2.83 (m, 1H), 2.52-2.59 (m, 1H), 2.08-2.12 (m, 1H).

(1H-1,2,3-Triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer II (60) LCMS: m/z found 433.4/435.4 [M+H]$^+$, RT=6.05 min; (Method A); HPLC: 98.09%, RT=7.47 min (Method B); Chiral SFC: RT: 5.30 min, Column: Chiralpak OJ-3 (4.6×250 mm, 5 μm). $^1$H NMR (400 MHz, DMSO-$d_6$): δ 14.90 (br s, 1H), 9.35 (s, 1H), 7.91-7.94 (m, 1H), 7.75 (bs, 1H), 7.54-7.59 (m, 2H), 7.36 (dd, 1H), 6.80 (s, 1H), 5.09 (s, 2H), 4.80-4.83 (m, 1H), 3.76 (s, 3H), 2.91-2.97 (m, 1H), 2.78-2.83 (m, 1H), 2.52-2.59 (m, 1H), 2.08-2.12 (m, 1H);

Example 21: (1-(Tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate (63)

1-(Tetrahydro-2H-pyran-2-yl)-1H-pyrazole-3-carbaldehyde

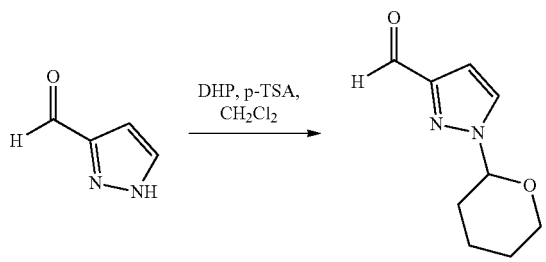 [SMILES: O=Cc1cc[nH]n1 ; O=Cc1ccn(C2CCCCO2)n1]

To the solution of 5.0 g (52.0 mmol, 1.0 eq.) of 1H-pyrazole-3-carbaldehyde in 50 mL of methylene chloride was added 5.3 g (62.4 mmol, 1.2 eq.) of 3,4-dihydro-2H-pyran (DHP) and 0.89 g (5.2 mmol, 0.1 eq.) of p-toluene sulfonic acid and the mixture was stirred at room temperature for 12 h. The mixture was basified with 2 mL of triethylamine and the solvent was removed in vacuo. The residue was purified by flash chromatography ($SiO_2$, eluting with 10% methanol in methylene chloride) to provide 4.0 g (22.2 mmol, 43%) of 1-(tetrahydro-2H-pyran-2-yl)-1H-pyrazole-3-carbaldehyde. LCMS: m/z found 181.40 [M+H]$^+$; $^1$H NMR (400 MHz, $CDCl_3$): δ 10.0 (s, 1H), 7.67 (d, 1H), 6.84 (d, 1H), 5.48-5.45 (m, 1H), 4.04-4.10 (m, 1H), 3.70-3.77 (m, 1H), 2.02-2.17 (m, 3H), 1.64-1.79 (m, 3H).

(1-(Tetrahydro-2H-pyran-2-yl)-1H-pyrazol-3-yl)
methanol: (XIIp)

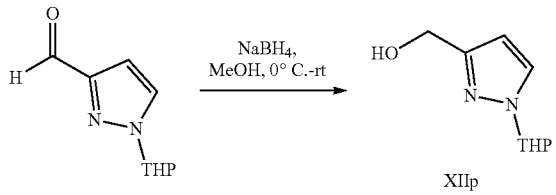

To a solution of 4.0 g (22.2 mmol, 1.0 eq.) of 1-(tetrahydro-2H-pyran-2-yl)-1H-pyrazole-3-carbaldehyde in 40 mL of methanol at 0° C. under a nitrogen atmosphere was added 2.4 g (66.7 mmol, 3.0 eq.) of sodium borohydride portion-wise. The mixture was allowed to warm to room temperature and stirred for 2 h. The reaction was quenched with 50 mL of ice-cold water and extracted with 3×75 mL of ethyl acetate. The combined organic extracts were washed with 80 mL of brine, dried ($Na_2SO_4$), filtered and the solvent was removed in vacuo to provide 3.9 g (21.40 mmol, 96%) of (1-(tetrahydro-2H-pyran-2-yl)-1H-pyrazol-3-yl)methanol (XIIp). $^1$H NMR (400 MHz, $CDCl_3$): δ 7.55 (d, 1H), 6.29 (d, 1H), 5.31-5.35 (m, 1H), 4.69 (s, 2H), 4.04-4.09 (m, 1H), 3.68-3.71 (m, 1H), 1.99-2.13 (m, 3H), 1.58-1.69 (m, 4H).

(1-(Tetrahydro-2H-pyran-2-yl)-1H-pyrazol-3-yl)
methyl 1H-imidazole-1-carboxylate (XIIIp)

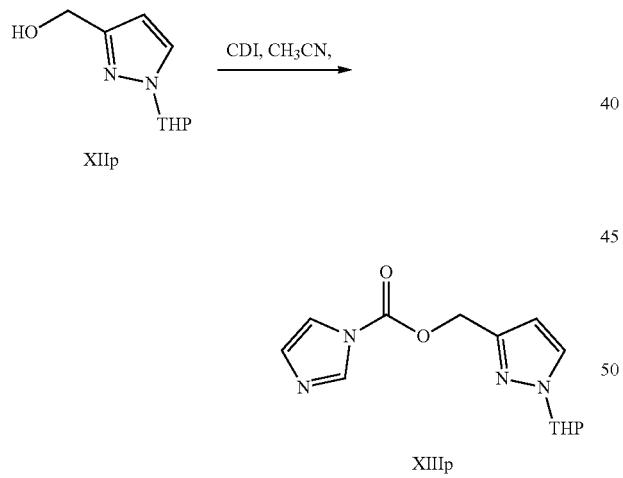

To a solution of 1.0 g (5.49 mmol, 1.0 eq.) of (1-(tetrahydro-2H-pyran-2-yl)-1H-pyrazol-3-yl)methanol (XIIp) in 10 mL of acetonitrile was added 1.3 g (8.02 mmol, 1.5 eq.) of 1,1'-carbonyl diimidazole and the mixture was stirred at room temperature for 2 h. The volatiles were removed in vacuo and the residue was redissolved in 40 mL of ethyl acetate, washed with 30 mL of brine, dried ($Na_2SO_4$), filtered and the solvent was removed in vacuo to provide 1.1 g of (1-(tetrahydro-2H-pyran-2-yl)-1H-pyrazol-3-yl)methyl 1H-imidazole-1-carboxylate (XIIIp). LCMS: m/z found 277.2 [M+H]$^+$.

(1-(Tetrahydro-2H-pyran-2-yl)-1H-pyrazol-3-yl)
methyl (1-((3-chloro-4-fluorophenyl) carbamoyl)-2-
methyl-2,4,5,6-tetrahydrocyclopenta[c]pyrrol-4-yl)
carbamate (63)

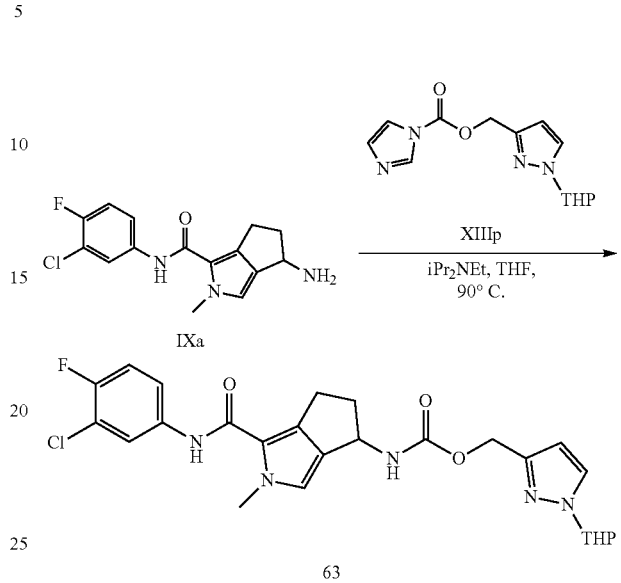

(1-(Tetrahydro-2H-pyran-2-yl)-1H-pyrazol-3-yl)methyl (1-((3-chloro-4-fluorophenyl) carbamoyl)-2-methyl-2,4,5,6-tetrahydrocyclopenta[c]pyrrol-4-yl)carbamate (63) was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (1-(tetrahydro-2H-pyran-2-yl)-1H-pyrazol-3-yl)methyl 1H-imidazole-1-carboxylate. LCMS: m/z found 516.4/518.4 [M+H]$^+$, RT=6.54 min (Method A); $^1$H NMR (400 MHz, DMSO-$d_6$): δ 9.38 (s, 1H), 7.91-7.94 (m, 1H), 7.83 (s, 1H), 7.55-7.59 (m, 1H), 7.52 (m, 1H), 7.36 (dd, 1H), 6.81 (s, 1H), 6.29 (s, 1H), 5.33-5.36 (m, 1H), 4.95 (s, 2H), 4.79-4.83 (m, 1H), 3.89-3.93 (m, 1H), 3.76 (s, 3H), 3.57-3.64 (m, 1H), 2.89-2.96 (m, 1H), 2.77-2.84 (m, 1H), 2.52-2.58 (m, 1H), 2.02-2.12 (m, 2H), 1.83-1.93 (m, 2H), 1.61-1.67 (m, 1H), 1.50-1.55 (m, 2H).

Example 22: (2-Methyl-2H-1,2,3-triazol-4-yl)
methyl (1-((3-chloro-4-fluorophenyl)carbamoyl)-2-
methyl-2,4,5,6-tetrahydrocyclopenta[c]pyrrol-4-yl)
carbamate (128, 129)

Ethyl 2-methyl-2H-1,2,3-triazole-4-carboxylate (A)

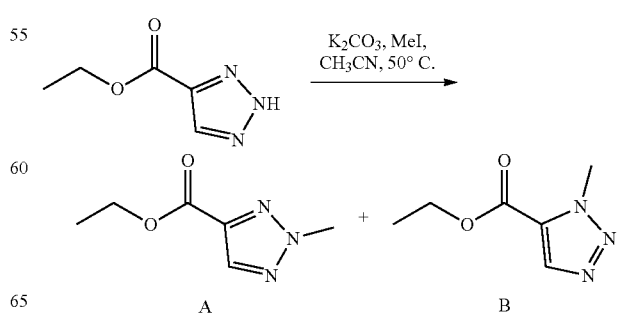

To a solution of 2.0 g (14.2 mmol, 1.0 eq.) of ethyl 2H-1,2,3-triazole-4-carboxylate in 20 mL of acetonitrile was added 3.9 g (28.4 mmol, 2.0 eq.) of potassium carbonate followed by 3.6 mL (56.7 mmol, 4.0 eq.) of iodomethane and the mixture was heated at 50° C. for 16 h. The mixture was allowed to cool to room temperature and quenched with 40 mL of water. The resulting solution was extracted with 3×40 mL of ethyl acetate and the combined organic extracts were washed with 40 mL of water, 40 mL of brine, dried (Na$_2$SO$_4$), filtered and the solvent was removed in vacuo. The residue comprising a mixture of regioisomers was purified by MPLC (REVELERIS® silica column, eluting with a linear gradient of 4-10% ethyl acetate in petroleum ether) to provide 350 mg of ethyl 2-methyl-2H-1,2,3-triazole-4-carboxylate (A) along with 540 mg of an isomeric mixture (41% & 55% of A and B respectively).

Ethyl 2-methyl-2H-1,2,3-triazole-4-carboxylate (A): LCMS: m/z found 156.4 [M+H]$^+$, RT=1.36 min; $^1$H NMR (400 MHz, DMSO-d$_6$): δ 8.24 (s, 1H), 4.32 (d, 2H), 4.24 (s, 3H), 1.30 (t, 3H).

(2-Methyl-2H-1,2,3-triazol-4-yl)methanol (XIIa)

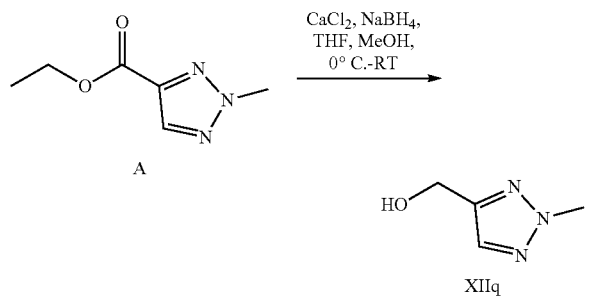

To a solution of 0.35 g (2.25 mmol, 1.0 eq.) ethyl 2-methyl-2H-1,2,3-triazole-4-carboxylate (A) in 6 mL of methanol at 0° C. was added 0.50 g (4.51 mmol, 2.0 eq.) of anhydrous calcium chloride followed by an additional 3 mL of methanol. The mixture was stirred at 0° C. for 15 min and 0.34 g (9.03 mmol, 4.0 eq.) of sodium borohydride was added portion-wise over approximately 15 min. The mixture was allowed to warm to room temperature, stirred for 4 h and then poured into 30 mL of ice-cold water. The resulting mixture was extracted with 3×30 mL of 20% methanol in methylene chloride and the combined organic extracts were dried (Na$_2$SO$_4$), filtered and the solvent was removed in vacuo to provide 0.18 g (1.57 mmol, 70%) of (2-methyl-2H-1,2,3-triazol-4-yl)methanol (XIIq). LCMS: m/z found 114.2 [M+H]$^+$, RT=1.04 min; $^1$H NMR (400 MHz, DMSO-d$_6$): δ 7.61 (s, 1H), 5.20 (t, 1H), 4.49 (d, 2H), 4.09 (s, 3H).

(2-Methyl-2H-1,2,3-triazol-4-yl)methyl 1H-imidazole-1-carboxylate (XIIIq)

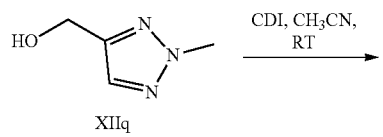

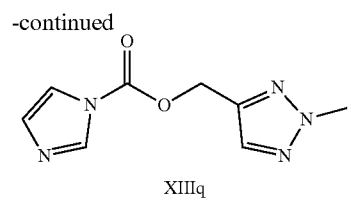

To a solution of 0.18 g (1.57 mmol, 1.0 eq.) of (2-methyl-2H-1,2,3-triazol-4-yl)methanol (XIIq) in 10 mL of acetonitrile was added 0.38 g (2.36 mmol, 1.5 eq.) of 1,1'-carbonyl and the mixture was stirred at room temperature for 2 h. The solvent was removed in vacuo and the residue was resuspended in 10 mL of water and extracted with 3×40 mL of ethyl acetate.

The combined organic extracts were washed with 30 mL of brine, dried (Na$_2$SO$_4$), filtered and the solvent was removed in vacuo to provide 250 mg of (2-methyl-2H-1,2,3-triazol-4-yl)methyl 1H-imidazole-1-carboxylate (XIIIq).

(2-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (128, 129)

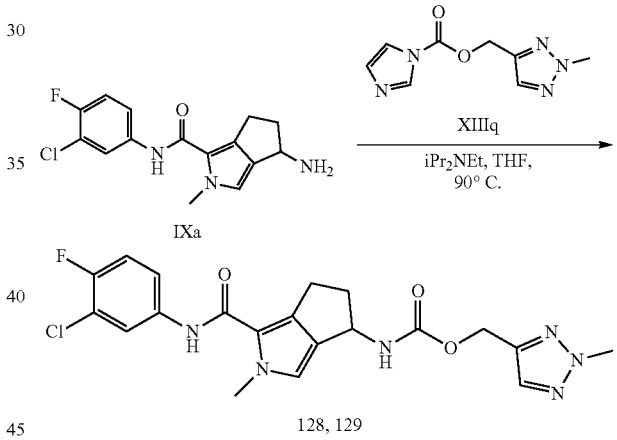

(2-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (2-methyl-2H-1,2,3-triazol-4-yl)methyl 1H-imidazole-1-carboxylate (XIIIq) The enantiomers were subsequently separated by SFC. Method: isocratic, Mobile phase MeOH:CO$_2$—40:60. Column: Chiralpak IA (30×250 mm), 5 μm, flow rate: 70 g/min.

(2-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer I (128) LCMS: m/z found 447.0/449.0 [M+H]$^+$, RT=8.66 min (Method A); Chiral SFC: RT: 1.24 min, Column: Chiralcel OJ-3 (4.6×250 mm, 5 μm); $^1$H NMR (400 MHz, DMSO-d$_6$): δ 9.35 (s, 1H), 7.91-7.94 (m, 1H), 7.72 (s, 1H), 7.55-7.60 (m, 2H), 7.36 (t, 1H), 6.80 (s, 1H), 5.05 (s, 2H), 4.79-4.83 (m, 1H), 4.09 (s, 3H), 3.77 (s, 3H), 2.90-2.97 (m, 1H), 2.79-2.85 (m, 1H), 2.53-2.61 (m, 1H), 2.06-2.12 (m, 1H).

(2-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer II (128) LCMS: m/z found 447.2/449.1 [M+H]$^+$, RT=8.60 min (Method A); Chiral SFC: RT: 3.65 min, Column: Chiralcel OJ-3 (4.6×250 mm, 5 μm); $^1$H NMR (400 MHz, DMSO-d$_6$): δ 9.35 (s, 1H), 7.91-7.94 (m, 1H), 7.72 (s, 1H), 7.55-7.60 (m, 2H), 7.36 (t, 1H), 6.80 (s, 1H), 5.05 (s, 2H), 4.79-4.83 (m, 1H), 4.09 (s, 3H), 3.77 (s, 3H), 2.90-2.97 (m, 1H), 2.79-2.85 (m, 1H), 2.53-2.61 (m, 1H), 2.06-2.12 (m, 1H).

Example 23: ((S)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate (118, 119)

(S)-4-Nitrophenyl ((5-oxopyrrolidin-2-yl)methyl) carbonate

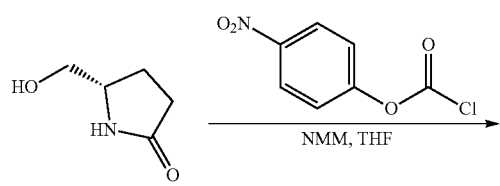

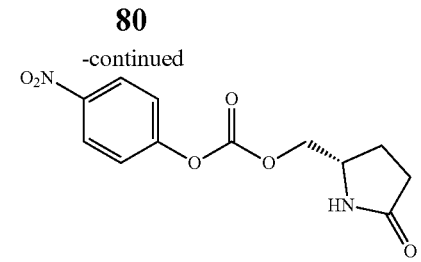

To a solution of 0.2 g (1.74 mmol, 1.0 eq.) of (S)-5-(hydroxymethyl)pyrrolidin-2-one in 2 mL of anhydrous THF under a nitrogen atmosphere at 0° C. was added 0.4 mL (3.48 mmol, 2.0 eq.) of N-methylmorpholine (NMM) followed by 0.42 g (2.09 mmol, 1.2 eq.) of 4-nitrophenylchloroformate and the mixture was stirred at room temperature for 8 h. The mixture was then diluted with 20 mL of water and extracted with 3×30 mL of ethyl acetate. The combined organic extracts were washed with 30 mL of water, 30 mL of brine, dried (Na$_2$SO$_4$), filtered and the solvent was removed in vacuo. The residue was triturated with 3 mL of methyl tert-butyl ether, filtered and the solids were dried under high vacuum to provide 0.27 g (0.96 mmol, 55%) of (S)-4-nitrophenyl ((5-oxopyrrolidin-2-yl)methyl) carbonate LCMS: m/z found 281.1 [M+H]$^+$; $^1$H NMR (400 MHz, CDCl$_3$): δ 8.27-8.31 (m, 2H), 7.37-7.41 (m, 2H), 5.88 (bs, 1H), 4.39-4.42 (m, 1H), 4.10-4.15 (m, 1H), 4.03-4.07 (m, 1H), 2.31-2.48 (m, 3H), 1.90-1.97 (m, 1H).

((S)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate (118, 119)

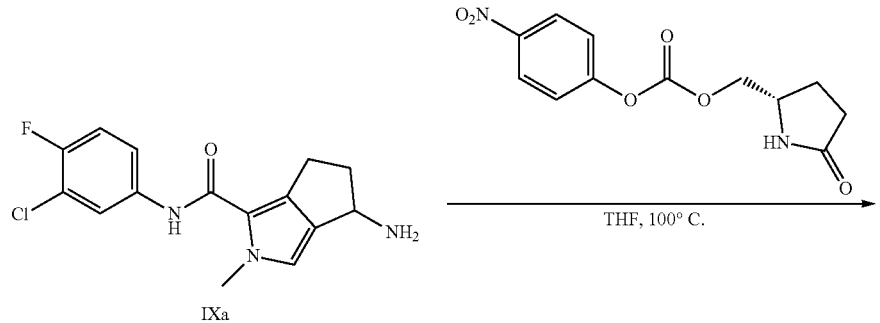

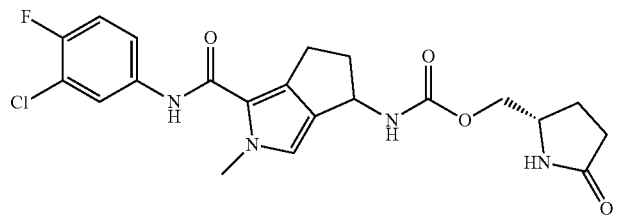

118, 119

A sealed tube containing 0.2 g (0.65 mmol, 1.0 eq.) of 4-amino-N-(3-chloro-4-fluorophenyl)-2-methyl-2,4,5,6-tetrahydrocyclopenta[c]pyrrole-1-carboxamide (IXa) and 0.22 g (0.78 mmol, 1.2 eq.) of (S)-4-nitrophenyl ((5-oxopyrrolidin-2-yl)methyl) in 2 mL of THF was heated to 100° C. for 16 h. The mixture was then allowed to cool to room temperature and diluted with 10 mL of ice-cold water. The resulting solution was extracted with 3×30 mL of ethyl acetate and the combined organic extracts were washed with 40 mL of water, 40 mL of brine, dried (Na$_2$SO$_4$), filtered and the solvent was removed in vacuo. The residue was purified by MPLC (SiO$_2$, eluting with a linear gradient of 0-3% methanol in methylene chloride) to provide 120 mg (0.26 mmol, 41%) of ((S)-5-oxopyrrolidin-2-yl)methyl chloro-4-fluorophenyl)carbamoyl)-2-methyl-2,4,5,6-tetrahydrocyclopenta[c]pyrrol-4-yl)carbamate. The diastereoisomers were subsequently separated by chiral SFC (Waters SFC investigator). Method isocratic, Mobile phase MeOH:CO$_2$—30:70. Column: Chiralpak AD-H (30×250 mm), 5 μm, flow rate: 100 g/min.

((S)-5-Oxopyrrolidin-2-yl)methyl(1-((3-chloro-4-fluorophenyl)carbamoyl)-2-methyl-2,4,5,6-tetrahydrocyclopenta[c]pyrrol-4-yl)carbamate Diastereoisomer I (118) LCMS: m/z found 449.2/451.2 [M+H]$^+$, RT=7.33 min (Method A); Chiral-SFC: RT=4.92 min, Chiralpak AD-3 (150 mm×4.6 mm, 3 μm); $^1$H NMR (400 MHz, DMSO-d$_6$): δ 9.39 (bs, 1H), 7.91-7.94 (m, 1H), 7.64 (bs, 1H), 7.55-7.60 (m, 1H), 7.46 (d, 1H), 7.37 (t, 1H), 6.80 (s, 1H), 4.77-4.80 (m, 1H), 3.84-3.97 (m, 2H), 3.77 (s, 3H), 3.68-3.72 (m, 1H), 2.90-2.97 (m, 1H), 2.78-2.86 (m, 1H), 2.54-2.60 (m, 1H), 2.20-2.26 (m, 1H), 2.00-2.15 (m, 3H), 1.75-1.80 (m, 1H).

((S)-5-Oxopyrrolidin-2-yl)methyl(1-((3-chloro-4-fluorophenyl)carbamoyl)-2-methyl-2,4,5,6-tetrahydrocyclopenta[c]pyrrol-4-yl)carbamate Diastereoisomer II (119) LCMS: m/z found 449.2/451.2 [M+H]$^+$, RT=7.33 min (Method A); Chiral-SFC: RT=7.55 min, Chiralpak AD-3 (150 mm×4.6 mm, 3 μm); $^1$H NMR (400 MHz, DMSO-d$_6$): δ 9.39 (bs, 1H), 7.91-7.94 (m, 1H), 7.64 (bs, 1H), 7.55-7.60 (m, 1H), 7.46 (d, 1H), 7.37 (t, 1H), 6.80 (s, 1H), 4.77-4.80 (m, 1H), 3.84-3.97 (m, 2H), 3.77 (s, 3H), 3.68-3.72 (m, 1H), 2.90-2.97 (m, 1H), 2.78-2.86 (m, 1H), 2.54-2.60 (m, 1H), 2.20-2.26 (m, 1H), 2.00-2.15 (m, 3H), 1.75-1.80 (m, 1H).

Example 24: ((R)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate (120, 121)

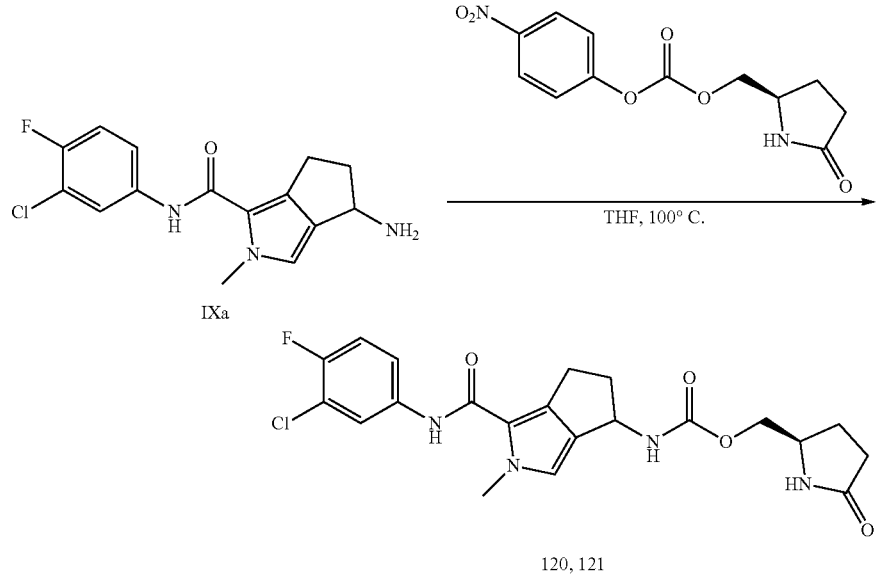

((R)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (R)-4-nitrophenyl ((5-oxopyrrolidin-2-yl)methyl). The diastereoisomers were subsequently separated by SFC (Waters SFC investigator). Method isocratic, Mobile phase MeOH:CO$_2$—40:60. Column: Chiralpak IC (30×250 mm, 5 μm), flow rate: 90 g/min.

((R)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate Diastereoisomer I (120) LCMS: m/z found 449.2/451.2 [M+H]$^+$, RT=7.29 min (Method A); Chiral-SFC: RT=6.49 min, Chiralpak IC-3 (150 mm×4.6 mm, 3 μm); $^1$H NMR (400 MHz, DMSO-d$_6$): δ 9.35 (bs, 1H), 7.92-7.94 (m, 1H), 7.64 (bs, 1H), 7.55-7.60 (m, 1H), 7.46 (bd, 1H), 7.37 (t, 1H), 6.80 (s, 1H), 4.78-4.82 (m, 1H), 3.89-3.97 (m, 2H), 3.77 (s, 3H), 3.69-3.72 (m, 1H), 2.90-2.98 (m, 1H), 2.78-2.86 (m, 1H), 2.54-2.61 (m, 1H), 2.19-2.26 (m, 1H), 2.00-2.16 (m, 3H), 1.73-1.81 (m, 1H).

((R)-5-Oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate Diastereoisomer II (121) LCMS: m/z found 449.2/451.2 [M+H]$^+$, RT=7.34 min (Method A); Chiral-SFC: RT=7.85 min, Chiralpak IC-3 (150 mm×4.6 mm, 3 μm); $^1$H NMR (400 MHz, DMSO-d$_6$): δ 9.35 (bs, 1H), 7.92-7.94 (m, 1H), 7.64 (bs, 1H), 7.55-7.60 (m, 1H), 7.46 (bd, 1H), 7.37 (t, 1H), 6.80 (s, 1H), 4.78-4.82 (m, 1H), 3.89-3.97 (m, 2H), 3.77 (s, 3H), 3.69-3.72 (m, 1H), 2.90-2.98 (m, 1H), 2.78-2.86 (m, 1H), 2.54-2.61 (m, 1H), 2.19-2.26 (m, 1H), 2.00-2.16 (m, 3H), 1.73-1.81 (m, 1H).

Example 25: (1-Methyl-1H-1,2,4-triazol-3-yl)methyl (1-((4-fluoro-3-methylphenyl) carbamoyl)-2-methyl-2,4,5,6-tetrahydrocyclopenta[c]pyrrol-4-yl) carbamate (62)

N-(4-Fluoro-3-methylphenyl)-2-methyl-4-oxo-2,4,5,6-tetrahydrocyclopenta[c]pyrrole-1-carboxamide (VIIIb)

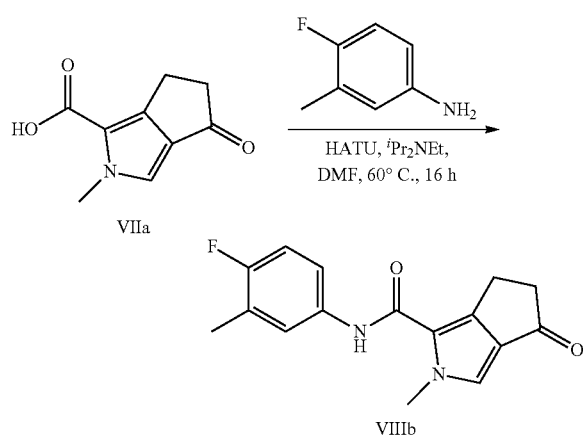

To a solution of 0.8 g (3.9 mmol, 1.0 eq.) of 2-methyl-4-oxo-2,4,5,6-tetrahydro cyclopenta [c]pyrrole-1-carboxylic acid (VIIa) in 9 mL of DMF at 0° C. was added 1.5 g (11.8 mmol, 3.0 eq.) of N,N-diisopropylethylamine followed by 2.2 g (7.5 mmol, 1.5 eq.) of hexafluorophosphate azabenzotriazole tetramethyl uronium (HATU) and 0.89 g (5.9 mmol, 1.2 eq.) of 3-chloro-4-fluoro aniline. The mixture was then heated at 90° C. for 16 h. The mixture was allowed to cool to room temperature, diluted with 100 mL of ice-cold water and extracted with 3×50 mL of ethyl acetate. The combined organic extracts were washed with 50 mL of brine, dried (Na$_2$SO$_4$) and the solvent was removed in vacuo. The residue was purified by flash chromatography (SiO$_2$, eluting with linear gradient of 20-30% ethyl acetate in petroleum ether) to provide 1.0 g (3.5 mmol, 72%) of N-(4-fluoro-3-methylphenyl)-2-methyl-4-oxo-2,4,5,6-tetrahydrocyclopenta[c]pyrrole-1-carboxamide (VIIIb). LCMS: m/z found 287.2 [M+H]$^+$; $^1$H NMR (400 MHz, CDCl$_3$): δ 9.51 (bs, 1H), 7.56-7.59 (m, 1H), 7.44-7.49 (m, 2H), 7.10 (dd, 1H), 3.90 (s, 3H), 3.12-3.16 (m, 2H), 2.72-2.76 (m, 2H), 2.22 (s, 3H).

4-(((R)-tert-Butylsulfinyl)amino)-N-(4-fluoro-3-methylphenyl)-2-methyl-2,4,5,6-tetrahydro cyclopenta[c]pyrrole-1-carboxamide (XIb)

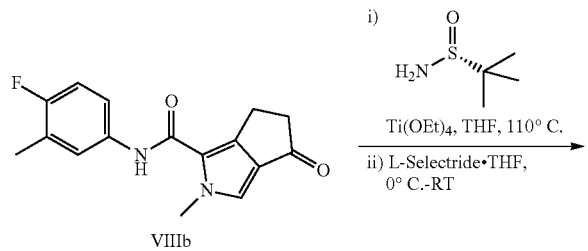

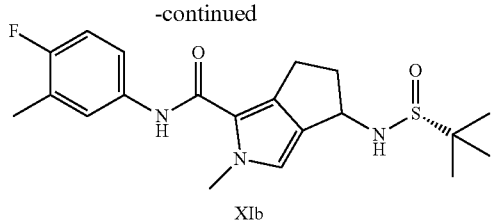

To a solution of 1.0 g (3.49 mmol, 1.0 eq.) of N-(4-fluoro-3-methylphenyl)-2-methyl-4-oxo-2,4,5,6-tetrahydrocyclopenta[c]pyrrole-1-carboxamide (VIIIb) in 10 mL of THF was added 0.63 g (5.2 mmol, 1.5 eq.) of (R)-2-methylpropane-2-sulfinamide followed by 4.1 mL (18.1 mmol, 5.0 eq.) of titanium tetraethoxide at room temperature. The vessel was sealed and the mixture was stirred at 110° C. for 16 h. The mixture was then cooled to 0° C. and diluted with 50 mL of ice-cold water. The heterogeneous mixture was filtered through CELITE® and the pad was washed with 40 mL of ethyl acetate. The organic phase was separated from the filtrate and the aqueous layer was extracted with 3×30 mL of ethyl acetate. The combined organic extracts were washed with 80 mL of brine, dried (Na$_2$SO$_4$), filtered and the solvent was removed in vacuo. The residue was redissolved in 10 mL of THF at 0° C. under a nitrogen atmosphere and 18 mL (18.0 mmol, 5 eq.) of a 1 M solution of L-selectride in THF was added drop wise over 10 min. The mixture was allowed to warm to room temperature and stirred for 24 h. The reaction was quenched with 50 mL of ice-cold water and the resultant heterogeneous mixture was filtered through CELITE®. The filtrate was extracted with 3×50-mL of ethyl acetate and the combined organic extracts were washed with 50 mL of brine, dried (Na$_2$SO$_4$), filtered and the solvent was removed in vacuo. The residue was purified by flash chromatography (SiO$_2$, eluting with linear gradient of 60-90% ethyl acetate in petroleum ether) to provide 0.8 g (2.04 mmol, 58%) 4-(((R)-tert-butylsulfinyl)amino)-N-(4-fluoro-3-methylphenyl)-2-methyl-2,4,5,6-tetrahydro cyclopenta[c]pyrrole-1-carboxamide (XIb) as a ~7:1 mixture of diastereoisomers. LCMS: m/z found 414.47 [M+H]$^+$, RT=2.06, 2.12 min.

4-Amino-N-(4-fluoro-3-methylphenyl)-2-methyl-2,4,5,6-tetrahydrocyclopenta[c]pyrrole-1-carboxamide (IXb)

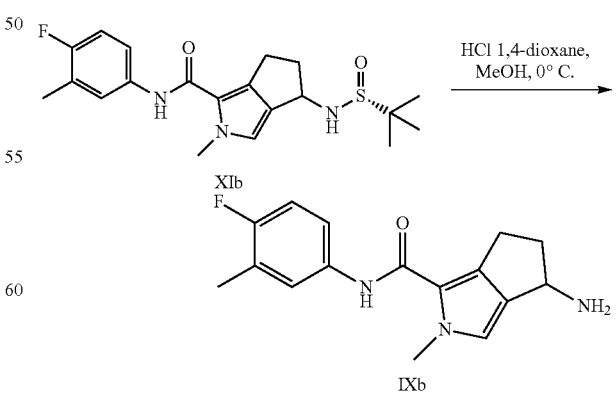

To a solution of 0.6 g (1.5 mmol, 1.0 eq.) of 4-(((R)-tert-butylsulfinyl)amino)-N-(4-fluoro-3-methylphenyl)-2- methyl-2,4,5,6-tetrahydrocyclopenta[c]pyrrole-1-carboxamide (XIb) in 6 mL of methanol at 0° C. was added 0.6 mL of 4 M HCl solution in 1,4-dioxane. The mixture was allowed warm to room temperature and stirred for 2 h. The solvent was removed in vacuo and the residue was triturated with 10 mL of 1:4 (v/v) ethyl acetate:diethyl ether. The resulting residue was dissolved in 50 mL of 1:4 (v/v) methanol:methylene chloride, washed with 2×30 mL of saturated sodium bicarbonate solution (2×30 mL), dried ($Na_2SO_4$), filtered and the solvent was removed in vacuo to provide 0.3 g (1.04 mmol, 67%) of 4-amino-N-(4-fluoro-3-methylphenyl)-2-methyl-2,4,5,6-tetrahydrocyclopenta[c]pyrrole-1-carboxamide (IXb) as a ~7:1 mixture of enantiomers.

(1-Methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate (62)

of (1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate—Enantiomer II (62). LCMS: m/z found 427.2 [M+H]$^+$, RT=6.01 min (Method A); HPLC: RT=7.12 min (Method B); Chiral SFC: RT=6.93 min, (Column: Chiralcel OJ-H (4.6×250 mm, 5 μm)); $^1$H NMR (400 MHz, DMSO-$d_6$) δ 9.12 (s, 1H), 8.43 (s, 1H), 7.53-7.58 (m, 2H), 7.43-7.47 (m, 1H), 7.06 (dd, 1H), 6.77 (s, 1H), 4.97-5.02 (m, 2H), 4.79-4.82 (m, 1H), 3.84 (s, 3H), 3.76 (s, 3H), 2.89-2.94 (m, 1H), 2.76-2.84 (m, 1H), 2.51-2.58 (m, 1H), 2.21 (s, 3H), 2.07-2.13 (m, 1H).

Example 26: (1-Methyl-1H-1,2,4-triazol-3-yl)methyl (2-methyl-1-((3,4,5-trifluorophenyl)carbamoyl)-2,4,5,6-tetrahydrocyclopenta[c]pyrrol-4-yl)carbamate (71)

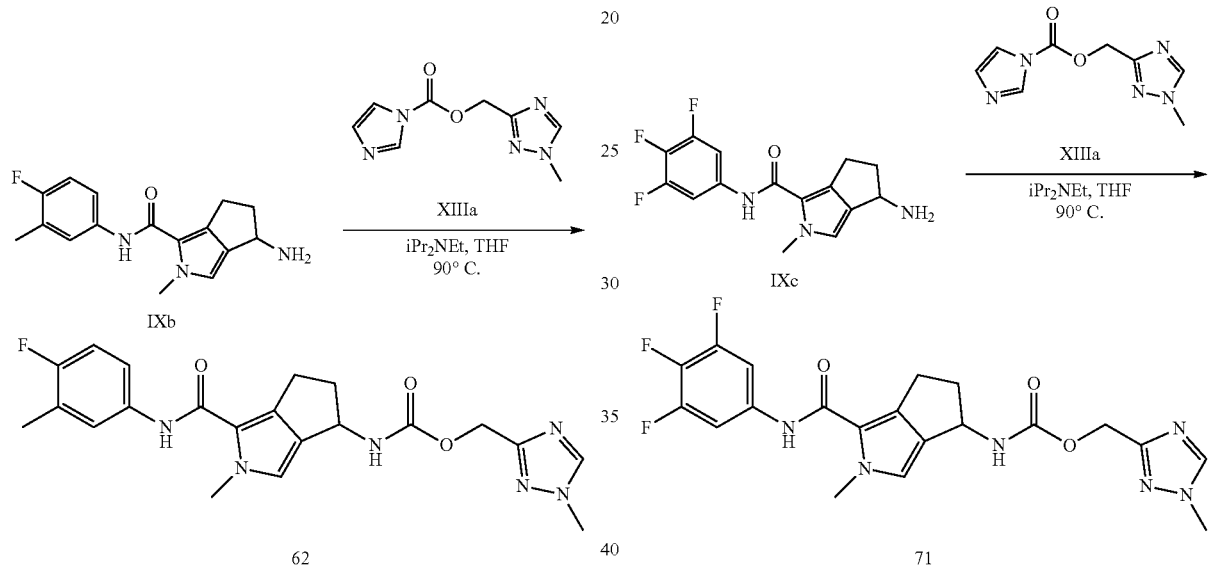

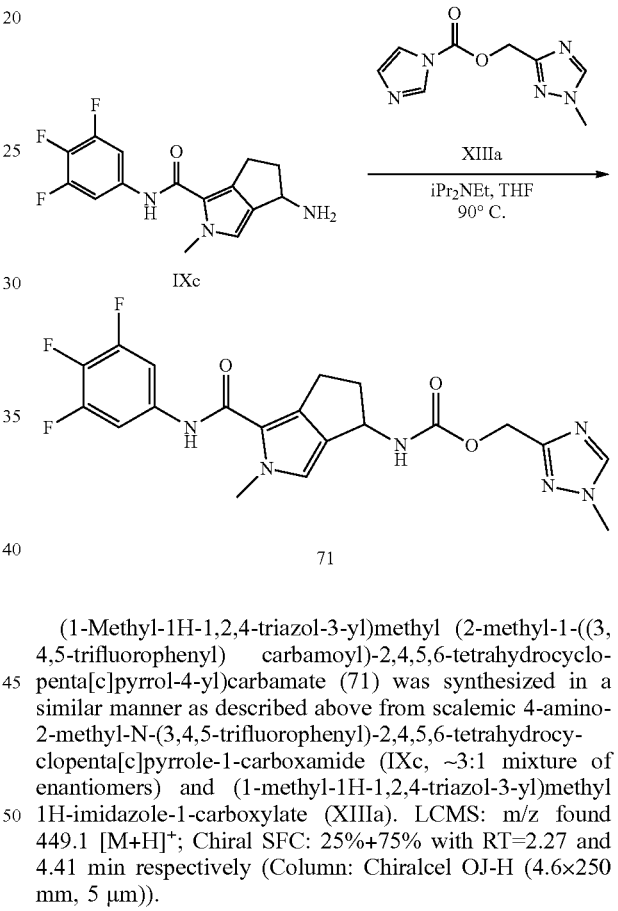

To a solution of 0.3 g (1.04 mmol, 1.0 eq.) of scalemic 4-amino-N-(4-fluoro-3-methylphenyl)-2-methyl-2,4,5,6-tetrahydrocyclopenta[c]pyrrole-1-carboxamide (IXb, ~7:1 mixture of enantiomers) and 0.32 g (1.56 mmol, 1.5 eq.) of (1-methyl-1H-1,2,4-triazol-3-yl)methyl 1H-imidazole-1-carboxylate (XIIIa) in 5 mL of THF under a nitrogen atmosphere was added 0.4 g (3.1 mmol, 3.0 eq.) of N,N-diisopropylethylamine and the mixture was heated at 90° C. for 16 h. The reaction was quenched with 30 mL of ice-cold water and extracted with 3×50 mL of ethyl acetate. The combined organic extracts were washed with 40 mL of brine, dried ($Na_2SO_4$), filtered the solvent was removed in vacuo. The residue was purified by flash chromatography ($SiO_2$, eluting with a linear gradient of 0-5% methanol in methylene chloride) to provide 0.23 g (0.54 mmol, 51%) of scalemic (1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate. LCMS: m/z found 427.44 [M+H]$^+$; Chiral SFC: 12%+78% with RT=2.08 and 6.97 min respectively, Column: Chiralcel OJ-H (4.6×250 mm, 5 μm).

The major enantiomer was subsequently isolated by preparative SFC (Waters SFC investigator). Method: isocratic, Mobile phase MeOH:CO$_2$—35:65. Column: Chiralcel OJ-H (30×250 mm), 5 μm, flow rate: 70 g/min to provide 92 mg (1-Methyl-1H-1,2,4-triazol-3-yl)methyl (2-methyl-1-((3,4,5-trifluorophenyl) carbamoyl)-2,4,5,6-tetrahydrocyclopenta[c]pyrrol-4-yl)carbamate (71) was synthesized in a similar manner as described above from scalemic 4-amino-2-methyl-N-(3,4,5-trifluorophenyl)-2,4,5,6-tetrahydrocyclopenta[c]pyrrole-1-carboxamide (IXc, ~3:1 mixture of enantiomers) and (1-methyl-1H-1,2,4-triazol-3-yl)methyl 1H-imidazole-1-carboxylate (XIIIa). LCMS: m/z found 449.1 [M+H]$^+$; Chiral SFC: 25%+75% with RT=2.27 and 4.41 min respectively (Column: Chiralcel OJ-H (4.6×250 mm, 5 μm)).

The major enantiomer was subsequently isolated by preparative SFC (Waters SFC investigator). Method: isocratic, Mobile phase MeOH:CO$_2$—15:85. Column: Chiralcel OJ-H (30×250 mm), 5 μm, flow rate: 60 g/min to provide (1-methyl-1H-1,2,4-triazol-3-yl)methyl (2-methyl-1-((3,4,5-trifluorophenyl)carbamoyl)-2,4,5,6-tetrahydrocyclopenta[c]pyrrol-4-yl)carbamate—Enantiomer II (71). LCMS: m/z found 449.1 [M+H]$^+$, RT=6.91 min, (Method A); HPLC: RT=7.52 min (Method B); Chiral SFC: RT=4.41 min, Column: Chiralcel OJ-H (4.6×250 mm, 5 μm)); $^1$H NMR (400 MHz, DMSO-$d_6$) δ 9.49 (s, 1H), 8.42 (s, 1H), 7.55-7.60 (m, 3H), 6.83 (s, 1H), 4.98-5.02 (m, 2H), 4.79-4.83 (m, 1H), 3.84 (s, 3H), 3.76 (s, 3H), 2.90-2.97 (m, 1H), 2.78-2.84 (m, 1H), 2.52-2.61 (m, 1H), 2.07-2.13 (m, 1H).

Example 27: (1-Methyl-1H-1,2,4-triazol-3-yl) methyl (1-((3,4-difluorophenyl)carbamoyl)-2-methyl-2,4,5,6-tetrahydrocyclopenta[c]pyrrol-4-yl) carbamate (64)

Example 28: (1-Methyl-1H-1,2,4-triazol-3-yl) methyl (1-((4-fluorophenyl)carbamoyl)-2-methyl-2,4,5,6-tetrahydrocyclopenta[c]pyrrol-4-yl)carbamate (65)

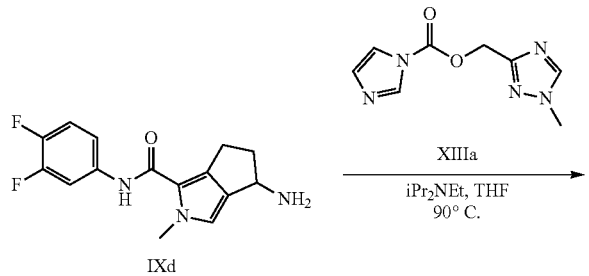

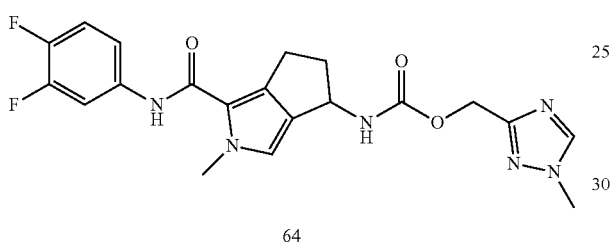

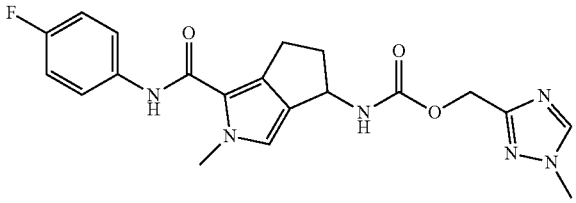

(1-Methyl-1H-1,2,4-triazol-3-yl)methyl(1-((3,4-difluorophenyl)carbamoyl)-2-methyl-2,4,5,6-tetrahydrocyclopenta[c]pyrrol-4-yl)carbamate was synthesized in a similar manner as described above from scalemic 4-amino-N-(3,4-difluorophenyl)-2-methyl-2,4,5,6-tetrahydro cyclopenta[c]pyrrole-1-carboxamide (IXd, ~10:1 mixture of enantiomers) and (1-methyl-1H-1,2,4-triazol-3-yl)methyl-1H-imidazole-1-carboxylate (XIIIa). LCMS: m/z found 431.4 [M+H]+; Chiral SFC: 90%+10% with RT=3.68 and 5.56 min respectively, Column: Chiralpak AD-H (4.6×250 mm, 5 μm).

The major enantiomer was subsequently isolated by preparative SFC (Waters SFC investigator). Method: isocratic, Mobile phase MeOH:CO₂—50:50. Column: Chiralpak AD-H (30×250 mm), 5 μm, flow rate: 90 g/min to provide (1-methyl-1H-1,2,4-triazol-3-yl)methyl (1-((3,4-difluorophenyl)carbamoyl)-2-methyl-2,4,5,6-tetrahydrocyclopenta[c]pyrrol-4-yl)carbamate—Enantiomer I (64). LCMS: m/z found 431.50 [M+H]+, RT=5.54 min (Method A); HPLC: RT=7.07 min (Method B); Chiral SFC: RT=3.86 min (Column: Chiralcel OJ-H (4.6×250 mm, 5 μm)); $^1$H NMR (400 MHz, DMSO-d₆): δ 9.39 (s, 1H), 8.43 (s, 1H), 7.77-7.82 (m, 1H), 7.59 (m, 1H), 7.35-7.39 (m, 2H), 6.81 (s, 1H), 4.98-5.02 (m, 2H), 4.79-4.82 (m, 1H), 3.84 (s, 3H), 3.76 (s, 3H), 2.89-2.96 (m, 1H), 2.77-2.84 (m, 1H), 2.51-2.59 (m, 1H), 2.07-2.12 (m, 1H).

(1-Methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate was synthesized in a similar manner as described above from scalemic 4-amino-N-(4-fluorophenyl)-2-methyl-2,4,5,6-tetrahydrocyclopenta[c]pyrrole-1-carboxamide (IXe, ~1:7 mixture of enantiomers) and (1-methyl-1H-1,2,4-triazol-3-yl)methyl 1H-imidazole-1-carboxylate (XIIIa) LCMS: m/z found 413.4 [M+H]+; Chiral SFC: 12%+88% with RT=2.07 and 6.19 min respectively, Column: Chiralcel OJ-H (4.6×250 mm, 5 μm).

The major enantiomer was subsequently isolated by preparative SFC (Waters SFC investigator). Method: isocratic, Mobile phase MeOH:CO₂—40:60. Column: Chiralcel OJ-H (21×250 mm), 5 μm, flow rate: 90 g/min to provide (1-methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate—Enantiomer II (65). LCMS: m/z found 413.3 [M+H]+, RT=5.70 min (Method A); HPLC: RT=6.77 min (Method B); Chiral SFC: RT=6.19 min, Column: Chiralcel OJ-H (4.6×250 mm, 5 μm); $^1$H NMR (400 MHz, DMSO-d₆): δ 9.24 (s, 1H), 8.43 (s, 1H), 7.62-7.66 (m, 2H), 7.58 (bd, 1H), 7.11-7.16 (m, 2H), 6.78 (s, 1H), 4.98-50.2 (m, 2H), 4.79-4.83 (m, 1H), 3.84 (s, 3H), 3.76 (s, 3H), 2.89-2.96 (m, 1H), 2.78-2.84 (m, 1H), 2.52-2.60 (m, 1H), 2.07-2.13 (m, 1H).

Example 29: (1-Methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate (66)

Example 30: (1-Methyl-1H-1,2,4-triazol-3-yl)methyl (1-((4-fluoro-3-(trifluoromethyl) phenyl)carbamoyl)-2-methyl-2,4,5,6-tetrahydrocyclopenta[c]pyrrol-4-yl)carbamate (69)

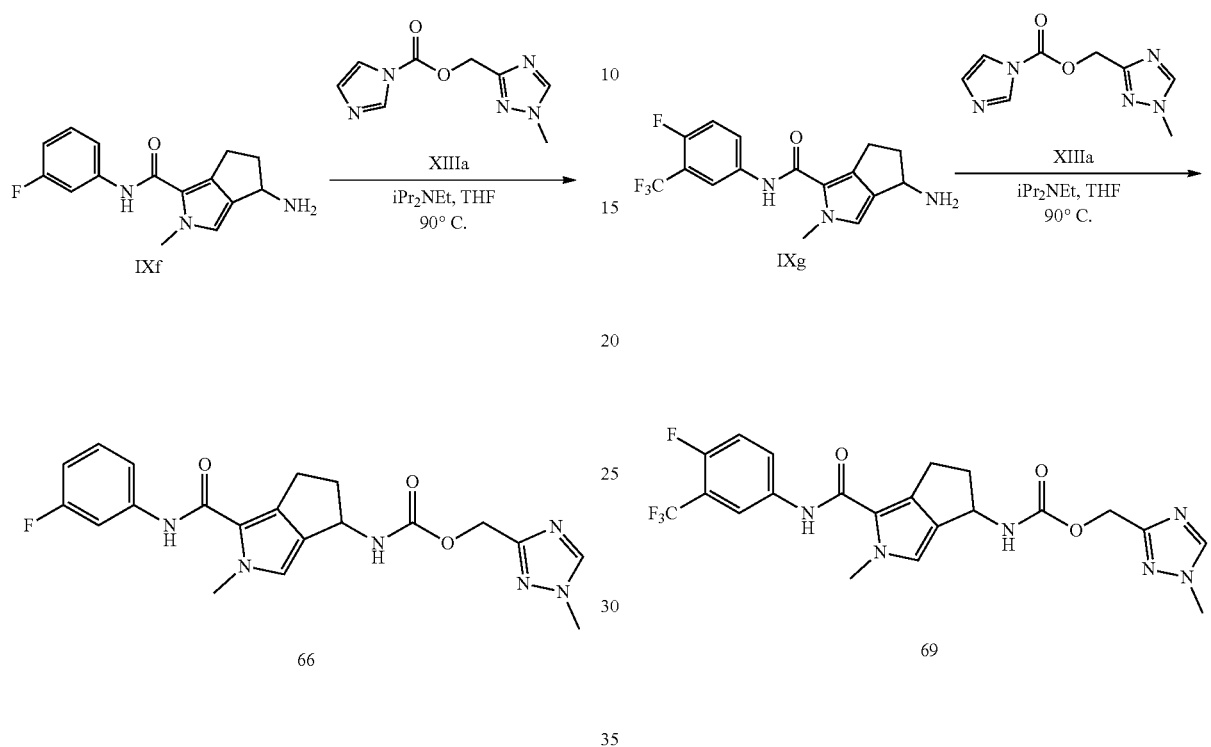

(1-Methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate was synthesized in a similar manner as described above from scalemic 4-amino-N-(3-fluorophenyl)-2-methyl-2,4,5,6-tetrahydrocyclopenta[c]pyrrole-1-carboxamide (IXf, ~1:7 mixture of enantiomers) and (1-methyl-1H-1,2,4-triazol-3-yl)methyl 1H-imidazole-1-carboxylate (XIIIa) LCMS: m/z found 413.4 [M+H]+; Chiral SFC: 13%+87% with RT=2.10 and 6.80 min respectively, Column: Chiralcel OJ-H (4.6×250 mm, 5 μm).

The major enantiomer was subsequently isolated by preparative SFC (Waters SFC investigator). Method: isocratic, Mobile phase MeOH:CO$_2$—40:60. Column: Chiralcel OJ-H (21×250 mm), 5 μm, flow rate: 90 g/min to provide (1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate—Enantiomer II (66). LCMS: m/z found 413.3 [M+H]+, RT=5.39 min (Method A); HPLC: RT=6.77 min (Method B); Chiral SFC: RT=6.91 min, Column: Chiralcel OJ-H (4.6×250 mm, 5 μm); $^1$H NMR (400 MHz, DMSO-d$_6$): δ 9.39 (s, 1H), 8.43 (s, 1H), 7.58-7.62 (m, 2H), 7.38-7.41 (m, 1H), 7.29-7.35 (m, 1H), 6.82-6.87 (m, 1H), 6.81 (s, 1H), 4.98-5.02 (m, 2H), 4.79-4.83 (m, 1H), 3.84 (s, 3H), 3.77 (s, 3H), 2.90-2.97 (m, 1H), 2.78-2.48 (m, 1H), 2.52-2.61 (m, 1H), 2.07-2.13 (m, 1H).

(1-Methyl-1H-1,2,4-triazol-3-yl)methyl (1-((4-fluoro-3-(trifluoromethyl)phenyl) carbamoyl)-2-methyl-2,4,5,6-tetrahydrocyclopenta[c]pyrrol-4-yl)carbamate was synthesized in a similar manner as described above from scalemic 4-amino-N-(4-fluoro-3-(trifluoromethyl) phenyl)-2-methyl-2,4,5,6-tetrahydrocyclopenta[c]pyrrole-1-carboxamide (IXg, ~1:10 mixture of enantiomers) and (1-methyl-1H-1,2,4-triazol-3-yl)methyl 1H-imidazole-1-carboxylate (XIIIa). LCMS: m/z found 413.4 [M+H]+; Chiral SFC: 8%+92% with RT=2.34 and 3.37 min respectively, Column: Chiralcel OJ-H (4.6×250 mm, 5 μm).

The major enantiomer was subsequently isolated by preparative SFC (Waters SFC investigator). Method: isocratic, Mobile phase MeOH:CO$_2$~15:85. Column: Chiralcel OJ-H (30×250 mm), 5 μm, flow rate: 90 g/min to provide (1-methyl-1H-1,2,4-triazol-3-yl)methyl (1-((4-fluoro-3-(trifluoromethyl)carbamoyl)-2-methyl-2,4,5,6-tetrahydrocyclopenta[c]pyrrol-4-yl)carbamate—Enantiomer II (69). LCMS: m/z found 481.3 [M+H]+, RT=7.65 min (Method A); HPLC: RT=6.77 min (Method B); Chiral SFC: RT=3.21 min, Column: Chiralcel OJ-H (4.6×250 mm, Sum)); $^1$H NMR (400 MHz, DMSO-d$_6$): δ 9.48 (s, 1H), 8.42 (s, 1H), 8.11-8.14 (m, 1H), 7.90-7.93 (m, 1H), 7.58 (bd, 1H), 7.44-7.49 (m, 1H), 6.82 (s, 1H), 4.96-5.03 (m, 2H), 4.79-4.83 (m, 1H), 3.84 (s, 3H), 3.77 (s, 3H), 2.92-2.98 (m, 1H), 2.80-2.86 (m, 1H), 2.52-2.61 (m, 1H), 2.07-2.14 (m, 1H).

Example 31: (1-Methyl-1H-1,2,4-triazol-3-yl)methyl (1-((3-(difluoromethyl)-4-fluoro phenyl)carbamoyl)-2-methyl-2,4,5,6-tetrahydrocyclopenta[c]pyrrol-4-yl)carbamate (70)

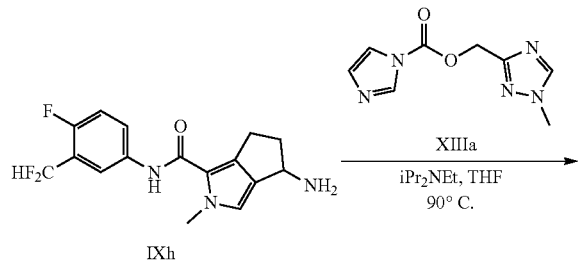

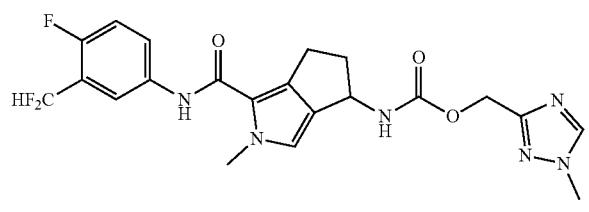

70

(1-Methyl-1H-1,2,4-triazol-3-yl)methyl (1-((3-(difluoromethyl)-4-fluorophenyl) carbamoyl)-2-methyl-2,4,5,6-tetrahydrocyclopenta[c]pyrrol-4-yl)carbamate was synthesized in a similar manner as described above from scalemic 4-amino-N-(4-fluoro-3-(difluoromethyl) phenyl)-2-methyl-2,4,5,6-tetrahydrocyclopenta [c]pyrrole-1-carboxamide (IXh, ~1:10 mixture of enantiomers) and (1-methyl-1H-1,2,4-triazol-3-yl)methyl 1H-imidazole-1-carboxylate (XIIIa).

The major enantiomer was subsequently isolated by preparative SFC (Waters SFC investigator). Method: isocratic, Mobile phase MeOH:CO$_2$—15:85. Column: Chiralcel OD-3 (30×250 mm), 5 μm, flow rate: 90 g/min to provide (1-methyl-1H-1,2,4-triazol-3-yl)methyl (1-((4-fluoro-3-(difluoromethyl)carbamoyl)-2-methyl-2,4,5,6-tetrahydrocyclopenta[c]pyrrol-4-yl)carbamate—Enantiomer II (70). LCMS: m/z found 463.3 [M+H]$^+$, RT=6.12 min (Method A); HPLC: RT=7.15 min (Method B); Chiral SFC: RT=1.25 min (Column: Chiralcel OD-3 (4.6×250 mm, 5 μm)); $^1$H NMR (400 MHz, DMSO-d$_6$): δ 9.39 (s, 1H), 8.42 (s, 1H), 7.97-7.99 (m, 1H), 7.75-7.79 (m, 1H), 7.58 (bd, 1H), 7.29-7.35 (m, 1H), 7.20 (dd, 1H), 6.80 (s, 1H), 4.98-5.02 (m, 2H), 4.79-4.83 (m, 1H), 3.84 (s, 3H), 3.77 (s, 3H), 2.91-2.98 (m, 1H), 2.79-2.85 (m, 1H), 2.52-2.61 (m, 1H), 2.08-2.13 (m, 1H).

Example 32: (1-Methyl-1H-1,2,4-triazol-3-yl)methyl (1-((3-cyano-4-fluorophenyl) carbamoyl)-2-methyl-2,4,5,6-tetrahydrocyclopenta[c]pyrrol-4-yl) carbamate (67)

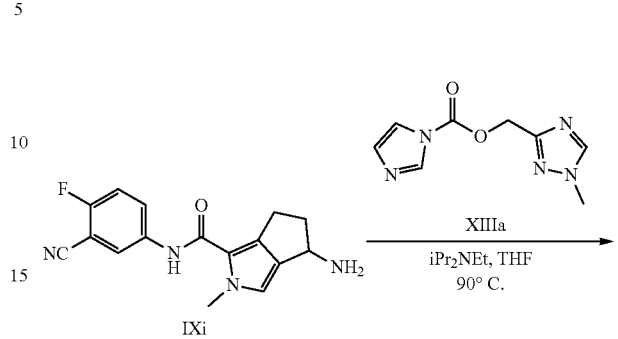

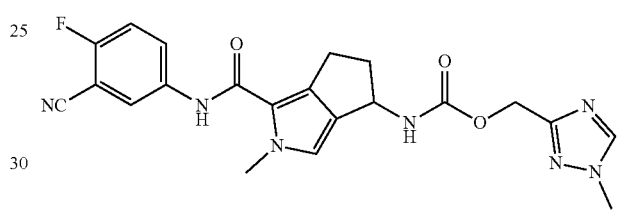

67

(1-Methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate was synthesized in a similar manner as described above from scalemic 4-amino-N-(3-cyano-4-fluorophenyl)-2-methyl-2,4,5,6-tetrahydrocyclopenta[c]pyrrole-1-carboxamide (IXi) and (1-methyl-1H-1,2,4-triazol-3-yl)methyl 1H-imidazole-1-carboxylate (XIIIa).

The major enantiomer was subsequently isolated by preparative SFC (Waters SFC investigator). Method: isocratic, Mobile phase MeOH:CO$_2$—15:85. Column: Chiralcel OD-3 (30×250 mm), 5 μm, flow rate: 90 g/min to provide (1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate—Enantiomer II (67). LCMS: m/z found 438.3 [M+H]$^+$, RT=5.43 min (Method A); HPLC: RT=6.82 min (Method B); Chiral SFC: RT=6.27 min, Column: Chiralpak IC-3 (4.6×250 mm, 5 μm); $^1$H NMR (400 MHz, DMSO-d$_6$) δ 9.49 (s, 1H), 8.43 (s, 1H), 8.12-8.14 (m, 1H), 7.91-7.95 (m, 1H), 7.60 (d, 1H), 7.50 (t, 1H), 6.83 (s, 1H), 4.97-5.02 (m, 2H), 4.79-4.83 (m, 1H), 3.84 (s, 3H), 3.77 (s, 3H), 2.91-2.98 (m, 1H), 2.77-2.85 (m, 1H), 2.52-2.61 (m, 1H), 2.07-2.14 (m, 1H).

Example 33: (1-Methyl-1H-1,2,4-triazol-3-yl) methyl (2-methyl-1-((2-(trifluoromethyl) pyridin-4-yl)carbamoyl)-2,4,5,6-tetrahydrocyclopenta[c]pyrrol-4-yl)carbamate (73)

Example 34: (1-Methyl-1H-1,2,4-triazol-3-yl) methyl (1-((2-chloropyridin-4-yl) carbamoyl)-2-methyl-2,4,5,6-tetrahydrocyclopenta[c]pyrrol-4-yl) carbamate (68)

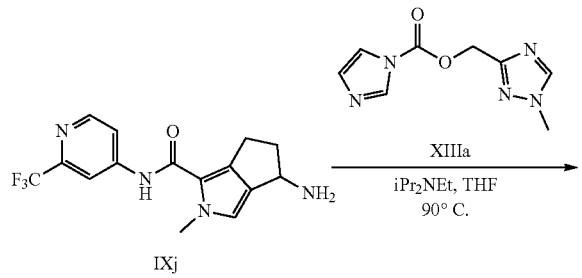

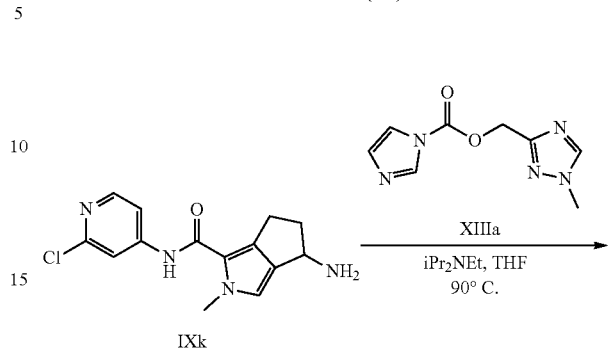

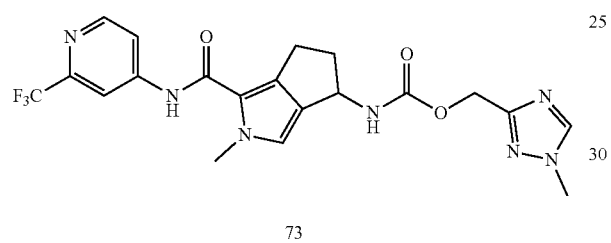

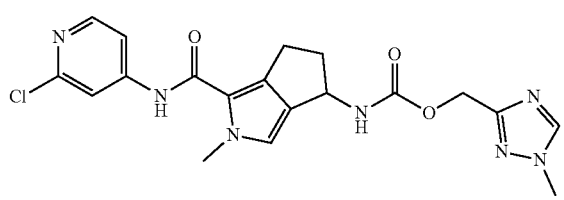

(1-Methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate was synthesized in a similar manner as described above from scalemic 4-amino-2-methyl-N-(2-(trifluoromethyl)pyridin-4-yl)-2,4,5,6-tetrahydrocyclopenta[c]pyrrole-1-carboxamide (IXj, ~9:1 mixture of enantiomers) and (1-methyl-1H-1,2,4-triazol-3-yl) methyl 1H-imidazole-1-carboxylate (XIIIa). LCMS: m/z found 464.08 [M+H]$^+$; Chiral SFC: 92%+8% with RT=4.23 and 5.67 min respectively, Column: Chiralcel OD-H (4.6× 250 mm, 5 μm).

The major enantiomer was subsequently isolated by preparative SFC (Waters SFC investigator). Method: isocratic, Mobile phase MeOH:CO$_2$—10:90. Column: Chiralcel OD-H (21×250 mm, 5 μm), flow rate: 70 g/min to provide ((1-methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate—Enantiomer I (73). LCMS: m/z found 464.3 [M+H]$^+$, RT=6.44 min (Method A); HPLC: RT=6.76 min (Method B); Chiral SFC: RT=4.52 min, Column: Chiralcel OD-H (4.6×250 mm, 5 μm); $^1$H NMR (400 MHz, DMSO-d$_6$): δ 9.86 (s, 1H), 8.58 (d, 1H), 8.43 (d, 1H), 8.15 (s, 1H), 7.86 (d, 1H), 7.61 (bs, 1H), 6.89 (s, 1H), 4.95-5.02 (m, 2H), 4.79-4.83 (m, 1H), 3.84 (s, 3H), 3.79 (s, 3H), 2.94-3.01 (m, 1H), 2.82-2.88 (m, 1H), 2.54-2.61 (m, 1H), 2.08-2.15 (m, 1H).

(1-Methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate was synthesized in a similar manner as described above from scalemic 4-amino-2-methyl-N-(2-chloropyridin-4-yl)-2,4,5,6-tetrahydrocyclopenta[c]pyrrole-1-carboxamide (IXk, ~1:3 mixture of enantiomers) and (1-methyl-1H-1,2,4-triazol-3-yl)methyl 1H-imidazole-1-carboxylate (XIIIa) LCMS: m/z found 430.3/432.3 [M+H]$^+$; Chiral SFC: 25%+75% with RT=2.95 and 5.91 min respectively, Column: Chiralcel OJ-H (4.6× 250 mm, 5 μm).

The major enantiomer was subsequently isolated by preparative SFC (Waters SFC investigator). Method: isocratic, Mobile phase MeOH:CO$_2$—25:75. Column: Chiralcel OD-H (21×250 mm, 5 μm), flow rate: 60 g/min to (1-methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate—Enantiomer II (68). LCMS: m/z found 430.3/432.3 [M+H]$^+$, RT=6.08 min (Method A); HPLC: RT=6.31 min (Method B); Chiral SFC: RT=5.86 min (Column: Chiralcel OJ-H (4.6×250 mm, 5 μm)); $^1$H NMR (400 MHz, DMSO-d$_6$): δ 9.76 (s, 1H), 8.43 (s, 1H), 8.23 (d, 1H), 7.76 (d, 1H), 7.56-7.61 (m, 2H), 6.88 (s, 1H), 4.99 (s, 2H), 4.79-4.82 (m, 1H), 3.84 (s, 3H), 3.78 (s, 3H), 2.89-2.96 (m, 1H), 2.77-2.84 (m, 1H), 2.51-2.59 (m, 1H), 2.13-2.07 (m, 1H).

Example 35: (1-Methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate (81)

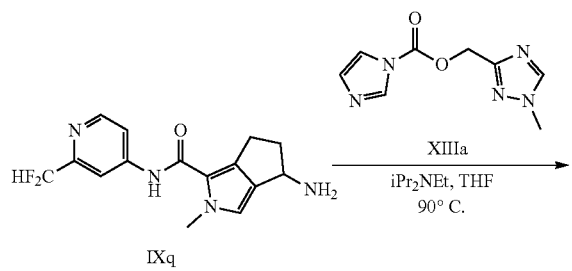

(1-Methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate was synthesized in a similar manner as described above from scalemic 4-amino-N-(2-(difluoromethyl)pyridin-4-yl)-2-methyl-2,4,5,6-tetrahydrocyclopenta[c]pyrrole-1-carboxamide (IXq, ~1:15 mixture of enantiomers) and (1-methyl-1H-1,2,4-triazol-3-yl)methyl 1H-imidazole-1-carboxylate (XIIIa). The major enantiomer was subsequently isolated by preparative SFC (Waters SFC investigator). Method: isocratic, Mobile phase MeOH:CO₂—25:75. Column: Chiralcel OX-H (21×250 mm), 5 μm, flow rate: 60 g/min to provide (1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate—Enantiomer II (81) LCMS: m/z found 446.4 [M+H]$^+$, RT=5.91 min (Method A); HPLC: RT=6.31 min (Method B); Chiral SFC: RT=14.79 min, Column: Chiralcel OX-H (4.6×250 mm, 5 μm); $^1$H NMR (400 MHz, DMSO-d₆): δ 9.77 (s, 1H), 8.50 (d, 1H), 8.42 (s, 1H), 7.98 (s, 1H), 7.74 (d, 1H), 7.61 (d, 1H), 6.75-7.03 (m, 2H), 4.99 (q, 2H), 4.79-4.83 (m, 1H), 3.84 (s, 3H), 3.79 (s, 3H), 2.93-2.99 (m, 1H), 2.83-2.91 (m, 1H), 2.50-2.61 (m, 1H), 2.07-2.13 (m, 1H).

Example 36: (5-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (138, 139)

Ethyl 5-methyl-2H-1,2,3-triazole-4-carboxylate

A sealed tube containing 1.6 g (14.28 mmol, 1.0 eq.) of ethyl but-2-ynoate and 5.8 g (35.74 mmol, 7.0 eq.) of azidotrimethylsilane in 16 mL of THF was heated to 100° C. for 30 h. The mixture was allowed to cool to room temperature and the solvent was removed in vacuo. The residue suspended in 40 mL of water and extracted with 3×40 mL of ethyl acetate. The combined organic extracts were washed with 30 mL of water, 40 mL of brine, dried (Na₂SO₄) and the solvent was removed in vacuo. The residue was purified by MPLC (REVELERIS® Silica column, eluting with a linear gradient of 0-30% ethyl acetate in petroleum ether) to provide 0.5 g of ethyl 5-methyl-2H-1,2,3-triazole-4-carboxylate. LCMS: m/z found 155.0 [M+H]$^+$; $^1$H NMR (400 MHz, CDCl₃): δ 4.44 (q, 2H), 2.64 (s, 3H), 1.40 (t, 3H). The above detailed reaction was conducted in multiple batches with consistent results.

Ethyl 5-methyl-2-trityl-2H-1,2,3-triazole-4-carboxylate

To a solution of 1.9 g (12.3 mmol, 1.0 eq.) of ethyl 5-methyl-2H-1,2,3-triazole-4-carboxylate in 19 mL of DMF at 0° C. was added 5.2 mL (36.77 mmol, 3.0 eq.) of triethylamine followed by 3.4 g (12.3 mmol, 1.0 eq.) of trityl chloride. The mixture was then allowed to warm to room temperature and stirred for 20 h. The reaction was diluted with 50 mL of ice-cold water and extracted with 3×80 mL of ethyl acetate. The combined organic extracts were dried (Na₂SO₄), filtered and the solvent was removed in vacuo. The residue was triturated with 20 mL of 5:1 v/v n-pentane:diethyl ether mixture to provide 1.1 g of ethyl 5-methyl-2-trityl-2H-1,2,3-triazole-4-carboxylate. $^1$H NMR (400 MHz, CDCl₃): δ 7.25-7.33 (m, 9H), 7.09-7.13 (m, 6H), 4.32-4.42 (m, 2H), 2.50 (s, 3H), 1.34-1.38 (t, 3H). The above detailed reaction was conducted in multiple batches with consistent results.

97

(5-Methyl-2-trityl-2H-1,2,3-triazol-4-yl)methanol (XIIr)

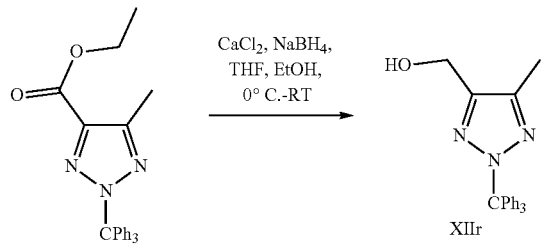

To a solution of 1.1 g (2.76 mmol, 1.0 eq.) of ethyl 5-methyl-2-trityl-2H-1,2,3-triazole-4-carboxylate in 10 mL of 1:1 v/v THF:ethanol at 0° C. under a nitrogen atmosphere was added 0.62 g (5.54 mmol, 2.0 eq.) of calcium chloride followed by the portions-wise addition over approximately 5 min of 0.53 g (13.9 mmol, 4.0 eq.) of sodium borohydride. The mixture was then allowed to warm to room temperature and stirred for 3 h. The reaction was quenched by the addition of 40 mL of ice-cold water and extracted with 3×75 mL of ethyl acetate. The combined organic extracts were washed with 80 mL of brine, dried (Na$_2$SO$_4$), filtered and the solvent was removed in vacuo. The residue was purified by MPLC (REVELERIS® Silica column, eluting with a linear gradient of 10-40% ethyl acetate/petroleum ether) to provide 0.4 g (1.13 mmol, 41%) of (5-methyl-2-trityl-2H-1,2,3-triazol-4-yl)methanol (XIIr). $^1$H NMR (400 MHz, CDCl$_3$): δ 7.25-7.31 (m, 9H), 7.10-7.15 (m, 6H), 4.69 (d, 2H), 2.32 (s, 3H), 1.73 (t, 1H).

98

(5-Methyl-2-trityl-2H-1,2,3-triazol-4-yl)methyl 1H-imidazole-1-carboxylate (XIIIr)

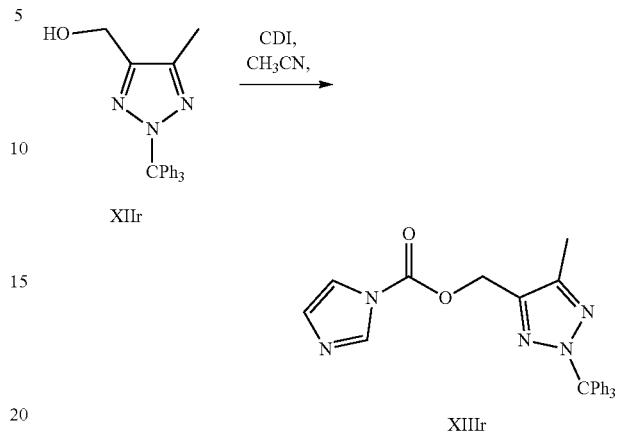

To a solution of 0.4 g (1.126 mmol, 1.0 eq.) of (5-methyl-2-trityl-2H-1,2,3-triazol-4-yl)methanol (XIIr) in 4 mL of acetonitrile was added 0.28 g (1.69 mmol, 1.5 eq.) of 1,1'-carbonyldiimidazole and the mixture was stirred at room temperature for 3 h. The solvent was removed in vacuo and the residue was suspended in 30 mL of ice-cold water and extracted with 2×30 mL of ethyl acetate. The combined organic extracts were washed with 30 mL of brine, dried (Na$_2$SO$_4$), filtered and the solvent was removed in vacuo to provide (5-methyl-2-trityl-2H-1,2,3-triazol-4-yl)methyl 1H-imidazole-1-carboxylate (XIIIr).

(5-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (138, 139)

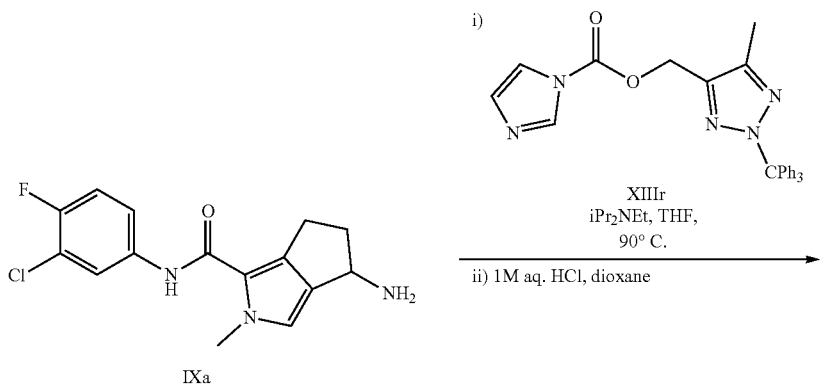

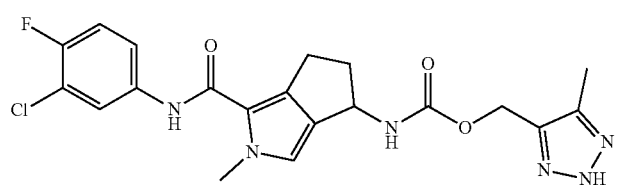

138, 139

(5-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (5-methyl-2-trityl-2H-1,2,3-triazol-4-yl)methyl 1H-imidazole-1-carboxylate (XIIIr) followed by acid mediated detritylation. The enantiomers were subsequently separated by SFC. Method: isocratic, Mobile phase MeOH:CO$_2$—30:70. Column: Chiralpak AD-H (30×250 mm, 5 μm), flow rate: 70 g/min. (5-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer I (138) LCMS: m/z found 447.1/449.0 [M+H]$^+$, RT=4.19 min (Method A); HPLC: RT=7.69 min (Method B); Chiral SFC: RT=2.16 min, Column: Chiralpak AD-H (4.6×250 mm, 5 μm); $^1$H NMR (400 MHz, DMSO-d$_6$): δ 14.74 (bs, 1H), 9.35 (s, 1H), 7.91-7.94 (m, 1H), 7.55-7.59 (m, 1H), 7.54 (d, 1H), 7.36 (t, 1H), 6.79 (s, 1H), 5.04-5.08 (m, 2H), 4.78-4.82 (m, 1H), 3.76 (s, 3H), 2.91-2.97 (m, 1H), 2.77-2.84 (m, 1H), 2.54-2.61 (m, 1H), 2.27 (s, 3H), 2.05-2.11 (m, 1H). (5-Methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer II (139) LCMS: m/z found 447.1/449.0 [M+H]$^+$, RT=4.19 min (Method A); HPLC: RT=7.68 min (Method B); Chiral SFC: RT=5.67 min, Column: Chiralpak AD-H (4.6×250 mm, 5 μm); $^1$H NMR (400 MHz, DMSO-d$_6$): δ 14.74 (bs, 1H), 9.35 (s, 1H), 7.91-7.94 (m, 1H), 7.55-7.59 (m, 1H), 7.54 (d, 1H), 7.36 (t, 1H), 6.79 (s, 1H), 5.04-5.08 (m, 2H), 4.78-4.82 (m, 1H), 3.76 (s, 3H), 2.91-2.97 (m, 1H), 2.77-2.84 (m, 1H), 2.54-2.61 (m, 1H), 2.27 (s, 3H), 2.05-2.11 (m, 1H).

Example 37: (5-Ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (140, 141)

(5-Ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (5-ethyl-2-trityl-2H-1,2,3-triazol-4-yl)methyl 1H-imidazole-1-carboxylate (XIIIs) followed by acid mediated detritylation. The enantiomers were subsequently separated by SFC. Method: isocratic, Mobile phase MeOH:CO$_2$—25:75. Column: Chiralcel OJ-H (30×250 mm, 5 μm), flow rate=90 g/min.

(5-Ethyl-2H-1,2,3-triazol-4-yl)methyl(1-((3-chloro-4-fluorophenyl)carbamoyl)-2-methyl-2,4,5,6-tetrahydrocyclopenta[c]pyrrol-4-yl)carbamate—Enantiomer I (140) LCMS: m/z found 461.1/463.2 [M+H]$^+$, RT=4.44 min (Method A); HPLC: RT=7.94 min (Method B); Chiral SFC: RT=1.36 min, Column: Chiralcel OJ-3 (4.6×250 mm, 5 μm); $^1$H NMR (400 MHz, DMSO-d$_6$): δ 9.34 (s, 1H), 7.91-7.94 (m, 1H), 7.55-7.59 (m, 1H), 7.51 (d, 1H), 7.36 (t, 1H), 6.79 (s, 1H), 5.06-5.09 (m, 2H), 4.78-4.82 (m, 1H), 3.76 (s, 3H), 2.91-2.97 (m, 1H), 2.77-2.84 (m, 1H), 2.69 (q, 2H), 2.54-2.61 (m, 1H), 2.05-2.11 (m, 1H), 1.17 (t, 3H).

(5-Ethyl-2H-1,2,3-triazol-4-yl)methyl(1-((3-chloro-4-fluorophenyl)carbamoyl)-2-methyl-2,4,5,6-tetrahydrocyclopenta[c]pyrrol-4-yl)carbamate—Enantiomer II (141) LCMS: m/z found 461.1/463.2 [M+H]$^+$, RT=4.44 min (Method A); HPLC: RT=7.94 min (Method B); Chiral SFC: RT=2.97 min, Column: Chiralcel OJ-3 (4.6×250 mm, 5 μm); $^1$H NMR (400 MHz, DMSO-d$_6$): δ 9.34 (s, 1H), 7.91-7.94 (m, 1H), 7.55-7.59 (m, 1H), 7.51 (d, 1H), 7.36 (t, 1H), 6.79 (s, 1H), 5.06-5.09 (m, 2H), 4.78-4.82 (m, 1H), 3.76 (s, 3H), 2.91-2.97 (m, 1H), 2.77-2.84 (m, 1H), 2.69 (q, 2H), 2.54-2.61 (m, 1H), 2.05-2.11 (m, 1H), 1.17 (t, 3H).

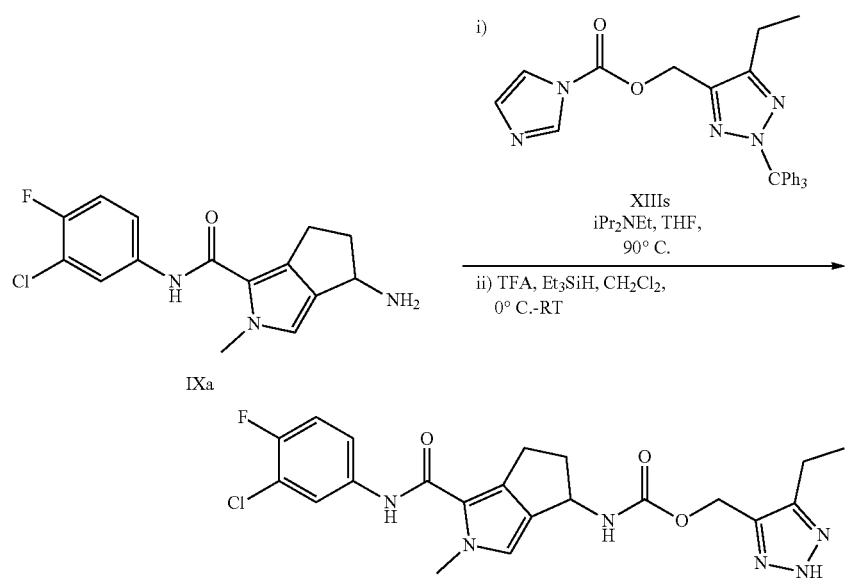

140, 141

Example 38: (5-Cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate (146, 147)

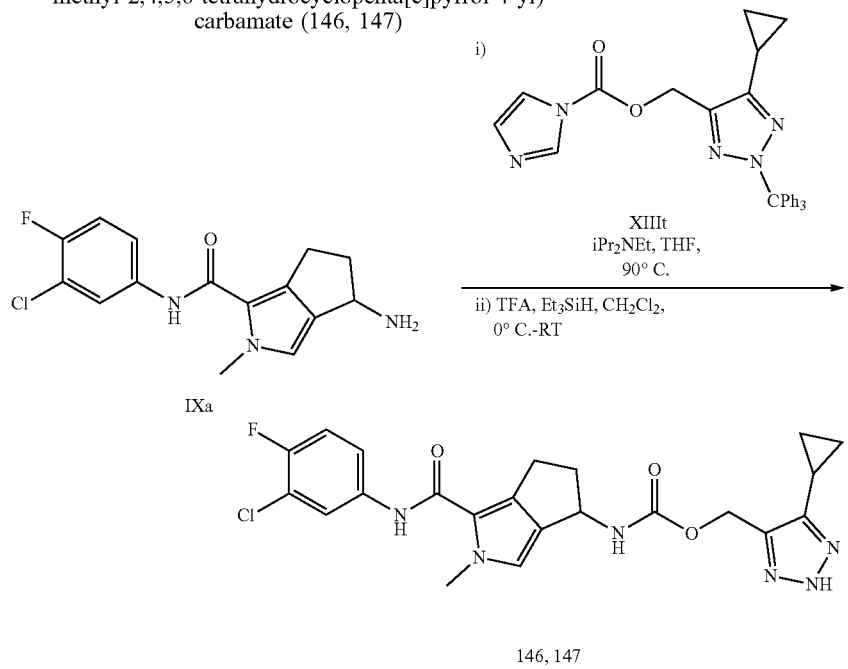

(5-Cyclopropyl-2H-1,2,3-triazol-4-yl)methyl(1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (5-cyclopropyl-2-trityl-2H-1,2,3-triazol-4-yl)methyl 1H-imidazole-1-carboxylate (XIIIt) followed by acid mediated detritylation. The enantiomers were subsequently separated by SFC. Method: isocratic, Mobile phase MeOH:$CO_2$—25:75. Column: Chiralcel OJ-H (30×250 mm, 5 μm), flow rate: 60 g/min.

(5-Ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate—Enantiomer I (146) LCMS: m/z found 473.1/475.2 [M+H]$^+$, RT=4.62 min (Method A); HPLC: RT=8.07 min (Method B); Chiral SFC: RT=1.83 min, Column: Chiralcel OJ-3 (4.6×250 mm, 5 μm); $^1$H NMR (400 MHz, DMSO-$d_6$): δ 9.35 (s, 1H), 7.91-7.94 (m, 1H), 7.53-7.59 (m, 2H), 7.36 (t, 1H), 6.79 (s, 1H), 5.12 (s, 2H), 4.78-4.82 (m, 1H), 3.76 (s, 3H), 2.91-2.97 (m, 1H), 2.77-2.84 (m, 1H), 2.54-2.61 (m, 1H), 2.05-2.12 (m, 1H), 1.98-2.04 (m, 1H), 0.92-0.96 (m, 2H), 0.75-0.79 (m, 2H).

(5-Ethyl-2H-1,2,3-triazol-4-yl)methyl(1-((3-chloro-4-fluorophenyl)carbamoyl)-2-methyl-2,4,5,6-tetrahydrocyclopenta[c]pyrrol-4-yl)carbamate—Enantiomer II (147) LCMS: m/z found 473.1/475.2 [M+H]$^+$, RT=4.63 min (Method A); HPLC: RT=8.07 min (Method B); Chiral SFC: RT=3.86 min, Column: Chiralcel OJ-3 (4.6×250 mm, 5 μm); $^1$H NMR (400 MHz, DMSO-$d_6$): δ 9.35 (s, 1H), 7.91-7.94 (m, 1H), 7.53-7.59 (m, 2H), 7.36 (t, 1H), 6.79 (s, 1H), 5.12 (s, 2H), 4.78-4.82 (m, 1H), 3.76 (s, 3H), 2.91-2.97 (m, 1H), 2.77-2.84 (m, 1H), 2.54-2.61 (m, 1H), 2.05-2.12 (m, 1H), 1.98-2.04 (m, 1H), 0.92-0.96 (m, 2H), 0.75-0.79 (m, 2H).

Example 39: (2H-Tetrazol-5-yl)methyl (1-((3-chloro-4-fluorophenyl)carbamoyl)-2-methyl-2,4,5,6-tetrahydrocyclopenta[c]pyrrol-4-yl)carbamate (148, 149, 150)

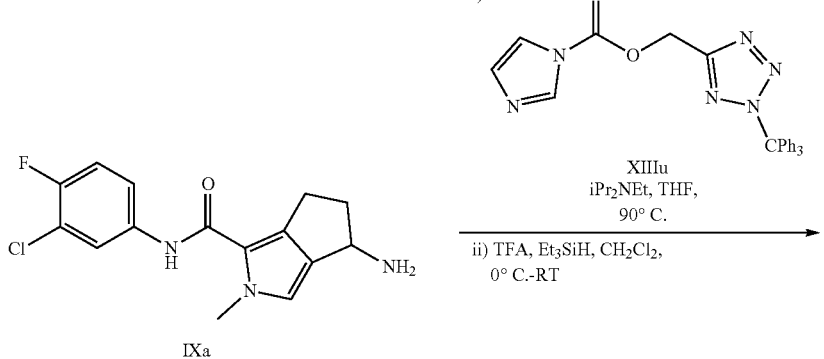

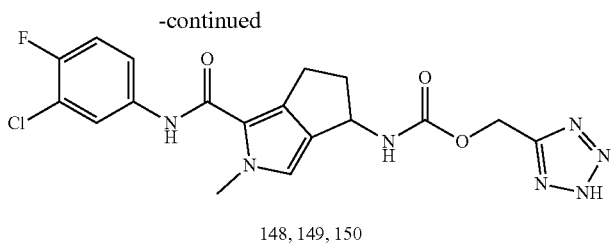

148, 149, 150

Racemic (2H-tetrazol-5-yl)methyl (1-((3-chloro-4-fluorophenyl)carbamoyl)-2-methyl-2,4,5,6-tetrahydrocyclopenta[c]pyrrol-4-yl)carbamate (148) was synthesized in a similar manner as described above from 4-amino-N-(3-chloro-4-fluorophenyl)-2-methyl-2,4,5,6-tetrahydrocyclopenta[c]pyrrole-1-carboxamide (IXa) and (2-trityl-2H-tetrazol-5-yl) methyl 1H-imidazole-1-carboxylate (XIIIu) followed by acid mediated detritylation. The enantiomers were subsequently separated by SFC. Method: isocratic, Mobile phase MeOH:CO$_2$—15:85. Column: Chiralpak IG (30×250 mm), 5 µm, flow rate: 60 g/min.

(2H-Tetrazol-5-yl)methyl(1-((3-chloro-4-fluorophenyl)carbamoyl)-2-methyl-2,4,5,6-tetrahydrocyclopenta[c]pyrrol-4-yl)carbamate—Enantiomer I (149) LCMS: m/z found 434.1/436.1 [M+H]$^+$; Chiral SFC: RT=2.04 min, Column: Chiralpak IG-3 (4.6×250 mm, 5 µm); $^1$H NMR (400 MHz, DMSO-d$_6$): δ 9.35 (s, 1H), 7.91-7.94 (m, 1H), 7.55-7.59 (m, 1H), 7.33-7.43 (m, 2H), 6.81 (s, 1H), 5.06 (s, 2H), 4.79-4.82 (m, 1H), 3.76 (s, 3H), 2.91-2.96 (m, 1H), 2.78-2.83 (m, 1H), 2.45-2.58 (m, 1H), 2.07-2.13 (m, 1H).

(2H-Tetrazol-5-yl)methyl(1-((3-chloro-4-fluorophenyl)carbamoyl)-2-methyl-2,4,5,6-tetrahydrocyclopenta[c]pyrrol-4-yl)carbamate—Enantiomer II (150) LCMS: m/z found 434.1/436.1 [M+H]$^+$; Chiral SFC: RT=2.65 min, Column: Chiralpak IG-3 (4.6×250 mm, 5 µm); $^1$H NMR (400 MHz, DMSO-d$_6$): δ 9.35 (s, 1H), 7.91-7.94 (m, 1H), 7.55-7.59 (m, 1H), 7.33-7.43 (m, 2H), 6.81 (s, 1H), 5.06 (s, 2H), 4.79-4.82 (m, 1H), 3.76 (s, 3H), 2.91-2.96 (m, 1H), 2.78-2.83 (m, 1H), 2.45-2.58 (m, 1H), 2.07-2.13 (m, 1H).

Example 40: (1-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate (144, 145)

Ethyl 2-methyl-2H-tetrazole-5-carboxylate (A) and ethyl 1-methyl-1H-tetrazole-5-carboxylate (B)

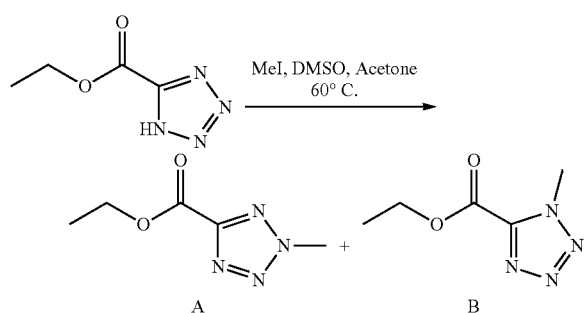

To a solution of 4.0 g (31.3 mmol, 1.0 eq.) of ethyl 1H-tetrazole-5-carboxylate in 20 mL of 1:1 v/v acetone: DMSO was added 7 mL (62.5 mmol, 2.0 eq.) of iodomethane and the mixture was heated to 60° C. for 16 h. The mixture was then allowed to cool to room temperature, quenched with 40 mL of ice-cold water and extracted with 3×50 mL of ethyl acetate. The combined organic extracts were washed with 40 mL of water, 40 mL of brine, dried (Na$_2$SO$_4$), filtered and the solvent was removed in vacuo to provide 2.5 g of an approximately 1:1 ratio of isomers A and B. LCMS: m/z found 157.1 [M+H]$^+$, RT=1.47, 1.55 min. The isomers were subsequently separated by SFC, Method: isocratic, Mobile phase MeOH:CO$_2$—10:90. Column: Lux Amylose-02 (30×250 mm), 5 µm, flow rate: 90 g/min to provide 0.7 g of ethyl 2-methyl-2H-tetrazole-5-carboxylate (A) and 1.0 g of ethyl 1-methyl-1H-tetrazole-5-carboxylate (B).

Ethyl 2-methyl-2H-tetrazole-5-carboxylate (A): LCMS: m/z found 157.10 [M+H]$^+$, RT=1.54 min; $^1$H NMR (400 MHz, CDCl$_3$): δ 4.55 (q, 2H), 4.46 (s, 3H), 1.46 (t, 3H). Ethyl 1-methyl-1H-tetrazole-5-carboxylate (B): LCMS: m/z found 157.03 [M+H]$^+$, RT=1.46 min; $^1$H NMR (400 MHz, CDCl$_3$): δ 4.54 (q, 2H), 4.38 (s, 3H), 1.48 (t, 3H).

(1-Methyl-1H-tetrazol-5-yl)methanol (XIIv)

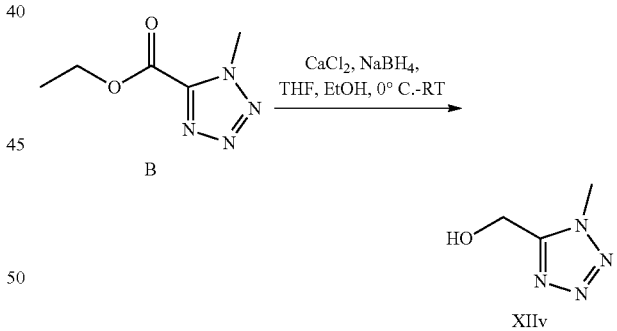

XIIv

To a stirred solution of 0.5 g (3.2 mmol, 1.0 eq.) of ethyl 1-methyl-1H-tetrazole-5-carboxylate (B) in 10 mL of 1:1 v/v ethanol:THF solution at 0° C. was added 0.71 g (6.4 mmol, 2.0 eq.) of anhydrous calcium chloride followed by 0.52 g (13.6 mmol, 4.0 eq.) of sodium borohydride. The mixture was allowed to warm to room temperature and stirred for 4 h. The reaction was quenched by the addition of 30 mL of ice-cold water and extracted with 3×30 mL of ethyl acetate. The combined organic extracts were dried (Na$_2$SO$_4$), filtered and the solvent was removed in vacuo to provide 20.2 g (2.1 mmol, 65%) of (1-methyl-1H-tetrazol-5-yl)methanol (XIIv). $^1$H NMR (400 MHz, DMSO-d$_6$): δ 5.83 (t, 1H), 4.78 (d, 2H), 4.06 (s, 3H).

(1-Methyl-1H-tetrazol-5-yl)methyl 1H-imidazole-1-carboxylate (XIIIv)

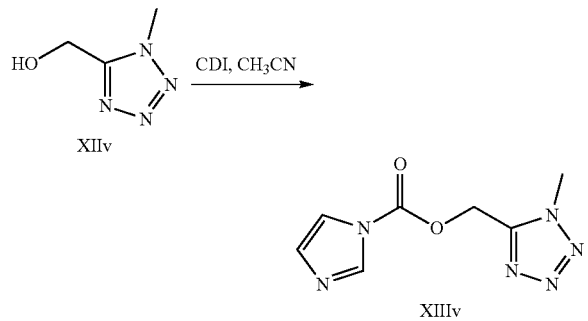

To a solution of 0.24 g (2.10 mmol, 1.0 eq.) of (1-methyl-1H-tetrazol-5-yl)methanol (XIIv) in 5 mL of acetonitrile was added 0.51 g (3.15 mmol, 1.5 eq.) of 1,1'-carbonyldiimidazole and the mixture was stirred at room temperature for 2 h. The mixture was then diluted with 10 mL of water and extracted with 3×40 mL of ethyl acetate. The combined organic extracts were washed with 30 mL of brine, dried (Na$_2$SO$_4$), filtered and the solvent was removed in vacuo to provide 0.38 g of (1-methyl-1H-tetrazol-5-yl)methyl 1H-imidazole-1-carboxylate.

(1-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate (144, 145)

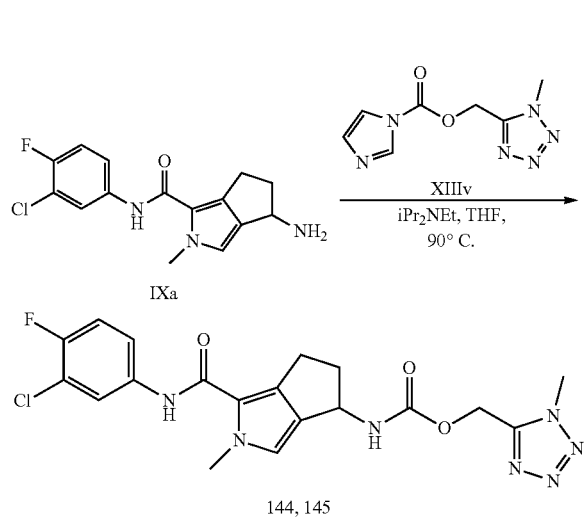

(1-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) (1-methyl-1H-tetrazol-5-yl) methyl 1H-imidazole-1-carboxylate (XIIIv). The enantiomers were subsequently separated by SFC. Method: isocratic, Mobile phase MeOH:CO$_2$—40:60. Column: Chiralpak AD-H (30×250 mm, 5 μm), flow rate: 70 g/min.

(1-Methyl-1H-tetrazol-5-yl)methyl(1-((3-chloro-4-fluorophenyl)carbamoyl)-2-methyl-2,4,5,6-tetrahydrocyclopenta[c]pyrrol-4-yl)carbamate—Enantiomer I (144) LCMS: m/z found 448.1/450.2 [M+H]$^+$, RT=4.30 min (Method A); HPLC RT=7.97 min (Method B); Chiral SFC: RT=3.04 min, Column: Chiralpak IG-3 (4.6×250 mm, 5 μm); $^1$H NMR (400 MHz, DMSO-d$_6$): δ 9.36 (s, 1H), 7.91-7.94 (m, 1H), 7.83 (d, 1H), 7.55-7.60 (m, 1H), 7.36 (t, 1H), 6.80 (s, 1H), 5.34-5.36 (m, 2H), 4.77-4.82 (m, 1H), 4.11 (s, 3H), 3.77 (s, 3H), 2.90-2.97 (m, 1H), 2.80-2.86 (m, 1H), 2.52-2.61 (m, 1H), 2.08-2.13 (m, 1H).

(1-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate—Enantiomer II (145) LCMS: m/z found 448.1/450.2 [M+H]$^+$, RT=4.30 min (Method A); HPLC RT=7.94 min (Method B); Chiral SFC: RT=5.67 min, Column: Chiralpak IG-3 (4.6×250 mm, 5 μm); $^1$H NMR (400 MHz, DMSO-d$_6$): δ 9.36 (s, 1H), 7.91-7.94 (m, 1H), 7.83 (d, 1H), 7.55-7.60 (m, 1H), 7.36 (t, 1H), 6.80 (s, 1H), 5.34-5.36 (m, 2H), 4.77-4.82 (m, 1H), 4.11 (s, 3H), 3.77 (s, 3H), 2.90-2.97 (m, 1H), 2.80-2.86 (m, 1H), 2.52-2.61 (m, 1H), 2.08-2.13 (m, 1H).

Example 41: (2-Methyl-1H-tetrazol-5-yl)methyl (1-((3-chloro-4-fluorophenyl) carbamoyl)-2-methyl-2,4,5,6-tetrahydrocyclopenta[c]pyrrol-4-yl)carbamate (142, 143)

(2-Methyl-2H-tetrazol-5-yl)methanol

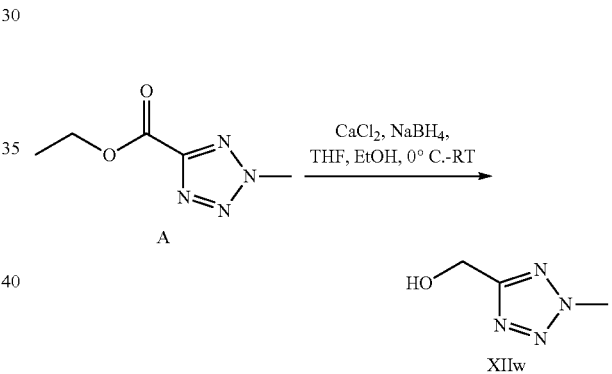

(2-Methyl-2H-tetrazol-5-yl)methanol (XIIw) was synthesized in a similar manner as described above from ethyl 2-methyl-2H-tetrazole-5-carboxylate (A). $^1$H NMR (400 MHz, CDCl$_3$): δ 495 (s, 2H), 4.35 (s, 3H), 2.54 (bs, 1H).

(2-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate (142, 143)

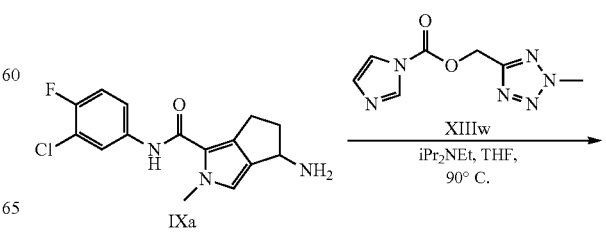

-continued

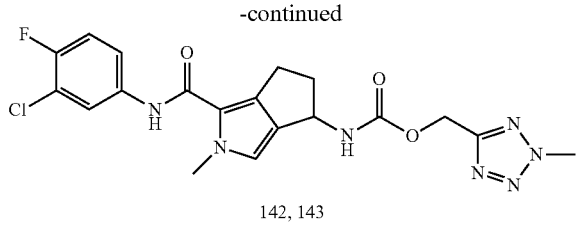

142, 143

(2-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-N-(3-chloro-4-fluorophenyl)-2-methyl-2,4,5,6-tetrahydrocyclopenta[c]pyrrole-1-carboxamide (IXa) (2-methyl-1H-tetrazol-5-yl)methyl 1H-imidazole-1-carboxylate (XIIIw). The enantiomers were subsequently separated by SFC. Method: isocratic, Mobile phase MeOH:CO$_2$—35:65. Column: Chiralpak OJ-H (30×250 mm, 5 μm), flow rate: 70 g/min.

(2-Methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate—Enantiomer I (142) LCMS: m/z found 448.1/450.1 [M+H]$^+$, RT=4.48 min (Method A); HPLC: RT=8.16 min (Method B); Chiral SFC: RT=2.33 min, Column: Chiralpak OJ-3 (4.6×250 mm, 5 μm); $^1$H NMR (400 MHz, DMSO-d$_6$): δ 9.36 (s, 1H), 7.91-7.94 (m, 1H), 7.72 (bd, 1H), 7.55-7.60 (m, 1H), 7.36 (t, 1H), 6.80 (s, 1H), 5.27-5.30 (m, 2H), 4.78-4.84 (m, 1H), 4.37 (s, 3H), 3.77 (s, 3H), 2.90-2.97 (m, 1H), 2.79-2.85 (m, 1H), 2.52-2.61 (m, 1H), 2.08-2.13 (m, 1H).

(2-Methyl-1H-tetrazol-5-yl)methyl(1-((3-chloro-4-fluorophenyl)carbamoyl)-2-methyl-2,4,5,6-tetrahydrocyclopenta[c]pyrrol-4-yl)carbamate—Enantiomer II (143) LCMS: m/z found 448.1/450.1 [M+H]$^+$, RT=4.48 min (Method A); HPLC: RT=8.14 min (Method B); Chiral SFC: RT=7.30 min, Column: Chiralpak OJ-3 (4.6×250 mm, 5 μm); $^1$H NMR (400 MHz, DMSO-d$_6$): δ 9.36 (s, 1H), 7.91-7.94 (m, 1H), 7.72 (bd, 1H), 7.55-7.60 (m, 1H), 7.36 (t, 1H), 6.80 (s, 1H), 5.27-5.30 (m, 2H), 4.78-4.84 (m, 1H), 4.37 (s, 3H), 3.77 (s, 3H), 2.90-2.97 (m, 1H), 2.79-2.85 (m, 1H), 2.52-2.61 (m, 1H), 2.08-2.13 (m, 1H)

Example 42: N-(3-Chloro-4-fluorophenyl)-4-(cyclopropanecarboxamido)-2-methyl-2,4,5,6-tetrahydro cyclopenta [c]pyrrole-1-carboxamide (23, 24)

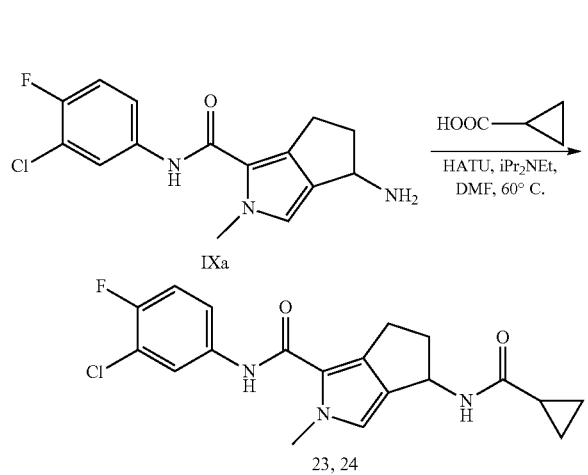

To a solution of 600 mg (1.94 mmol, 1.0 eq.) of 4-amino-N-(3-chloro-4-fluorophenyl)-2-methyl-2,4,5,6-tetrahydrocyclopenta[c]pyrrole-1-carboxamide (IXa) in 10 mL of DMF was added 0.98 mL (5.88 mmol, 3.0 eq.) of N,N-diisopropylethylamine followed by 1.12 g (2.92 mmol, 1.5 eq.) of HATU and 0.20 g (2.34 mmol, 1.2 eq.) of cyclopropane carboxylic acid and mixture was heated at 60° C. for 16 h. The mixture was allowed to cool to room temperature and diluted with 70 mL of ice-cold water. The resulting precipitate was collected by filtration and washed with 10 mL of water and 20 mL of n-pentane. The crude product was subsequently purified by flash chromatography (SiO$_2$, eluting with a linear gradient of 10-30% ethyl acetate/petroleum ether) to provide 174 mg (0.46 mmol, 24%) of N-(3-chloro-4-fluorophenyl)-4-(cyclopropane carboxamido)-2-methyl-2,4,5,6-tetrahydrocyclopenta[c]pyrrole-1-carboxamide (23, 24) as a white solid. The enantiomers were subsequently separated by SFC (Waters SFC investigator). Method isocratic, Mobile phase MeOH:CO$_2$—30:70. Column: Lux-Amylose-2 (30×250 mm, 5 μm), flow rate: 60 g/min.

N-(3-Chloro-4-fluorophenyl)-4-(cyclopropanecarboxamido)-2-methyl-2,4,5,6-tetrahydrocyclopenta [c]pyrrole-1-carboxamide Enantiomer I (23) LCMS: m/z found 376.1/378.1 [M+H]$^+$, RT=6.33 min (Method A); Chiral SFC: RT=2.49 min (Column: Lux-amylose-2, 250 mm×4.6 mm, 5 μm); $^1$H NMR (400 MHz, DMSO-d$_6$): δ 9.36 (s, 1H), 8.29 (d, 1H), 7.94 (dd, 1H), 7.57-7.61 (m, 1H), 7.37 (dd, 1H), 6.81 (s, 1H), 5.01 (q, 1H), 3.78 (s, 3H), 2.84-2.99 (m, 2H), 2.50-2.67 (m, 1H), 2.05-2.10 (m, 1H), 1.52-1.58 (m, 1H), 0.61-0.69 (m, 4H).

N-(3-Chloro-4-fluorophenyl)-4-(cyclopropanecarboxamido)-2-methyl-2,4,5,6-tetrahydrocyclopenta [c]pyrrole-1-carboxamide Enantiomer II (24) LCMS: m/z found 376.1/378.1 [M+H]$^+$, RT=6.33 min (Method A); Chiral SFC: RT=3.63 min (Column: Lux-amylose-2, 250 mm×4.6 mm, 5 μm); $^1$H NMR (400 MHz, DMSO-d$_6$): δ 9.35 (s, 1H), 8.28 (d, 1H), 7.94 (dd, 1H), 7.56-7.61 (m, 1H), 7.37 (dd, 1H), 6.81 (s, 1H), 5.01 (q, 1H), 3.78 (s, 3H), 2.84-2.99 (m, 2H), 2.50-2.67 (m, 1H), 2.05-2.10 (m, 1H), 1.52-1.58 (m, 1H), 0.61-0.69 (m, 4H).

Example 43: N-(3-Chloro-4-fluorophenyl)-4-(cyclopropanesulfonamido)-2-methyl-2,4,5,6-tetrahydrocyclopenta [c]pyrrole-1-carboxamide (13, 14)

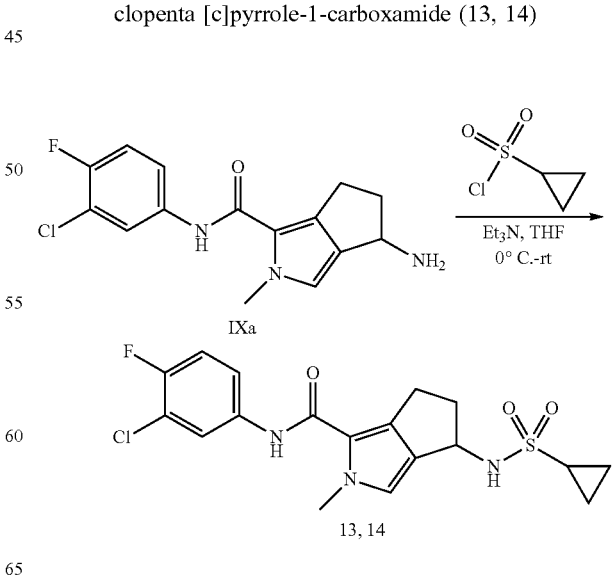

To a solution of 0.3 g (0.97 mmol, 1.0 eq) of 4-amino-N-(3-chloro-4-fluorophenyl)-2-methyl-2,4,5,6-tetrahydrocyclopenta[c]pyrrole-1-carboxamide (IXa) in 6 mL of THF at 0° C. was added 0.4 mL (2.94 mmol, 3.0 eq.) of triethylamine followed by 0.2 g (1.47 mmol, 1.5 eq.) of cyclopropanesulfonyl chloride. The mixture was allowed to warm to room temperature and stirred for 16 h. The mixture was diluted with 70 mL of water and extracted with 3×50 mL of ethyl acetate. The combined organic extracts were washed with 50 mL of water, 50 mL of brine, dried ($Na_2SO_4$), filtered and the solvent was removed in vacuo. The residue was purified by flash chromatography ($SiO_2$, eluting with a linear gradient of 20-35% ethyl acetate/petroleum ether) to provide 0.27 g (0.66 mmol, 66%) of N-(3-chloro-4-fluorophenyl)-4-(cyclopropanesulfonamido)-2-methyl-2,4,5,6-tetrahydrocyclopenta[c]pyrrole-1-carboxamide. The enantiomers were subsequently separated by SFC (Waters SFC investigator). Method isocratic, Mobile phase MeOH:$CO_2$—40:60. Column: Chiralpak AD-H (30×250 mm, 5 nm), flow rate: 90 g/min.

N-(3-Chloro-4-fluorophenyl)-4-(cyclopropanesulfonamido)-2-methyl-2,4,5,6-tetrahydrocyclopenta [c]pyrrole-1-carboxamide Enantiomer I (13) LCMS: m/z found 412.1/414.1 [M+H]$^+$, RT=4.45 min (Method A); Chiral SFC: RT=3.05 min, Column: Chiralpak AD-H (250 mm×4.6 mm, 5 μm); $^1$H NMR (400 MHz, DMSO-$d_6$): δ 9.39 (s, 1H), 7.93 (dd, 1H), 7.57-7.60 (m, 1H), 7.35-7.41 (m, 2H), 6.89 (s, 1H), 4.68 (m, 1H), 3.79 (s, 3H), 2.92-2.95 (m, 1H), 2.80-2.82 (m, 1H), 2.55-2.68 (m, 2H), 2.18-2.21 (m, 1H), 0.95-1.01 (m, 4H).

N-(3-Chloro-4-fluorophenyl)-4-(cyclopropanesulfonamido)-2-methyl-2,4,5,6-tetrahydrocyclopenta [c]pyrrole-1-carboxamide Enantiomer II (14) LCMS: m/z found 412.1/414.1 [M+H]$^+$, RT=4.45 min (Method A); Chiral SFC: RT=4.07 min, Column: Chiralpak AD-H (250 mm×4.6 mm, 5 μm); $^1$H NMR (400 MHz, DMSO-$d_6$): δ 9.39 (s, 1H), 7.93 (dd, 1H), 7.57-7.60 (m, 1H), 7.35-7.41 (m, 2H), 6.89 (s, 1H), 4.68 (m, 1H), 3.79 (s, 3H), 2.92-2.95 (m, 1H), 2.80-2.82 (m, 1H), 2.55-2.68 (m, 2H), 2.18-2.21 (m, 1H), 0.95-1.01 (m, 4H).

Scheme 4.

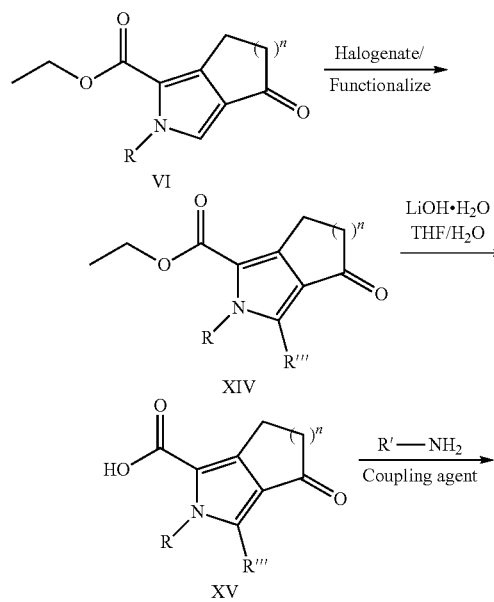

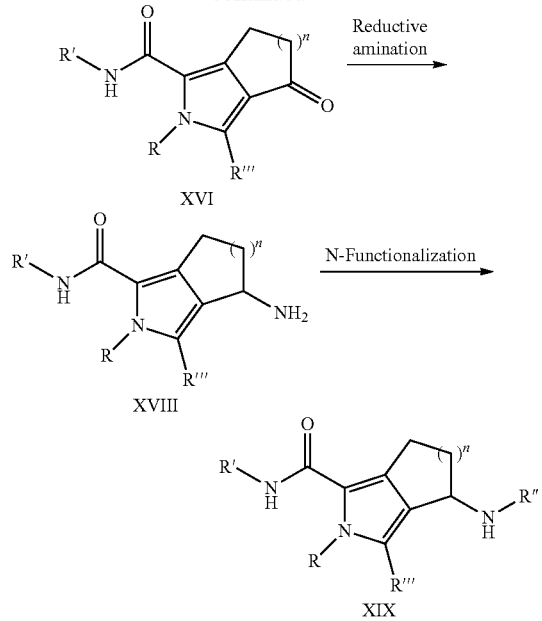

Compounds of the present invention can be further elaborated according to the route outlined in Scheme 4. Halogenation of VI with, for example N-chlorosuccinimide or N-bromosuccinimide, provides XIV (R'''=Hal). Optional further functionalization of XIV (R'''=Hal) can be achieved through, for example transition metal catalyzed coupling of XIV with, for example boronic acids or trifluoroborates. Ester hydrolysis of XIV to generate XV followed by carboxylic acid functionalization provides XVI (or alternatively, XIV can be converted directly to XVI through direct amination of the ester) followed by reductive amination to provide XVIII allows for N-functionalization to provide XIX.

Example 44: (1-Methyl-1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate (51, 52)

Ethyl 3-chloro-2-methyl-4-oxo-2,4,5,6-tetrahydrocyclopenta[c]pyrrole-1-carboxylate (XIVa)

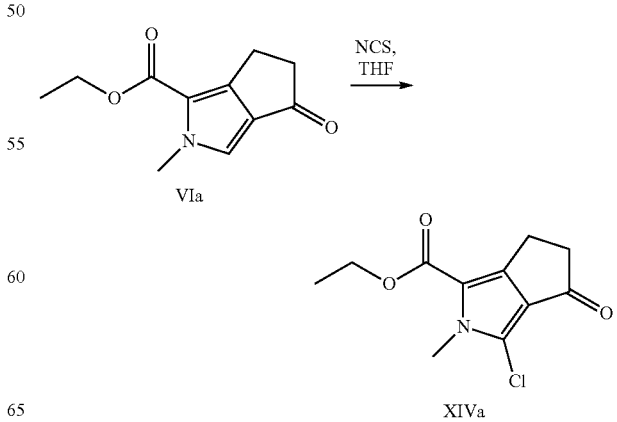

To a solution of 2.5 g (12.1 mmol, 1.0 eq.) of ethyl 2-methyl-4-oxo-2,4,5,6-tetrahydro cyclopenta[c]pyrrole-1-carboxylate (VIa) in 25 mL of anhydrous THF was added 2.0 g (15.7 mmol, 1.3 eq.) of N-chlorosuccinimide and the mixture was stirred at room temperature for 16 h. The mixture was then diluted with 100 mL of ice-cold water and extracted with 2×100 mL of ethyl acetate. The combined organic extracts were washed with 100 mL of brine, dried ($Na_2SO_4$), filtered and the solvent was removed in vacuo. The residue was purified by flash chromatography ($SiO_2$, eluting with linear gradient of 10-30% ethyl acetate in petroleum ether) to provide 2.5 g (10.3 mmol, 85%) of ethyl 3-chloro-2-methyl-4-oxo-2,4,5,6-tetrahydrocyclopenta[c]pyrrole-1-carboxylate (XIVa). LCMS: m/z found 242.0/244.1 [M+H]$^+$; $^1$H NMR (400 MHz, $CDCl_3$): δ 4.31 (q, 2H), 3.96 (s, 3H), 3.04-3.07 (m, 2H), 2.83-2.86 (m, 2H), 1.36 (t, 3H).

3-Chloro-N-(3-chloro-4-fluorophenyl)-2-methyl-4-oxo-2,4,5,6-tetrahydrocyclopenta [c]pyrrole-1-carboxamide (XVIa)

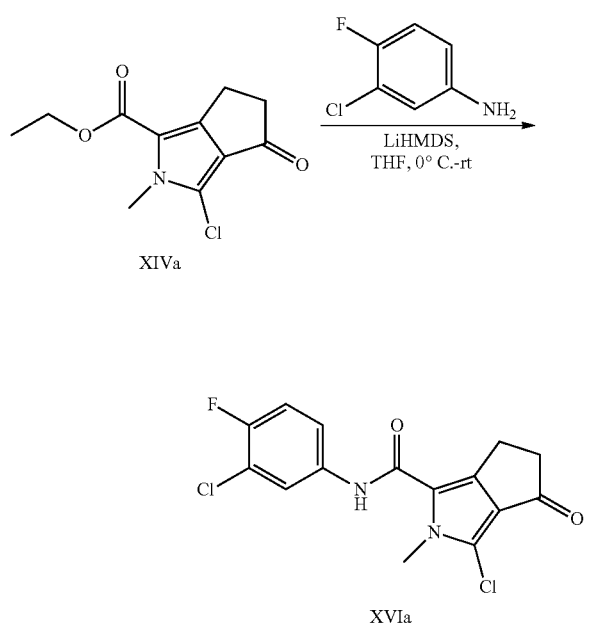

To a solution of 1.0 g (4.16 mmol, 1.0 eq.) of ethyl 3-chloro-2-methyl-4-oxo-2,4,5,6-tetrahydrocyclopenta[c]pyrrole-1-carboxylate (XIVa) in 10 mL of anhydrous THF under a nitrogen atmosphere at 0° C. was added 0.9 g (6.25 mmol, 1.5 eq.) of 3-chloro-4-fluoroaniline followed by 25 mL (25.0 mmol, 6 eq.) of a 1 M solution of lithium bis(trimethylsilyl)amide in THF. The mixture was allowed to warm to room temperature stirred at for 2 h. The reaction was quenched with 50 mL of saturated ammonium chloride solution and extracted with 3×50 mL of ethyl acetate. The combined organic extracts were washed with 100 mL of brine, dried ($Na_2SO_4$), filtered and the solvent was removed in vacuo. The residue was purified by flash chromatography ($SiO_2$, eluting with linear gradient of 30-80% ethyl acetate in petroleum ether) to provide 0.8 g (2.35 mmol, 56%) of 3-chloro-N-(3-chloro-4-fluorophenyl)-2-methyl-4-oxo-2,4,5,6-tetrahydro cyclopenta[c]pyrrole-1-carboxamide (XVIa). LCMS: m/z found 341.0/343.0 [M+H]$^+$; $^1$H NMR (400 MHz, $CDCl_3$): δ 7.71-7.73 (m, 1H), 7.31-7.35 (m, 1H), 7.11-7.17 (m, 2H), 4.01 (s, 3H), 3.12-3.16 (m, 2H), 2.96-2.98 (m, 2H).

4-Amino-3-chloro-N-(3-chloro-4-fluorophenyl)-2-methyl-2,4,5,6-tetrahydrocyclopenta [c]pyrrole-1-carboxamide (XVIIIa)

4-((tert-Butylsulfinyl)amino)-3-chloro-N-(3-chloro-4-fluorophenyl)-2-methyl-2,4,5,6-tetrahydro cyclopenta[c]pyrrole-1-carboxamide (XVIIa)

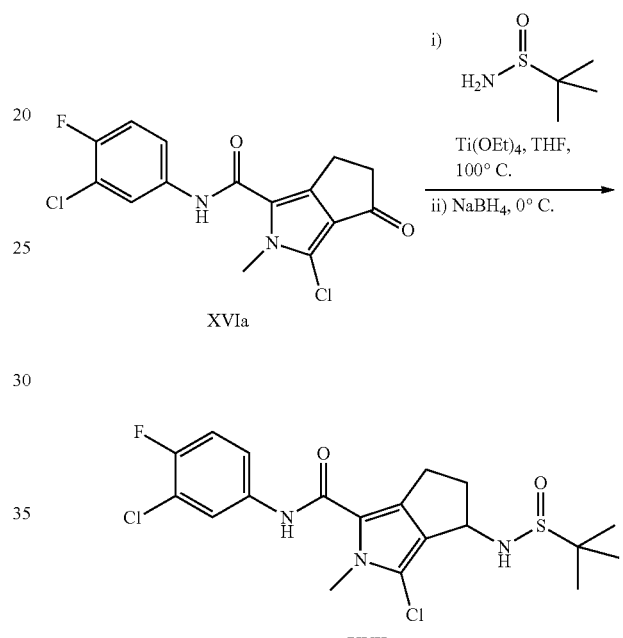

To a solution of 0.6 g (1.76 mmol, 1.0 eq.) of 3-chloro-N-(3-chloro-4-fluorophenyl)-2-methyl-4-oxo-2,4,5,6-tetrahydrocyclopenta[c]pyrrole-1-carboxamide (XVIa) in 8 mL of THF was added 0.43 g (3.52 mmol, 2.0 eq.) of (±)-2-methylpropane-2-sulfinamide followed by 2.4 g (10.58 mmol, 6.0 eq.) of titanium tetraethoxide at room temperature. The reaction vessel was sealed and the mixture was heated at 90° C. for 48 h. The mixture was cooled to 0° C. and 0.27 g (7.10 mmol, 4.0 eq.) of sodium borohydride was added. The mixture was then stirred at 0° C. for 4 h. The mixture was diluted with 100 mL of ice-cold water and extracted with 3×100 mL of ethyl acetate. The combined organic extracts were washed with 100 mL of brine, dried ($Na_2SO_4$), filtered and the solvent was removed in vacuo. The residue was purified by flash chromatography ($SiO_2$, eluting with linear gradient of 20-70% ethyl acetate in petroleum ether) to provide 0.55 g (1.23 mmol, 70%) of 4-((tert-butylsulfinyl)amino)-3-chloro-N-(3-chloro-4-fluorophenyl)-2-methyl-2,4,5,6-tetrahydrocyclopenta[c]pyrrole-1-carboxamide (XVIIa). LCMS: m/z found 446.3/448.3 [M+H]$^+$; $^1$H NMR (400 MHz, $CDCl_3$) δ 7.72-7.74 (m, 1H), 7.31-7.33 (m, 2H), 7.08-7.12 (m, 1H), 4.83-4.87 (m, 1H), 4.30 (m, 1H), 3.92 (s, 3H), 3.14-3.20 (m, 1H), 2.72-2.90 (m, 2H), 2.49-2.54 (m, 1H), 1.21 (s, 9H).

4-Amino-3-chloro-N-(3-chloro-4-fluorophenyl)-2-methyl-2,4,5,6-tetrahydrocyclopenta[c]pyrrole-1-carboxamide (XVIIIa)

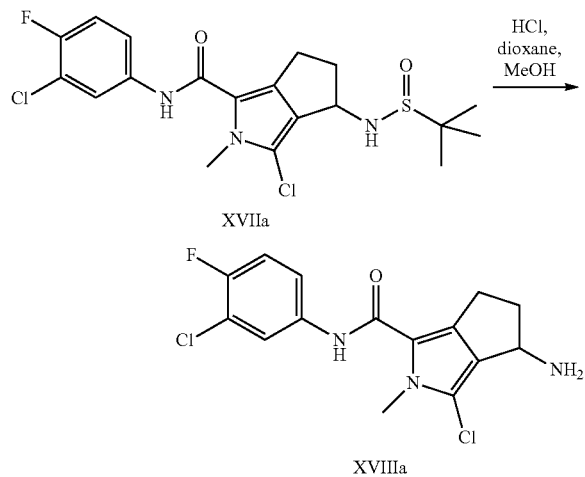

To a solution of 0.55 g (1.23 mmol, 1.0 eq.) of 4-((tert-butylsulfinyl)amino)-3-chloro-N-(3-chloro-4-fluorophenyl)-2-methyl-2,4,5,6-tetrahydrocyclopenta[c]pyrrole-1-carboxamide (XVIIa) in 5 mL of methanol at 0° C. was added 1.8 mL of a 4 M HCl solution in 1,4-dioxane. The resulting mixture was allowed to warm to room temperature and stirred for 2 h. The solvent was removed in vacuo and the residue was redissolved in 10 mL of water and 10 mL of saturated sodium bicarbonate solution and stirred for 20 min. The resulting precipitate was collected by filtration and dried under high vacuum to provide 0.35 g (1.02 mmol, 58%) of 4-amino-3-chloro-N-(3-chloro-4-fluorophenyl)-2-methyl-2,4,5,6-tetrahydrocyclopenta[c]pyrrole-1-carboxamide (XVIIIa). $^1$H NMR (400 MHz, CDCl$_3$): δ 7.70-7.73 (m, 1H), 7.29-7.32 (m, 1H), 7.13-7.20 (m, 1H), 7.08-7.12 (m, 1H), 4.42-4.43 (m, 1H), 3.91 (s, 3H), 3.04-3.08 (m, 1H), 2.81-2.86 (m, 2H), 2.08-2.14 (m, 1H), 1.50 (bs, 2H).

(1-Methyl-1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate (51, 52)

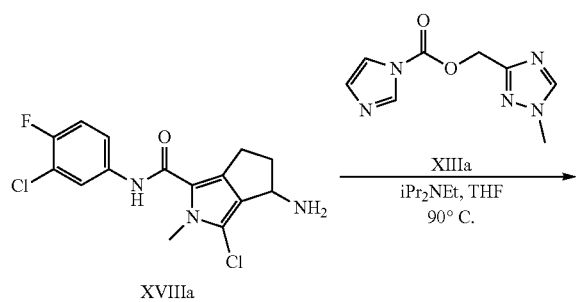

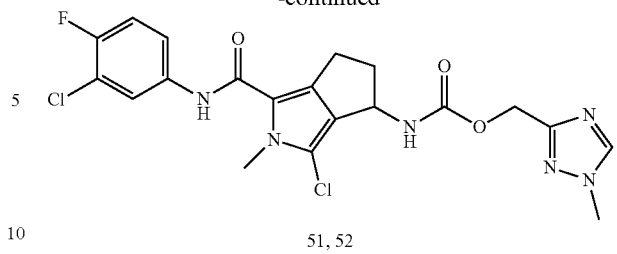

To a solution of 0.35 g (1.02 mmol, 1.0 eq.) of 4-amino-3-chloro-N-(3-chloro-4-fluorophenyl)-2-methyl-2,4,5,6-tetrahydrocyclopenta[c]pyrrole-1-carboxamide (XVIIIa) in 6 mL of anhydrous THF at 0° C. under inert atmosphere was added 0.39 g (3.06 mmol, 3.0 eq.) of N,N-diisopropylethylamine followed by 0.30 g (1.43 mmol, 1.5 eq.) of (1-methyl-1H-1,2,4-triazol-3-yl)methyl 1H-imidazole-1-carboxylate (XIIIa). The reaction vessel was sealed and the mixture was heated at 90° C. for 16 h. The mixture was allowed to cool to room temperature, diluted with 100 mL of water and extracted with 3×100 mL of ethyl acetate. The combined organic extracts were washed with 80 mL of water, 60 mL of brine, dried (Na$_2$SO$_4$) and the solvent was removed in vacuo. The residue was purified by flash chromatography (SiO$_2$, eluting with a linear gradient of 0-5% methanol in methylene chloride) to provide 0.35 g (0.72 mmol, 71%) of racemic(1-methyl-1H-1,2,4-triazol-3-yl)methyl(3-chloro-1-((3-chloro-4-fluorophenyl)carbamoyl)-2-methyl-2,4,5,6-tetrahydrocyclopenta[c]pyrrol-4-yl)carbamate. The enantiomers were subsequently separated by SFC (Waters SFC investigator). Method: isocratic, Mobile phase MeOH:CO$_2$—35:65. Column: Chiralpak IA (30×250 mm), 5 nm, flow rate: 100 g/min.

(1-Methyl-1H-1,2,4-triazol-3-yl)methyl (3-chloro-1-((3-chloro-4-fluorophenyl) carbamoyl)-2-methyl-2,4,5,6-tetrahydrocyclopenta[c]pyrrol-4-yl)carbamate—Enantiomer I (51) LCMS: m/z found 481.2/483.2 [M+H]$^+$, RT=6.15 min (Method A); HPLC: RT=7.69 min (Method B); Chiral SFC: RT=7.51 min (Chiralpak IA 4.6×250 mm); $^1$H NMR (400 MHz, DMSO-d$_6$) δ 9.56 (s, 1H), 8.43 (s, 1H), 7.91-7.93 (m, 1H), 7.56-7.64 (m, 2H), 7.37 (dd, 1H), 4.95-5.04 (m, 3H), 3.84 (s, 3H), 3.71 (s, 3H), 2.91-2.95 (m, 1H), 2.79-2.85 (m, 1H), 2.58-2.64 (m, 1H), 2.06-2.09 (m, 1H).

(1-Methyl-1H-1,2,4-triazol-3-yl)methyl (3-chloro-1-((3-chloro-4-fluorophenyl) carbamoyl)-2-methyl-2,4,5,6-tetrahydrocyclopenta[c]pyrrol-4-yl)carbamate—Enantiomer II (52) LCMS: m/z found 481.2/483.2 [M+H]$^+$, RT=6.13 min (Method A); HPLC: RT=7.69 min (Method B); Chiral SFC: RT=9.61 min (Chiralpak IA 4.6×250 mm); $^1$H NMR (400 MHz, DMSO-d$_6$) δ 9.56 (s, 1H), 8.43 (s, 1H), 7.91-7.93 (m, 1H), 7.56-7.64 (m, 2H), 7.37 (dd, 1H), 4.95-5.04 (m, 3H), 3.84 (s, 3H), 3.71 (s, 3H), 2.91-2.95 (m, 1H), 2.79-2.85 (m, 1H), 2.58-2.64 (m, 1H), 2.06-2.09 (m, 1H).

Example 45: (1H-1,2,4-Triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate (103, 104, 105)

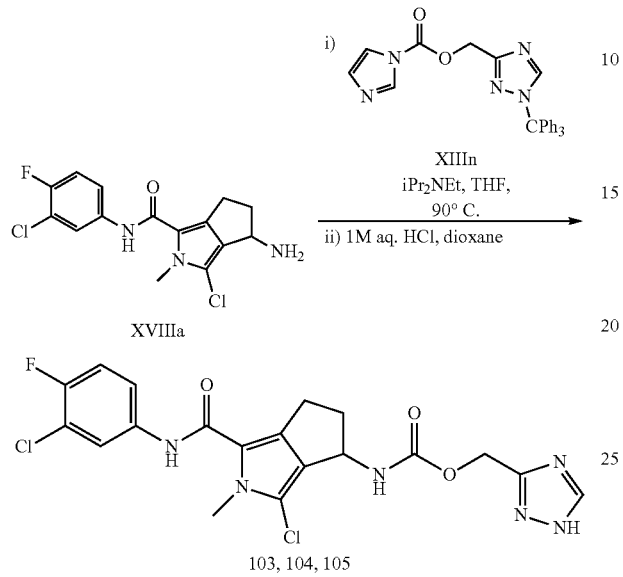

(1H-1,2,4-Triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-3-chloro-N-(3-chloro-4-fluorophenyl)-2-methyl-2,4,5,6-tetrahydrocyclopenta[c]pyrrole-1-carboxamide (XVIIIa) and (1-trityl-1H-1,2,4-triazol-3-yl)methyl 1H-imidazole-1-carboxylate (XIIIn) followed by acid mediated detritylation. The enantiomers were subsequently separated by SFC (Waters SFC investigator). Method: isocratic, Mobile phase MeOH:CO$_2$—20:80. Column: Chiralcel OJ-H (30×250 mm), 5 μm, flow rate: 70 g/min.

(1H-1,2,4-Triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate—Enantiomer I (104) LCMS: m/z found 467.1/469.1 [M+H]$^+$, RT=7.81 min (Method A); HPLC: RT=7.64 min (Method B); Chiral SFC: RT: 1.82 min, Column: Chiralpak OJ-H (4.6×250 mm, 5 μm). $^1$H NMR (400 MHz, DMSO-d$_6$): δ 14.03 (bs, 1H), 9.56 (s, 1H), 8.49 (s, 1H), 7.91-7.94 (m, 1H), 7.64-7.67 (d, 1H), 7.56-7.61 (m, 1H), 7.38 (t, 1H), 5.02-5.10 (m, 2H), 4.93-4.98 (m, 1H), 3.71 (s, 3H), 2.91-2.99 (m, 1H), 2.80-2.87 (m, 1H), 2.56-2.67 (m, 1H), 2.07-2.12 (m, 1H).

(1H-1,2,4-Triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate—Enantiomer II (105) LCMS: m/z found 467.1/469.1 [M+H]$^+$, RT=7.88 min (Method A); HPLC: RT=7.67 min (Method B); Chiral SFC: RT: 4.02 min, Column: Chiralpak OJ-H (4.6×250 mm, 5 μm). $^1$H NMR (400 MHz, DMSO-d$_6$): δ 14.03 (bs, 1H), 9.56 (s, 1H), 8.49 (s, 1H), 7.91-7.94 (m, 1H), 7.64-7.67 (d, 1H), 7.56-7.61 (m, 1H), 7.38 (t, 1H), 5.02-5.10 (m, 2H), 4.93-4.98 (m, 1H), 3.71 (s, 3H), 2.91-2.99 (m, 1H), 2.80-2.87 (m, 1H), 2.56-2.67 (m, 1H), 2.07-2.12 (m, 1H).

Example 46: (2H-1,2,3-Triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate (106, 107)

Prop-2-yn-1-yl (3-chloro-1-((3-chloro-4-fluorophenyl)carbamoyl)-2-methyl-2,4,5,6-tetrahydrocyclopenta[c]pyrrol-4-yl)carbamate (XIXa)

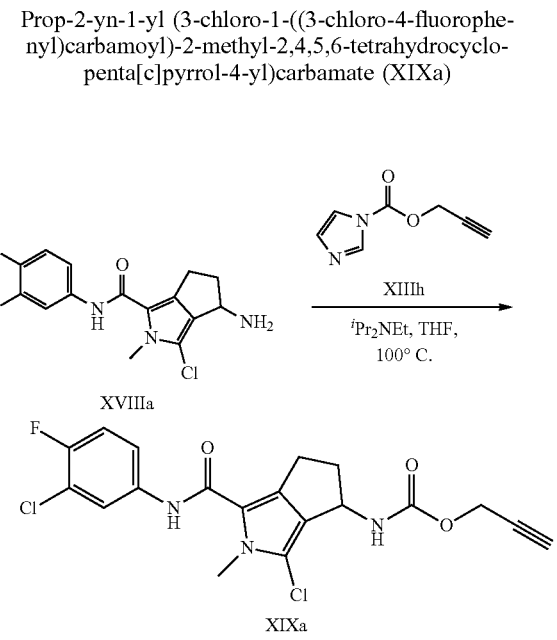

Prop-2-yn-1-yl (3-chloro-1-((3-chloro-4-fluorophenyl)carbamoyl)-2-methyl-2,4,5,6-tetrahydrocyclopenta[c]pyrrol-4-yl)carbamate (XIXa) was synthesized in a similar manner as described above from 4-amino-3-chloro-N-(3-chloro-4-fluorophenyl)-2-methyl-2,4,5,6-tetrahydrocyclopenta[c]pyrrole-1-carboxamide (XVIIIa) and prop-2-yn-1-yl 1H-imidazole-1-carboxylate (XIIIh) LCMS: m/z found 424.03 [M+H]$^+$; $^1$H NMR (400 MHz, DMSO-d$_6$): δ 9.56 (s, 1H), 7.91-7.94 (dd, 1H), 7.71 (bd, 1H), 7.56-7.61 (m, 1H), 7.38 (m, 1H), 4.91-4.95 (m, 1H), 4.64 (s, 2H), 3.71 (s, 3H), 3.48 (t, 1H), 2.92-2.98 (m, 1H), 2.81-2.88 (m, 1H), 2.56-2.67 (m, 1H), 2.04-2.12 (m, 1H).

(2H-1,2,3-Triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate (106, 107)

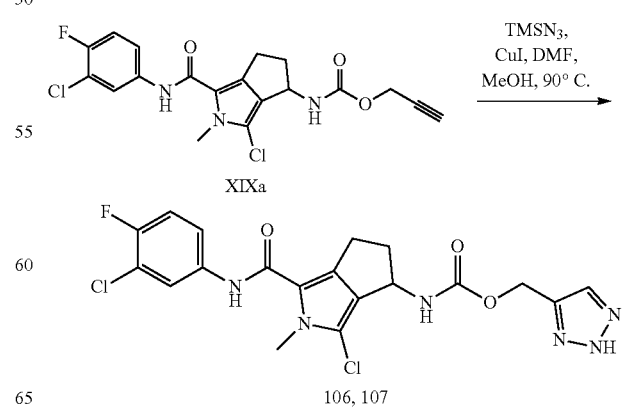

To a solution of 0.5 g (1.18 mmol, 1.0 eq.) of prop-2-yn-1-yl (3-chloro-14(3-chloro-4-fluorophenyl)carbamoyl)-2-methyl-2,4,5,6-tetrahydrocyclopenta[c]pyrrol-4-yl)carbamate (XIXa) in 10 mL of 4:1 v/v DMF:methanol was added 22 mg (0.12 mmol, 0.1 eq.) of copper(I)iodide followed by 1.36 g (5.91 mmol, 10.0 eq.) of trimethylsilyl azide and the mixture was heated at 90° C. for 5 h. The mixture was then allowed to cool to room temperature, diluted with 15 mL of water and the resulting solids collected by filtration and dried under high vacuum. The solids were then triturated with 80 mL of 10% methanol in methylene chloride and filtered. The crude product was purified by reverse phase preparative HPLC (Column: XBRIDGE C18 (250×19) mm, 5 μm to provide 75 mg (0.16 mmol, 14% yield) of (2H-1,2,3-triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate. LCMS: m/z found 467.2/469.2 [M+H]⁺. The enantiomers were subsequently separated by SFC (Waters SFC investigator). Method isocratic, Mobile phase MeOH:CO₂—30:70. Column: Chiralcel OJ-H (21× 250 mm), 5 μm, flow rate: 70 g/min.

(2H-1,2,3-Triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate—Enantiomer I (106) LCMS: m/z found 467.2/469.2 [M+H]⁺, RT=7.64 min (Method A); Chiral-SFC: RT=1.57 min (Chiralpak OJ-H (150 mm×4.6 mm, 3 μm); ¹H NMR (400 MHz, DMSO-d₆): δ 9.55 (s, 1H), 7.90-7.93 (m, 1H), 7.80 (s, 1H), 7.55-7.60 (m, 2H), 7.37 (t, 1H), 5.10 (s, 2H), 4.93-4.99 (m, 1H), 3.71 (s, 3H), 2.90-2.98 (m, 1H), 2.80-2.87 (m, 1H), 2.54-2.65 (m, 1H), 2.03-2.10 (m, 1H).

(2H-1,2,3-Triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate—Enantiomer II (107) LCMS: m/z found 467.2/469.2 [M+H]⁺, RT=7.68 min (Method A); Chiral-SFC: RT=4.62 min (Chiralpak OJ-H (150 mm×4.6 mm, 3 μm); ¹H NMR (400 MHz, DMSO-d₆): δ 9.55 (s, 1H), 7.90-7.93 (m, 1H), 7.80 (s, 1H), 7.55-7.60 (m, 2H), 7.37 (t, 1H), 5.10 (s, 2H), 4.93-4.99 (m, 1H), 3.71 (s, 3H), 2.90-2.98 (m, 1H), 2.80-2.87 (m, 1H), 2.54-2.65 (m, 1H), 2.03-2.10 (m, 1H).

Example 47: (1-Methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate (47, 48)

4-Amino-3-bromo-N-(3-chloro-4-fluorophenyl)-2-methyl-2,4,5,6-tetrahydrocyclopenta [c]pyrrole-1-carboxamide (XVIIIb)

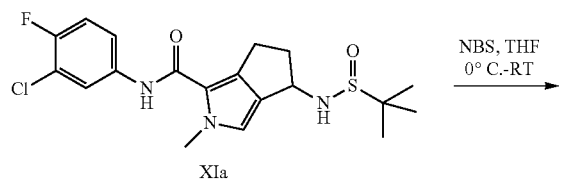

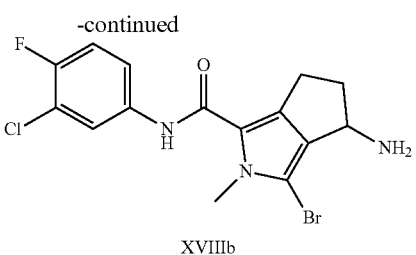

XVIIIb

To a solution of 0.5 g (1.20 mmol, 1.0 eq.) of ethyl 4-((tert-butylsulfinyl)amino)-N-(3-chloro-4-fluorophenyl)-2-methyl-2,4,5,6-tetrahydrocyclopenta[c]pyrrole-1-carboxamide (XIa) in 15 mL of THF at 0° C. under inert atmosphere was added 0.24 g (1.33 mmol, 1.1 eq.) of N-bromosuccinimide. The mixture was allowed to warm to room temperature and stirred for 2 h. The solvent was removed in vacuo and the residue was dissolved in 10 mL of water and 10 mL of saturated NaHCO₃ solution and stirred at room temperature for 10 min. The precipitate was collected by filtration and dried under high vacuum to provide 250 mg (0.63 mmol, 53%) of 4-amino-3-bromo-N-(3-chloro-4-fluorophenyl)-2-methyl-2,4,5,6-tetrahydrocyclopenta[c]pyrrole-1-carboxamide (XVIIIb). ¹H NMR (300 MHz, DMSO-d₆): δ 9.53 (s, 1H), 7.92 (dd, 1H), 7.55-7.60 (m, 1H), 7.34-7.40 (m, 1H), 4.14-4.18 (m, 1H), 3.72 (s, 3H), 3.02-2.92 (m, 2H), 3.02-2.92 (m, 2H), 2.81-2.73 (m, 1H), 1.93-1.90 (m, 1H).

(1-Methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate (47, 48)

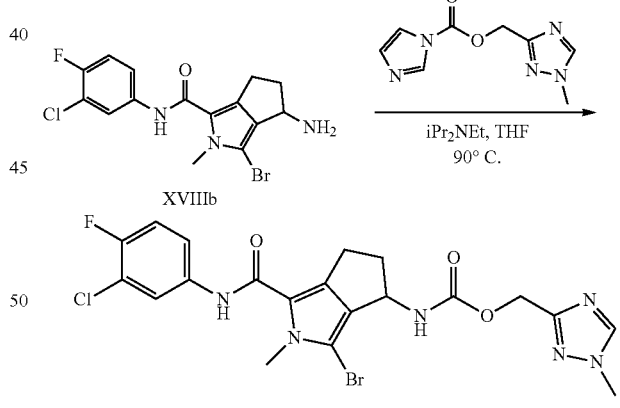

(1-Methyl-1H-1,2,4-triazol-3-yl)methyl (3-bromo-1-((3-chloro-4-fluorophenyl) carbamoyl)-2-methyl-2,4,5,6-tetrahydrocyclopenta[c]pyrrol-4-yl)carbamate was synthesized in a similar manner as described above from 4-amino-3-bromo-N-(3-chloro-4-fluorophenyl)-2-methyl-2,4,5,6-tetrahydrocyclopenta[c]pyrrole-1-carboxamide (XVIIIb) and (1-methyl-1H-1,2,4-triazol-3-yl)methyl 1H-imidazole-1-carboxylate. The enantiomers were subsequently separated by SFC (Waters SFC investigator). Method isocratic, Mobile phase MeOH:CO₂ 20:80. Column: Chiralcel OJ-H (21×250 mm), 5 μm, flow rate: 60 g/min.

(1-Methyl-1H-1,2,4-triazol-3-yl)methyl (3-bromo-1-((3-chloro-4-fluorophenyl) carbamoyl)-2-methyl-2,4,5,6-tetrahydrocyclopenta[c]pyrrol-4-yl)carbamate—Enantiomer I (47) LCMS: m/z found 525.1/527.1/529.2 [M+H]$^+$, RT=5.41 min, (Method A); HPLC: RT=7.74 min, (Method B); Chiral SFC: RT=2.38 min (CHIRALCEL OJ-H (4.6× 250 mm), 5 µm; $^1$H NMR (400 MHz, DMSO-d$_6$) δ 9.58 (s, 1H), 8.43 (s, 1H), 7.91-7.94 (m, 1H), 7.56-7.61 (m, 2H), 7.38 (dd, 1H), 4.91-5.05 (m, 3H), 3.84 (s, 3H), 3.72 (s, 3H), 2.91-2.96 (m, 1H), 2.82-2.88 (m, 1H), 2.58-2.63 (m, 1H), 2.04-2.09 (m, 1H).

(1-Methyl-1H-1,2,4-triazol-3-yl)methyl (3-bromo-1-((3-chloro-4-fluorophenyl) carbamoyl)-2-methyl-2,4,5,6-tetrahydrocyclopenta[c]pyrrol-4-yl)carbamate—Enantiomer II (48) LCMS: m/z found 525.1/527.1/529.2 [M+H]$^+$, RT=5.42 min, (Method A); HPLC: RT=7.74 min, (Method A); Chiral SFC: RT=5.05 min (CHIRALCEL OJ-H (4.6× 250 mm), 5 µm; $^1$H NMR (400 MHz, DMSO-d$_6$) δ 9.58 (s, 1H), 8.43 (s, 1H), 7.91-7.94 (m, 1H), 7.56-7.61 (m, 2H), 7.38 (dd, 1H), 4.91-5.05 (m, 3H), 3.84 (s, 3H), 3.72 (s, 3H), 2.91-2.96 (m, 1H), 2.82-2.88 (m, 1H), 2.58-2.63 (m, 1H), 2.04-2.09 (m, 1H).

Example 48: (1H-1,2,4-Triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate (124, 125)

((1H-1,2,4-Triazol-3-yl)methyl(3-bromo-1-((3-chloro-4-fluorophenyl)carbamoyl)-2-methyl-2,4,5,6-tetrahydrocyclopenta[c]pyrrol-4-yl)carbamate was synthesized in a similar manner as described above from 4-amino-3-bromo-N-(3-chloro-4-fluorophenyl)-2-methyl-2,4,5,6-tetrahydrocyclopenta[c]pyrrole-1-carboxamide (XVIIIb) and (1-trityl-1H-1,2,4-triazol-3-yl)methyl 1H-imidazole-1-carboxylate (XIIIn) followed by acid mediated detritylation. The enantiomers were subsequently separated by SFC (Waters SFC investigator). Method: isocratic, Mobile phase MeOH:CO$_2$—30:70. Column: Chiralcel OJ-H (30×250 mm), 5 µm, flow rate: 70 g/min.

((1H-1,2,4-Triazol-3-yl)methyl(3-bromo-1-((3-chloro-4-fluorophenyl)carbamoyl)-2-methyl-2,4,5,6-tetrahydrocyclopenta[c]pyrrol-4-yl)carbamate—Enantiomer I (124) LCMS: m/z found 511.1/513.2/515.2 [M+H]$^+$, (Method A); Chiral SFC: RT: 1.85 min, Column: Chiralpak OJ-H (4.6× 250 mm, 5 µm). $^1$H NMR (400 MHz, DMSO-d$_6$): δ 14.68 (bs, 1H), 9.57 (bs, 1H), 7.91-7.94 (m, 1H), 7.84 (bs, 1H), 7.56-7.61 (m, 2H), 7.38 (t, 1H), 5.11 (s, 2H), 4.90-4.95 (m, 1H), 3.72 (s, 3H), 2.81-2.97 (m, 2H), 2.50-2.62 (m, 1H), 2.03-2.10 (m, 1H).

((1H-1,2,4-Triazol-3-yl)methyl(3-bromo-1-((3-chloro-4-fluorophenyl)carbamoyl)-2-methyl-2,4,5,6-tetrahydrocyclopenta[c]pyrrol-4-yl)carbamate—Enantiomer II (125) LCMS: m/z found 511.1/513.2/515.2 [M+H]$^+$, (Method A); Chiral SFC: RT: 6.10 min, Column: Chiralpak OJ-H (4.6× 250 mm, 5 µm). $^1$H NMR (400 MHz, DMSO-d$_6$): δ 14.68 (bs, 1H), 9.57 (bs, 1H), 7.91-7.94 (m, 1H), 7.84 (bs, 1H), 7.56-7.61 (m, 2H), 7.38 (t, 1H), 5.11 (s, 2H), 4.90-4.95 (m, 1H), 3.72 (s, 3H), 2.81-2.97 (m, 2H), 2.50-2.62 (m, 1H), 2.03-2.10 (m, 1H).

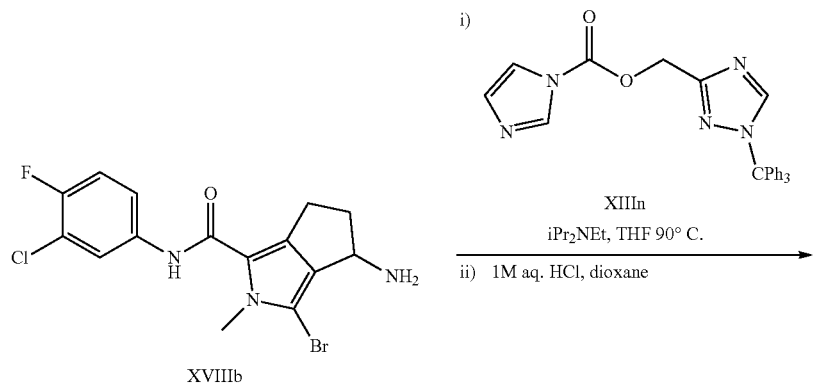

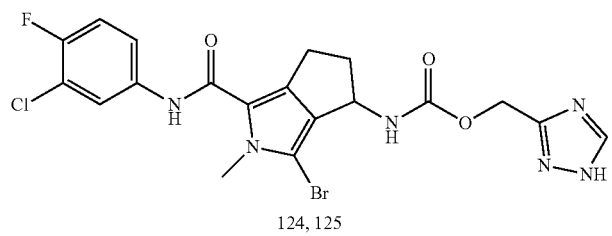

124, 125

Example 49: (1-Methyl-1H-1,2,4-triazol-3-yl)
methyl (1-((3-chloro-4-fluorophenyl) carbamoyl)-2,
3-dimethyl-2,4,5,6-tetrahydrocyclopenta[c]pyrrol-4-
yl)carbamate (61, 82, 83)

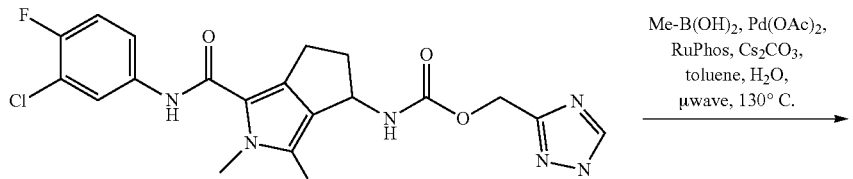

47, 48

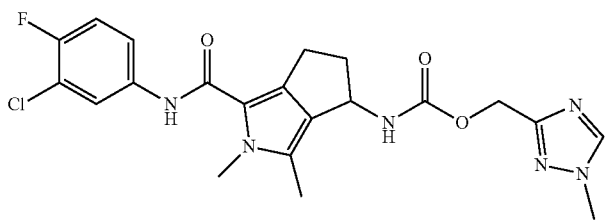

61, 82, 83

A solution of 120 mg (0.22 mmol, 1.0 eq.) of racemic (1-methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate in 2 mL of toluene in a microwave vial was degassed with argon gas for 10 min. To the degassed solution was added 68 mg (1.14 mmol, 5.0 eq.) of methyl boronic acid followed by 3 mg (0.011 mmol, 0.05 eq.) of Pd(OAc)$_2$, 10.6 mg (0.022 mmol, 0.1 eq.) of Ruphos and 220 mg (0.68 mmol, 3.0 eq.) of cesium carbonate. The mixture was degassed with argon for a further 5 min and then subjected to microwave irradiation maintaining a reaction temperature of 130° C. for 30 min. The mixture was allowed to cool to room temperature, diluted with 20 mL of water and extracted with 3×50 mL of ethyl acetate. The combined organic extracts were washed with 50 mL of water, 40 mL of brine, dried (Na$_2$SO$_4$), filtered and the solvent was removed in vacuo. The residue was purified by semi-preparative HPLC to provide 15 mg (0.032 mmol, 14%) of racemic (1-methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate (61). LCMS: m/z found 461.1/463.1 [M+H]$^+$, RT=6.88 min (Method A); $^1$H NMR (400 MHz, CDCl$_3$): δ 8.01 (s, 1H), 7.71-7.74 (m, 1H), 7.28-7.32 (m, 1H), 7.18 (s, 1H), 7.08 (dd, 1H), 5.17-5.25 (m, 2H), 5.11-5.14 (m, 1H), 4.94 (m, 1H), 3.92 (s, 3H), 3.85 (s, 3H), 2.96-3.02 (m, 1H), 2.83-2.89 (m, 2H), 2.26-2.32 (m, 1H), 2.21 (s, 3H). The above detailed synthetic procedure was repeated, and the enantiomers were subsequently separated by preparative SFC (Waters SFC investigator). Method: isocratic, Mobile phase MeOH:CO$_2$—25:75. Column: Chiralpak AD (21×250 mm, 5 μm), flow rate: 60 g/min.

(1-Methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate—Enantiomer I (82) LCMS: m/z found 461.1/463.1 [M+H]$^+$, RT=6.85 min (Method A); Chiral SFC: RT=3.05 min (Column: Chiralcel AD-3 (4.6×250 mm, 5 μm)); $^1$H NMR (400 MHz, CDCl$_3$): δ 8.01 (s, 1H), 7.71-7.74 (m, 1H), 7.28-7.32 (m, 1H), 7.18 (s, 1H), 7.08 (dd, 1H), 5.17-5.25 (m, 2H), 5.11-5.14 (m, 1H), 4.94 (m, 1H), 3.92 (s, 3H), 3.85 (s, 3H), 2.96-3.02 (m, 1H), 2.83-2.89 (m, 2H), 2.26-2.32 (m, 1H), 2.21 (s, 3H).

(1-Methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate—Enantiomer II (83) LCMS: m/z found 461.1/463.1 [M+H]$^+$, RT=6.85 min (Method A); Chiral SFC: RT=4.86 min (Column: Chiralcel AD-3 (4.6×250 mm, 5 μm)); $^1$H NMR (400 MHz, CDCl$_3$): δ 8.01 (s, 1H), 7.71-7.74 (m, 1H), 7.28-7.32 (m, 1H), 7.18 (s, 1H), 7.08 (dd, 1H), 5.17-5.25 (m, 2H), 5.11-5.14 (m, 1H), 4.94 (m, 1H), 3.92 (s, 3H), 3.85 (s, 3H), 2.96-3.02 (m, 1H), 2.83-2.89 (m, 2H), 2.26-2.32 (m, 1H), 2.21 (s, 3H).

Example 50: (1-Methyl-1H-1,2,4-triazol-3-yl)methyl (1-((3-chloro-4-fluorophenyl)carbamoyl)-2-methyl-3-phenyl-2,4,5,6-tetrahydrocyclopenta[c]pyrrol-4-yl)carbamate (108, 109)

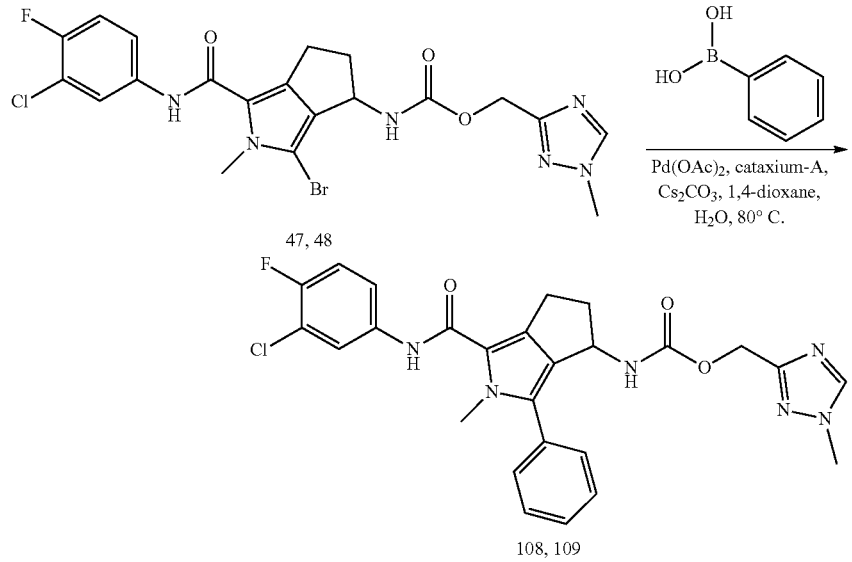

A sealed tube was charged with 0.25 g (0.47 mmol, 1.0 eq.) of racemic (1-methyl-1H-1,2,4-triazol-3-yl)methyl (3-bromo-1-((3-chloro-4-fluorophenyl)carbamoyl)-2-methyl-2,4,5,6-tetrahydrocyclopenta [c]pyrrol-4-yl)carbamate (48, 49), 69 mg (0.57 mmol, 1.2 eq.) of benzeneboronic acid and 2.5 mL of 1,4-dioxane. The mixture was purged with argon for 5 min and 0.46 g (1.42 mmol, 3.0 eq.) of cesium carbonate was added followed by 0.5 mL of water. The mixture was purged with argon for an additional 5 min and 16 mg (0.023 mmol, 5 mol %) of palladium acetate was added followed by 16 mg (0.047 mmol, 10 mol %) of Cataxium-A. The mixture was then heated to 80° C. for 3 h. On cooling to room temperature, the mixture was filtered through CELITE®, washed with 20 mL of ethyl acetate and the filtrate was concentrated in vacuo. The residue was diluted with 50 mL of ethyl acetate and washed with 30 mL of water, 30 mL of brine, dried ($Na_2SO_4$), filtered and the solvent was removed in vacuo. The residue was purified by reverse phase preparative HPLC (Column: KROMOSIL C18 (150×25) mm, 7 μm) to provide 0.24 g of racemic (1-methyl-1H-1,2,4-triazol-3-yl)methyl (1-((3-chloro-4-fluorophenyl)carbamoyl)-2-methyl-3-phenyl-2,4,5,6-tetrahydrocyclopenta[c]pyrrol-4-yl)carbamate. The enantiomers were subsequently separated by SFC (Waters SFC investigator). Method isocratic, Mobile phase MeOH:$CO_2$—40:60. Column: Chiralpak IG (30×250 mm, 5 μm), flow rate: 100 g/min.

(1-Methyl-1H-1,2,4-triazol-3-yl)methyl (1-((3-chloro-4-fluorophenyl)carbamoyl)-2-methyl-3-phenyl-2,4,5,6-tetrahydrocyclopenta[c]pyrrol-4-yl)carbamate—Enantiomer I (108) LCMS: m/z found 523.3/525.3 [M+H]$^+$, RT=8.03 min (Method A); Chiral-SFC: RT=2.38 min, Chiralpak IG-3 (150 mm×4.6 mm, 3 μm); $^1$H NMR (400 MHz, DMSO-d$_6$): δ 9.54 (s, 1H), 8.41 (s, 1H), 7.95-7.98 (m, 1H), 7.58-7.64 (m, 1H), 7.36-7.51 (m, 7H), 4.98-5.02 (m, 1H), 4.92 (d, 1H), 4.81 (d, 1H), 3.83 (s, 3H), 3.68 (s, 3H), 2.93-2.88 (m, 2H), 2.56-2.65 (m, 1H), 2.16-2.13 (m, 1H).

(1-Methyl-1H-1,2,4-triazol-3-yl)methyl (1-((3-chloro-4-fluorophenyl)carbamoyl)-2-methyl-3-phenyl-2,4,5,6-tetrahydrocyclopenta[c]pyrrol-4-yl)carbamate—Enantiomer II (109) LCMS: m/z found 523.3/525.3 [M+H]$^+$, RT=8.03 min (Method A); Chiral-SFC: RT=2.87 min, Chiralpak IG-3 (150 mm×4.6 mm, 3 μm); $^1$H NMR (400 MHz, DMSO-d$_6$): δ 9.54 (s, 1H), 8.41 (s, 1H), 7.95-7.98 (m, 1H), 7.58-7.64 (m, 1H), 7.36-7.51 (m, 7H), 4.98-5.02 (m, 1H), 4.92 (d, 1H), 4.81 (d, 1H), 3.83 (s, 3H), 3.68 (s, 3H), 2.93-2.88 (m, 2H), 2.56-2.65 (m, 1H), 2.16-2.13 (m, 1H).

Example 51: (1H-1,2,3-Triazol-4-yl)methyl (1-((3-chloro-4-fluorophenyl)carbamoyl)-2,3-dimethyl-2,4,5,6-tetrahydrocyclopenta[c]pyrrol-4-yl)carbamate (130, 131)

Ethyl 2,3-dimethyl-4-oxo-2,4,5,6-tetrahydrocyclopenta[c]pyrrole-1-carboxylate (XIVc)

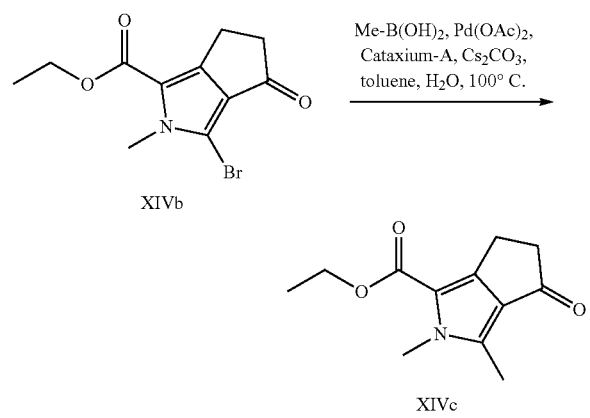

A solution of 2.8 g (9.8 mmol, 1.0 eq.) of ethyl 3-bromo-2-methyl-4-oxo-2,4,5,6-tetrahydrocyclopenta[c]pyrrole-1-carboxylate (XIVb) in 10 mL of toluene and 3 mL of water was degassed by purging with argon gas for 10 min. To the degassed solution was added 2.9 g (49.1 mmol, 5.0 eq.) of methylboronic acid followed by 0.33 g (0.49 mmol, 0.05 eq.) of Pd(OAc)$_2$, 0.35 g (0.98 mmol, 0.1 eq.) of Cataxium-A and 9.5 g (29.4 mmol, 3.0 eq.) of cesium carbonate. The mixture was degassed with argon for a further 5 min and then heated at 100° C. for 30 min. The mixture was allowed to cool to room temperature, filtered through CELITE® and the pad was washed with 10 mL of ethyl acetate. The filtrate was diluted with 30 mL of water and extracted with 3×50 mL of ethyl acetate. The combined organic extracts were dried (Na$_2$SO$_4$), filtered and the solvent was removed in vacuo. The above detailed reaction was conducted in duplicate and the crude products combined prior to purification by MPLC (REVELERIS® silica column, eluting with a linear gradient of 20-30% ethyl acetate/petroleum ether) to provide 2.5 g (11.30 mmol, 57%) of ethyl 2,3-dimethyl-4-oxo-2,4,5,6-tetrahydrocyclopenta[c]pyrrole-1-carboxylate (XIVc) as a brown solid. LCMS: m/z found 222.2 [M+H]$^+$; $^1$H NMR (400 MHz, CDCl$_3$): δ 4.29 (q, 2H), 3.87 (s, 3H), 3.00-3.03 (m, 2H), 2.78-2.82 (m, 2H), 2.43 (s, 3H), 1.36 (t, 3H).

2,3-Dimethyl-4-oxo-2,4,5,6-tetrahydrocyclopenta[c]pyrrole-1-carboxylic acid (XVc)

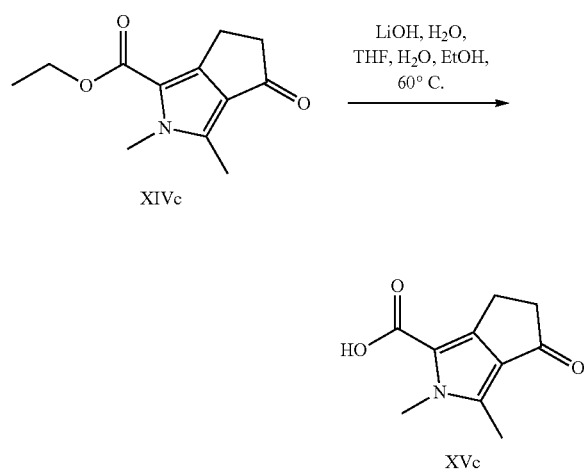

To a solution of 2.5 g (11.30 mmol, 57%) of ethyl 2,3-dimethyl-4-oxo-2,4,5,6-tetrahydrocyclopenta[c]pyrrole-1-carboxylate (XIVc) in 25 mL of 2:2:1 v/v/v THF:water:ethanol was added 4.7 g (113.1 mmol, 10.0 eq.) of lithium hydroxide monohydrate and the mixture was heated at 60° C. for 16 h. The mixture was allowed to cool to room temperature and acidified to pH-3 with 3 M aqueous HCl. The resulting precipitate was collected by filtration, washed with 30 mL of n-pentane and dried under high vacuum to provide 2.4 g of 2,3-dimethyl-4-oxo-2,4,5,6-tetrahydrocyclopenta[c]pyrrole-1-carboxylic acid (XVc). LCMS: m/z found 194.1 [M+H]$^+$; $^1$H NMR (400 MHz, DMSO-d$_6$): δ 12.28 (bs, 1H), 3.81 (s, 3H), 2.88-2.92 (m, 2H), 2.65-2.68 (m, 2H), 2.35 (s, 3H).

N-(3-Chloro-4-fluorophenyl)-2,3-dimethyl-4-oxo-2,4,5,6-tetrahydrocyclopenta[c]pyrrole-1-carboxamide (XVIc)

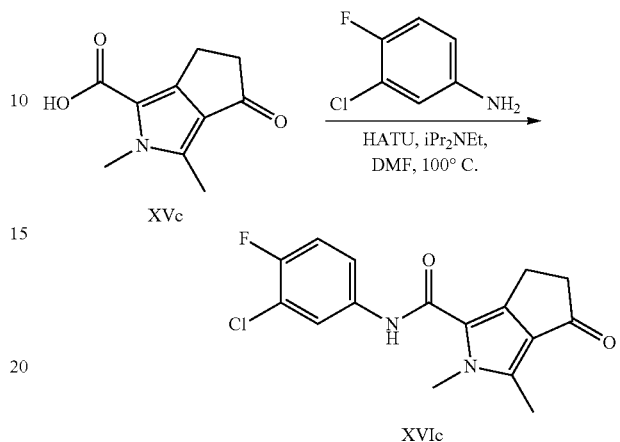

To a solution of 2.4 g of 2,3-dimethyl-4-oxo-2,4,5,6-tetrahydrocyclopenta[c]pyrrole-1-carboxylic acid (XVc) in 12 mL of DMF was added 6.6 mL (37.4 mmol, 3.0 eq.) of IV, N-diisopropylethylamine followed by 7.1 g (18.6 mmol, 1.5 eq.) of 1-[bis(dimethylamino) methylene]-1H-1,2,3-triazolo[4,5-b]pyridinium 3-oxide hexafluorophosphate (HATU) and 2.24 g (15.5 mmol, 1.25 eq.) of 4-fluoro-3-chloro aniline, and the mixture was heated to 100° C. for 16 h. The mixture was then allowed to cool to room temperature and diluted with 200 mL of ice-cold water. The precipitated solid was collected by filtration, dried under vacuum and washed with 30 mL of 1:1 v/v n-pentane:diethyl ether to provide 2.0 g (6.25 mmol) of N-(3-chloro-4-fluorophenyl)-2,3-dimethyl-4-oxo-2,4,5,6-tetrahydrocyclopenta[c]pyrrole-1-carboxamide (XVIc). LCMS: m/z found 321.1 [M+H]$^+$; $^1$H NMR (300 MHz, DMSO-d$_6$): δ 9.64 (bs, 1H), 7.92-7.97 (m, 1H), 7.56-7.63 (m, 1H), 7.39 (t, 1H), 3.76 (s, 3H), 3.07-3.12 (m, 2H), 2.68-2.74 (m, 2H), 2.38 (s, 3H).

N-(3-Chloro-4-fluorophenyl)-4-(hydroxyimino)-2,3-dimethyl-2,4,5,6-tetrahydrocyclopenta[c]pyrrole-1-carboxamide

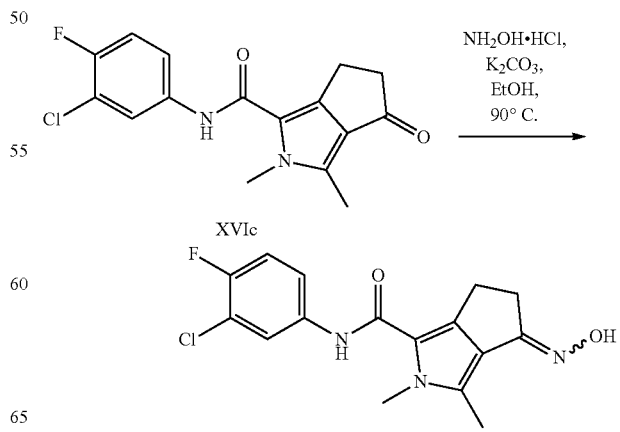

To a solution of 2.0 g (6.25 mmol, 1.0 eq.) of N-(3-chloro-4-fluorophenyl)-2,3-dimethyl-4-oxo-2,4,5,6-tetrahydrocyclopenta[c]pyrrole-1-carboxamide (XVIc) in 20 mL of ethanol was added 1.7 g (25.0 mmol, 4.0 eq.) of hydroxylamine hydrochloride followed by 5.2 g (37.5 mmol, 6.0 eq.) of potassium carbonate and the mixture heated at 90° C. for 16 h. The mixture was allowed to cool to room temperature and diluted with 100 mL of ice-cold water. The resulting precipitate was collected by filtration, washed with 20 mL of n-pentane and dried under high vacuum to provide 1.7 g (5.07 mmol, 81%) of N-(3-chloro-4-fluorophenyl)-4-(hydroxyimino)-2,3-dimethyl-2,4,5,6-tetrahydrocyclopenta[c]pyrrole-1-carboxamide. LCMS: m/z found 336.1/338.1 [M+H]$^+$; $^1$H NMR (300 MHz, DMSO-d$_6$): δ 10.26 (s, 1H), 9.43 (s, 1H), 7.91-7.96 (m, 1H), 7.55-7.61 (m, 1H), 7.37 (t, 1H), 3.72 (s, 3H), 2.96-3.04 (m, 4H), 2.34 (s, 3H).

4-Amino-N-(3-chloro-4-fluorophenyl)-2,3-dimethyl-2,4,5,6-tetrahydro cyclopenta[c]pyrrole-1-carboxamide (XVIIIc)

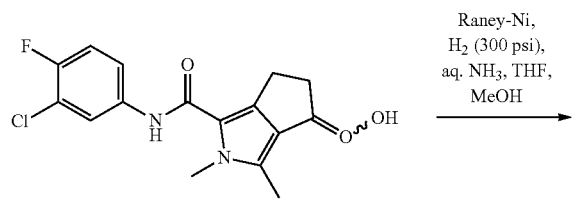

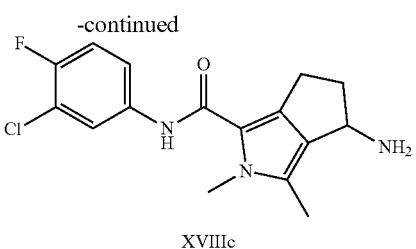

To a solution of 0.85 g (2.53 mmol, 1.0 eq.) of N-(3-chloro-4-fluorophenyl)-4-(hydroxyimino)-2,3-dimethyl-2,4,5,6-tetrahydrocyclopenta[c]pyrrole-1-carboxamide in 60 mL of 1:1 v/v THF:methanol was added 1.7 g (50% slurry in water) of Raney nickel and 30 mL of 25% ammonium hydroxide solution. The resulting mixture was stirred at room temperature under 300 psi of hydrogen for 16 h. The mixture was then filtered through CELITE® and the pad was washed with 20 mL of methanol and the filtrate was concentrated under reduce pressure. The above detailed reaction was carried out in duplicate and the crude products combined prior to purification by flash chromatography (SiO$_2$, eluting with a linear gradient of 2-10% of methanol in methylene chloride) to provide 1.0 g (3.10 mmol, 61%) of 4-amino-N-(3-chloro-4-fluorophenyl)-2,3-dimethyl-2,4,5,6-tetrahydrocyclopenta[c]pyrrole-1-carboxamide (XVIIIc). $^1$H NMR (400 MHz, DMSO-d$_6$): δ 9.17 (s, 1H), 7.91-7.94 (m, 1H), 7.54-7.58 (m, 1H), 7.35 (t, 1H), 4.13-4.17 (m, 1H), 3.66 (s, 3H), 2.87-2.93 (m, 1H), 2.68-2.76 (m, 1H), 2.49-2.54 (m, 1H), 2.21 (s, 3H), 1.85-1.96 (m, 3H).

(1H-1,2,3-Triazol-4-yl)methyl (1-((3-chloro-4-fluorophenyl)carbamoyl)-2,3-dimethyl-2,4,5,6-tetrahydrocyclopenta[c]pyrrol-4-yl)carbamate (130, 131)

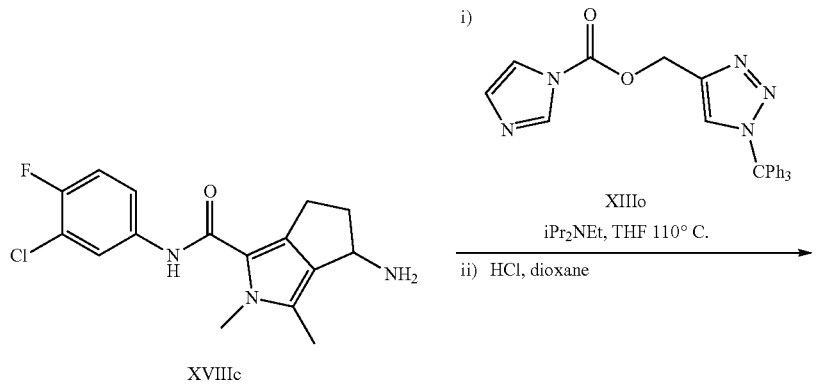

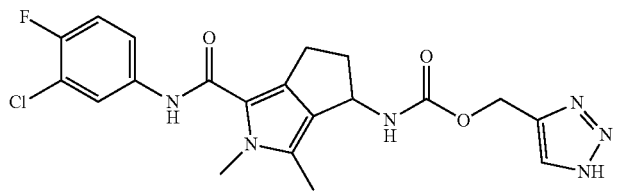

(1H-1,2,3-Triazol-4-yl)methyl (1-((3-chloro-4-fluorophenyl)carbamoyl)-2,3-dimethyl-2,4,5,6-tetrahydrocyclopenta[c]pyrrol-4-yl)carbamate was synthesized in a similar manner as described above from 4-amino-3-chloro-N-(3-chloro-4-fluorophenyl)-2-methyl-2,4,5,6-tetrahydrocyclopenta[c]pyrrole-1-carboxamide (XVIIIc) and (1-trityl-1H-1,2,3-triazol-4-yl)methyl 1H-imidazole-1-carboxylate (XIIIo) followed by acid mediated detritylation. The enantiomers were subsequently separated by SFC (Waters SFC investigator). Method: isocratic, Mobile phase MeOH:$CO_2$—35:65, Column: Chiralcel OJ-H (30×250 mm, 5 μm), flow rate: 70 g/min.

(1H-1,2,3-Triazol-4-yl)methyl (1-((3-chloro-4-fluorophenyl)carbamoyl)-2,3-dimethyl-2,4,5,6-tetrahydrocyclopenta[c]pyrrol-4-yl)carbamate—Enantiomer I (130) LCMS: m/z found 447.1/449.1 $[M+H]^+$, RT=6.97 min (Method A); HPLC: RT=8.15 min (Method B); Chiral SFC: RT: 2.81 min, Column, Chiralpak OJ-H (4.6×250 mm, 5 μm). $^1$H NMR (400 MHz, DMSO-$d_6$): δ 9.44 (s, 1H), 7.96-7.93 (m, 1H), 7.69 (s, 1H), 7.57-7.61 (m, 1H), 7.37 (t, 1H), 6.61 (bs, 2H), 5.95-5.97 (m, 1H), 4.98 (s, 2H), 3.66 (s, 3H), 3.20-3.26 (s, 1H), 2.84-2.93 (m, 2H), 2.71-2.77 (m, 1H), 2.04 (s, 3H).

(1H-1,2,3-Triazol-4-yl)methyl (1-((3-chloro-4-fluorophenyl)carbamoyl)-2,3-dimethyl-2,4,5,6-tetrahydrocyclopenta[c]pyrrol-4-yl)carbamate—Enantiomer II (131) LCMS: m/z found 447.1/449.1 $[M+H]^+$, RT=6.97 min (Method A); HPLC: RT=8.14 min (Method B); Chiral SFC: RT=5.35 min, Column: Chiralpak OJ-H (4.6×250 mm, 5 μm). $^1$H NMR (400 MHz, DMSO-$d_6$): δ 9.44 (s, 1H), 7.96-7.93 (m, 1H), 7.69 (s, 1H), 7.57-7.61 (m, 1H), 7.37 (t, 1H), 6.61 (bs, 2H), 5.95-5.97 (m, 1H), 4.98 (s, 2H), 3.66 (s, 3H), 3.20-3.26 (s, 1H), 2.84-2.93 (m, 2H), 2.71-2.77 (m, 1H), 2.04 (s, 3H).

Example 52: (1-Methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate (90, 91)

Ethyl 3-cyclopropyl-2-methyl-4-oxo-2,4,5,6-tetrahydrocyclopenta[c]pyrrole-1-carboxylate (XIVd)

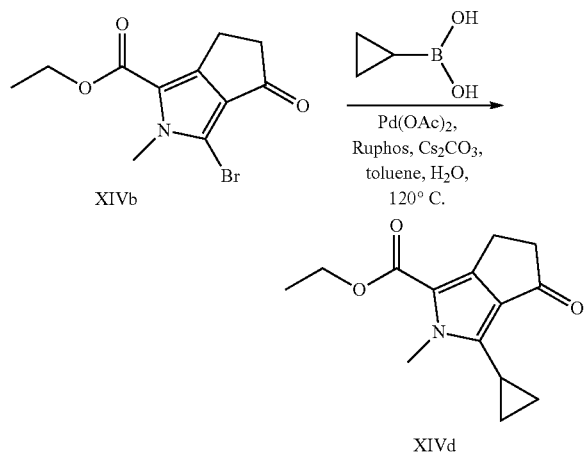

In a sealed tube, a solution of 1.0 g (3.5 mmol, 1.0 eq.) of ethyl 3-bromo-2-methyl-4-oxo-2,4,5,6-tetrahydrocyclopenta[c]pyrrole-1-carboxylate (XIVb) in 12 mL of 5:1 v/v of toluene:water was degassed with argon gas for 10 min. To this degassed solution was added 0.91 g (10.5 mmol, 3.0 eq.) of cyclopropylboronic acid followed by 0.12 g (0.18 mmol, 0.05 eq.) of $Pd(OAc)_2$, 0.16 g (0.35 mmol, 0.1 eq.) of Ruphos and 3.4 g (10.5 mmol, 3.0 eq.) of cesium carbonate, and degassing was continued for a further 5 min. The vessel was sealed, and the mixture was stirred at 110° C. for 16 h. The mixture was allowed to cool to room temperature, diluted with 50 mL of water and then extracted with 3×50 mL of ethyl acetate. The combined organic extracts were washed with 50 mL of water, 50 mL of brine, dried ($Na_2SO_4$), filtered and the solvent was removed in vacuo. The residue was purified by flash chromatography ($SiO_2$, eluting with a linear gradient of 10-30% ethyl acetate/hexanes) to provide 0.60 g (2.42 mmol, 69%) of ethyl 3-cyclopropyl-2-methyl-4-oxo-2,4,5,6-tetrahydrocyclopenta[c]pyrrole-1-carboxylate (XIVd). LCMS: m/z found 248.2 $[M+H]^+$; $^1$H NMR (400 MHz, $CDCl_3$): δ 4.28 (q, 2H), 4.03 (s, 3H), 2.98-3.01 (m, 2H), 2.74-2.77 (m, 2H), 1.68-1.73 (m, 1H), 1.35 (t, 3H), 1.28 (q, 2H), 1.06 (q, 2H).

N-(3-Chloro-4-fluorophenyl)-3-cyclopropyl-2-methyl-4-oxo-2,4,5,6-tetrahydrocyclopenta[c]pyrrole-1-carboxamide (XVId)

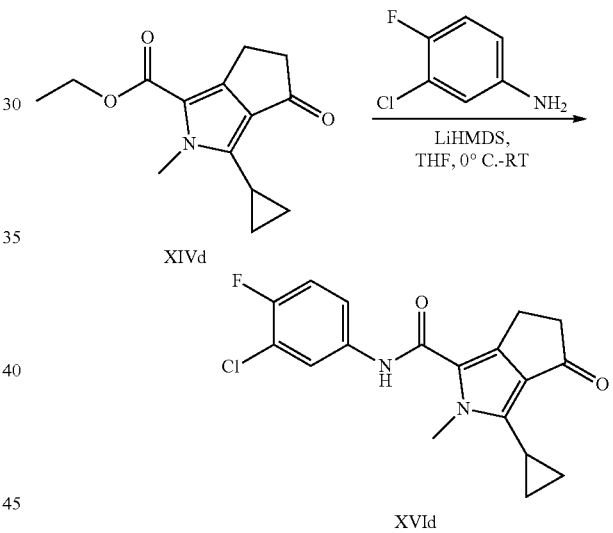

To a solution of 0.6 g (2.42 mmol, 1.0 eq.) of ethyl 3-cyclopropyl-2-methyl-4-oxo-2,4,5,6-tetrahydrocyclopenta[c]pyrrole-1-carboxylate (XIVd) in 6 mL of THF at 0° C. was added 0.53 g (3.69 mmol, 1.5 eq.) of 3-chloro-4-fluoroaniline followed by 14.5 mL (14.5 mmol, 6 eq.) of a 1 M solution of lithium bis(trimethylsilyl)amide in THF. The reaction mixture was allowed to warm to room temperature and stirred for 3 h. The mixture was then quenched with 50 mL of saturated ammonium chloride solution and extracted with 3×50 mL of ethyl acetate. The combined organic extracts were washed with 100 mL of brine (100 mL), dried ($Na_2SO_4$), filtered and the solvent was removed in vacuo. The residue was purified by flash chromatography ($SiO_2$, eluting with a linear gradient of 30-80% ethyl acetate in petroleum ether) to provide 0.65 g (1.87 mmol, 77%) of N-(3-chloro-4-fluorophenyl)-3-cyclopropyl-2-methyl-4-oxo-2,4,5,6-tetrahydrocyclopenta[c]pyrrole-1-carboxamide (XVId). LCMS: m/z found 347.31 $[M+H]^+$; $^1$H NMR (400 MHz, $CDCl_3$): δ 7.72 (dd, 1H), 7.30-7.34 (m, 1H), 7.09-7.16

(m, 2H), 4.08 (s, 3H), 3.07-3.09 (m, 2H), 2.87-2.90 (m, 2H), 1.71-1.74 (m, 1H), 1.27-1.30 (m, 2H), 1.07-1.12 (m, 2H).

N-(3-Chloro-4-fluorophenyl)-3-cyclopropyl-4-(hydroxyimino)-2-methyl-2,4,5,6-tetrahydro cyclopenta[c]pyrrole-1-carboxamide (XVId)

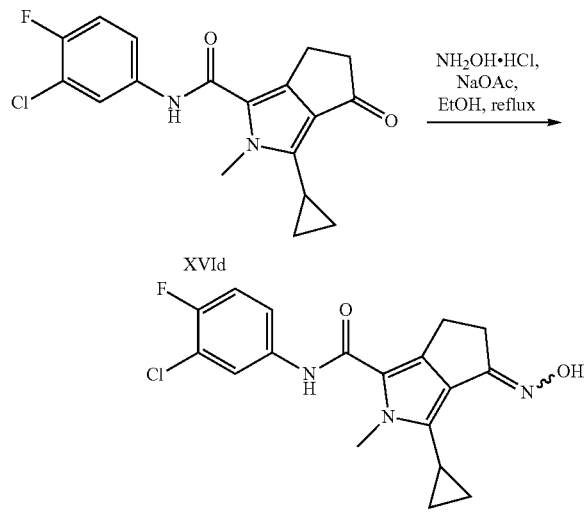

To a solution of 1.1 g (3.18 mmol, 1.0 eq.) of N-(3-chloro-4-fluorophenyl)-3-cyclopropyl-2-methyl-4-oxo-2,4,5,6-tetrahydrocyclopenta[c]pyrrole-1-carboxamide (XVId) in 11 mL of ethanol and 1.1 mL of water was added 0.88 g (12.71 mmol, 4.0 eq.) of hydroxylamine hydrochloride followed by 1.5 g (19.1 mmol, 6.0 eq.) of sodium acetate and the mixture was heated at 90° C. for 16 h. The reaction was quenched with 50 mL of ice-cold water and extracted with 3×100 mL of ethyl acetate. The combined organic extracts were washed with 100 mL of brine, dried (Na$_2$SO$_4$), filtered and the solvent was removed in vacuo. The residue was triturated with diethyl ether to provide 0.75 g (2.07 mmol, 56%) of N-(3-chloro-4-fluorophenyl)-3-cyclopropyl-4-(hydroxyimino)-2-methyl-2,4,5,6-tetrahydrocyclopenta[c]pyrrole-1-carboxamide. LCMS: m/z found 362.3/364.3 [M+14]$^+$; $^1$H NMR (400 MHz, DMSO-d$_6$): δ 10.30 (s, 1H), 9.46 (s, 1H), 7.91 (dd, 1H), 7.54-7.58 (m, 1H), 7.37 (t, 2H), 3.85 (s, 3H), 3.12-3.16 (s, 2H), 2.65-2.71 (m, 2H), 1.82-1.86 (m, 1H), 1.07-1.10 (m, 2H), 0.91-0.95 (m, 2H).

4-Amino-N-(3-chloro-4-fluorophenyl)-3-cyclopropyl-2-methyl-2,4,5,6-tetrahydrocyclopenta[c]pyrrole-1-carboxamide (XVIIId)

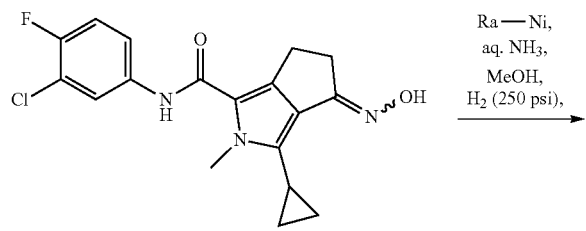

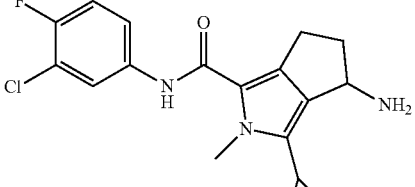

To a solution of 0.25 g (0.69 mmol, 1.0 eq.) of N-(3-chloro-4-fluorophenyl)-3-cyclopropyl-4-(hydroxyimino)-2-methyl-2,4,5,6-tetrahydrocyclopenta[c]pyrrole-1-carboxamide in 6 mL of THF and 6 mL of methanol was added 250 mg of Raney nickel (50% slurry in water) and 3 mL of ammonium hydroxide and the resulting mixture was stirred at under 250 psi of hydrogen at room temperature for 16 h. The mixture was filtered through CELITE® and the pad was washed with 10 mL of methanol. The filtrate was then concentrated in vacuo to provide 170 mg of 4-amino-N-(3-chloro-4-fluorophenyl)-3-cyclopropyl-2-methyl-2,4,5,6-tetrahydrocyclopenta[c]pyrrole-1-carboxamide (XVIIId).

(1-Methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate (90, 91)

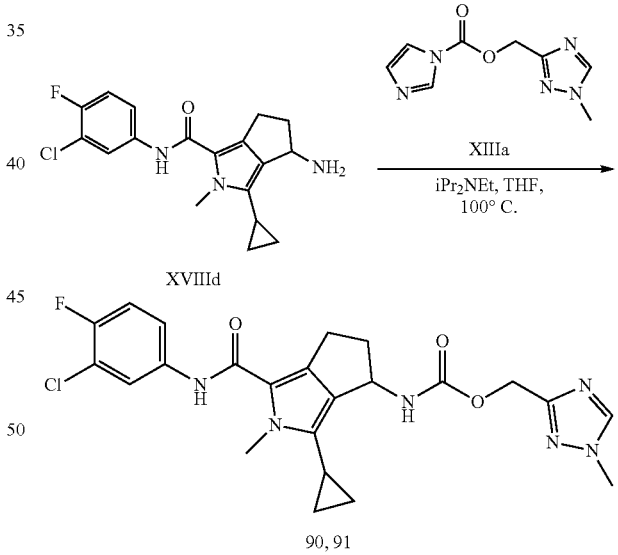

(1-Methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate was synthesized in a similar manner as described above from 4-amino-N-(3-chloro-4-fluorophenyl)-3-cyclopropyl-2-methyl-2,4,5,6-tetrahydrocyclopenta[c]pyrrole-1-carboxamide (XVIIId) and (1-methyl-1H-1,2,4-triazol-3-yl)methyl 1H-imidazole-1-carboxylate (XIIIa). The enantiomers were subsequently separated by SFC (Waters SFC investigator). Method isocratic, Mobile phase MeOH:CO$_2$ 45:55. Column: Chiralpak IC (21×250 mm), 5 μm, flow rate: 100 g/min.

(1-Methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate—Enantiomer I (90) LCMS: m/z found 487.3/489.4 [M+H]$^+$, RT=7.27 min (Method A); HPLC: RT=7.92 min (Method B); Chiral SFC: RT=6.56 min, column Chiralpak IC (150 mm×4.6 mm, 5 μm); $^1$H NMR (400 MHz, DMSO-d$_6$): δ 9.30 (s, 1H), 8.42 (s, 1H), 7.92 (dd, 1H), 7.53-7.59 (m, 1H), 7.46 (d, 1H), 7.35 (t, 1H), 4.99 (s, 2H), 4.86-4.90 (m, 1H), 3.84 (s, 3H), 3.78 (s, 3H), 2.78-2.87 (m, 2H), 2.49-2.57 (m, 1H), 2.00-2.05 (m, 1H), 1.69-1.74 (m, 1H), 0.81-0.84 (m, 2H), 0.58-0.68 (m, 2H).

(1-Methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate—Enantiomer I (91) LCMS: m/z found 487.3/489.3 [M+H]$^+$, RT=7.23 min (Method A); HPLC: RT=7.93 min (Method B); Chiral-SFC: RT=10.22 min, column Chiralpak IC (150 mm×4.6 mm, 5 μm); $^1$H NMR (400 MHz, DMSO-d$_6$): δ 9.30 (s, 1H), 8.42 (s, 1H), 7.92 (dd, 1H), 7.53-7.59 (m, 1H), 7.46 (d, 1H), 7.35 (t, 1H), 4.99 (s, 2H), 4.86-4.90 (m, 1H), 3.84 (s, 3H), 3.78 (s, 3H), 2.78-2.87 (m, 2H), 2.49-2.57 (m, 1H), 2.00-2.05 (m, 1H), 1.69-1.74 (m, 1H), 0.81-0.84 (m, 2H), 0.58-0.68 (m, 2H).

Example 53: (1H-1,2,4-Triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate (98, 99)

(1H-1,2,4-Triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate was synthesized in a similar manner as described above from 4-amino-N-(3-chloro-4-fluorophenyl)-3-cyclopropyl-2-methyl-2,4,5,6-tetrahydrocyclopenta[c]pyrrole-1-carboxamide (XVIIId) and (1-trityl-1H-1,2,4-triazol-3-yl)methyl 1H-imidazole-1-carboxylate (XIIIn) followed by acid mediated detritylation. The enantiomers were isolated by SFC. Method: isocratic, Mobile phase MeOH:CO$_2$—50:50. Column: Chiralpak AD (30×250 mm), 5 μm, flow rate: 100 g/min. (1H-1,2,4-Triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate—Enantiomer I (98) LCMS: m/z found 473.3/475.3 [M+H]$^+$, RT=7.42 min; (Method A); HPLC: RT=7.64 min (Method B); Chiral SFC: RT=1.60 min, Column: Chiralpak AD-3 (4.6×250 mm, 5 μm). $^1$H NMR (400 MHz, DMSO-d$_6$): δ 14.01 (bs, 1H), 9.29 (s, 1H), 8.53 (bs, 1H), 7.90-7.93 (m, 1H), 7.54-7.58 (m, 1H), 7.42-7.48 (m, 1H), 7.35 (t, 1H), 5.04 (s, 2H), 4.86-4.90 (m, 1H), 3.78 (s, 3H), 2.73-2.86 (m, 2H), 2.49-2.50 (m, 1H), 2.01-2.07 (m, 1H), 1.68-1.74 (m, 1H), 0.79-0.84 (m, 2H), 0.61-0.68 (m, 1H), 0.58-0.52 (m, 1H).

(1H-1,2,4-Triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate—Enantiomer II (99) LCMS: m/z found 473.5/475.5 [M+H]$^+$, RT=7.42 min; (Method A); HPLC: RT=7.64 min (Method B); Chiral SFC: RT=2.27 min, Column: Chiralpak AD-3 (4.6×250 mm, 5

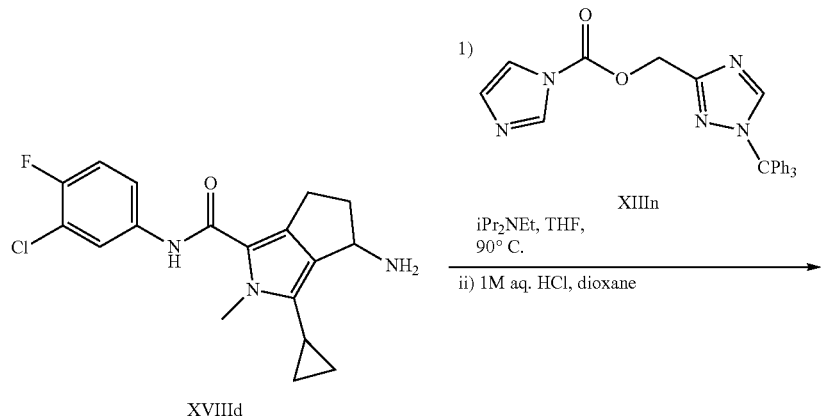

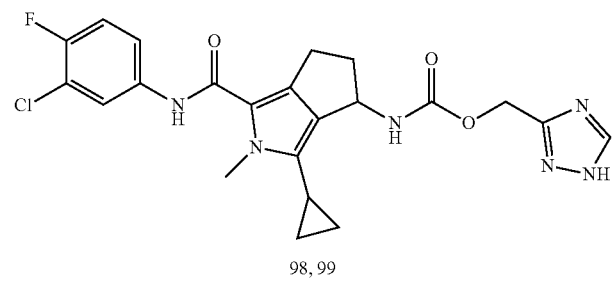

μm). $^1$H NMR (400 MHz, DMSO-$d_6$): δ 14.01 (bs, 1H), 9.29 (s, 1H), 8.53 (bs, 1H), 7.90-7.93 (m, 1H), 7.54-7.58 (m, 1H), 7.42-7.48 (m, 1H), 7.35 (t, 1H), 5.04 (s, 2H), 4.86-4.90 (m, 1H), 3.78 (s, 3H), 2.73-2.86 (m, 2H), 2.49-2.50 (m, 1H), 2.01-2.07 (m, 1H), 1.68-1.74 (m, 1H), 0.79-0.84 (m, 2H), 0.61-0.68 (m, 1H), 0.58-0.52 (m, 1H).

Example 54: (1-Methyl-1H-1,2,4-triazol-3-yl) methyl (1-((3-chloro-4-fluorophenyl)carbamoyl)-3-cyclobutyl-2-methyl-2,4,5,6-tetrahydrocyclopenta[c] pyrrol-4-yl)carbamate (96, 97)

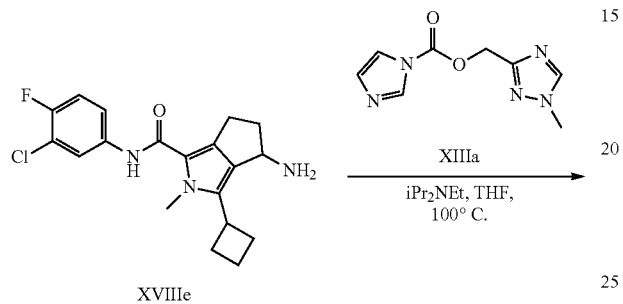

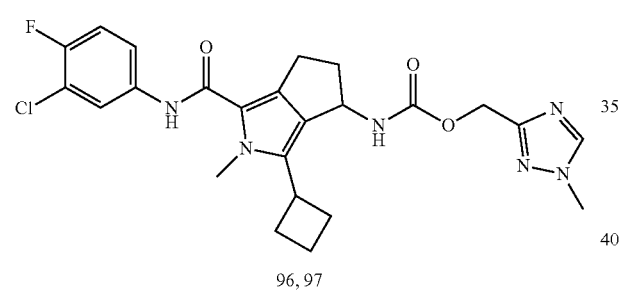

(1-Methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate was synthesized in a similar manner as described above from 4-amino-N-(3-chloro-4-fluorophenyl)-3-cyclobutyl-2-methyl-2,4,5,6-tetrahydrocyclopenta[c]pyrrole-1-carboxamide (XVIIIe) and (1-methyl-1H-1,2,4-triazol-3-yl)methyl 1H-imidazole-1-carboxylate (XIIIa) The enantiomers were subsequently separated by SFC (Waters SFC investigator). Method isocratic, Mobile phase MeOH:CO$_2$—10:90, Column: Chiralpak IA (21×250 mm), 5 μm, flow rate: 100 g/min.

(1-Methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate—Enantiomer I (96) LCMS: m/z found 501.3/503.3 [M+H]$^+$, RT=7.62 min (Method A); HPLC: RT=8.32 min (Method B); Chiral SFC: RT=3.67 min; Chiralpak IA (150 mm×4.6 mm, 5 μm); $^1$H NMR (400 MHz, DMSO-$d_6$): δ 9.31 (s, 1H), 8.41 (s, 1H), 7.92 (dd, 1H), 7.52-7.58 (m, 2H), 7.35 (t, 1H), 5.02-5.05 (m, 1H), 4.97 (s, 2H), 3.83 (s, 3H), 3.60 (s, 3H), 3.51-3.55 (m, 1H), 2.79-2.90 (m, 2H), 2.59-2.60 (m, 1H), 2.16-2.27 (m, 4H), 2.04-2.08 (m, 1H), 1.91-1.96 (m, 1H), 1.74-1.76 (m, 1H).

(1-Methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate—Enantiomer II (97) LCMS: m/z found 501.3/503.4 [M+H]$^+$, RT=7.63 min (Method A); HPLC: RT=8.33 min (Method B); Chiral SFC: RT=5.21 min; Chiralpak IA (150 mm×4.6 mm, 5 μm); $^1$H NMR (400 MHz, DMSO-$d_6$): δ 9.31 (s, 1H), 8.41 (s, 1H), 7.92 (dd, 1H), 7.52-7.58 (m, 2H), 7.35 (t, 1H), 5.02-5.05 (m, 1H), 4.97 (s, 2H), 3.83 (s, 3H), 3.60 (s, 3H), 3.51-3.55 (m, 1H), 2.79-2.90 (m, 2H), 2.59-2.60 (m, 1H), 2.16-2.27 (m, 4H), 2.04-2.08 (m, 1H), 1.91-1.96 (m, 1H), 1.74-1.76 (m, 1H).

Example 55: 1-Methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c] pyrrol-4-yl)carbamate (122, 123)

Ethyl 2-methyl-4-oxo-3-(trifluoromethyl)-2,4,5,6-tetrahydrocyclopenta[c]pyrrole-1-carboxylate (XIVf)

To a solution of 2.0 g (7.0 mmol, 1.0 eq.) of ethyl 3-bromo-2-methyl-4-oxo-2,4,5,6-tetrahydrocyclopenta[c] pyrrole-1-carboxylate (XIVb) in 25 mL of DMF in a seal tube was added 5.3 mL (42.1 mmol, 6.0 eq) of methyl 2,2-difluoro-2-(fluorosulfonyl)acetate followed by 5.4 g (28.1 mmol, 4.0 eq.) of copper (I) iodide. The vessel was sealed, and the mixture was heated to 100° C. for 16 h. The mixture was then allowed to cool to room temperature and quenched with 50 mL ice-cold water and diluted with 100 mL of ethyl acetate. The resulting solution was filtered, and the filtrate was washed with 50 mL of water. The aqueous phase was extracted with 2×50 mL of ethyl acetate and the combined organic extracts were dried (Na$_2$SO$_4$), filtered and the solvent was removed in vacuo. The residue was purified by trituration with 2×40 mL of n-pentane to provide 1.3 g (4.72 mmol, 67%) of ethyl 2-methyl-4-oxo-3-(trifluoromethyl)-2,4,5,6-tetrahydrocyclopenta[c]pyrrole-1-carboxylate (XIVf). LCMS: m/z found 276.2 [M+H]$^+$; $^1$H NMR (400 MHz, CDCl$_3$): δ 4.35 (q, 2H), 4.12 (s, 3H), 3.06-3.09 (m, 2H), 2.87-2.90 (m, 2H), 1.38 (t, 3H).

2-Methyl-4-oxo-3-(trifluoromethyl)-2,4,5,6-tetrahydrocyclopenta[c]pyrrole-1-carboxylic acid (XVI)

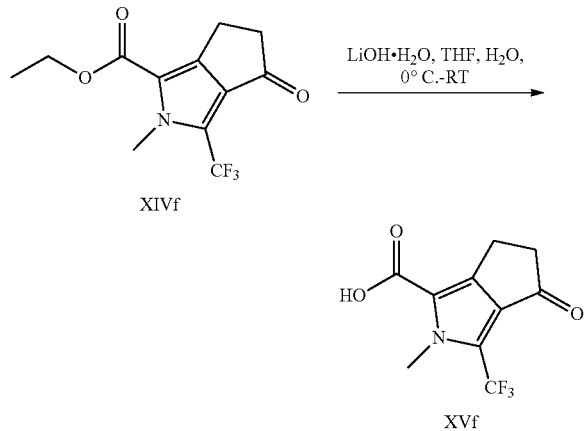

To a solution of 1.3 g (4.7 mmol, 1.0 eq.) of ethyl 2-methyl-4-oxo-3-(trifluoromethyl)-2,4,5,6-tetrahydrocyclopenta[c]pyrrole-1-carboxylate (XIVf) in 50 mL of 1:1 v/v THF:water was added 1.8 g (42.8 mmol, 9.1 eq.) of lithium hydroxide monohydrate and the mixture was stirred at room temperature for 48 h. The mixture was then acidified to pH 3 using 3 M aqueous hydrochloric acid and extracted with 3×30 mL of ethyl acetate. The combined organic extracts were dried (Na$_2$SO$_4$), filtered and the solvent was removed in vacuo. The residue was triturated with 30 mL of n-pentane, filtered and dried under high vacuum to provide 1.0 g (4.0 mmol, 85%) of 2-methyl-4-oxo-3-(trifluoromethyl)-2,4,5,6-tetrahydrocyclopenta[c]pyrrole-1-carboxylic acid (XVf). LCMS: m/z found 248.1 [M+H]$^+$; $^1$H NMR (400 MHz, CDCl$_3$): δ 4.13 (s, 3H), 3.12-3.15 (m, 2H), 2.90-2.93 (m, 2H).

N-(3-Chloro-4-fluorophenyl)-2-methyl-4-oxo-3-(trifluoromethyl)-2,4,5,6-tetrahydrocyclopenta[c]pyrrole-1-carboxamide (XVII)

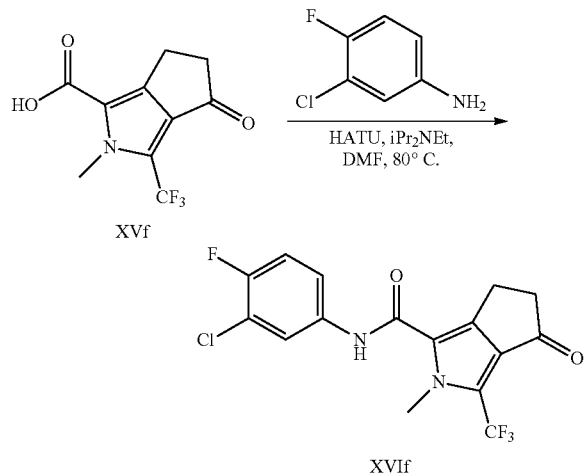

To a solution of 1.0 g (4.0 mmol, 1.0 eq.) of 2-methyl-4-oxo-3-(trifluoromethyl)-2,4,5,6-tetrahydrocyclopenta[c]pyrrole-1-carboxylic acid (XVI) in 10 mL of DMF at 0° C. under a nitrogen atmosphere was added 1.6 g (12.2 mmol, 3.0 eq.) of N,N-diisopropylethylamine followed by 2.3 g (6.1 mmol, 1.5 eq.) of 1-[bis(dimethylamino)methylene]-1H-1,2,3-triazolo[4,5-b]pyridinium 3-oxide hexafluorophosphate and 0.74 g (5.06 mmol, 1.25 eq.) of 4-fluoro-3-chloro aniline. The mixture was allowed to warm to room temperature and then heated at 80° C. for 16 h. The mixture was allowed to cool to room temperature and diluted with 100 mL of ice-cold water. The obtained solids were collected by filtration, dried under vacuum and washed with 30 mL of 1:1 v/v n-pentane:diethyl ether to provide 1.2 g (3.2 mmol, 79%) of N-(3-chloro-4-fluorophenyl)-2-methyl-4-oxo-3-(trifluoromethyl)-2,4,5,6-tetrahydrocyclopenta[c]pyrrole-1-carboxamide (XIVf). LCMS: m/z found 375.1 [M+H]$^+$; $^1$H NMR (400 MHz, CDCl$_3$): δ 7.73-7.76 (m, 1H), 7.31-7.38 (m, 2H), 7.16 (t, 1H), 4.14 (s, 3H), 3.14-3.18 (m, 2H), 2.99-3.02 (m, 2H).

N-(3-Chloro-4-fluorophenyl)-4-(hydroxyimino)-2-methyl-3-(trifluoromethyl)-2,4,5,6-tetrahydro cyclopenta[c]pyrrole-1-carboxamide

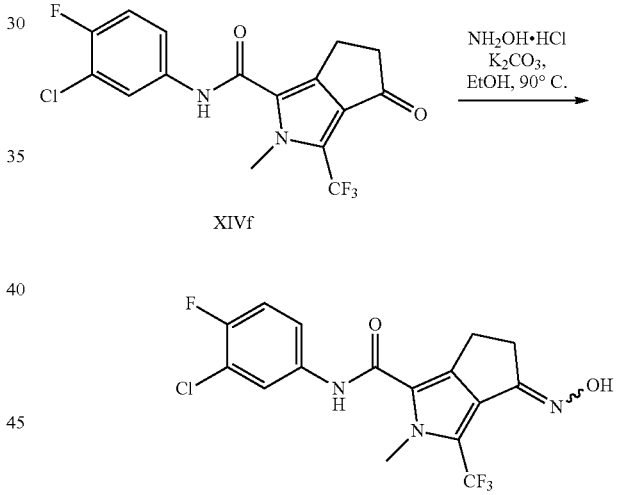

To a solution of 1.2 g (3.3 mmol, 1.0 eq.) of N-(3-chloro-4-fluorophenyl)-2-methyl-4-oxo-3-(trifluoromethyl)-2,4,5,6-tetrahydrocyclopenta[c]pyrrole-1-carboxamide (XIVf) in 40 mL of ethanol was added 0.89 g (12.9 mmol, 4.0 eq.) of hydroxylamine hydrochloride followed by 2.6 g (19.0 mmol, 6 eq.) of potassium carbonate and the mixture was heated at 90° C. for 16 h. The mixture was allowed to cool to room temperature and quenched with 80 mL of ice-cold water. The obtained solids were collected by filtration, washed with 20 mL of n-pentane and dried under high vacuum to provide 1.1 g (2.87 mmol, 88%) of N-(3-chloro-4-fluorophenyl)-4-(hydroxyimino)-2-methyl-3-(trifluoromethyl)-2,4,5,6-tetrahydro cyclopenta[c]pyrrole-1-carboxamide. LCMS: m/z found 390.2/392.2 [M+14]$^+$; $^1$H NMR (400 MHz, DMSO-d$_6$): δ 10.96 (s, 1H), 10.17 (s, 1H), 7.94-7.97 (m, 1H), 7.58-7.63 (m, 1H), 7.43 (t, 1H), 3.89 (s, 3H), 2.99-3.06 (m, 4H).

4-Amino-N-(3-chloro-4-fluorophenyl)-2-methyl-3-(trifluoromethyl)-2,4,5,6-tetrahydrocyclopenta[c]pyrrole-1-carboxamide (XVIIIf)

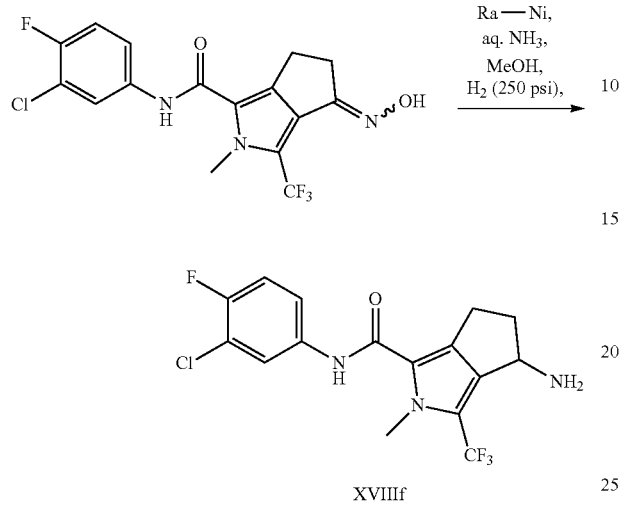

XVIIIf

To a solution of 0.75 g (1.92 mmol, 1.0 eq.) of N-(3-chloro-4-fluorophenyl)-4-(hydroxyimino)-2-methyl-3-(trifluoromethyl)-2,4,5,6-tetrahydrocyclopenta[c]pyrrole-1-carboxamide in 22 mL of THF and 22 mL of methanol was added 750 mg of Raney nickel (50% suspension in water) followed by 22 mL of 25% ammonium hydroxide solution and the resulting mixture was stirred at under 250 psi of hydrogen at room temperature for 48 h. The mixture was filtered through CELITE® and the pad was washed with 10 mL of methanol. The residue was purified by reverse phase HPLC to provide 170 mg (0.45 mmol, 23%) of 4-amino-N-(3-chloro-4-fluorophenyl)-2-methyl-3-(trifluoromethyl)-2,4,5,6-tetrahydrocyclopenta[c]pyrrole-1-carboxamide (XVIIIf). LCMS: m/z found 376.1/378.1 [M+H]$^+$; $^1$H NMR (400 MHz, DMSO-d$_6$): δ 10.02 (s, 1H), 7.94-7.97 (m, 1H), 7.58-7.64 (m, 1H), 7.41 (t, 1H), 4.28-4.31 (m, 1H), 3.80 (s, 3H), 2.92-3.01 (m, 1H), 2.68-2.78 (m, 1H), 2.51-2.59 (m, 1H), 1.95-2.03 (m, 1H), 1.80 (bs, 2H).

1-Methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate (122, 123)

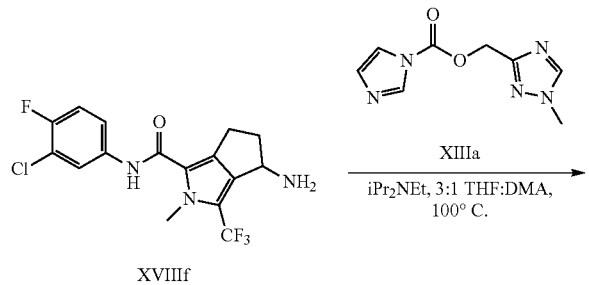

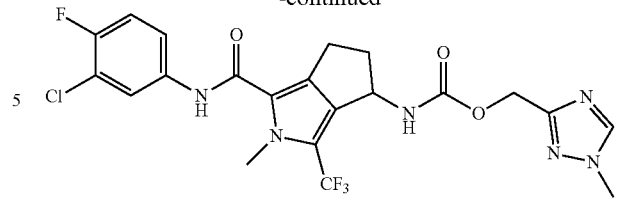

122, 123

1-Methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate was synthesized in a similar manner as described above from 4-amino-N-(3-chloro-4-fluorophenyl)-2-methyl-3-(trifluoromethyl)-2,4,5,6-tetrahydrocyclopenta[c]pyrrole-1-carboxamide (XVIIIf) and (1-methyl-1H-1,2,4-triazol-3-yl) methyl 1H-imidazole-1-carboxylate (XIIIa) The enantiomers were subsequently separated by SFC. Method isocratic, Mobile phase MeOH:CO$_2$—10:90. Column: Chiralcel OD-H (21×250 mm, 5 μm), flow rate: 70 g/min.

1-Methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate—Enantiomer I (122) LCMS: m/z found 515.3/511.3 [M+H]$^+$; Chiral SFC: RT=2.32 min, Chiralcel OD-H (150 mm×4.6 mm, 5 μm); $^1$H NMR (400 MHz, DMSO-d$_6$): δ10.04 (s, 1H), 8.42 (s, 1H), 7.94-7.97 (m, 1H), 7.71 (d, 1H), 7.58-7.63 (m, 1H), 7.41 (t, 1H), 4.92-5.07 (m, 3H), 3.84 (s, 3H), 3.81 (s, 3H), 2.87-2.93 (m, 1H), 2.76-2.85 (m, 1H), 2.59-2.68 (m, 1H), 2.07-2.14 (m, 1H).

1-Methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate—Enantiomer II (123) LCMS: m/z found 515.3/511.3 [M+H]$^+$; Chiral-SFC: RT=3.27 min, Chiralcel OD-H (150 mm×4.6 mm, 5 μm); $^1$H NMR (400 MHz, DMSO-d$_6$): δ10.04 (s, 1H), 8.42 (s, 1H), 7.94-7.97 (m, 1H), 7.71 (d, 1H), 7.58-7.63 (m, 1H), 7.41 (t, 1H), 4.92-5.07 (m, 3H), 3.84 (s, 3H), 3.81 (s, 3H), 2.87-2.93 (m, 1H), 2.76-2.85 (m, 1H), 2.59-2.68 (m, 1H), 2.07-2.14 (m, 1H).

Example 56: (1H-1,2,4-Triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate (126, 127)

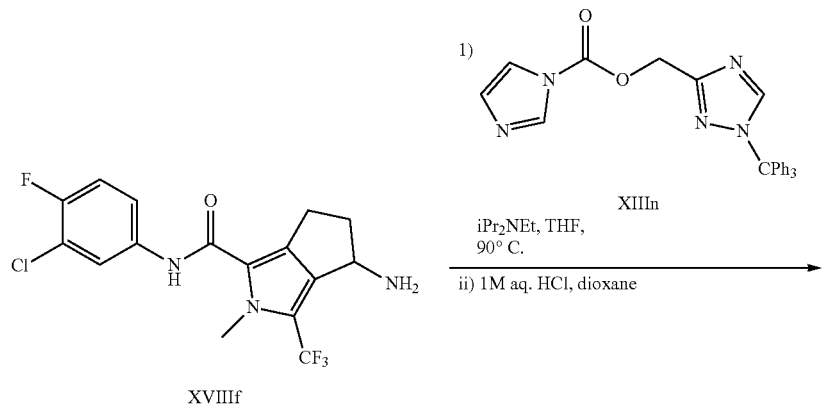

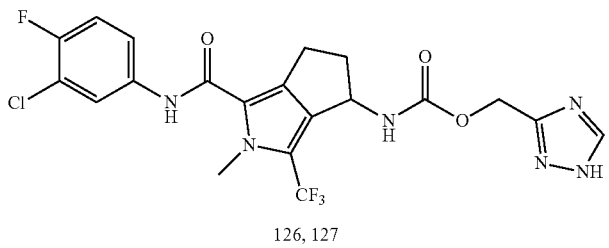

126, 127

(1H-1,2,4-Triazol-3-yl)methyl (1-((3-chloro-4-fluorophenyl)carbamoyl-2-methyl-3-(trifluoromethyl)-2,4,5,6-tetrahydrocyclopenta[c]pyrrol-4-yl)carbamate was synthesized in a similar manner as described above from N-(3-chloro-4-fluorophenyl)-4-(hydroxyimino)-2-methyl-3-(trifluoromethyl)-2,4,5,6-tetrahydrocyclopenta[c]pyrrole-1-carboxamide (XVIIIf) and (1-trityl-1H-1,2,4-triazol-3-yl)methyl 1H-imidazole-1-carboxylate (XIIIn) followed by acid mediated detritylation. The enantiomers were isolated by SFC, Method: isocratic, Mobile phase MeOH:$CO_2$—15:85. Column: Chiralpak IG (30×250 mm, 5 μm), flow rate: 60 g/min.

(1H-1,2,4-Triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate (126) LCMS: m/z found 501.3/503.3 [M+H]$^+$, RT=7.13 min (Method A); HPLC: RT=7.84 min (Method B); Chiral SFC: RT=2.51 min, Column: Chiralpak IG-3 (4.6×250 mm, 5 μm). $^1$H NMR (400 MHz, DMSO-$d_6$): δ 14.02 (bs, 1H), 10.05 (s, 1H), 8.42 (s, 1H), 7.94-7.97 (m, 1H), 7.74 (d, 1H), 7.58-7.63 (m, 1H), 7.41 (t, 1H), 4.98-5.08 (m, 3H), 3.81 (s, 3H), 2.77-2.94 (m, 2H), 2.60-2.67 (m, 1H), 2.08-2.13 (m, 1H).

(1H-1,2,4-Triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate—Enantiomer II (127) LCMS: m/z found 501.3/503.3 [M+H]$^+$, RT=7.13 min (Method A); HPLC: RT=7.84 min (Method B); Chiral SFC: RT=3.45 min, Column: Chiralpak IG-3 (4.6×250 mm, 5 μm). $^1$H NMR (400 MHz, DMSO-$d_6$): δ 14.02 (bs, 1H), 10.05 (s, 1H), 8.42 (s, 1H), 7.94-7.97 (m, 1H), 7.74 (d, 1H), 7.58-7.63 (m, 1H), 7.41 (t, 1H), 4.98-5.08 (m, 3H), 3.81 (s, 3H), 2.77-2.94 (m, 2H), 2.60-2.67 (m, 1H), 2.08-2.13 (m, 1H).

Example 57: (2H-1,2,3-Triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate (132, 133)

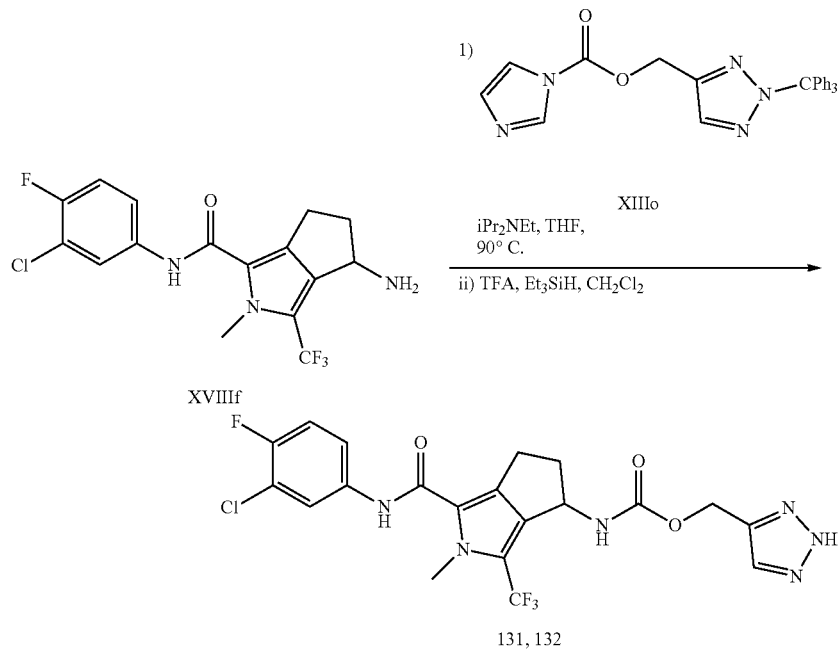

(2H-1,2,3-Triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate was synthesized in a similar manner as described above from N-(3-chloro-4-fluorophenyl)-4-(hydroxyimino)-2-methyl-3-(trifluoromethyl)-2,4,5,6-tetrahydrocyclopenta[c]pyrrole-1-carboxamide (XVIIIf) and (2-trityl-2H-1,2,3-triazol-4-yl)methyl 1H-imidazole-1-carboxylate (XIIIo) followed by acid mediated detritylation. The enantiomers were isolated by SFC, Method: isocratic, Mobile phase MeOH:CO₂—30:70. Column: Chiralcel OJ-H (30×250 mm), 5 μm, flow rate: 90 g/min.

(2H-1,2,3-Triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate—Enantiomer I (131) LCMS: m/z found 501.3/503.3 [M+H]⁺, RT=4.71 min (Method A); HPLC: RT=8.25 min (Method B); Chiral SFC: RT=1.79 min, Column: Chiralcel OJ-H (4.6×250 mm, 5 μm); $^1$H NMR (400 MHz, DMSO-d₆): δ 15.04 (bs, 1H), 10.04 (s, 1H), 7.94-7.97 (m, 1H), 7.81 (s, 1H), 7.68-7.71 (m, 1H), 7.60-7.63 (m, 1H), 7.39 (t, 1H), 5.05-5.12 (m, 3H), 3.81 (s, 3H), 2.77-2.93 (m, 2H), 2.58-2.67 (m, 1H), 2.05-2.13 (m, 1H).

(2H-1,2,3-Triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate—Enantiomer II (132) LCMS: m/z found 501.3/503.3 [M+H]⁺, RT=4.71 min (Method A); HPLC: RT=8.25 min (Method B); Chiral SFC: RT=4.57 min, Column: Chiralcel OJ-H (4.6×250 mm, 5 μm); $^1$H NMR (400 MHz, DMSO-d₆): δ 15.04 (bs, 1H), 10.04 (s, 1H), 7.94-7.97 (m, 1H), 7.81 (s, 1H), 7.68-7.71 (m, 1H), 7.60-7.63 (m, 1H), 7.39 (t, 1H), 5.05-5.12 (m, 3H), 3.81 (s, 3H), 2.77-2.93 (m, 2H), 2.58-2.67 (m, 1H), 2.05-2.13 (m, 1H).

Example 58: (1-Methyl-1H-1,2,4-triazol-3-yl)methyl (1-((3-chloro-4-fluorophenyl) carbamoyl)-2-ethyl-2,4,5,6-tetrahydrocyclopenta[c]pyrrol-4-yl) carbamate (19, 20)

1-Bromo-2-ethyl-5,6-dihydrocyclopenta[c]pyrrol-4(2H)-one (Vb)

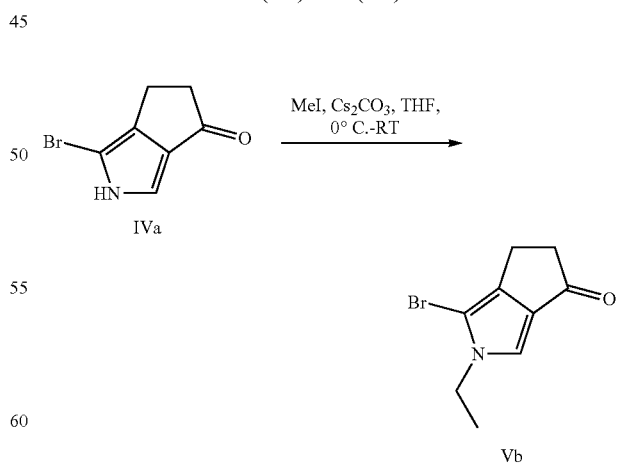

To a solution of 5.0 g (25.1 mmol, 1.0 eq) of 1-bromo-5,6-dihydrocyclopenta[c]pyrrol-4(2H)-one (IVa) in 50 mL of THF at 0° C. was added 24.4 g (75.3 mmol, 3.0 eq.) of cesium carbonate and 7.79 g (50.3 mmol, 2.0 eq) of ethyl iodide. The mixture was allowed to warm to room temperature and stirred for 16 h. The mixture was then diluted with 150 mL of water and extracted with 3×100 mL of ethyl acetate. The combined organic extracts were washed with 100 mL of water, 100 mL of brine, dried (Na$_2$SO$_4$) and the solvent was removed in vacuo. The reaction was performed on 2×5.0 g batches as described above. The combined crude product from the two batches was purified by flash chromatography (SiO$_2$, eluting with a linear gradient of 0-20% ethyl acetate/petroleum ether) to provide 8.5 g (37.3 mmol, 74%) of 1-bromo-2-ethyl-5,6-dihydrocyclopenta[c]pyrrol-4(2H)-one (Vb) as a white solid. LCMS: m/z found 228.3/230.3 [M+H]$^+$, RT=1.94 min; $^1$H NMR (300 MHz, CDCl$_3$) δ 7.16 (s, 1H), 4.00 (q, 2H), 2.78-2.86 (m, 4H), 1.42 (t, 3H).

Ethyl 2-ethyl-4-oxo-2,4,5,6-tetrahydrocyclopenta[c]pyrrole-1-carboxylate (VIb)

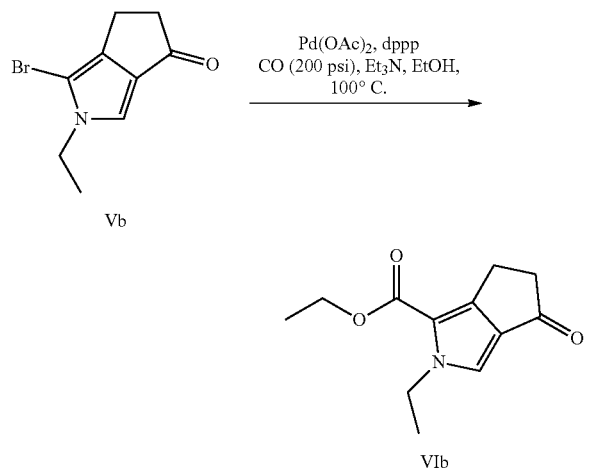

Ethyl 2-ethyl-4-oxo-2,4,5,6-tetrahydrocyclopenta[c]pyrrole-1-carboxylate (VIb) was synthesized in a similar manner as described above, and detailed in Scheme 1, from 1-bromo-2-ethyl-5,6-dihydrocyclopenta[c]pyrrol-4 (2H)-one (Vb). LCMS: m/z found 222.4 [M+H]$^+$, RT=1.94 min; $^1$H NMR (400 MHz, CDCl$_3$) δ 7.18 (s, 1H), 4.41 (q, 2H), 4.31 (q, 2H), 3.06-3.10 (m, 2H), 2.81-2.85 (m, 2H), 1.45 (t, 3H), 1.37 (t, 3H).

2-Ethyl-4-oxo-2,4,5,6-tetrahydrocyclopenta[c]pyrrole-1-carboxylic acid (VIIb)

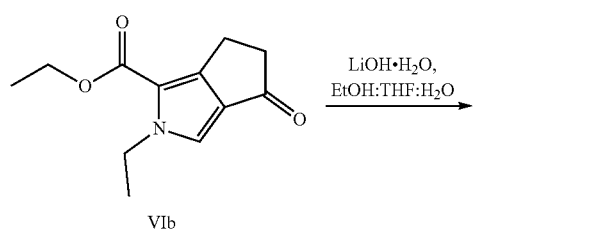

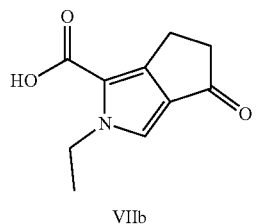

2-Ethyl-4-oxo-2,4,5,6-tetrahydrocyclopenta[c]pyrrole-1-carboxylic acid (VIIb) was synthesized in a similar manner as described above, and detailed in Scheme 1, from ethyl 2-ethyl-4-oxo-2,4,5,6-tetrahydrocyclopenta[c]pyrrole-1-carboxylate (VIb). LCMS: m/z found 194.04 [M+H]$^+$, RT=1.53 min.

N-(3-Chloro-4-fluorophenyl)-2-ethyl-4-oxo-2,4,5,6-tetrahydrocyclopenta[c]pyrrole-1-carboxamide (VIIIc)

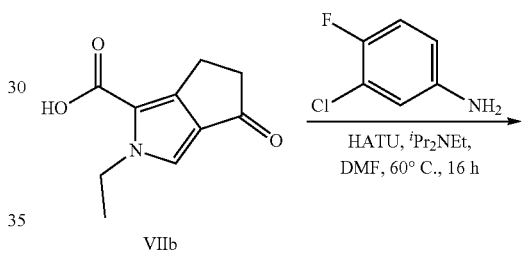

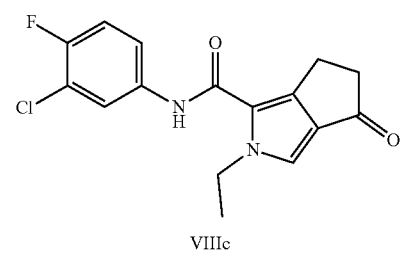

N-(3-Chloro-4-fluorophenyl)-2-ethyl-4-oxo-2,4,5,6-tetrahydrocyclopenta[c]pyrrole-1-carboxamide (VIIIc) was synthesized in a similar manner as described above, and detailed in Scheme 1, from 2-ethyl-4-oxo-2,4,5,6-tetrahydrocyclopenta[c]pyrrole-1-carboxylic acid (VIIb). LCMS: m/z found 321.4/323.4 [M+H]$^+$, RT=2.13 min; $^1$H NMR (400 MHz, CDCl$_3$) δ 7.73-7.76 (m, 1H), 7.32-7.36 (m, 1H), 7.23-7.26 (m, 2H), 7.13 (dd, 1H), 4.49 (q, 2H), 3.18 (m, 2H), 2.96 (m, 2H), 1.48 (t, 3H).

4-Amino-N-(3-chloro-4-fluorophenyl)-2-ethyl-2,4,5,6-tetrahydrocyclopenta[c]pyrrole-1-carboxamide (IXm)

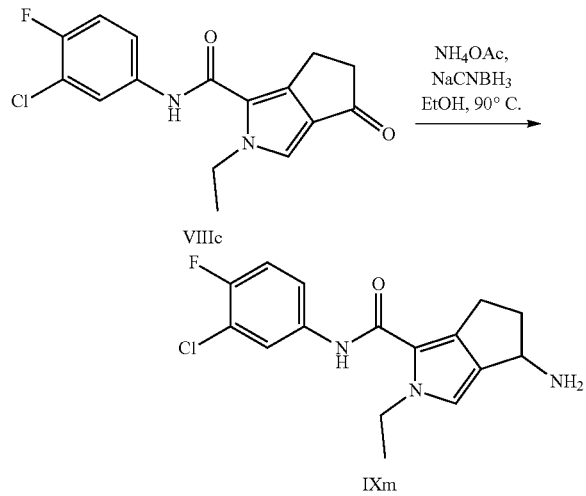

4-Amino-N-(3-chloro-4-fluorophenyl)-2-ethyl-2,4,5,6-tetrahydrocyclopenta[c]pyrrole-1-carboxamide (IXm) was synthesized in a similar manner as described above from N-(3-chloro-4-fluorophenyl)-2-ethyl-4-oxo-2,4,5,6-tetrahydrocyclopenta[c]pyrrole-1-carboxamide (VIIIe) and ammonium acetate. LCMS: m/z found 322.1/324.1 [M+H]$^+$, RT=1.76 min. (1-Methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate (19, 20):

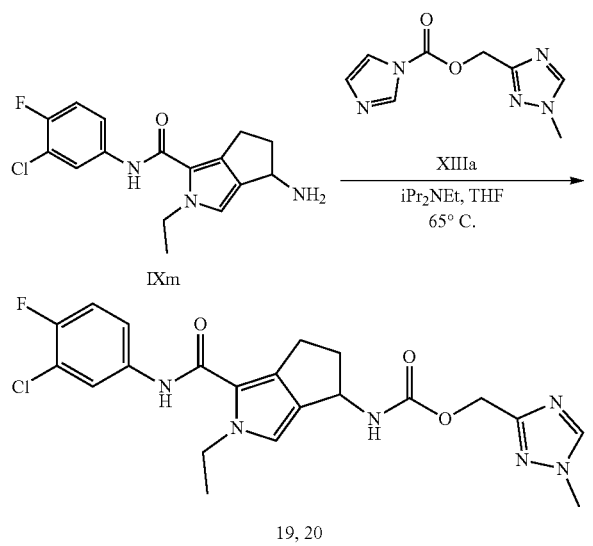

(1-Methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate was synthesized in a similar manner as described above from 4-amino-N-(3-chloro-4-fluorophenyl)-2-ethyl-2,4,5,6-tetrahydrocyclopenta[c]pyrrole-1-carboxamide (IXm) and (1-methyl-1H-1,2,4-triazol-3-yl)methyl 1H-imidazole-1-carboxylate (XIIIa) The enantiomers were subsequently separated by SFC (Waters SFC investigator). Method isocratic, Mobile phase MeOH:CO$_2$ 40:60. Column: Chiralcel OJ-H (30×250 mm, 5 μm), flow rate: 60 g/min.

(1-Methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate—Enantiomer I (19) LCMS: m/z found 461.2/463.2 [M+H]$^+$, RT=4.28 min (Method A); Chiral SFC: RT=2.71 min, Column: Chiralcel OJ-H (250 mm×4.6 mm, 5 μm); $^1$H NMR (400 MHz, DMSO-d$_6$) δ 9.40 (s, 1H), 8.43 (s, 1H), 7.92-7.94 (m, 1H), 7.54-7.59 (m, 2H), 7.36 (dd, 1H), 6.88 (s, 1H), 4.99 (s, 2H), 4.82-4.84 (m, 1H), 4.16-4.25 (m, 2H), 3.84 (s, 3H), 2.89-2.96 (m, 1H), 2.78-2.85 (m, 1H), 2.53-2.61 (m, 1H), 2.07-2.12 (m, 1H), 1.26 (t, 3H).

(1-Methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate—Enantiomer II (20) LCMS: m/z found 461.2/463.2 [M+H]$^+$, RT=4.27 min (Method A); Chiral SFC: RT=5.13 min, Column: Chiralcel OJ-H (250 mm×4.6 mm, 5 μm); $^1$H NMR (400 MHz, DMSO-d$_6$) δ 9.40 (s, 1H), 8.43 (s, 1H), 7.92-7.94 (m, 1H), 7.54-7.59 (m, 2H), 7.36 (dd, 1H), 6.88 (s, 1H), 4.99 (s, 2H), 4.82-4.84 (m, 1H), 4.16-4.25 (m, 2H), 3.84 (s, 3H), 2.89-2.96 (m, 1H), 2.78-2.85 (m, 1H), 2.53-2.61 (m, 1H), 2.07-2.12 (m, 1H), 1.26 (t, 3H).

Example 59: (1-Methyl-1H-pyrazol-3-yl)methyl (1-((3-chloro-4-fluorophenyl) carbamoyl)-2-ethyl-2,4,5,6-tetrahydrocyclopenta[c]pyrrol-4-yl)carbamate (27, 28)

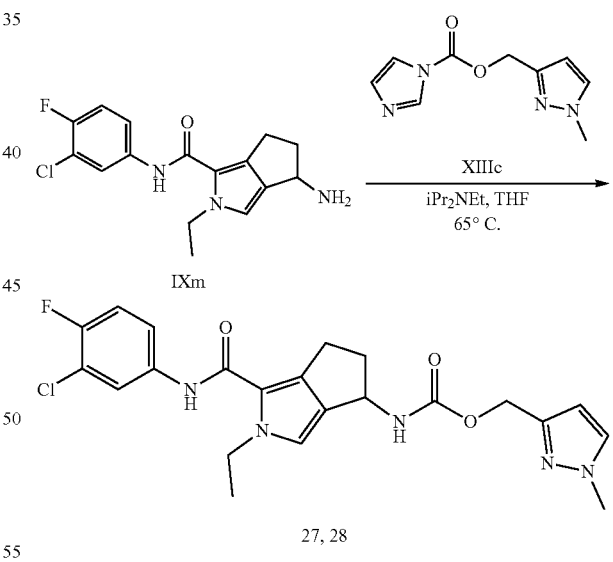

(1-Methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate was synthesized in a similar manner as described above from 4-amino-N-(3-chloro-4-fluorophenyl)-2-ethyl-2,4,5,6-tetrahydrocyclopenta[c]pyrrole-1-carboxamide (IXm) and (1-methyl-1H-pyrazol-3-yl)methyl 1H-imidazole-1-carboxylate (XIIIc) The enantiomers were subsequently separated by SFC (Waters SFC investigator. Method isocratic, Mobile phase MeOH:CO$_2$—40:60. Column: Chiralcel OJ-H (30×250 mm), 5 μm, flow rate: 60 g/min.

(1-Methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate—Enantiomer I (27) LCMS: m/z found 460.2/462.2 [M+H]$^+$, RT=4.76 min (Method A); Chiral SFC: RT=2.70 min (Chiralcel OJ-H (250 mm×4.6 mm, 5 μm); $^1$H NMR (400 MHz, DMSO-d$_6$): δ 9.40 (s, 1H), 7.91-7.94 (m, 1H), 7.63 (s, 1H), 7.54-7.59 (m, 1H), 7.45-7.48 (m, 1H), 7.36 (dd, 1H), 6.87 (s, 1H), 6.22 (s, 1H), 4.93 (s, 2H), 4.82-4.84 (m, 1H), 4.15-4.26 (m, 2H), 3.80 (s, 3H), 2.89-2.96 (m, 1H), 2.76-2.83 (m, 1H), 2.52-2.61 (m, 1H), 2.07-2.11 (m, 1H), 1.25 (t, 3H).

(1-Methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate—Enantiomer II (28) LCMS: m/z found 460.2/462.2 [M+H]$^+$, RT=4.76 min (Method A); Chiral SFC: RT=6.48 min (Chiralcel OJ-H (250 mm×4.6 mm, 5 μm); $^1$H NMR (400 MHz, DMSO-d$_6$): δ 9.40 (s, 1H), 7.91-7.94 (m, 1H), 7.63 (s, 1H), 7.54-7.59 (m, 1H), 7.45-7.48 (m, 1H), 7.36 (dd, 1H), 6.87 (s, 1H), 6.22 (s, 1H), 4.93 (s, 2H), 4.82-4.84 (m, 1H), 4.15-4.26 (m, 2H), 3.80 (s, 3H), 2.89-2.96 (m, 1H), 2.76-2.83 (m, 1H), 2.52-2.61 (m, 1H), 2.07-2.11 (m, 1H), 1.25 (t, 3H).

Example 60: N-(3-Chloro-4-fluorophenyl)-4-(cyclopropanesulfonamido)-2-ethyl-2,4,5,6-tetrahydrocyclopenta[c]pyrrole-1-carboxamide (12, 15, 16)

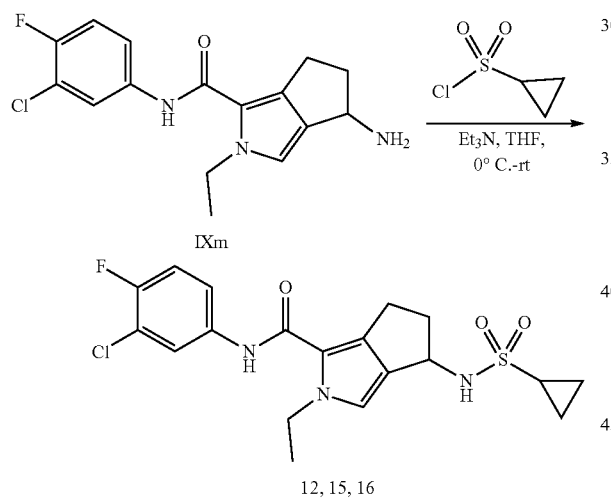

N-(3-Chloro-4-fluorophenyl)-4-(cyclopropanesulfonamido)-2-ethyl-2,4,5,6-tetrahydrocyclopenta[c]pyrrole-1-carboxamide (12) was synthesized in a similar manner as described above from 4-amino-N-(3-chloro-4-fluorophenyl)-2-ethyl-2,4,5,6-tetrahydrocyclopenta [c]pyrrole-1-carboxamide (IXm) and cyclopropane sulfonyl chloride. The enantiomers were subsequently separated by SFC (Waters SFC investigator. Method isocratic, Mobile phase MeOH:CO$_2$—30:70. Column: Chiralcel OJ-H (30×250 mm), 5 μm, flow rate: 90 g/min.

N-(3-Chloro-4-fluorophenyl)-4-(cyclopropanesulfonamido)-2-ethyl-2,4,5,6-tetrahydrocyclopenta[c]pyrrole-1-carboxamide Enantiomer I (15) LCMS: m/z found 426.2/428.2 [M+H]$^+$, RT=4.85 min (Method A); Chiral SFC: RT=3.66 min (Chiralcel OJ-H (250 mm×4.6 mm, 5 μm); $^1$H NMR (300 MHz, DMSO-d$_6$) δ 9.41 (s, 1H), 7.92-7.95 (m, 1H), 7.56-7.60 (m, 1H), 7.35-7.40 (m, 2H), 6.96 (s, 1H), 4.65-4.71 (m, 1H), 4.19-4.26 (m, 2H), 2.91-2.97 (m, 1H), 2.78-2.86 (m, 1H), 2.56-2.70 (m, 2H), 2.17-2.22 (m, 1H), 1.27 (t, 3H), 0.94-1.02 (m, 4H);

N-(3-Chloro-4-fluorophenyl)-4-(cyclopropanesulfonamido)-2-ethyl-2,4,5,6-tetrahydrocyclopenta[c]pyrrole-1-carboxamide Enantiomer II (16) LCMS: m/z found 426.2/428.2 [M+H]$^+$, RT=4.85 min (Method A); Chiral SFC: RT=4.97 min (Chiralcel OJ-H (250 mm×4.6 mm, 5 μm); $^1$H NMR (300 MHz, DMSO-d$_6$) δ 9.41 (s, 1H), 7.92-7.95 (m, 1H), 7.56-7.60 (m, 1H), 7.35-7.40 (m, 2H), 6.96 (s, 1H), 4.65-4.71 (m, 1H), 4.19-4.26 (m, 2H), 2.91-2.97 (m, 1H), 2.78-2.86 (m, 1H), 2.56-2.70 (m, 2H), 2.17-2.22 (m, 1H), 1.27 (t, 3H), 0.94-1.02 (m, 4H).

Example 61: N-(3-Chloro-4-fluorophenyl)-4-(cyclopropanecarboxamido)-2-ethyl-2,4,5,6-tetrahydrocyclopenta[c]pyrrole-1-carboxamide (17, 18)

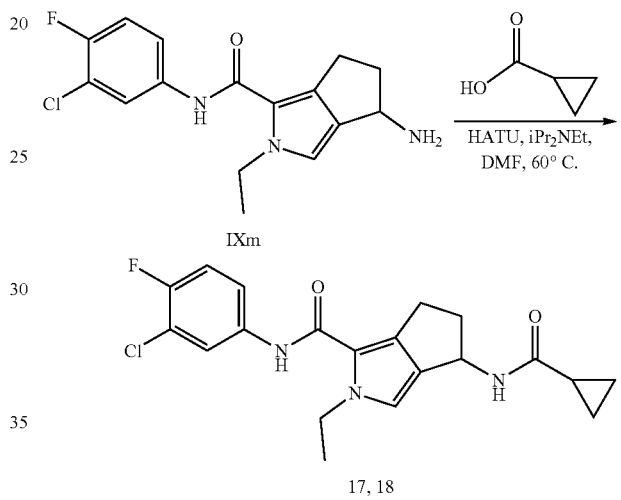

N-(3-Chloro-4-fluorophenyl)-4-(cyclopropanecarboxamido)-2-ethyl-2,4,5,6-tetrahydrocyclopenta[c]pyrrole-1-carboxamide was synthesized in a similar manner as described above from 4-amino-N-(3-chloro-4-fluorophenyl)-2-ethyl-2,4,5,6-tetrahydrocyclopenta [c]pyrrole-1-carboxamide (IXm) and cyclopropane carboxylic acid. The enantiomers were subsequently separated by SFC (Waters SFC investigator. Method isocratic, Mobile phase MeOH:CO$_2$—15:85. Column: Chiralcel OJ-H (30×250 mm), 5 μm, flow rate: 90 g/min.

N-(3-Chloro-4-fluorophenyl)-4-(cyclopropanecarboxamido)-2-ethyl-2,4,5,6-tetrahydrocyclopenta[c]pyrrole-1-carboxamide Enantiomer I (17) LCMS: m/z found 390.2/392.3 [M+H]$^+$, RT=4.62 min (Method A); Chiral SFC: RT=2.58 min (Chiralcel OJ-H (250 mm×4.6 mm, 5 μm); $^1$H NMR (400 MHz, DMSO-d$_6$) δ 9.41 (s, 1H), 8.31 (d, 1H), 7.93-7.96 (m, 1H), 7.56-7.60 (m, 1H), 7.37 (dd, 1H), 6.89 (s, 1H), 5.00-5.05 (m, 1H), 4.15-4.28 (m, 2H), 2.93-2.98 (m, 2H), 2.50-2.67 (m, 1H), 2.03-2.08 (m, 1H), 1.53-1.58 (m, 1H), 1.26 (t, 3H), 0.61-0.69 (m, 4H).

N-(3-Chloro-4-fluorophenyl)-4-(cyclopropanecarboxamido)-2-ethyl-2,4,5,6-tetrahydro cyclopenta[c]pyrrole-1-carboxamide Enantiomer II (18) LCMS: m/z found 390.2/392.3 [M+H]$^+$, RT=4.62 min (Method A); Chiral SFC: RT=3.79 min (Chiralcel OJ-H (250 mm×4.6 mm, 5 μm); $^1$H NMR (400 MHz, DMSO-d$_6$) δ 9.41 (s, 1H), 8.31 (d, 1H), 7.93-7.96 (m, 1H), 7.56-7.60 (m, 1H), 7.37 (dd, 1H), 6.89 (s, 1H), 5.00-5.05 (m, 1H), 4.15-4.28 (m, 2H), 2.93-2.98 (m, 2H), 2.50-2.67 (m, 1H), 2.03-2.08 (m, 1H), 1.53-1.58 (m, 1H), 1.26 (t, 3H), 0.61-0.69 (m, 4H).

Example 62: Methyl 1-(3-chloro-4-fluorophenylcarbamoyl)-2,4,5,6-tetrahydrocyclopenta[c]pyrrol-4-ylcarbamate (9)

1-Bromo-2-tosyl-5,6-dihydrocyclopenta[c]pyrrol-4(2H)-one (Vc)

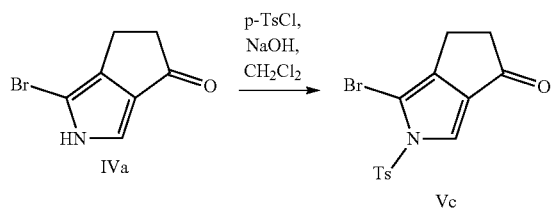

To a solution of 3.0 g (15.0 mmol, 1.0 eq.) of 1-bromo-5,6-dihydrocyclopenta[c]pyrrol-4(2H)-one (IVa) in 30 mL of anhydrous methylene chloride at 0° C. was added 1.2 g (30.0 mmol, 2.0 eq.) of sodium hydroxide followed by 3.1 g (16.5 mmol, 1.1 eq.) of p-toluene sulphonyl chloride. The mixture was allowed to warm to room temperature and stirred for 2 h. The solvent was removed in vacuo and the residue was diluted with 100 mL of water and extracted with 2×250 mL of methylene chloride. The combined organic extracts were washed with 100 mL of water, 100 mL of brine dried ($Na_2SO_4$), filtered and the solvent was removed in vacuo. The residue was purified by flash chromatography (eluting with a linear gradient of 0-30% ethyl acetate/petroleum ether) to provide 3.0 g (8.4 mmol, 56%) of 1-bromo-2-tosyl-5,6-dihydrocyclopenta[c]pyrrol-4(2H)-one (Vc). LCMS: m/z found 354.2/356.2 [M+H]; $^1$H NMR (500 MHz, $CDCl_3$) δ 7.85-7.88 (m, 3H), 7.35-7.37 (m, 2H), 2.45 (s, 3H), 2.72-2.75 (m, 2H), 2.81-2.85 (m, 2H).

Ethyl 4-oxo-2-tosyl-2,4,5,6-tetrahydrocyclopenta[c]pyrrole-1-carboxylate (VIc)

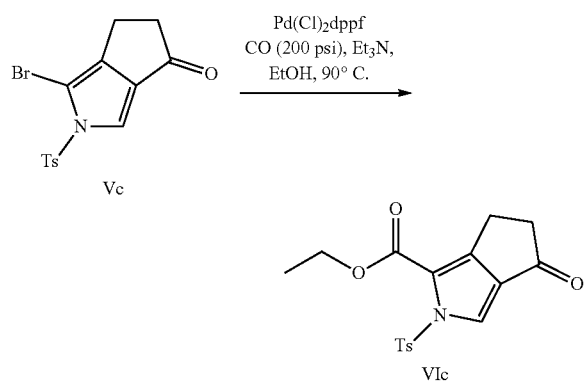

To a solution of 3.0 g (8.4 mmol, 1.0 eq.) of 1-bromo-2-tosyl-5,6-dihydrocyclopenta[c]pyrrol-4(2H)-one (Vc) in 30 mL of ethanol in a steel pressure vessel was added 2.5 g (25 mmol, 3.0 eq.) of triethylamine. The mixture was degassed with argon gas for 10 min and 1.2 g (1.6 mmol, 0.2 eq.) of $Pd(Cl)_2$ dppf was added. The mixture was degassed with argon gas for a further 10 min and the mixture was then stirred under 150 psi of carbon monoxide gas 90° C. for 16 h. The mixture was allowed to cool to room temperature and the volatiles were removed in vacuo. The residue was suspended in 50 mL of water and extracted with 2×250 mL of ethyl acetate. The combined organics extracts were washed with 100 mL of water, 100 mL of brine, dried ($Na_2SO_4$), filtered and the solvent was removed in vacuo. The residue was purified by flash chromatography (eluting with a linear gradient of 0-10% ethyl acetate/petroleum ether) to provide 2.0 g (5.7 mmol, 68%) of ethyl 4-oxo-2-tosyl-2,4,5,6-tetrahydrocyclopenta[c]pyrrole-1-carboxylate (VIc). LCMS: m/z found 348.2 [M+H]$^+$; $^1$H NMR (500 MHz, $CDCl_3$): δ 8.05 (s, 1H), 7.92 (d, 2H), 7.33-7.35 (d, 2H), 4.22 (q, 2H), 3.05-3.08 (m, 2H), 2.84 (m, 2H), 2.44 (s, 3H), 1.29 (t, 3H).

N-(3-Chloro-4-fluorophenyl)-4-oxo-2-tosyl-2,4,5,6-tetrahydrocyclopenta[c]pyrrole-1-carboxamide (VIIId)

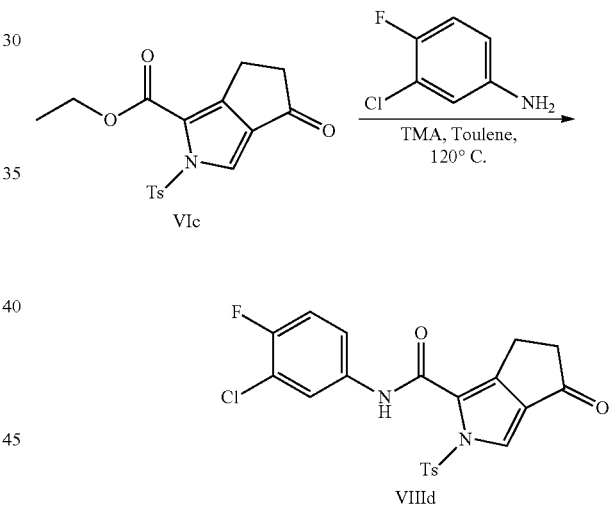

To a solution of 1.0 g (2.89 mmol, 1.0 eq.) of ethyl 4-oxo-2-tosyl-2,4,5,6-tetrahydrocyclopenta [c]pyrrole-1-carboxylate (VIc) in 10 mL of toluene was added 0.63 g (4.3 mmol, 1.5 eq.) of 3-chloro-4-fluoroaniline followed by 3.6 mL (7.2 mmol, 2.5 eq.) of a 2 M trimethyl aluminum in toluene and the mixture was heated at 110° C. for 16 h. The mixture was allowed to cool to room temperature, quenched with 50 mL of cold water and extracted with 2×100 mL of ethyl acetate. The combined organic extracts were washed with 50 mL of water, 50 mL of brine, dried ($Na_2SO_4$), filtered and the solvent was removed in vacuo. The residue was purified by semi preparative HPLC to provide 0.30 g (24%, 0.66 mmol) of N-(3-chloro-4-fluorophenyl)-4-oxo-2-tosyl-2,4,5,6-tetrahydrocyclopenta[c]pyrrole-1-carboxamide (VIIId). LCMS: m/z found 448.1/450.1 [M+H]$^+$, RT=2.29 min.

4-Amino-N-(3-chloro-4-fluorophenyl)-2-tosyl-2,4,5,6-tetrahydrocyclopenta[c]pyrrole-1-carboxamide (IXn)

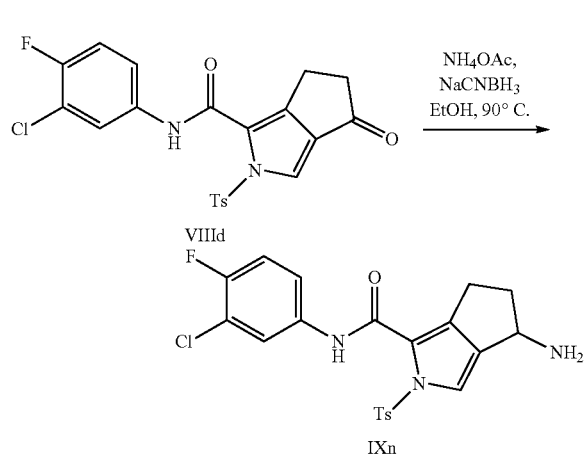

To a solution of 0.1 g (0.22 mmol, 1.0 eq.) of N-(3-chloro-4-fluorophenyl)-4-oxo-2-tosyl-2,4,5,6-tetrahydrocyclopenta[c]pyrrole-1-carboxamide (VIIId) in 10 mL of ethanol was added 0.29 g (4.4 mmol, 20.0 eq.) of ammonium acetate followed by 0.34 g (0.44 mmol, 2.0 eq.) of sodium cyanoborohydride. The mixture was then heated to 90° C. for 16 h. The solvent was removed in vacuo and the residue was resuspended in 20 mL of water and extracted with 2×50 mL of ethyl acetate. The combined organic extracts were washed with 50 mL of water, 50 mL of brine, dried (Na$_2$SO$_4$) and the solvent was removed in vacuo to provide 0.1 g (0.22 mmol) of 4-amino-N-(3-chloro-4-fluorophenyl)-2-tosyl-2,4,5,6-tetrahydrocyclopenta[c]pyrrole-1-carboxamide (IXn).

Methyl 1-(3-chloro-4-fluorophenylcarbamoyl)-2-tosyl-2,4,5,6-tetrahydrocyclopenta [c]pyrrol-4-ylcarbamate (Xc)

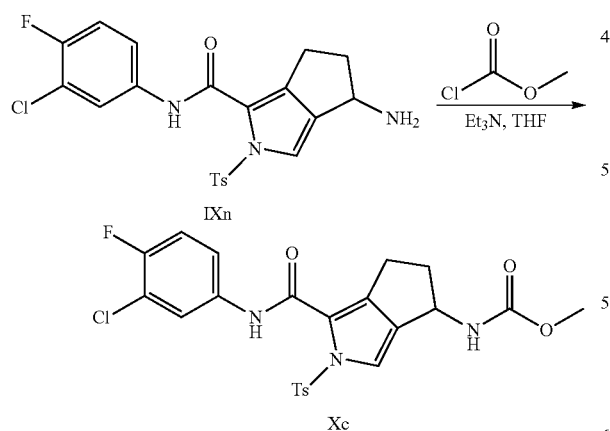

Methyl 1-(3-chloro-4-fluorophenylcarbamoyl)-2,4,5,6-tetrahydrocyclopenta[c]pyrrol-4-ylcarbamate (Xc) was synthesized in a similar manner as described above from 4-amino-N-(3-chloro-4-fluorophenyl)-2-tosyl-2,4,5,6-tetrahydrocyclopenta[c]pyrrole-1-carboxamide (IXn) and methyl chloroformate.

Methyl 1-(3-chloro-4-fluorophenylcarbamoyl)-2,4,5,6-tetrahydrocyclopenta[c]pyrrol-4-ylcarbamate (9)

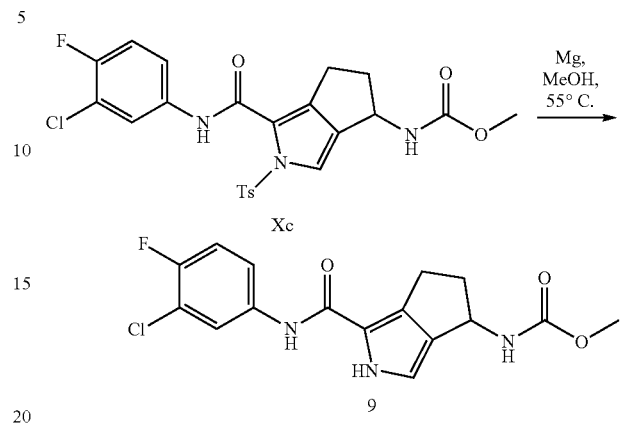

To a solution 0.09 g (0.17 mmol, 1.0 eq.) of methyl 1-(3-chloro-4-fluorophenyl carbamoyl)-2-tosyl-2,4,5,6-tetrahydrocyclopenta[c]pyrrol-4-ylcarbamate (Xc) in 10 mL of methanol was added 0.04 g (1.7 mmol, 10.0 eq.) of magnesium metal. The mixture was degassed with argon gas for 15 min and then heated at 50° C. for 16 h. The mixture was allowed to cool to room temperature and was filter through CELITE®. The pad was wash with 20 mL of methanol and the solvent was removed in vacuo. The residue was purified by semi-preparative HPLC to methyl 1-(3-chloro-4-fluorophenylcarbamoyl)-2,4,5,6-tetrahydrocyclopenta[c]pyrrol-4-ylcarbamate (9). $^1$H NMR (400 MHz, DMSO-d$_6$) δ 9.31 (m, 1H), 8.53 (s, 1H), 7.87 (dd, 1H), 7.56-7.60 (m, 1H), 7.35-7.39 (m, 2H), 6.74 (d, 1H), 4.80-4.81 (m, 1H), 3.53 (s, 3H), 2.76-2.79 (m, 1H), 2.66-2.67 (m, 1H), 2.60-2.63 (m, 1H), 2.27-2.33 (m, 1H).

Example 63: N-(3-Chloro-4-fluorophenyl)-4-(3-methylureido)-2,4,5,6-tetrahydrocyclopenta[c]pyrrole-1-carboxamide (8, 10, 11)

N-(3-Chloro-4-fluorophenyl)-4-(3-methylureido)-2-tosyl-2,4,5,6-tetrahydrocyclopenta [c]pyrrole-1-carboxamide (Xd)

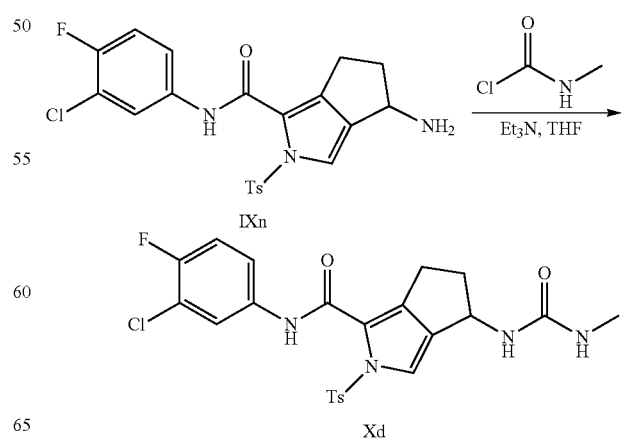

N-(3-Chloro-4-fluorophenyl)-4-(3-methylureido)-2-to-syl-2,4,5,6-tetrahydrocyclopenta [c]pyrrole-1-carboxamide (Xd) was synthesized in a similar manner as described above from 4-amino-N-(3-chloro-4-fluorophenyl)-2-tosyl-2,4,5,6-tetrahydrocyclopenta[c]pyrrole-1-carboxamide (IXn) and N-methyl carbamoyl chloride.

N-(3-Chloro-4-fluorophenyl)-4-(3-methylureido)-2,4,5,6-tetrahydrocyclopenta[c]pyrrole-1-carboxamide (8, 10, 11)

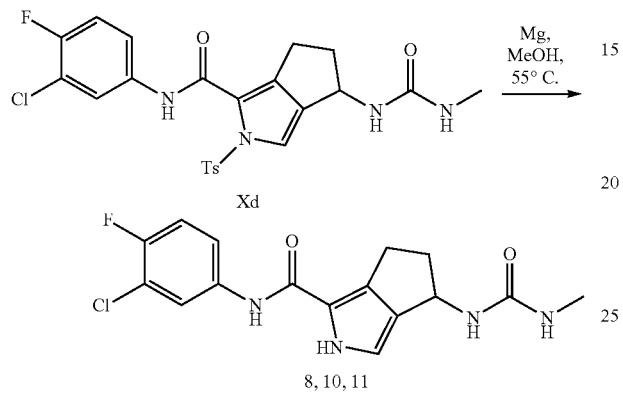

To a solution of 0.15 g (0.30 mmol, 1.0 eq.) of N-(3-chloro-4-fluorophenyl)-4-(3-methylureido)-2-tosyl-2,4,5,6-tetrahydrocyclopenta[c]pyrrole-1-carboxamide (Xd) in 10 mL of methanol was added 0.07 g (2.97 mmol, 10 eq.) of magnesium metal. The mixture was degassed with argon gas for 15 minutes and then heated to 50° C. for 16 h. The mixture was allowed to cool to room temperature and filtered through CELITE®. The pad was wash with 20 mL of methanol and the solvent was removed in vacuo. The residue was subsequently purified by semi-preparative HPLC to provide racemic N-(3-chloro-4-fluorophenyl)-4-(3-methylureido)-2,4,5,6-tetrahydrocyclopenta[c]pyrrole-1-carboxamide (8). LCMS: m/z found 351.2/353.2 [M+H]$^+$, RT=5.84 min (Method A); HPLC: RT=5.84 min (Method B); $^1$H NMR (400 MHz, DMSO-d$_6$) δ11.31 (s, 1H), 9.30 (s, 1H), 7.96-7.98 (m, 1H), 7.56-7.60 (m, 1H), 7.35-7.40 (m, 1H), 6.74 (d, 1H), 6.03 (d, 1H), 5.58 (d, 1H), 4.83-4.88 (m, 1H), 2.89-2.94 (m, 1H), 2.74-2.82 (m, 1H), 2.54-2.55 (m, 4H), 1.99-2.00 (m, 1H).

The enantiomers were subsequently separated by SFC (Waters SFC investigator. Method isocratic, Mobile phase MeOH:CO$_2$ 15:85. Column: Chiralcel OJ-H (30×250 mm, 5 μm), flow rate: 90 g/min.

N-(3-Chloro-4-fluorophenyl)-4-(3-methylureido)-2,4,5,6-tetrahydrocyclopenta[c]pyrrole-1-carboxamide—Enantiomer I (10) LCMS: m/z found 351.2/353.2 [M+H]$^+$, RT=5.84 min (Method A); Chiral SFC: RT=2.25 min, Chiralcel OJ-H (250 mm×4.6 mm, 5 μm); HPLC: RT=5.84 min (Method B); $^1$H NMR (400 MHz, DMSO-d$_6$): δ11.31 (s, 1H), 9.30 (s, 1H), 7.96-7.98 (m, 1H), 7.56-7.60 (m, 1H), 7.35-7.40 (m, 1H), 6.74 (d, 1H), 6.03 (d, 1H), 5.58 (d, 1H), 4.83-4.88 (m, 1H), 2.89-2.94 (m, 1H), 2.74-2.82 (m, 1H), 2.54-2.55 (m, 4H), 1.99-2.00 (m, 1H).

N-(3-Chloro-4-fluorophenyl)-4-(3-methylureido)-2,4,5,6-tetrahydrocyclopenta[c]pyrrole-1-carboxamide Enantiomer II (11) LCMS: m/z found 351.2/353.2 [M+H]$^+$, RT=5.84 min (Method A); Chiral SFC: RT=3.30 min, Chiralcel OJ-H (250 mm×4.6 mm, 5 μm); HPLC: RT=5.84 min (Method B); $^1$H NMR (400 MHz, DMSO-d$_6$): δ11.31 (s, 1H), 9.30 (s, 1H), 7.96-7.98 (m, 1H), 7.56-7.60 (m, 1H), 7.35-7.40 (m, 1H), 6.74 (d, 1H), 6.03 (d, 1H), 5.58 (d, 1H), 4.83-4.88 (m, 1H), 2.89-2.94 (m, 1H), 2.74-2.82 (m, 1H), 2.54-2.55 (m, 4H), 1.99-2.00 (m, 1H).

Example 64: N-(3-Chloro-4-fluorophenyl)-2-methyl-4-oxo-4,5,6,7-tetrahydro-2H-isoindole-1-carboxamide (45, VIIId)

2,5,6,7-Tetrahydro-4H-isoindol-4-one (IIIb)

To a stirred suspension of 3.4 g (85.0 mmol, 1.6 eq.) of a 60% dispersion of sodium hydride in mineral oil in 80 mL of 3:1 (v/v) diethyl ether:DMSO was added a solution of 5.0 g (52.2 mmol, 1.0 eq.) of cyclohex-2-en-1-one and 11.5 g (59.0 mmol, 1.1 eq.) of p-tolylsulfonyl) methyl isocyanide in 80 mL of 3:1 (v/v) diethyl ether:DMSO over approximately 20 min. The mixture was then stirred at room temperature for 16 h. The solvent was removed in vacuo and the residue was purified by flash chromatography (SiO$_2$, eluting with a linear gradient of 20-35% ethyl acetate/petroleum ether) to provide 2.6 g (19.25 mmol, 23%) of 2,5,6,7-tetrahydro-4H-isoindol-4-one (IIIb). $^1$H NMR (300 MHz, CDCl$_3$) δ 8.83 (bs, 1H), 7.36-7.39 (m, 1H), 6.55-6.58 (m, 1H), 2.72 (t, 2H), 2.49 (t, 2H), 2.03-2.11 (m, 2H).

1-Bromo-2,5,6,7-tetrahydro-4H-isoindol-4-one (IVb)

To a solution of 2.0 g (14.8 mmol, 1.0 eq.) of 2,5,6,7-tetrahydro-4H-isoindol-4-one (Mb) in 60 mL of anhydrous THF at −78° C. under a nitrogen atmosphere, was added a solution of 2.64 g (14.8 mmol, 1.0 eq.) of N-bromosuccinimide in 60 ml of THF over approximately 30 min. The mixture was stirred at −78° C. for an additional 2 h and then quenched 50 mL of ice-cold water. The mixture was then extracted with 3×50 mL of ethyl acetate and the combined organic extracts dried (Na$_2$SO$_4$), filtered and the solvent was removed in vacuo. The residue was purified by flash chromatography (SiO$_2$, eluting with a linear gradient of 20% ethyl acetate in methylene chloride) to provide 1.8 g (8.4 mmol, 56%) of 1-bromo-2,5,6,7-tetrahydro-4H-isoindol-4-one (IVb). $^1$H NMR (300 MHz, DMSO-d$_6$) δ 12.17 (bs, 1H), 7.36 (s, 1H), 2.47-2.51 (m, 2H), 2.31-2.36 (m, 2H), 1.90-

1.98 (m, 2H). The above reaction was performed in multiple batches with comparable results.

1-Bromo-2-methyl-2,5,6,7-tetrahydro-4H-isoindol-4-one (Vd)

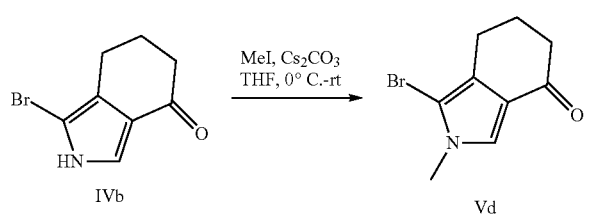

To a solution of 8.0 g (37.7 mmol, 1.0 eq.) of 1-bromo-2,5,6,7-tetrahydro-4H-isoindol-4-one (IVb) in 80 mL of THF at 0° C. under a nitrogen atmosphere was added 24.5 g (75.47 mmol, 2.0 eq.) of cesium carbonate followed by 8.0 g (56.6 mmol, 1.5 eq) of iodomethane. The mixture was allowed to warm to room temperature and stirred for 16 h. The mixture was poured into 100 mL of ice-cold water and extracted with 3×100 mL of ethyl acetate. The combined organic extracts were dried ($Na_2SO_4$), filtered and the solvent was removed in vacuo. The residue was purified by flash chromatography ($SiO_2$, eluting with 25% ethyl acetate/petroleum ether) to provide 7.0 g (30.7 mmol, 81%) of 1-bromo-2-methyl-2,5,6,7-tetrahydro-4H-isoindol-4-one (Vd). LCMS: m/z found 228.3/230.3 [M+H]$^+$; $^1$H NMR (400 MHz, DMSO-$d_6$) δ 7.54 (s, 1H), 3.60 (s, 3H), 2.47-2.51 (m 2H), 2.31-2.35 (m, 2H), 1.92-1.97 (m, 2H).

Ethyl 2-methyl-4-oxo-4,5,6,7-tetrahydro-2H-isoindole-1-carboxylate (VId)

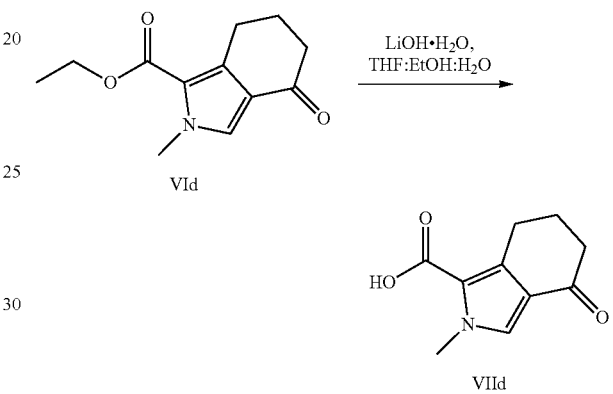

A solution of 1.0 g (4.38 mmol, 1.0 eq.) of 1-bromo-2-methyl-2,5,6,7-tetrahydro-4H-isoindol-4-one (Vd) in 10 mL of ethanol in a steel pressure vessel was degassed with argon for 10 min and 1.8 mL (13.14 mmol, 3.0 eq.) of triethylamine was added. Degassing was continued for a further 5 min and 0.1 g (0.44 mmol, 0.1 eq.) of palladium(II)acetate and 0.27 g (0.657 mmol, 0.15 eq.) of 1,3-bis(diphenylphosphino)propane were added. The mixture was degassed with argon for an additional 10 min and then stirred under 200 psi of carbon monoxide at 110° C. for 16 h. The mixture was allowed to cool to room temperature and filtered through CELITE®. The pad was washed with 20 mL of ethanol and the filtrate was concentrated in vacuo. The residue was purified by flash chromatography ($SiO_2$, eluting with linear gradient of 25-30% ethyl acetate in petroleum ether) to provide 0.7 g (3.17 mmol, 72%) of ethyl 2-methyl-4-oxo-4,5,6,7-tetrahydro-2H-isoindole-1-carboxylate (VId). LCMS: m/z found 222.3 [M+H]$^+$; $^1$H NMR (400 MHz, $CDCl_3$) δ 7.34 (s, 1H), 4.31 (q, 2H), 3.93 (s, 3H), 2.96-2.99 (m 2H), 2.45-2.49 (m, 2H), 2.04-2.11 (m, 2H), 1.38 (s, 3H). The above reaction was performed in multiple batches with comparable results.

2-Methyl-4-oxo-4,5,6,7-tetrahydro-2H-isoindole-1-carboxylic acid (VIId)

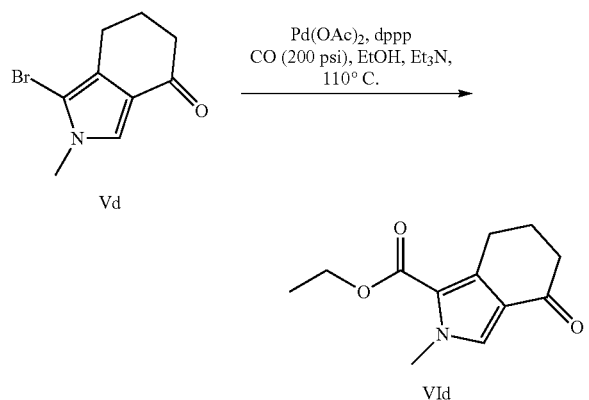

To a solution of 8.0 g (36.2 mmol, 1.0 eq.) of ethyl 2-methyl-4-oxo-4,5,6,7-tetrahydro-2H-isoindole-1-carboxylate (VId) in 50 mL of 2:2:1 (v/v/v) THF:ethanol:water was added 15.0 g (36.2 mmol, 10.0 eq.) of lithium hydroxide monohydrate and the mixture was stirred at room temperature for 16 h. The solvent was removed in vacuo and the residue was resuspended in 50 mL of water and washed with 30 mL of ethyl acetate. The aqueous phase was acidified with 20 mL of 3 M aqueous HCl and the resulting precipitated was collected by filtration. The solids were washed with 30 mL of diethyl ether and dried under high vacuum to provide 5.5 g (28.5 mmol, 78%) of 2-methyl-4-oxo-4,5,6,7-tetrahydro-2H-isoindole-1-carboxylic acid (VIId). LCMS: m/z found 194.25 [M+H]$^+$.

N-(3-Chloro-4-fluorophenyl)-2-methyl-4-oxo-4,5,6,7-tetrahydro-2H-isoindole-1-carboxamide (45, VIIIe)

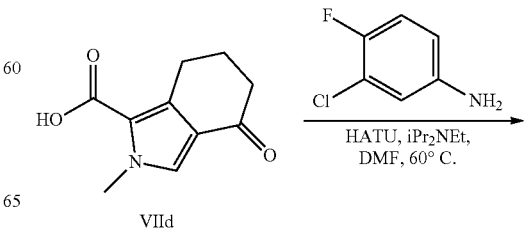

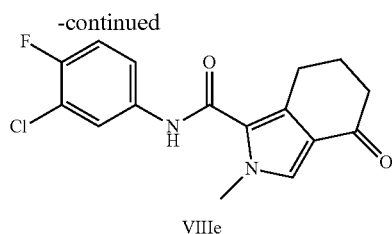

VIIIe

To a solution of 2.0 g (10.4 mmol, 1.0 eq.) of 2-methyl-4-oxo-4,5,6,7-tetrahydro-2H-isoindole-1-carboxylic acid (VIId) in 30 mL of DMF was added 4.03 g (31.1 mmol, 3.0 eq.) of N,N-diisopropylethylamine followed by 5.9 g (15.5 mmol, 1.5 eq.) of HATU. The mixture was stirred at room temperature and 1.81 g (12.4 mmol, 1.2 eq.) of 3-chloro-4-fluoroaniline was added. The mixture was then heated at 60° C. for 16 h. The mixture was allowed to cool to room temperature and diluted with 100 mL of ice-cold water. The resulting precipitate was collected by filtration, washed with 30 mL of n-pentane and dried under high vacuum. The solids were triturated with 2×30 mL of diethyl ether to provide 1.6 g (5.0 mmol, 48%) of N-(3-chloro-4-fluorophenyl)-2-methyl-4-oxo-4,5,6,7-tetrahydro-2H-isoindole-1-carboxamide (45, VIIIe). LCMS: m/z found 321.2/323.2 [M+H]$^+$, RT=5.97 min (Method A); HPLC: RT=7.70 min (Method B); $^1$H NMR (300 MHz, CDCl$_3$): δ 7.73-7.77 (m, 1H), 7.34-7.40 (m, 2H), 7.22-7.25 (m, 1H), 7.14 (dd, 1H), 3.95 (s, 3H), 2.94-2.98 (m, 2H), 2.49-2.54 (m, 2H), 2.14-2.22 (m, 2H).

Example 65: 4-Amino-N-(3-chloro-4-fluorophenyl)-2-methyl-4,5,6,7-tetrahydro-2H-isoindole-1-carboxamide (75)

4-(((R)-tert-Butylsulfinyl)amino)-N-(3-chloro-4-fluorophenyl)-2-methyl-4,5,6,7-tetrahydro-2H-isoindole-1-carboxamide (XIe)

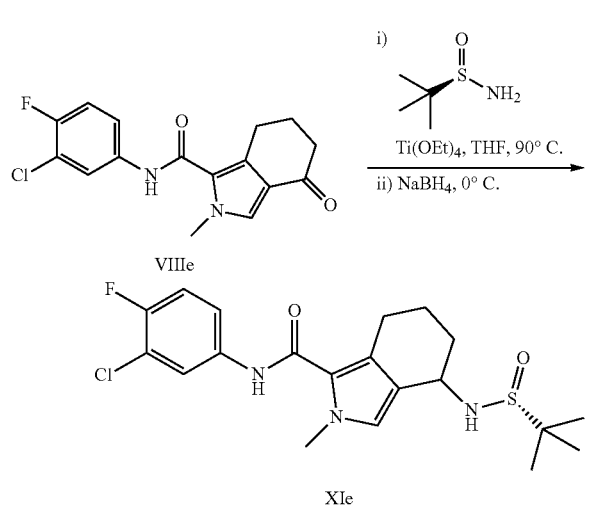

To a solution of 2.5 g (7.8 mmol, 1.0 eq.) of N-(3-chloro-4-fluorophenyl)-2-methyl-4-oxo-4,5,6,7-tetrahydro-2H-isoindole-1-carboxamide (VIIIe) in 12.5 mL of THF in a sealed tube was added 1.9 g (15.6 mmol, 2.0 eq.) of (R)-2-methylpropane-2-sulfinamide followed by 12.5 g (54.7 mmol, 7.0 eq.) of titanium tetraethoxide and the mixture was stirred at 90° C. for 48 h. The mixture was allowed to cool to room temperature, further cooled to 0° C., and 0.84 g (23.4 mmol, 3.0 eq.) of sodium borohydride was added. After stirring at 0° C. for 3 h, the mixture was poured into 70 mL of water and extracted with 3×100 mL of ethyl acetate. The combined organic extracts were washed with 100 mL of brine, dried (Na$_2$SO$_4$), filtered, and the solvent was removed in vacuo. The residue was purified by flash chromatography (SiO$_2$, eluting with a linear gradient of 40-60% ethyl acetate in petroleum ether) to provide 2.2 g (5.16 mmol, 66%) of 4-(((R)-tert-butylsulfinyl)amino)-N-(3-chloro-4-fluorophenyl)-2-methyl-4,5,6,7-tetrahydro-2H-isoindole-1-carboxamide (XIe) as an approximately 4:1 ratio of diastereoisomers. LCMS: m/z found 426.0 [M+H]$^+$, RT=2.09, 2.17 min; $^1$H NMR (300 MHz, DMSO-d$_6$): δ 9.60 (s, 1H), 7.95 (dd, 1H), 7.54-7.62 (m, 1H), 7.37 (t, 1H), 6.97 (s, 1H), 5.16 (d, 1H), 4.20-4.26 (m, 1H), 3.72 (s, 3H), 2.69-2.73 (m, 2H), 1.88-1.93 (m, 2H), 1.57-1.63 (m, 2H), 1.14 (s, 9H).

4-Amino-N-(3-chloro-4-fluorophenyl)-2-methyl-4,5,6,7-tetrahydro-2H-isoindole-1-carboxamide (75)

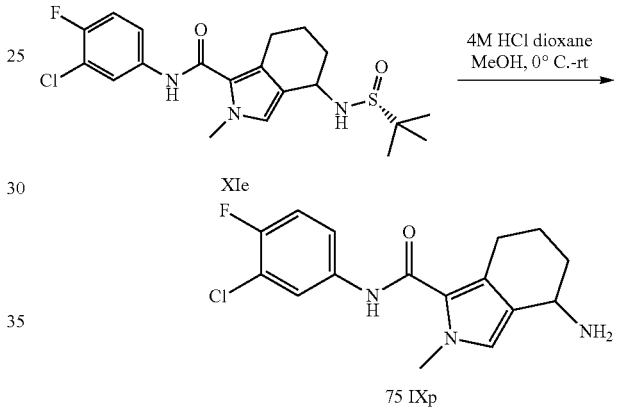

To a solution of 0.85 g (2.0 mmol, 1.0 eq) of 4-(((R)-tert-butylsulfinyl)amino)-N-(3-chloro-4-fluorophenyl)-2-methyl-4,5,6,7-tetrahydro-2H-isoindole-1-carboxamide (XIe) in 4.25 mL of methanol at 0° C. was added 1.7 mL of a 4 M solution of HCl in 1,4-dioxane. The mixture was allowed to warm to room temperature and stirred for 1 h. The solvent was removed in vacuo and the residue was triturated with 2 mL of diethyl ether and dried under high vacuum. The resulting solid was treated with 20 mL of saturated sodium bicarbonate solution for 10 min and then extracted with 3×30 mL of 10% methanol in methylene chloride. The combined organic extracts were dried (Na$_2$SO$_4$), filtered and the solvent was removed in vacuo to provide 0.56 g (1.74 mmol, 87%) of 4-amino-N-(3-chloro-4-fluorophenyl)-2-methyl-4,5,6,7-tetrahydro-2H-isoindole-1-carboxamide (IXp). Chiral SFC: 77% & 23% at RT=1.70, 3.02 min respectively (Method: Column: Chiralpak AD-H (250 mm×4.6 mm) 5 μm); The major enantiomer was subsequently isolated by chiral SFC, Method: isocratic, Mobile phase MeOH:CO$_2$—30:70. Column: Chiralpak AD-H (30×250 mm, 5 μm), flow rate: 90 g/min.

4-Amino-N-(3-chloro-4-fluorophenyl)-2-methyl-4,5,6,7-tetrahydro-2H-isoindole-1-carboxamide (75) Enantiomer I, HPLC: RT=6.44 min (Method B); Chiral SFC: RT: 2.47 min, Column Chiralpak AD-H (250×4.6 mm, 5 μm); $^1$H NMR (400 MHz, DMSO-d$_6$): δ 9.53 (s, 1H), 7.92 (m, 1H), 7.55-7.57 (m, 1H), 7.36 (t, 1H), 6.88 (s, 1H), 3.68-3.71 (m, 4H), 2.63-2.69 (m, 2H), 1.82-1.88 (m, 4H), 1.52-1.58 (m, 1H), 1.24-1.31 (m, 1H).

Example 66: Methyl (1-((3-chloro-4-fluorophenyl)carbamoyl)-2-methyl-4,5,6,7-tetrahydro-2H-isoindol-4-yl)carbamate (74)

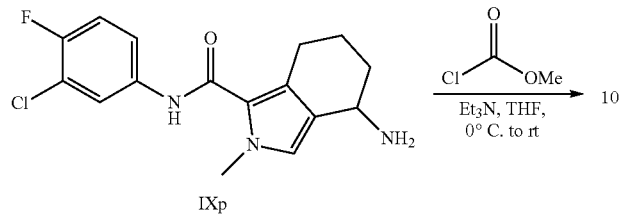

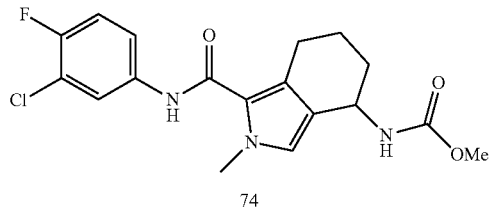

Methyl (1-((3-chloro-4-fluorophenyl)carbamoyl)-2-methyl-4,5,6,7-tetrahydro-2H-isoindol-4-yl)carbamate was synthesized in a similar manner as described above from 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) and methyl chloroformate. The major enantiomer was isolated by SFC. (Waters SFC investigator). Method: isocratic, Mobile phase MeOH:$CO_2$—20:80. Column: Chiralcel OD-H (30×250 mm, 5 µm), flow rate=70 g/min Methyl (1-((3-chloro-4-fluorophenyl)carbamoyl)-2-methyl-4,5,6,7-tetrahydro-2H-isoindol-4-yl)carbamate—Enantiomer II (74) LCMS: m/z found 380.2/382.2 [M+H]$^+$, RT=5.22 min (Method A); HPLC: RT=8.32 min (Method B); $^1$H NMR (400 MHz, DMSO-$d_6$): δ 9.60 (bs, 1H), 7.93-7.95 (m, 1H), 7.55-7.59 (m, 1H), 7.33-7.39 (m, 2H), 6.82 (s, 1H), 4.51-4.55 (m, 1H), 3.70 (s, 3H), 3.55 (s, 3H), 2.64-2.72 (m, 2H), 1.84-1.89 (m, 2H), 1.49-1.63 (m, 2H).

Example 67: (1-Methyl-1H-1,2,4-triazol-3-yl)methyl (1-((3-chloro-4-fluorophenyl) carbamoyl)-2-methyl-4,5,6,7-tetrahydro-2H-isoindol-4-yl)carbamate (33)

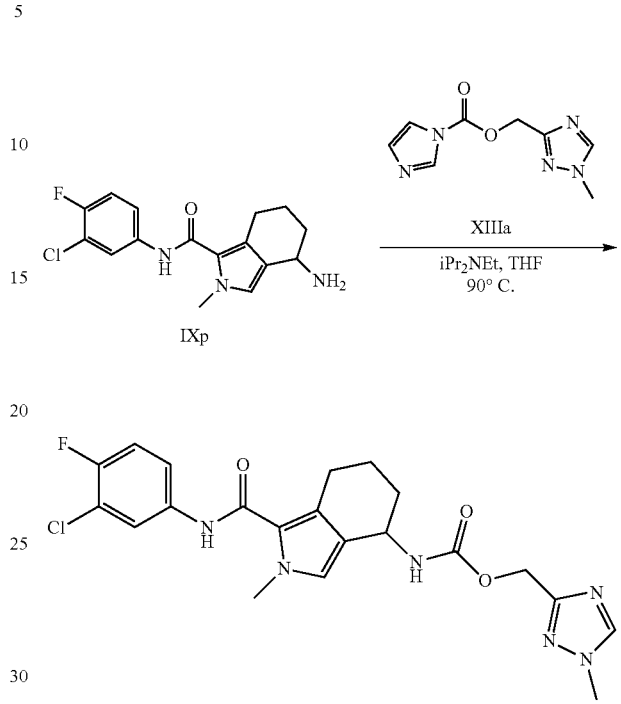

(1-Methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate was synthesized in a similar manner as described above from 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) and (1-methyl-1H-1,2,4-triazol-3-yl)methyl 1H-imidazole-1-carboxylate (XIIIa) The major enantiomer was isolated by SFC. Method: isocratic, Mobile phase MeOH:$CO_2$ 20:80. Column: Chiralcel AD-H (30×250 mm, 5 µm), flow rate=70 g/min.

(1-Methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate—Enantiomer II (33) LCMS: m/z found 461.2/463.2 [M+H]+, RT=6.83 min (Method A); HPLC: RT=7.50 min (Method B); Chiral SFC: RT=6.77 min (Column: Chiralcel AD-H (250×4.6 mm, 5 µm)); 1H NMR (400 MHz, DMSO-$d_6$): δ 9.60 (s, 1H), 8.44 (s, 1H), 7.92-7.95 (m, 1H), 7.55-7.59 (m, 1H), 7.50 (d, 1H), 7.37 (dd, 1H), 6.84 (s, 1H), 5.01 (s, 2H), 4.53-4.58 (m, 1H), 3.85 (s, 3H), 3.70 (s, 3H), 2.66-2.71 (m, 2H), 1.83-1.89 (m, 2H), 1.50-1.60 (m, 2H).

Example 68: (1H-1,2,4-Triazol-3-yl)methyl (1-((3-chloro-4-fluorophenyl)carbamoyl)-2-methyl-4,5,6,7-tetrahydro-2H-isoindol-4-yl)carbamate (88)

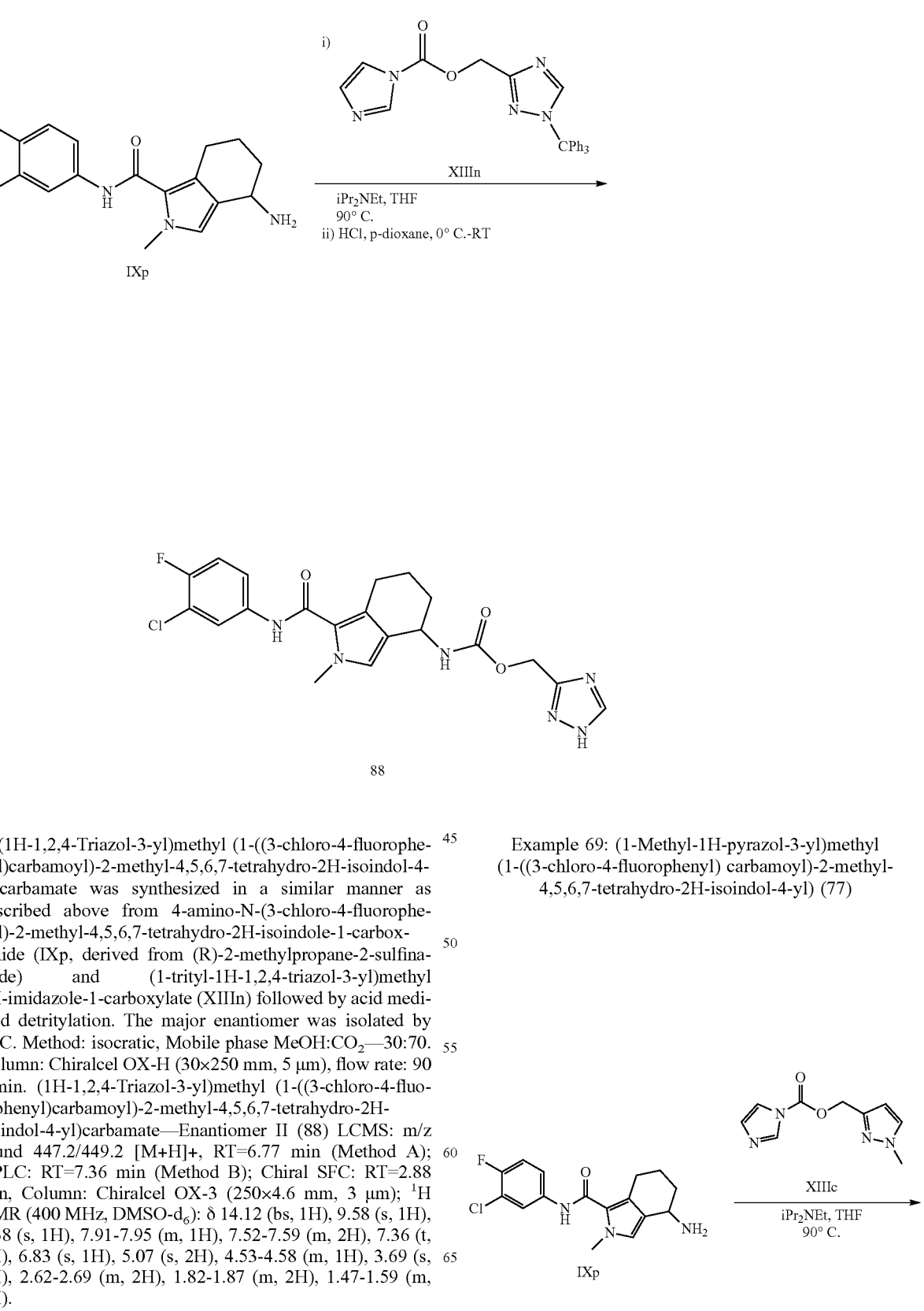

88

(1H-1,2,4-Triazol-3-yl)methyl (1-((3-chloro-4-fluorophenyl)carbamoyl)-2-methyl-4,5,6,7-tetrahydro-2H-isoindol-4-yl)carbamate was synthesized in a similar manner as described above from 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) and (1-trityl-1H-1,2,4-triazol-3-yl)methyl 1H-imidazole-1-carboxylate (XIIIn) followed by acid mediated detritylation. The major enantiomer was isolated by SFC. Method: isocratic, Mobile phase MeOH:$CO_2$—30:70. Column: Chiralcel OX-H (30×250 mm, 5 μm), flow rate: 90 g/min. (1H-1,2,4-Triazol-3-yl)methyl (1-((3-chloro-4-fluorophenyl)carbamoyl)-2-methyl-4,5,6,7-tetrahydro-2H-isoindol-4-yl)carbamate—Enantiomer II (88) LCMS: m/z found 447.2/449.2 [M+H]+, RT=6.77 min (Method A); HPLC: RT=7.36 min (Method B); Chiral SFC: RT=2.88 min, Column: Chiralcel OX-3 (250×4.6 mm, 3 μm); $^1$H NMR (400 MHz, DMSO-$d_6$): δ 14.12 (bs, 1H), 9.58 (s, 1H), 8.38 (s, 1H), 7.91-7.95 (m, 1H), 7.52-7.59 (m, 2H), 7.36 (t, 1H), 6.83 (s, 1H), 5.07 (s, 2H), 4.53-4.58 (m, 1H), 3.69 (s, 3H), 2.62-2.69 (m, 2H), 1.82-1.87 (m, 2H), 1.47-1.59 (m, 2H).

Example 69: (1-Methyl-1H-pyrazol-3-yl)methyl (1-((3-chloro-4-fluorophenyl) carbamoyl)-2-methyl-4,5,6,7-tetrahydro-2H-isoindol-4-yl) (77)

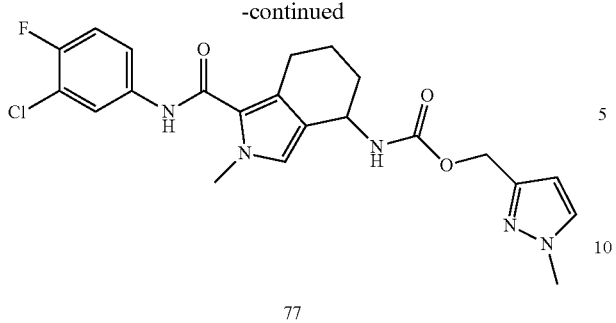

77

(1-Methyl-1H-pyrazol-3-yl)methyl(1-((3-chloro-4-fluorophenyl) carbamoyl)-2-methyl-4,5,6,7-tetrahydro-2H-isoindol-4-yl) was synthesized in a similar manner as described above from 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) and (1-methyl-1H-pyrazol-3-yl)methyl 1H-imidazole-1-carboxylate (XIIIc) The major enantiomer was isolated by SFC. Method: isocratic, Mobile phase MeOH:CO$_2$—35:65. Column: Chiralcel AD-H (30×250 mm, 5 μm), flow rate=70 g/min.

(1-Methyl-1H-pyrazol-3-yl)methyl(1-((3-chloro-4-fluorophenyl)carbamoyl)-2-methyl-4,5,6,7-tetrahydro-2H-isoindol-4-yl)carbamate—Enantiomer II (77) LCMS: m/z found 460.2/462.2 [M+H]$^+$, RT=5.40 min (Method A); HPLC: RT=8.04 min (Method B); Chiral SFC: RT: 8.03 min, Column: Chiralcel AD-H (250×4.6 mm, 5 μm); $^1$H NMR (400 MHz, DMSO-d$_6$): δ 9.58 (bs, 1H), 7.92-7.95 (m, 1H), 7.63 (d, 1H), 7.54-7.59 (m, 1H), 7.33-7.38 (m, 2H), 6.81 (s, 1H), 6.23 (d, 1H), 4.95 (s, 2H), 4.54-4.57 (m, 1H), 3.81 (s, 3H), 3.69 (s, 3H), 2.66-2.71 (m, 2H), 1.84-1.88 (m, 2H), 1.52-1.61 (m, 2H).

Example 70: N-(3-Chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide (84)

N-((1-Methyl-1H-1,2,4-triazol-3-yl)methyl)-1H-imidazole-1-carboxamide

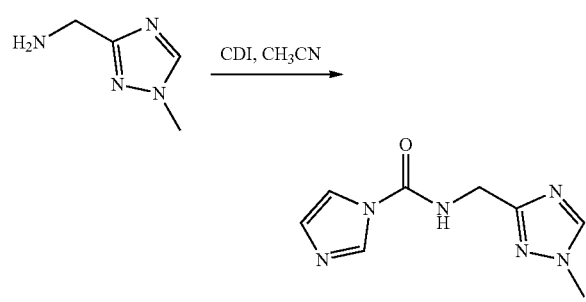

To a solution of 0.38 g (3.38 mmol, 1.0 eq.) of (1-methyl-1H-1,2,4-triazol-3-yl)methanamine in 5 mL of acetonitrile was added 0.29 g (1.75 mmol, 1.5 eq.) of 1,1'-carbonyl diimidazole and the mixture was stirred at room temperature for 2 h. The solvent was removed in vacuo and the residue was diluted with water and extracted with 3×50 mL of 5% methanol in methylene chloride. The combined organic extracts were washed with 30 mL of brine, dried (Na$_2$SO$_4$), filtered and the solvent was removed in vacuo to provide 0.27 g of N-((1-methyl-1H-1,2,4-triazol-3-yl)methyl)-1H-imidazole-1-carboxamide. LCMS: m/z found 207.2 [M+H]$^+$.

N-(3-Chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide (84)

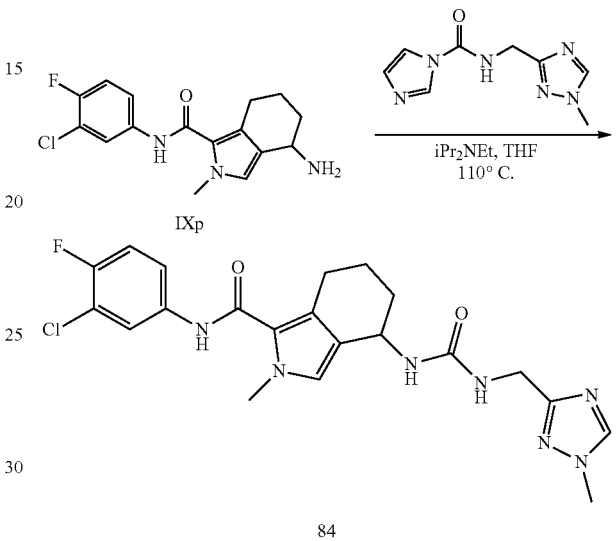

84

To a solution of 0.35 g (1.09 mmol, 1.0 eq.) of 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) in 3 mL of THF in a sealed tube was added 0.57 mL (3.27 mmol, 3.0 eq.) of N,N-diisopropylethylamine followed by a solution of 0.27 g (1.30 mmol, 1.2 eq.) of N-((1-methyl-1H-1,2,4-triazol-3-yl)methyl)-1H-imidazole-1-carboxamide in 2 mL of THF and the mixture was heated to 110° C. for 16 h. The mixture was allowed to cool to room temperature, diluted with 50 mL of water and extracted with 3×100 mL of ethyl acetate. The combined organic extracts were washed with 50 mL of brine, dried (Na$_2$SO$_4$), filtered and the solvent was removed in vacuo. The residue was purified by flash chromatography (Al$_2$O$_3$, eluting with a linear gradient of 0-3% methanol in methylene chloride) to provide 0.25 g (0.54 mmol, 49%) of N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide. The major enantiomer was isolated by SFC. Method: isocratic, Mobile phase MeOH:CO$_2$—40:60. Column: Chiralpak IA (30×250 mm, 5 μm), flow rate: 60 g/min. N-(3-Chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide Enantiomer II (84) LCMS: m/z found 460.3/462.3 [M+H]$^+$, RT=7.34 min (Method A); HPLC: RT=8.27 min (Method B); Chiral SFC: RT=5.86 min, Column: Chiralpak IA (250×4.6 mm, 5 μm); $^1$H NMR (400 MHz, DMSO-d$_6$): δ 9.56 (s, 1H), 8.37 (s, 1H), 7.92-7.95 (m, 1H), 7.55-7.59 (s, 1H), 7.36 (t, 1H), 6.83 (s, 1H), 6.12-6.16 (m, 2H), 4.60-4.64 (m, 1H), 4.24 (d, 2H), 3.82 (s, 3H), 3.70 (s, 3H), 2.65-2.71 (m, 2H), 1.74-1.90 (m, 2H), 1.57-1.66 (m, 1H), 1.42-1.49 (m, 1H).

Example 71: N-(3-Chloro-4-fluorophenyl)-4-(cyclopropanesulfonamido)-2-methyl-4,5,6,7-tetrahydro-2H-isoindole-1-carboxamide (78)

Example 72: N-(3-Chloro-4-fluorophenyl)-4-(cyclopropanecarboxamido)-2-methyl-4,5,6,7-tetrahydro-2H-isoindole-1-carboxamide (76)

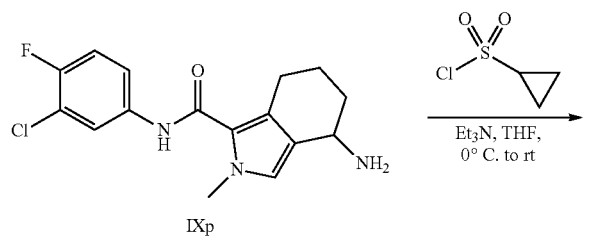

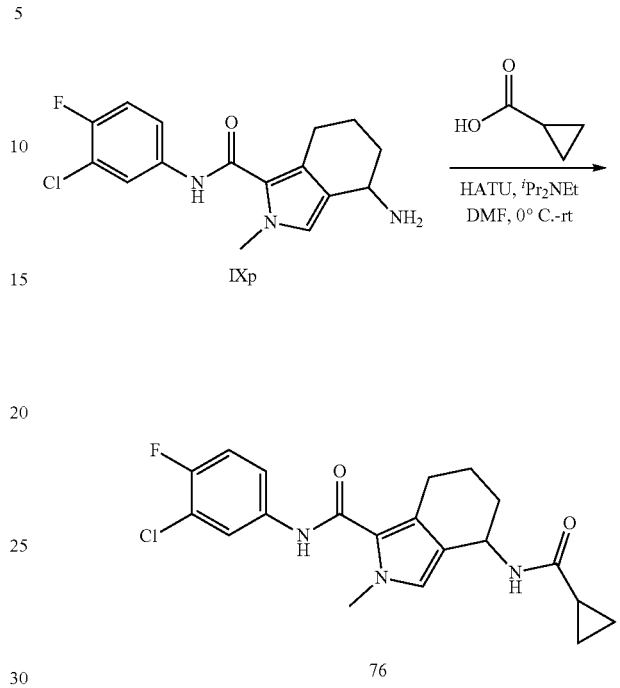

To a solution of 0.30 g (0.93 mmol 1.0 eq.) 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) in 3 mL of anhydrous THF at 0° C. was added 0.28 g (2.80 mmol, 3.0 eq.) of triethylamine followed by 0.20 g (1.40 mmol, 1.5 eq.) of cyclopropylsulfonyl chloride. The mixture was allowed to warm to room temperature and stirred for 16 h. The mixture was then diluted with 5 mL of water and extracted with 2×25 mL of ethyl acetate. The combined organic extracts were washed with 5 mL of brine, dried ($Na_2SO_4$), filtered and the solvent was removed in vacuo. The residue was purified by flash chromatography ($SiO_2$, eluting with linear gradient of 30-40% ethyl acetate in petroleum ether) to provide 0.15 g of N-(3-chloro-4-fluorophenyl)-4-(cyclopropanesulfonamido)-2-methyl-4,5,6,7-tetrahydro-2H-isoindole-1-carboxamide. The major enantiomer was subsequently isolated by SFC (Waters SFC investigator). Method isocratic, Mobile phase MeOH:$CO_2$—25:75. Column: Chiralcel OD-H (30× 250 mm), 5 µm, flow rate: 70 g/min.

N-(3-Chloro-4-fluorophenyl)-4-(cyclopropanesulfonamido)-2-methyl-4,5,6,7-tetrahydro-2H-isoindole-1-carboxamide Enantiomer II (78) LCMS: m/z found 426.3/428.3 [M+14]$^+$, RT=7.29 min (Method A); Chiral-SFC: RT=3.75 min (Chiralcel OJ-H (150 mm×4.6 mm, 5 µm); $^1$H NMR (400 MHz, DMSO-$d_6$): δ 9.60 (bs, 1H), 7.93-7.95 (m, 1H), 7.55-7.59 (m, 1H), 7.33-7.39 (m, 2H), 6.92 (s, 1H), 4.34-4.37 (m, 1H), 3.73 (s, 3H), 2.62-2.69 (m, 3H), 1.97-2.01 (m, 1H), 1.86-1.91 (m, 1H), 1.64-1.59 (m, 2H), 0.95-1.00 (m, 4H).

To a solution of 0.3 g (0.93 mmol, 1.0 eq.) of 4-amino-N-(3-chloro-4-fluorophenyl)-2-methyl-4,5,6,7-tetrahydro-2H-isoindole-1-carboxamide (IXp, derived from (R)-2-methylpropane-2-sulfinamide) in 2 mL of DMF at 0° C. under a nitrogen atmosphere was added 96 mg (1.12 mmol, 1.2 eq.) of cyclopropane carboxylic acid followed by 0.8 mL (4.67 mmol, 5.0 eq.) of N,N-diisopropylethylamine and 0.53 g (0.93 mmol, 1.5 eq.) of 1-[bis(dimethylamino)methylene]-1H-1,2,3-triazolo[4,5-b]pyridinium 3-oxid hexafluorophosphate (HATU). The reaction mixture was allowed to warm to room temperature and stirred for 16 h. The mixture was then diluted with 50 mL of ice-cold water and extracted with 2×100 mL of ethyl acetate. The combined organic extracts were washed with 50 mL of water, 50 mL of brine, dried ($Na_2SO_4$), filtered and the solvent was removed in vacuo. The residue was purified by trituration with tert-butyl methyl ether to provide 0.14 g (0.35 mmol, 38%) of N-(3-chloro-4-fluorophenyl)-4-(cyclopropanecarboxamido)-2-methyl-4,5,6,7-tetrahydro-2H-isoindole-1-carboxamide. The major enantiomer was subsequently isolated by SFC (Waters SFC investigator). Method isocratic, Mobile phase MeOH:$CO_2$ 35:65. Column: Chiralpak IG (30×250 mm, 5 µm), flow rate: 100 g/min, isolating the later eluting enantiomer.

N-(3-chloro-4-fluorophenyl)-4-(cyclopropanecarboxamido)-2-methyl-4,5,6,7-tetrahydro-2H-isoindole-1-carboxamide Enantiomer II (76) LCMS: m/z found 390.5/392.5 [M+H]$^+$, RT=7.14 min (Method A); Chiral-SFC: RT=3.38 min, Chiralcel IG-3 (150 mm×4.6 mm, 3 µm); $^1$H NMR (400 MHz, DMSO-$d_6$): δ 9.56 (s, 1H), 8.21 (d, 1H), 7.94-7.96 (m, 1H), 7.56-7.60 (m, 1H), 7.37 (t, 1H), 6.82 (s, 1H), 4.76-4.83 (m, 1H), 3.71 (s, 3H), 2.65-2.80 (m, 2H), 1.79-1.85 (m, 2H), 1.51-1.63 (m, 3H), 0.61-0.73 (m, 4H).

Example 73: Methyl (1-((3-chloro-4-fluorophenyl)carbamoyl)-2-methyl-4,5,6,7-tetrahydro-2H-isoindol-4-yl)carbamate (29)

4-((((S)-tert-Butylsulfinyl)amino)-N-(3-chloro-4-fluorophenyl)-2-methyl-4,5,6,7-tetrahydro-2H-isoindole-1-carboxamide (XIe)

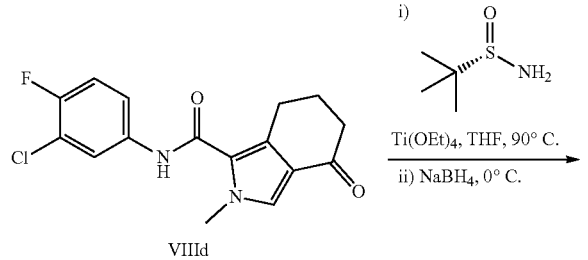

To a solution of 0.3 g (0.94 mmol, 1.0 eq.) of N-(3-chloro-4-fluorophenyl)-2-methyl-4-oxo-4,5,6,7-tetrahydro-2H-isoindole-1-carboxamide (VIIId) in 3.0 mL of THF in a sealed tube was added 0.23 g (1.87 mmol, 2.0 eq.) of (S)-2-methylpropane-2-sulfinamide followed by 1.5 g (6.58 mmol, 7.0 eq.) of titanium tetraethoxide and the mixture was stirred at 90° C. for 48 h. The mixture was allowed to cool to room temperature, further cooled to 0° C., and 100 mg (2.81 mmol, 3.0 eq.) of sodium borohydride was added. After stirring at 0° C. for 3 h, the mixture was poured into 50 mL of water and extracted with 3×50 mL of ethyl acetate. The combined organic extracts were washed with 50 mL of brine, dried ($Na_2SO_4$), filtered, and the solvent was removed in vacuo. The residue was purified by flash chromatography ($SiO_2$, eluting with a linear gradient of 40-60% ethyl acetate in petroleum ether) to provide 0.26 g (0.61 mmol, 65%) of 4-(((S)-tert-butylsulfinyl)amino)-N-(3-chloro-4-fluorophenyl)-2-methyl-4,5,6,7-tetrahydro-2H-isoindole-1-carboxamide (XIe) as an approximately 10:1 ratio of diastereoisomers. LCMS: m/z found 426.3/428.3 [M+14]$^+$, RT=2.13, 2.20 min; $^1$H NMR (300 MHz, DMSO-$d_6$): δ 7.72-7.74 (m, 1H), 7.32-7.36 (m, 1H), 7.24-7.26 (m, 1H), 7.10 (t, 1H), 7.00 (s, 1H), 4.44-4.47 (m, 1H), 3.77 (s, 3H), 3.20-3.22 (m, 1H), 2.78-2.80 (m, 2H), 1.96-2.01 (m, 2H), 1.76-1.87 (m, 2H), 1.21 (s, 9H).

4-Amino-N-(3-chloro-4-fluorophenyl)-2-methyl-4,5,6,7-tetrahydro-2H-isoindole-1-carboxamide (IXp)

To a solution of 0.26 g (0.61 mmol, 1.0 eq.) of 4-(((S)-tert-butylsulfinyl)amino)-N-(3-chloro-4-fluorophenyl)-2-methyl-4,5,6,7-tetrahydro-2H-isoindole-1-carboxamide (XIe) in 5 mL of methanol at 0° C. was added 0.5 mL of a 4 M solution of HCl in 1,4-dioxane. The mixture was allowed to warm to room temperature and stirred for 1 h. The solvent was removed in vacuo and the residue was triturated with 2 mL of diethyl ether and dried under high vacuum. The resulting solid was treated with 10 mL of saturated sodium bicarbonate solution for 10 min and then extracted with 3×20 mL of 10% methanol in methylene chloride. The combined organic extracts were dried ($Na_2SO_4$), filtered and the solvent was removed in vacuo to provide 0.20 g (0.55 mmol, 90%) of 4-amino-N-(3-chloro-4-fluorophenyl)-2-methyl-4,5,6,7-tetrahydro-2H-isoindole-1-carboxamide. $^1$H NMR (400 MHz, DMSO-$d_6$): δ 9.53 (s, 1H), 7.92 (m, 1H), 7.55-7.57 (m, 1H), 7.36 (t, 1H), 6.88 (s, 1H), 3.68-3.71 (m, 4H), 2.63-2.69 (m, 2H), 1.82-1.88 (m, 4H), 1.52-1.58 (m, 1H), 1.24-1.31 (m, 1H).

Methyl (1-((3-chloro-4-fluorophenyl)carbamoyl)-2-methyl-4,5,6,7-tetrahydro-2H-isoindol-4-yl)carbamate (29)

Methyl (1-((3-chloro-4-fluorophenyl)carbamoyl)-2-methyl-4,5,6,7-tetrahydro-2H-isoindol-4-yl)carbamate was synthesized in a similar manner as described above from 4-amino-N-(3-chloro-4-fluorophenyl)-2-methyl-4,5,6,7-tetrahydro-2H-isoindole-1-carboxamide (IXp, derived from (S)-2-methylpropane-2-sulfinamide) and methyl chloroformate. The major enantiomer was isolated by SFC. (Waters SFC investigator). Method: isocratic, Mobile phase MeOH:CO$_2$—20:80. Column: Chiralcel OD-H (30×250 mm, 5 μm), flow rate: 70 g/min. Methyl (1-((3-chloro-4-fluorophenyl)carbamoyl)-2-methyl-4,5,6,7-tetrahydro-2H-isoindol-4-yl)carbamate—Enantiomer I (29) LCMS: m/z found 380.2/382.2 [M+H]$^+$, RT=5.22 min (Method A); HPLC: RT=8.32 min (Method B); Chiral SFC: RT: 2.47 min, Column: Chiralcel OD-H (250×4.6 mm, 5 μm); $^1$H NMR (400 MHz, DMSO-d$_6$): δ 9.60 (bs, 1H), 7.93-7.95 (m, 1H), 7.55-7.59 (m, 1H), 7.33-7.39 (m, 2H), 6.82 (s, 1H), 4.51-4.55 (m, 1H), 3.70 (s, 3H), 3.55 (s, 3H), 2.64-2.72 (m, 2H), 1.84-1.89 (m, 2H), 1.49-1.63 (m, 2H).

Example 74: (1-Methyl-1H-1,2,4-triazol-3-yl)methyl (1-((3-chloro-4-fluorophenyl) carbamoyl)-2-methyl-4,5,6,7-tetrahydro-2H-isoindol-4-yl)carbamate (32)

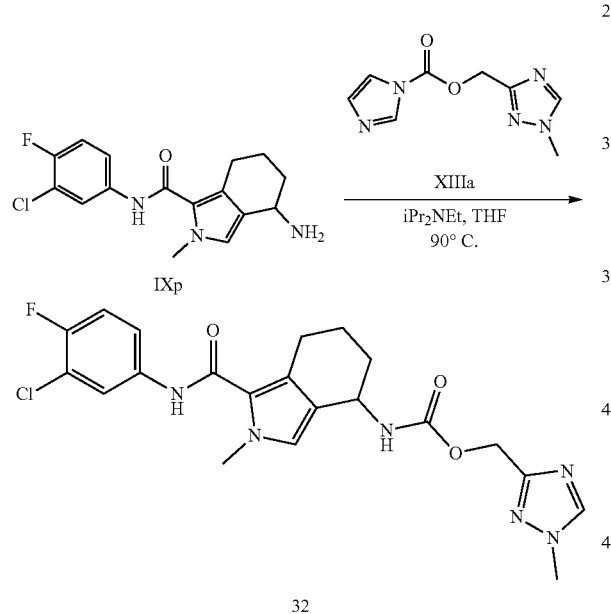

(1-Methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate was synthesized in a similar manner as described above from 4-amino-N-(3-chloro-4-fluorophenyl)-2-methyl-4,5,6,7-tetrahydro-2H-isoindole-1-carboxamide (IXp, derived from (S)-2-methylpropane-2-sulfinamide) and (1-methyl-1H-1,2,4-triazol-3-yl)methyl 1H-imidazole-1-carboxylate (XIIIa) The major enantiomer was isolated by SFC. Method: isocratic, Mobile phase MeOH:CO$_2$ 20:80.

Column: Chiralcel AD-H (30×250 mm, 5 μm), flow rate=70 g/min.

(1-Methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate—Enantiomer I (32) LCMS: m/z found 461.2/463.2 [M+H]$^+$, RT=5.74 min (Method A); HPLC: RT=7.50 min (Method B); Chiral SFC: RT: 5.36 min (Column: Chiralcel AD-H, 250×4.6 mm, 5 μm); $^1$H NMR (400 MHz, DMSO-d$_6$): δ 9.60 (s, 1H), 8.44 (s, 1H), 7.92-7.95 (m, 1H), 7.55-7.59 (m, 1H), 7.50 (d, 1H), 7.37 (dd, 1H), 6.84 (s, 1H), 5.01 (s, 2H), 4.53-4.58 (m, 1H), 3.85 (s, 3H), 3.70 (s, 3H), 2.66-2.71 (m, 2H), 1.83-1.89 (m, 2H), 1.50-1.60 (m, 2H).

Example 75: (1-Methyl-1H-pyrazol-3-yl)methyl (1-((3-chloro-4-fluorophenyl) carbamoyl)-2-methyl-4,5,6,7-tetrahydro-2H-isoindol-4-yl) (31)

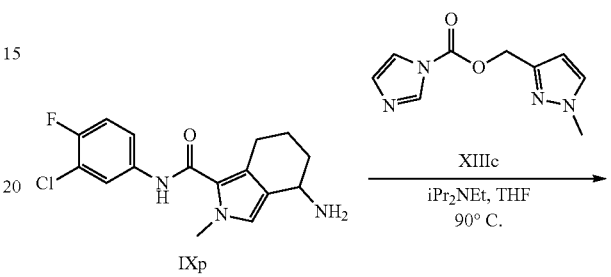

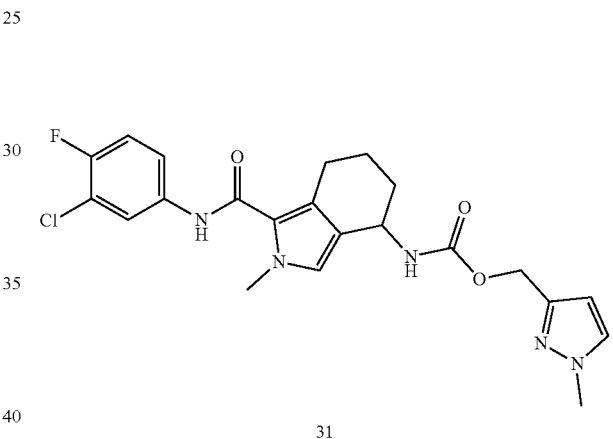

(1-Methyl-1H-pyrazol-3-yl)methyl(1-((3-chloro-4-fluorophenyl) carbamoyl)-2-methyl-4,5,6,7-tetrahydro-2H-isoindol-4-yl) was synthesized in a similar manner as described above from 4-amino-N-(3-chloro-4-fluorophenyl)-2-methyl-4,5,6,7-tetrahydro-2H-isoindole-1-carboxamide (IXp, derived from (S)-2-methylpropane-2-sulfinamide) and (1-methyl-1H-pyrazol-3-yl)methyl 1H-imidazole-1-carboxylate (XIIIc) The major enantiomer was isolated by SFC. Method: isocratic, Mobile phase MeOH:CO$_2$—35:65. Column: Chiralcel AD-H (30×250 mm), 5 μm, flow rate: 70 g/min.

(1-(1-Methyl-1H-pyrazol-3-yl)methyl (1-((3-chloro-4-fluorophenyl)carbamoyl)-2-methyl-4,5,6,7-tetrahydro-2H-isoindol-4-yl)carbamate—Enantiomer I (31) LCMS: m/z found 460.2/462.2 [M+H]$^+$, RT=5.40 min (Method A); HPLC: RT=8.04 min (Method B); Chiral SFC: RT: 6.70 min (Column: Chiralcel AD-H (250×4.6 mm, 5 μm)); $^1$H NMR (400 MHz, DMSO-d$_6$): δ 9.58 (br s, 1H), 7.92-7.95 (m, 1H), 7.63 (d, 1H), 7.54-7.59 (m, 1H), 7.33-7.38 (m, 2H), 6.81 (s, 1H), 6.23 (d, 1H), 4.95 (s, 2H), 4.54-4.57 (m, 1H), 3.81 (s, 3H), 3.69 (s, 3H), 2.66-2.71 (m, 2H), 1.84-1.88 (m, 2H), 1.52-1.61 (m, 2H).

Example 76: N-(3-Chloro-4-fluorophenyl)-4-(cyclopropanesulfonamido)-2-methyl-4,5,6,7-tetrahydro-2H-isoindole-1-carboxamide (30)

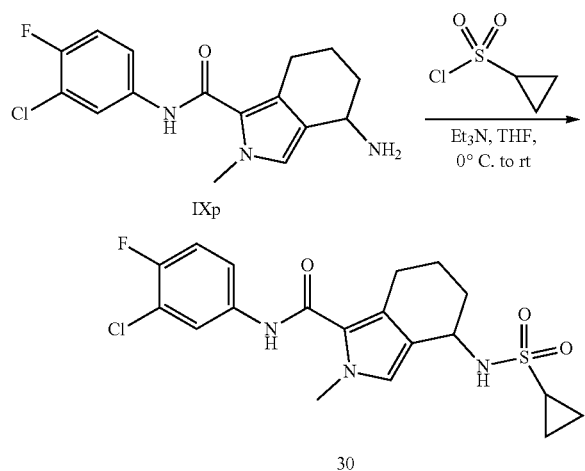

N-(3-Chloro-4-fluorophenyl)-4-(cyclopropanesulfonamido)-2-methyl-4,5,6,7-tetrahydro-2H-isoindole-1-carboxamide was synthesized in a similar manner as described above from 4-amino-N-(3-chloro-4-fluorophenyl)-2-methyl-4,5,6,7-tetrahydro-2H-isoindole-1-carboxamide (IXp, derived from (S)-2-methylpropane-2-sulfinamide) and cyclopropane sulfonyl chloride. The major enantiomer was subsequently isolated by SFC (Waters SFC investigator). Method isocratic, Mobile phase MeOH:CO$_2$—25:75. Column: Chiralcel OD-H (30×250 mm), 5 μm, flow rate: 70 g/min.

N-(3-Chloro-4-fluorophenyl)-4-(cyclopropanesulfonamido)-2-methyl-4,5,6,7-tetrahydro-2H-isoindole-1-carboxamide Enantiomer I (30) LCMS: m/z found 426.3/428.3 [M+H]$^+$, RT=7.29 min (Method A); $^1$H NMR (400 MHz, DMSO-d$_6$): δ 9.60 (bs, 1H), 7.93-7.95 (m, 1H), 7.55-7.59 (m, 1H), 7.33-7.39 (m, 2H), 6.92 (s, 1H), 4.34-4.37 (m, 1H), 3.73 (s, 3H), 2.62-2.69 (m, 3H), 1.97-2.01 (m, 1H), 1.86-1.91 (m, 1H), 1.64-1.59 (m, 2H), 0.95-1.00 (m, 4H).

Example 77: (1-Methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate (92, 93)

Ethyl 3-methyl-4-oxo-4,5,6,7-tetrahydro-2H-isoindole-1-carboxylate (XIVg)

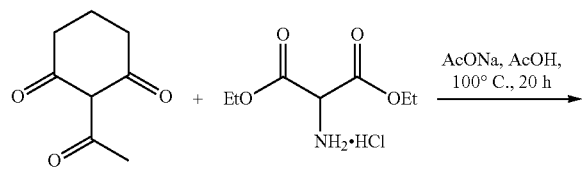

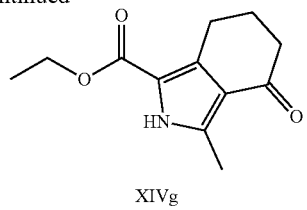

To a solution of 3.0 g (19.5 mmol, 1.0 eq.) of 2-acetylcyclohexane-1,3-dione in 15 mL of glacial acetic acid under a nitrogen atmosphere was added 10.6 g (77.9 mmol, 4.0 eq.) of anhydrous sodium acetate and the mixture was heated to 100° C. To this preheated mixture was slowly added a solution of 8.2 g (39.0 mmol, 2.0 eq.) of diethyl 2-aminomalonate hydrochloride in 15 mL of glacial acetic acid and the mixture was stirred at 100° C. for 20 h. The mixture was then allowed to cool to room temperature and poured into 100 mL of ice-cold water. The resulting solution was extracted with 3×80 mL of ethyl acetate and the combined organic extracts were washed with 60 mL of 10% aqueous sodium hydroxide solution, 60 mL of brine, dried (Na$_2$SO$_4$), filtered and the solvent was removed in vacuo to provide 3.0 g (13.6 mmol, 69%) of ethyl 3-methyl-4-oxo-4,5,6,7-tetrahydro-2H-isoindole-1-carboxylate (XIVg). LCMS: m/z found 222.3 [M+H]$^+$; $^1$H NMR (300 MHz, DMSO-d$_6$): δ 12.09 (bs, 1H), 4.24 (q, 2H), 2.84-2.89 (m, 2H), 2.43 (s, 3H), 2.30-2.35 (m, 2H), 1.91-1.98 (m, 2H), 1.29 (t, 3H).

Ethyl 2,3-dimethyl-4-oxo-4,5,6,7-tetrahydro-2H-isoindole-1-carboxylate (XIVh)

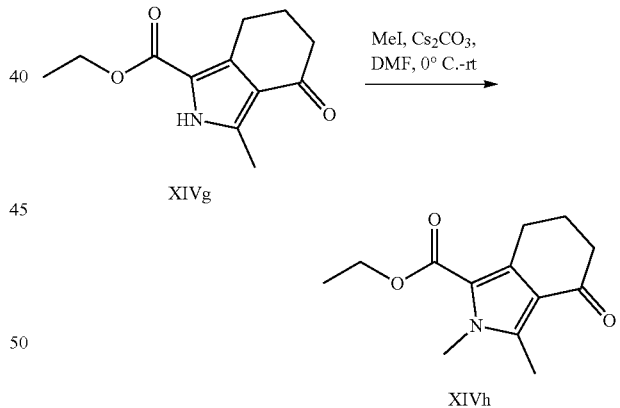

To a solution of 3.0 g (13.6 mmol, 1.0 eq.) of ethyl 3-methyl-4-oxo-4,5,6,7-tetrahydro-2H-isoindole-1-carboxylate (XIVg) in 20 mL of DMF at 0° C. was added 13.3 g (40.7 mmol, 3.0 eq.) of cesium carbonate followed by 4.8 g (33.9 mmol, 2.5 eq.) of iodomethane. The resulting mixture allowed to warm to room temperature and stirred for 8 h. The mixture was quenched with 50 mL of ice-cold water and stirred for a further 10 min. The resulting precipitated was collected by filtration, washed with 20 mL of ice-cold water followed by 20 mL of n-pentane and dried under high vacuum to provide 3.0 g (12.8 mmol, 94%) of ethyl 2,3-dimethyl-4-oxo-4,5,6,7-tetrahydro-2H-isoindole-1-carboxylate (XIVh). LCMS: m/z found 236.1 [M+H]$^+$; $^1$H NMR (300 MHz, DMSO-d$_6$): δ 4.23 (q, 2H), 3.75 (s, 3H), 2.91-2.87 (m, 2H), 2.51 (s, 3H), 2.36-2.31 (m, 2H), 1.96-1.90 (m, 2H), 1.29 (t, 3H).

N-(3-Chloro-4-fluorophenyl)-2,3-dimethyl-4-oxo-4,5,6,7-tetrahydro-2H-isoindole-1-carboxamide (XVIh)

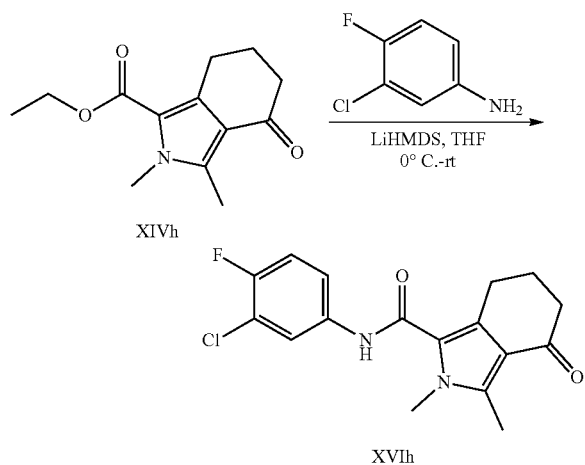

To a solution of 3.0 g (12.8 mmol, 1.0 eq.) of ethyl 2,3-dimethyl-4-oxo-4,5,6,7-tetrahydro-2H-isoindole-1-carboxylate (XIVh) and 2.77 g (19.14 mmol, 1.5 eq.) of 3-chloro-4-fluoroaniline in 30 mL of anhydrous THF at 0° C. under a nitrogen atmosphere was added 89.4 mL (89.4 mmol, 7.0 eq.) of a 1 M solution of lithium bis(trimethylsilyl)amide in THF. The mixture was then allowed to warm to room temperature and stirred for 3 h. The reaction was quenched with 150 mL of ice-cold water and extracted with 3×150 mL of ethyl acetate. The combined organic extracts were washed with 150 mL of brine, dried (Na$_2$SO$_4$), filtered and the solvent was removed in vacuo. The residue was triturated with 40 mL of diethyl ether and dried under high vacuum to provide 1.6 g (4.7 mmol, 37%) of N-(3-chloro-4-fluorophenyl)-2,3-dimethyl-4-oxo-4,5,6,7-tetrahydro-2H-isoindole-1-carboxamide (XVIh). LCMS: m/z found 335.3 [M+H]$^+$; $^1$H NMR (300 MHz, DMSO-d$_6$): δ 9.99 (bs, 1H), 7.95-7.98 (m, 1H), 7.57-7.63 (m, 1H), 7.40 (t, 1H), 3.64 (s, 3H), 2.81-2.85 (m, 2H), 2.53 (s, 3H), 2.31-2.36 (m, 2H), 1.90-1.98 (m, 2H).

N-(3-Chloro-4-fluorophenyl)-4-(hydroxyimino)-2,3-dimethyl-4,5,6,7-tetrahydro-2H-isoindole-1-carboxamide

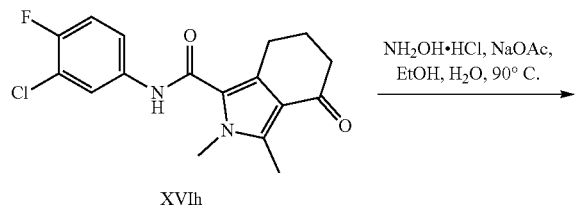

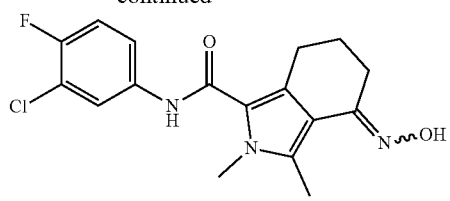

To a solution of 0.8 g (2.4 mmol, 1.0 eq.) of N-(3-chloro-4-fluorophenyl)-2,3-dimethyl-4-oxo-4,5,6,7-tetrahydro-2H-isoindole-1-carboxamide (XVIh) in 15 mL of 1:1 v/v ethanol:water was added 1.0 g (14.4 mmol, 6.0 eq.) of hydroxylamine hydrochloride and 1.2 g (14.4 mmol, 6.0 eq.) of sodium acetate and the mixture was heated at 90° C. for 16 h. The mixture was then allowed to cool to room temperature, diluted with 30 mL of ice-cold water and extracted with 3×50 mL of ethyl acetate. The combined organic extracts were washed with 100 mL of brine, dried (Na$_2$SO$_4$), filtered and the solvent was removed in vacuo to provide 0.49 g (1.4 mmol, 58%) N-(3-chloro-4-fluorophenyl)-4-(hydroxyimino)-2,3-dimethyl-4,5,6,7-tetrahydro-2H-isoindole-1-carboxamide. LCMS: m/z found 350.5/352.5 [M+H]$^+$; $^1$H NMR (400 MHz, DMSO-d$_6$) δ 10.35 (s, 1H), 9.78 (s, 1H), 7.94-7.96 (m, 1H), 7.56-7.60 (m, 1H), 7.38 (t, 1H), 3.63 (s, 3H), 2.68-2.71 (m, 2H), 2.55-2.59 (m, 2H), 2.47 (s, 3H), 1.68-1.71 (m, 2H).

4-Amino-N-(3-chloro-4-fluorophenyl)-2,3-dimethyl-4,5,6,7-tetrahydro-2H-isoindole-1-carboxamide (XVIIIh)

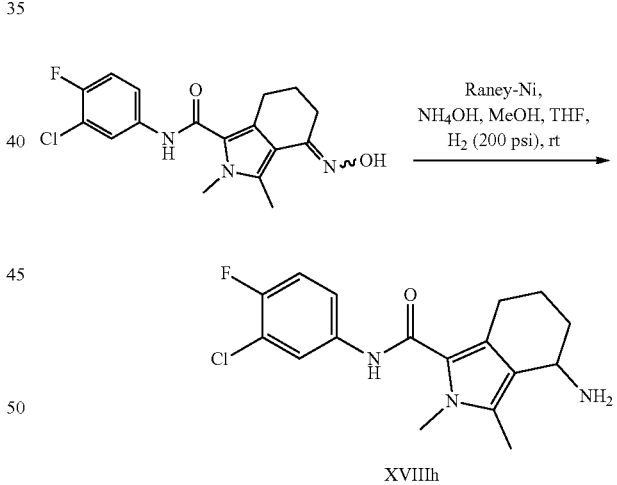

To a solution of 0.4 g (1.1 mmol, 1.0 eq.) of N-(3-chloro-4-fluorophenyl)-4-(hydroxyimino)-2,3-dimethyl-4,5,6,7-tetrahydro-2H-isoindole-1-carboxamide in 30 mL of 1:1 v/v THF:methanol in a steel pressure vessel was added 0.4 g (50% dispersion in water) of Raney nickel followed by 5 mL of ammonium hydroxide and the mixture was stirred at room temperature under 200 psi of hydrogen for 16 h. The mixture was filtered through CELITE® and the pad was washed with 10 mL of methanol. The filtrate was concentrated in vacuo to provide 0.36 g of 4-amino-N-(3-chloro-4-fluorophenyl)-2,3-dimethyl-4,5,6,7-tetrahydro-2H-isoindole-1-carboxamide (XVIIIh).

(1-Methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate (92, 93)

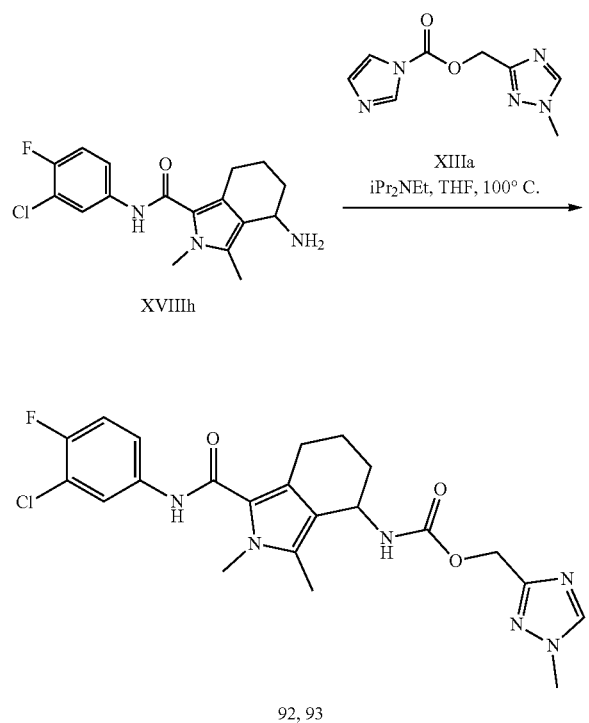

(1-Methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate was synthesized in a similar manner as described above from 4-amino-N-(3-chloro-4-fluorophenyl)-2,3-dimethyl-4,5,6,7-tetrahydro-2H-isoindole-1-carboxamide (XVIIIh) and (1-methyl-1H-1,2,4-triazol-3-yl)methyl 1H-imidazole-1-carboxylate (XIIIa) The enantiomers were subsequently separated by chiral SFC. Method: isocratic, Mobile phase MeOH:CO₂—45:55. Column Chiralpak IC (30×250 mm, 5 μm), flow rate: 70 g/min.

(1-Methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate—Enantiomer I (92) LCMS: m/z found 475.4/477.3 [M+H]⁺, RT=7.13 min (Method A); HPLC: RT=7.71 min (Method B); Chiral SFC: RT=4.59 min, Column: Chiralpak IC-3 (4.6×150 mm, 3 μm); ¹H NMR (400 MHz, DMSO-d₆): δ 9.46 (bs, 1H), 8.42 (s, 1H), 7.92-7.95 (m, 1H), 7.55-7.58 (m, 1H), 7.42 (d, 1H), 7.36 (t, 1H), 4.99 (s, 2H), 4.63-4.67 (m, 1H), 3.84 (s, 3H), 3.59 (s, 3H), 2.63-2.67 (m, 2H), 2.11 (s, 3H), 1.48-1.79 (m, 4H).

(1-Methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate—Enantiomer II (93) LCMS: m/z found 475.4/477.4 [M+H]⁺, RT=7.10 min (Method A); HPLC: RT=7.71 min (Method B); Chiral SFC: RT=7.32 min, Column: Chiralpak IC-3 (4.6×150 mm, 3 μm); ¹H NMR (400 MHz, DMSO-d₆): δ 9.46 (bs, 1H), 8.42 (s, 1H), 7.92-7.95 (m, 1H), 7.55-7.58 (m, 1H), 7.42 (d, 1H), 7.36 (t, 1H), 4.99 (s, 2H), 4.63-4.67 (m, 1H), 3.84 (s, 3H), 3.59 (s, 3H), 2.63-2.67 (m, 2H), 2.11 (s, 3H), 1.48-1.79 (m, 4H).

Example 78: (1H-1,2,4-Triazol-3-yl)methyl (3-chloro-1-((3-chloro-4-fluorophenyl)carbamoyl)-2-methyl-4,5,6,7-tetrahydro-2H-isoindol-4-yl)carbamate (134, 135)

Ethyl 3-chloro-2-methyl-4-oxo-4,5,6,7-tetrahydro-2H-isoindole-1-carboxylate (XIVi)

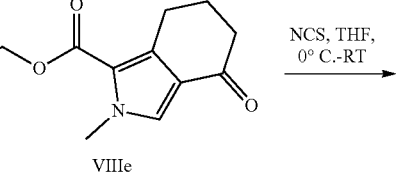

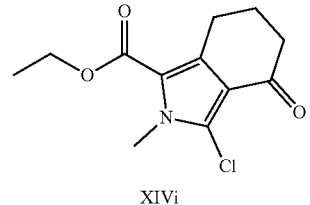

To a solution of 3.0 g (13.6 mmol, 1.0 eq.) of ethyl 2-methyl-4-oxo-4,5,6,7-tetrahydro-2H-isoindole-1-carboxylate (VIIIe) in 20 mL of THF at 0° C. under a nitrogen atmosphere was added a solution of 2.2 g (16.3 mmol, 1.2 eq.) of N-chlorosuccinimide in 10 mL of THF drop-wise over approximately 20 min. The mixture was then allowed to warm to room temperature and stirred for 16 h. The mixture was diluted with 40 mL of water and extracted with 3×100 mL of ethyl acetate. The combined organic extracts were washed with 80 mL of brine, dried (Na₂SO₄), filtered and the solvent was removed in vacuo. The above detailed reaction was conducted in duplicate and the combined residues were purified by flash chromatography (SiO₂, eluting with a linear gradient of 10-15% ethyl acetate/petroleum ether) to provide 5.0 g (19.6 mmol, 72%) of ethyl 3-chloro-2-methyl-4-oxo-4,5,6,7-tetrahydro-2H-isoindole-1-carboxylate (XIVi). LCMS: m/z found 256.0/258.0 [M+H]⁺; ¹H NMR (300 MHz, CDCl₃): δ 4.33 (q, 2H), 3.92 (s, 3H), 2.99 (t, 2H), 2.49 (t, 2H), 2.08-2.03 (m, 2H), 1.38 (t, 3H).

3-Chloro-N-(3-chloro-4-fluorophenyl)-2-methyl-4-oxo-4,5,6,7-tetrahydro-2H-isoindole-1-carboxamide (XVIi)

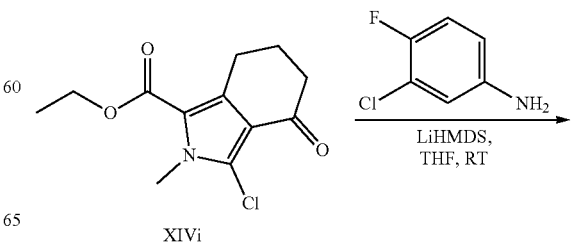

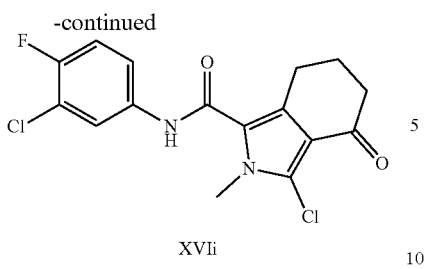

XVIi

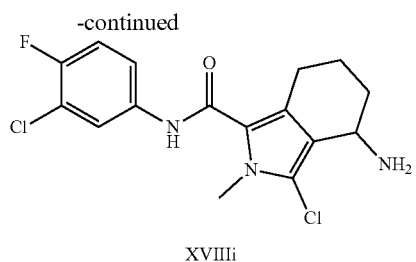

XVIIIi

To a solution of 6.0 g (23.5 mmol, 1.0 eq.) of ethyl 3-chloro-2-methyl-4-oxo-4,5,6,7-tetrahydro-2H-isoindole-1-carboxylate (XIVi) and 4.1 g (28.3 mmol, 1.2 eq.) of 3-chloro-4-fluoroaniline in 60 mL of THF under a nitrogen atmosphere was added 141 mL (141 mmol, 6.0 eq.) of a 1 M solution of lithium bis(trimethylsilyl)amide and the resulting mixture was stirred at room temperature for 3 h. The reaction mixture was poured into 200 mL of ice-cold water and extracted with 3×250 mL of ethyl acetate. The combined organic extracts were washed with 350 mL of brine, dried over (Na$_2$SO$_4$), filtered and the solvent was removed in vacuo. The residue was washed with 30 mL of diethyl ether followed by 20 mL of n-pentane and the resulting solid dried under high vacuum to provide 5.9 g (16.6 mmol, 70%) of 3-chloro-N-(3-chloro-4-fluorophenyl)-2-methyl-4-oxo-4,5,6,7-tetrahydro-2H-isoindole-1-carboxamide (XVIi). LCMS: m/z found 355.1/337.1 [M+H]$^+$; $^1$H NMR (400 MHz, DMSO-d$_6$): δ 10.20 (bs, 1H), 7.95-7.98 (m, 1H), 7.59-7.63 (m, 1H), 7.42 (t, 1H), 3.73 (s, 3H), 2.85-2.88 (m, 2H), 2.38-2.42 (m, 2H), 1.95-2.00 (m, 2H).

4-Amino-3-chloro-N-(3-chloro-4-fluorophenyl)-2-methyl-4,5,6,7-tetrahydro-2H-isoindole-1-carboxamide (XVIIIi)

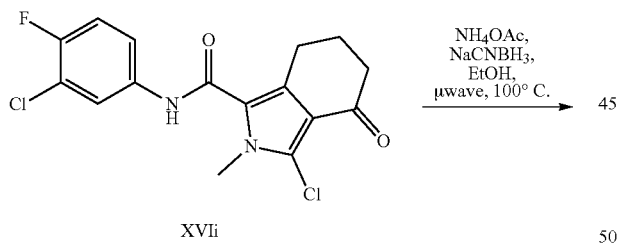

XVIi

A microwave tube was charged with 0.35 g (0.98 mmol, 1.0 eq.) of 3-chloro-N-(3-chloro-4-fluorophenyl)-2-methyl-4-oxo-4,5,6,7-tetrahydro-2H-isoindole-1-carboxamide (XVIi), 3.5 mL of ethanol, 1.51 g (19.71 mmol, 20.0 eq.) of ammonium acetate and 0.24 g (3.94 mmol, 4.0 eq.) of sodium cyanoborohydride and the mixture was subjected to microwave irradiation maintaining a reaction temperature of 100° C. for 2 h. The above detailed reaction was conducted in duplicate and the mixtures combined, diluted with 50 mL of 2% aqueous sodium hydroxide solution and extracted with 3×30 mL of 10% methanol in methylene chloride. The combined organic extracts were washed with 50 mL of brine, dried (Na$_2$SO$_4$), filtered and the solvent was removed in vacuo. The residue was purified by MPLC (REVELERIS® Silica gel column, eluting with a linear gradient 30-50% of [20% methanol in methylene chloride]/methylene chloride) to provide 190 mg (0.53 mmol, 27%) of 4-amino-3-chloro-N-(3-chloro-4-fluorophenyl)-2-methyl-4,5,6,7-tetrahydro-2H-isoindole-1-carboxamide (XVIIIi). $^1$H NMR (400 MHz, DMSO-d$_6$): δ 9.77 (bs, 1H), 7.92-7.95 (m, 1H), 7.55-7.59 (m, 1H), 7.38 (t, 1H), 3.93-3.95 (m, 1H), 3.66 (s, 3H), 2.60-2.71 (m, 2H), 1.58-1.90 (m, 4H), 1.23 (bs, 2H). The above detailed reaction was repeated on multiple 0.35 g batches with consistent results.

(1H-1,2,4-Triazol-3-yl)methyl (3-chloro-1-((3-chloro-4-fluorophenyl)carbamoyl)-2-methyl-4,5,6,7-tetrahydro-2H-isoindol-4-yl)carbamate (134, 135)

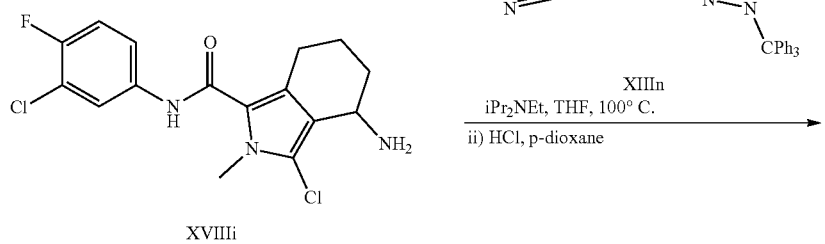

XVIIIi

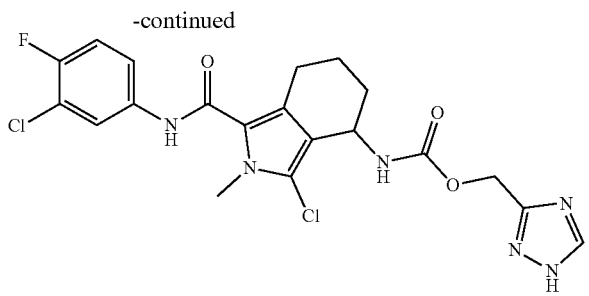

134, 135

(1H-1,2,4-Triazol-3-yl)methyl (3-chloro-1-((3-chloro-4-fluorophenyl)carbamoyl)-2-methyl-4,5,6,7-tetrahydro-2H-isoindol-4-yl)carbamate was synthesized in a similar manner as described above from 4-amino-3-chloro-N-(3-chloro-4-fluorophenyl)-2-methyl-4,5,6,7-tetrahydro-2H-isoindole-1-carboxamide (XVIIIi) and (1-trityl-1H-1,2,4-triazol-3-yl) methyl 1H-imidazole-1-carboxylate (XIIIn) followed by acid mediated detritylation. The enantiomers were subsequently separated by SFC. Method: isocratic, Mobile phase MeOH:CO$_2$— 35:65. Column: Chiralpak IG (30×250 mm, 5 μm), flow rate: 70 g/min.

(1H-1,2,4-Triazol-3-yl)methyl (3-chloro-1-((3-chloro-4-fluorophenyl)carbamoyl)-2-methyl-4,5,6,7-tetrahydro-2H-isoindol-4-yl)carbamate—Enantiomer I (134) LCMS: m/z found 481.1/483.2 [M+H]$^+$, RT=4.19 min (Method A); HPLC: RT=7.62 min (Method B); Chiral SFC: RT=2.14 min, Column: Chiralpak IG-3 (4.6×250 mm, 3 μm); $^1$H NMR (400 MHz, DMSO-d$_6$): δ 14.01 (bs, 1H), 9.75 (s, 1H), 8.36 (s, 1H), 7.92-7.95 (m, 1H), 7.52-7.60 (m, 2H), 7.38 (t, 1H), 5.01-5.09 (m, 2H), 4.63-4.66 (m, 1H), 3.66 (s, 3H), 2.65-2.67 (m, 2H), 1.62-1.76 (m, 4H).

(1H-1,2,4-Triazol-3-yl)methyl (3-chloro-1-((3-chloro-4-fluorophenyl)carbamoyl)-2-methyl-4,5,6,7-tetrahydro-2H-isoindol-4-yl)carbamate—Enantiomer II (135) LCMS: m/z found 481.1/483.2 [M+H]$^+$, RT=4.19 min (Method A); HPLC: RT=7.62 min (Method B); Chiral SFC: RT=3.33 min, Column: Chiralpak IG-3 (4.6×250 mm, 3 μm); $^1$H NMR (400 MHz, DMSO-d$_6$): δ 14.01 (bs, 1H), 9.75 (s, 1H), 8.36 (s, 1H), 7.92-7.95 (m, 1H), 7.52-7.60 (m, 2H), 7.38 (t, 1H), 5.01-5.09 (m, 2H), 4.63-4.66 (m, 1H), 3.66 (s, 3H), 2.65-2.67 (m, 2H), 1.62-1.76 (m, 4H).

Example 79: (2H-1,2,3-Triazol-4-yl)methyl (3-chloro-1-((3-chloro-4-fluorophenyl)carbamoyl)-2-methyl-4,5,6,7-tetrahydro-2H-isoindol-4-yl)carbamate (136, 137)

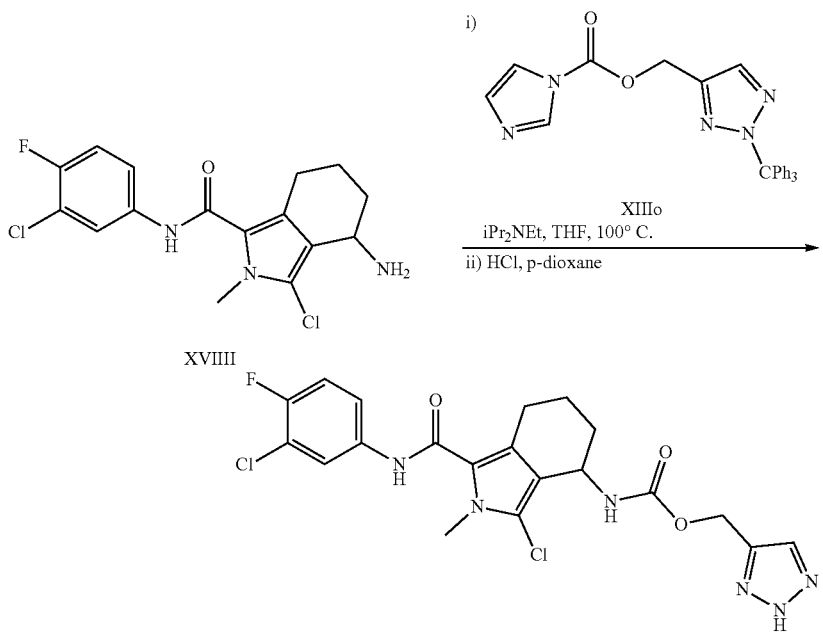

136, 137

(2H-1,2,3-Triazol-4-yl)methyl (3-chloro-1-((3-chloro-4-fluorophenyl)carbamoyl)-2-methyl-4,5,6,7-tetrahydro-2H-isoindol-4-yl)carbamate was synthesized in a similar manner as described above from 4-amino-3-chloro-N-(3-chloro-4-fluorophenyl)-2-methyl-4,5,6,7-tetrahydro-2H-isoindole-1-carboxamide (XVIIIi) and (2-trityl-2H-1,2,3-triazol-4-yl) methyl 1H-imidazole-1-carboxylate (XIIIo) followed by acid mediated detritylation. The enantiomers were subsequently separated by SFC. Method: isocratic, Mobile phase MeOH:CO$_2$—40:60. Column: Chiralpak IG (30×250 mm, 5 µm), flow rate: 70 g/min.

(2H-1,2,3-Triazol-4-yl)methyl (3-chloro-1-((3-chloro-4-fluorophenyl)carbamoyl)-2-methyl-4,5,6,7-tetrahydro-2H-isoindol-4-yl)carbamate—Enantiomer I (136) LCMS: m/z found 481.1/483.2 [M+H]$^+$, RT=4.51 min (Method A); HPLC: RT=8.03 min (Method B); Chiral SFC: RT=2.20 min, Column: Chiralpak IG-3 (4.6×250 mm, 3 µm); $^1$H NMR (400 MHz, DMSO-d$_6$): δ 13.96 (bs, 1H), 9.74 (s, 1H), 7.92-7.95 (m, 1H), 7.80 (s, 1H), 7.55-7.60 (m, 1H), 7.48 (d, 1H), 7.38 (t, 1H), 5.10-5.13 (m, 2H), 4.63-4.66 (m, 1H), 3.65 (s, 3H), 2.65-2.67 (m, 2H), 1.62-1.76 (m, 4H);

(2H-1,2,3-Triazol-4-yl)methyl (3-chloro-1-((3-chloro-4-fluorophenyl)carbamoyl)-2-methyl-4,5,6,7-tetrahydro-2H-isoindol-4-yl)carbamate—Enantiomer II (137) LCMS: m/z found 481.1/483.2 [M+H]$^+$, RT=4.50 min (Method A); HPLC: RT=8.02 min (Method B); Chiral SFC: RT=5.20 min, Column: Chiralpak IG-3 (4.6×250 mm, 3 µm); $^1$H NMR (400 MHz, DMSO-d$_6$): δ 13.96 (bs, 1H), 9.74 (s, 1H), 7.92-7.95 (m, 1H), 7.80 (s, 1H), 7.55-7.60 (m, 1H), 7.48 (d, 1H), 7.38 (t, 1H), 5.10-5.13 (m, 2H), 4.63-4.66 (m, 1H), 3.65 (s, 3H), 2.65-2.67 (m, 2H), 1.62-1.76 (m, 4H).

Example 80: (1-Methyl-1H-1,2,4-triazol-3-yl) methyl (3-chloro-1-((3-chloro-4-fluorophenyl)carbamoyl)-2-methyl-4,5,6,7-tetrahydro-2H-isoindol-4-yl)carbamate (94)

4-(((R)-tert-Butylsulfinyl)amino)-3-chloro-N-(3-chloro-4-fluorophenyl)-2-methyl-4,5,6,7-tetrahydro-2H-isoindole-1-carboxamide (XVIIi)

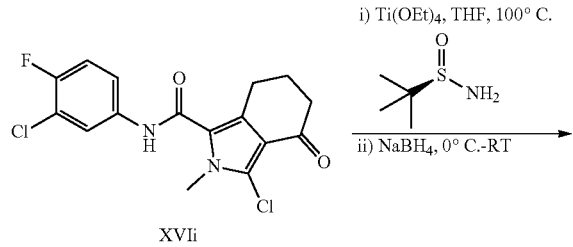

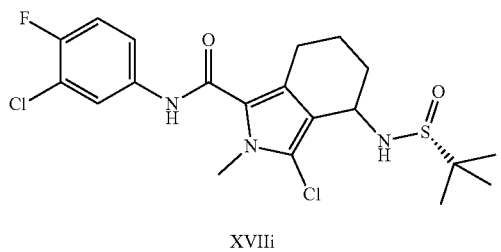

To a solution of 1.7 g (4.8 mmol, 1.0 eq.) of 3-chloro-N-(3-chloro-4-fluorophenyl)-2-methyl-4-oxo-4,5,6,7-tetrahydro-2H-isoindole-1-carboxamide (XVIi) in 17 mL of anhydrous THF in a sealed tube was added 1.16 g (9.6 mmol, 2.0 eq.) of (R)-2-methylpropane-2-sulfinamide followed by 7.7 g (33.6 mmol, 7.0 eq.) of titanium tetraethoxide. The vessel was sealed, and the mixture was heated at 100° C. for 72 h. The mixture was then allowed to cool to room temperature, further cooled to 0° C., and 0.36 g (9.6 mmol, 20 eq.) of sodium borohydride was added and stirring was continued for a further 2 h. The mixture was then poured into 100 mL of water and the resulting heterogeneous mixture was filtered. The filtrate was extracted with 3×80 mL of ethyl acetate and the combined organic extracts were washed with 50 mL of brine, dried (Na$_2$SO$_4$), filtered, and the solvent was removed in vacuo. The residue was purified by column chromatography (neutral alumina, eluting with linear gradient of 10-30% ethyl acetate in petroleum ether) to provide 0.2 g (approximately 9:1 mixture of diastereoisomers) of 4-(((R)-tert-butylsulfinyl)amino)-3-chloro-N-(3-chloro-4-fluorophenyl)-2-methyl-4,5,6,7-tetrahydro-2H-isoindole-1-carboxamide (XVIIi). LCMS: m/z found 460.0/462.0 [M+H]$^+$.

4-Amino-3-chloro-N-(3-chloro-4-fluorophenyl)-2-methyl-4,5,6,7-tetrahydro-2H-isoindole-1-carboxamide hydrochloride (XVIIIi)

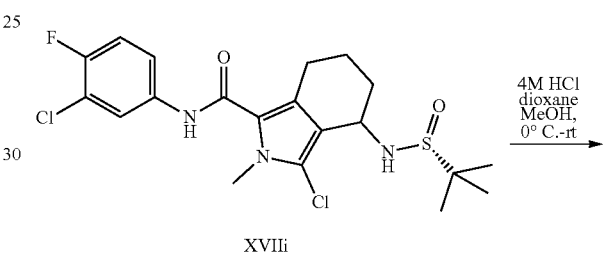

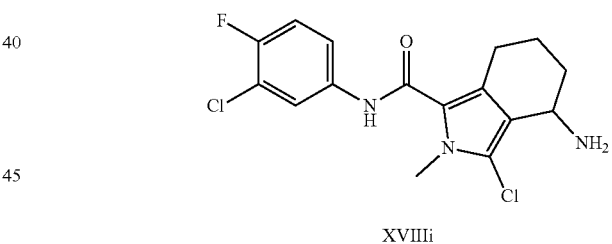

To a solution of 100 mg (approximately 9:1 mixture of diastereoisomers) of 4-(((R)-tert-butylsulfinyl)amino)-3-chloro-N-(3-chloro-4-fluorophenyl)-2-methyl-4,5,6,7-tetrahydro-2H-isoindole-1-carboxamide (XVIIi) in 1 mL of methanol at 0° C. was added 0.2 mL of a 4 M solution of HCl in 1,4-dioxane and the mixture was stirred at 0° C. for 2 h. The solvent was removed in vacuo and the residue was triturated with 5 mL of n-pentane and dried under high vacuum. The residue was then treated with 20 mL of saturated sodium bicarbonate solution and stirred at room temperature for 10 min. The resulting solution was extracted with 3×30 mL of 10% methanol in methylene chloride, the combined organic extracts washed with 30 mL of water, 30 mL of brine, dried (Na$_2$SO$_4$), filtered and the solvent removed in vacuo to provide 50 mg of 4-amino-3-chloro-N-(3-chloro-4-fluorophenyl)-2-methyl-4,5,6,7-tetrahydro-2H-isoindole-1-carboxamide

(1-Methyl-1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate (94)

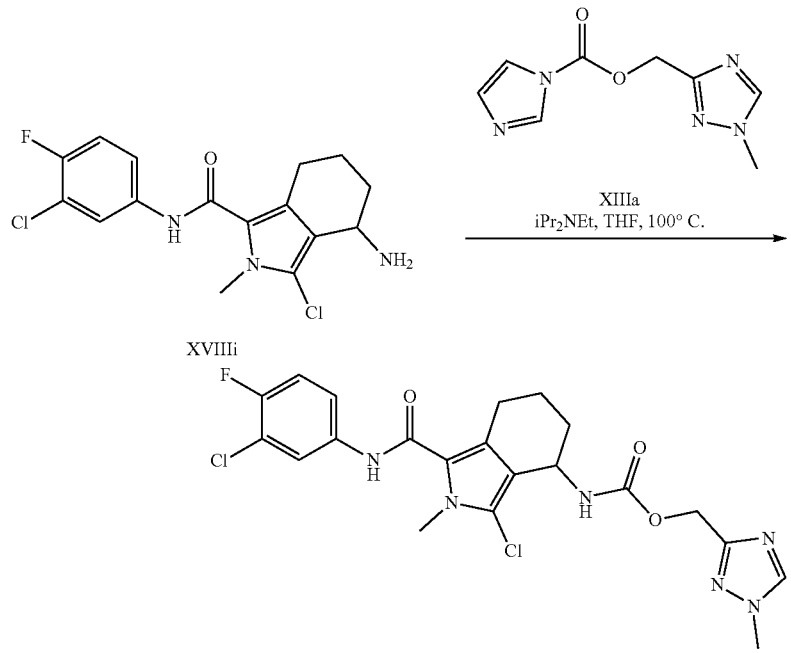

(1-Methyl-1H-1,2,4-triazol-3-yl)methyl (3-chloro-1-((3-chloro-4-fluorophenyl) carbamoyl)-2-methyl-4,5,6,7-tetrahydro-2H-isoindol-4-yl)carbamate was synthesized in a similar manner as described above from 4-amino-3-chloro-N-(3-chloro-4-fluorophenyl)-2-methyl-4,5,6,7-tetrahydro-2H-isoindole-1-carboxamide derived from (R)-2-methyl-propane-2-sulfinamide) and (1-methyl-1H-1,2,4-triazol-3-yl)methyl 1H-imidazole-1-carboxylate (XIIIa). Chiral SFC: 8% & 92% at RT=5.60 min and 6.76 min respectively (Method: Column: Chiralpak AD-H (4.6×250 mm, 5 μm). The major enantiomer was isolated by SFC. Method: isocratic, Mobile phase MeOH:CO$_2$—40:60. Column Chiralpak AD-H (30×250 mm), 5 μm, flow rate=70 g/min.

(1-Methyl-1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate—Enantiomer II (94) LCMS: m/z found 495.3/497.3/499.3 [M+H]$^+$, RT=7.06 min; (Method A); HPLC: RT=7.93 min (Method B); Chiral SFC: RT=6.76 min, Column: Chiralpak AD-H (4.6×250 mm, 5 μm); $^1$H NMR (400 MHz, DMSO-d$_6$): δ 9.75 (s, 1H), 8.43 (s, 1H), 7.92-7.95 (m, 1H), 7.54-7.60 (m, 1H), 7.50 (d, 1H), 7.38 (t, 1H), 4.94-5.03 (m, 2H), 4.62-4.66 (m, 1H), 3.84 (s, 3H), 3.66 (s, 3H), 2.65-2.69 (m, 2H), 1.63-1.77 (m, 4H).

Example 81: N-(3-Chloro-4-fluorophenyl)-2-methyl-4-oxo-2,4,5,6,7,8-hexahydrocyclohepta[c]pyrrole-1-carboxamide (72, VIIIe)

5,6,7,8-Tetrahydrocyclohepta[c]pyrrol-4(2H)-one (IIIc)

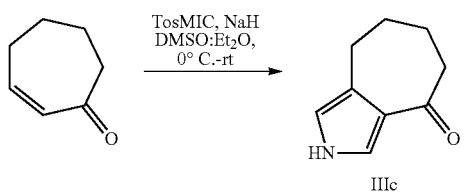 [SMILES: O=C1C=CCCCC1 ; "TosMIC, NaHDMSO:Et2O,0° C.-rt" ; O=C1CCCCc2c[nH]cc21]

To a stirred suspension of 1.58 g (39.6 mmol, 1.6 eq.) of a 60% dispersion of sodium hydride in mineral oil in 50 mL of 3:1 (v/v) diethyl ether:DMSO at 0° C. under a nitrogen atmosphere was added a solution of 2.72 g (24.7 mmol, 1.0 eq) of cyclohept-2-en-1-one and 4.85 g (24.7 mmol, 1.1 eq) of p-tolylsulfonyl)methyl isocyanide in 20 mL of 3:1 (v/v) diethyl ether:DMSO over approximately 20 min. The mixture was then allowed to warm to room temperature and stirred for 16 h. The solvent was removed in vacuo and the residue was purified by flash chromatography (SiO$_2$, eluting with linear gradient of 20-40% ethyl acetate/petroleum ether) to provide 1.2 g (8.04 mmol) of 5,6,7,8-tetrahydrocyclohepta[c]pyrrol-4(2H)-one (IIIc). LCMS: m/z found 150.14 [M+H]$^+$; $^1$H NMR (400 MHz, CDCl$_3$): δ 8.46 (bs, 1H), 7.38-7.40 (m, 1H), 6.54-6.55 (m, 1H), 2.77-2.80 (m, 2H), 2.64-2.73 (m, 2H), 1.83-1.90 (m, 4H).

1-Bromo-5,6,7,8-tetrahydrocyclohepta[c]pyrrol-4 (2H)-one (IVc)

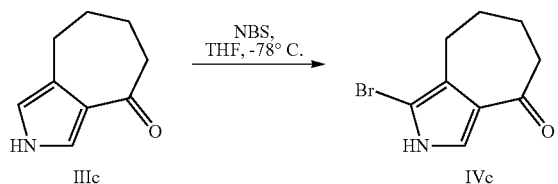 [SMILES: O=C1CCCCc2c[nH]cc21 ; "NBS,THF, -78° C." ; O=C1CCCCc2c1c[nH]c2Br]

To a solution of 1.1 g (7.4 mmol, 1.0 eq.) of 5,6,7,8-tetrahydrocyclohepta[c]pyrrol-4(2H)-one (IIIc) in 50 mL of anhydrous THF at −78° C. under a nitrogen atmosphere, was added a solution of 1.31 g (7.4 mmol, 1.0 eq.) of N-bromosucciminide in 10 ml of THF over approximately 30 min. The mixture was stirred at −78° C. for an additional 1 h and then quenched 50 mL of ice-cold water. The mixture was then extracted with 3×50 mL of ethyl acetate and the combined organic extracts dried ($Na_2SO_4$), filtered and the solvent was removed in vacuo. The residue was purified by flash chromatography ($SiO_2$, eluting with a linear gradient of 20% ethyl acetate in methylene chloride) to provide 0.62 g (2.71 mmol, 37%) of 1-bromo-5,6,7,8-tetrahydrocyclohepta[c]pyrrol-4(2H)-one (IVe) as an off-white solid. LCMS: m/z found 228.29/230.3 $[M+H]^+$; $^1$H NMR (300 MHz, DMSO-$d_6$): δ 12.06 (bs, 1H), 7.32 (s, 1H), 2.60-2.66 (m, 2H), 2.51-2.57 (m, 2H), 1.71-1.80 (m, 4H).

1-Bromo-2-methyl-5,6,7,8-tetrahydrocyclohepta[c]pyrrol-4(2H)-one (Ve)

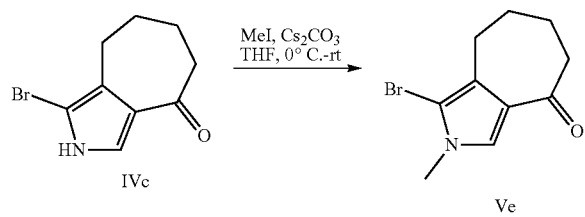

To a solution of 0.6 g (2.63 mmol, 1.0 eq.) of 1-bromo-5,6,7,8-tetrahydrocyclohepta[c]pyrrol-4(2H)-one (IVc) in 20 mL of THF under a nitrogen atmosphere at 0° C. was added 1.71 g (5.26 mmol, 2.0 eq) of cesium carbonate followed by 0.56 g (3.94 mmol, 1.5 eq.) of iodomethane. The mixture was allowed to warm to room temperature and stirred for 4 h. The mixture was filtered through CELITE® and the pad washed with 20 mL of ethyl acetate. The filtrate was diluted with 200 mL of ice-cold water and extracted with 3×30 mL of ethyl acetate. The combined organic extracts were washed with 30 mL of brine, dried ($Na_2SO_4$), filtered and the solvent was removed in vacuo to provide 0.58 g (2.39 mmol, 91%) of 1-bromo-2-methyl-5,6,7,8-tetrahydrocyclohepta[c]pyrrol-4(2H)-one (4) as a brown liquid. LCMS: m/z found 242.2/244.2 $[M+H]^+$; $^1$H NMR (400 MHz, CDCl$_3$): δ 7.35 (s, 1H), 3.60 (s, 3H), 2.69-2.73 (m, 2H), 2.64-2.67 (m, 2H), 1.83-1.89 (m, 4H).

Ethyl 2-methyl-4-oxo-2,4,5,6,7,8-hexahydrocyclohepta[c]pyrrole-1-carboxylate (VIe)

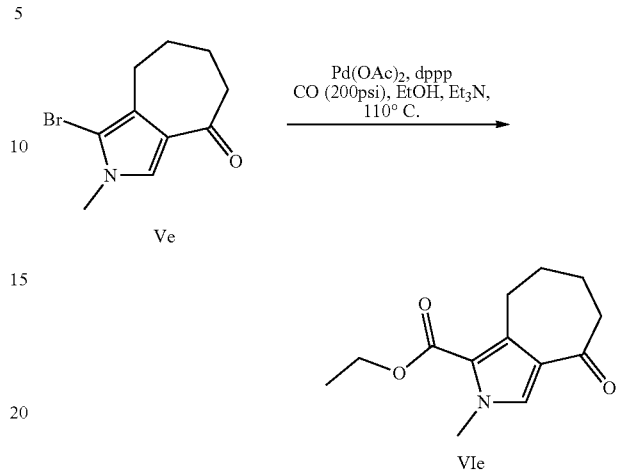

A solution of 0.58 g (2.39 mmol, 1.0 eq.) of 1-bromo-2-methyl-5,6,7,8-tetrahydrocyclohepta [c]pyrrol-4(2H)-one (Ve) in 8 mL of ethanol in a steel pressure vessel was degassed with argon for 10 min and 1.2 g (12.0 mmol, 3.0 eq.) of triethylamine was added. Degassing was continued for a further 5 min and 0.197 g (0.48 mmol, 0.2 eq.) of palladium(II)acetate and 0.156 g (0.24 mmol, 0.1 eq.) of 1,3-bis(diphenylphosphino)propane were added. The mixture was degassed with argon for an additional 10 min and then stirred under 200 psi of carbon monoxide at 110° C. for 16 h. The mixture was allowed to cool to room temperature and filtered through CELITE®. The pad was washed with 50 mL of ethyl acetate. The filtrate was diluted with 30 mL of ice-cold water and 50 mL of ethyl acetate and the layers were separated. The organic phase was washed with 50 mL of brine, dried ($Na_2SO_4$), filtered and the solvent was removed in vacuo. The residue was purified by flash chromatography ($SiO_2$, eluting with linear gradient of 0-15% ethyl acetate in petroleum ether) to provide 0.35 g (1.5 mmol, 62%) of ethyl 2-methyl-4-oxo-2,4,5,6,7,8-hexahydrocyclohepta[c]pyrrole-1-carboxylate (VIe). LCMS: m/z found 236.1 $[M+H]^+$; $^1$H NMR (400 MHz, CDCl$_3$): δ 7.35 (s, 1H), 4.34 (q, 2H), 3.88 (s, 3H), 3.16-3.19 (m 2H), 2.65-2.68 (m, 2H), 1.83-1.89 (m, 4H), 1.38 (s, 3H).

N-(3-Chloro-4-fluorophenyl)-2-methyl-4-oxo-2,4,5,6,7,8-hexahydrocyclohepta[c]pyrrole-1-carboxamide (VIIIf, 72)

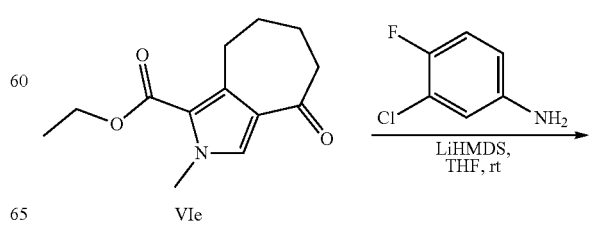

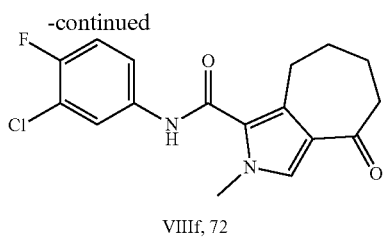

VIIIf, 72

To solution of 0.3 g (1.28 mmol, 1.0 eq.) of ethyl 2-methyl-4-oxo-2,4,5,6,7,8-hexahydrocyclohepta[c]pyrrole-1-carboxylate (VIe) and 0.22 g (1.53 mmol, 1.2 eq.) of 3-chloro-4-fluoroaniline in 15 mL of anhydrous THF under a nitrogen atmosphere was added 10.2 mL (10.2 mmol, 8.0 eq) of a 1 M solution of LiHMDS in THF and the mixture was stirred at room temperature for 2 h. The mixture was quenched with 20 mL of ice-cold water and extracted with 2×30 mL of ethyl acetate. The combined organic extracts were washed with 2×30 mL of water, 50 mL of brine, dried ($Na_2SO_4$), filtered and the solvent was removed in vacuo. The residue was purified by flash chromatography ($SiO_2$, eluting with linear gradient of 30-40% ethyl acetate in petroleum ether) to provide 0.3 g (0.89 mmol, 70%) of N-(3-chloro-4-fluorophenyl)-2-methyl-4-oxo-2,4,5,6,7,8-hexahydrocyclohepta[c]pyrrole-1-carboxamide (72, VIIIf). LCMS: m/z found 335.3/337.3 $[M+H]^+$, RT=6.78 min (Method A); HPLC: RT=8.06 min (Method B); $^1$H NMR (400 MHz, DMSO-$d_6$): δ 10.32 (s, 1H), 7.97-7.99 (m, 1H), 7.58-7.62 (m, 1H), 7.51 (s, 1H), 7.41 (dd, 1H), 3.72 (s, 3H), 2.86-2.89 (m, 2H), 2.55-2.58 (m, 2H), 1.74-1.81 (m, 4H).

Example 82: 4-Amino-N-(3-chloro-4-fluorophenyl)-2-methyl-2,4,5,6,7,8-hexahydrocyclohepta [c]pyrrole-1-carboxamide (80)

(R)-4-((tert-Butylsulfinyl)imino)-N-(3-chloro-4-fluorophenyl)-2-methyl-2,4,5,6,7,8-hexahydro cyclohepta[c]pyrrole-1-carboxamide

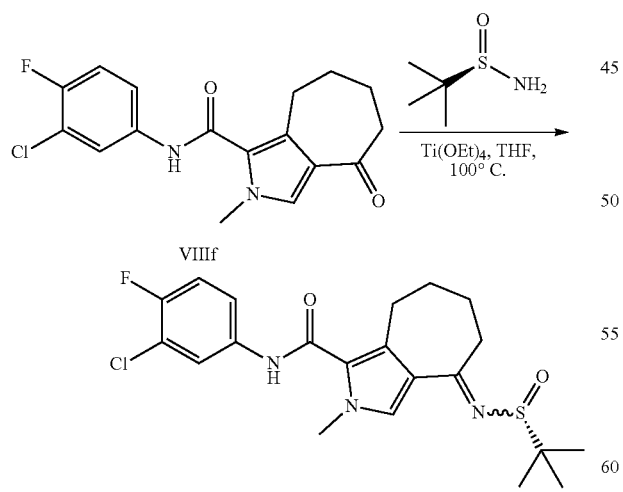

To a solution of 1.0 g (2.99 mmol, 1.0 eq.) of N-(3-chloro-4-fluorophenyl)-2-methyl-4-oxo-2,4,5,6,7,8-hexahydrocyclohepta[c]pyrrole-1-carboxamide (VIIIf) in 25 mL of THF in a sealed tube was added 0.54 g (4.49 mmol, 1.5 eq.) of (R)-2-methylpropane-2-sulfinamide and 4.7 g (20.93 mmol, 7.0 eq.) of titanium tetraethoxide and the mixture was heated at 100° C. for 32 h. The mixture was allowed to cool to room temperature and further cooled to −10° C. and then diluted with 200 mL of ice-cold water and 300 mL of methylene chloride. The heterogeneous mixture was filtered through CELITE® and washed with 40 mL of methylene chloride. The organic phase was washed with 3×300 mL of water, dried ($Na_2SO_4$), filtered and the solvent was removed in vacuo. The residue was purified by reverse phase chromatography (REVELERIS® C-18 column, eluting with a linear gradient of 10-60% acetonitrile in water) to provide 0.9 g (2.05 mmol, 68%) of (R)-4-((tert-butylsulfinyl)imino)-N-(3-chloro-4-fluorophenyl)-2-methyl-2,4,5,6,7,8-hexahydro cyclohepta[c]pyrrole-1-carboxamide. LCMS: m/z found 438.5 $[M+H]^+$, RT=2.16 min; $^1$H NMR (400 MHz, CDCl$_3$): δ 7.80 (dd, 1H), 7.55 (bs, 1H), 7.39-7.42 (m, 1H), 7.25-7.26 (m, 1H), 7.13 (t, 1H), 3.84 (s, 3H), 3.12-3.17 (m, 1H), 3.01-3.07 (m, 1H), 2.88-2.96 (m, 2H), 1.81-1.92 (m, 4H), 1.27 (s, 9H).

4-(((R)-tert-Butylsulfinyl)amino)-N-(3-chloro-4-fluorophenyl)-2-methyl-2,4,5,6,7,8-hexahydro cyclohepta[c]pyrrole-1-carboxamide (XII)

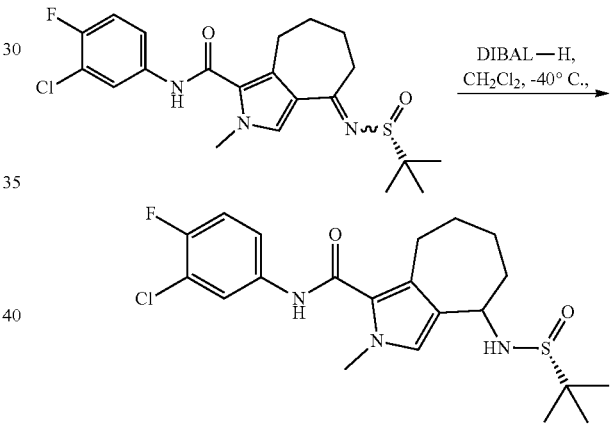

XIf

To a solution of 0.9 g (2.05 mmol, 1.0 eq) of (R)-4-((tert-butylsultinyl)imino)-N-(3-chloro-4-fluorophenyl)-2-methyl-2,4,5,6,7,8-hexahydro cyclohepta[c]pyrrole-1-carboxamide in 100 mL of methylene chloride at −40° C. under a nitrogen atmosphere was added 12.35 mL (12.35 mmol, 6.0 eq) of a 1 M solution of DIBAL-H in THF drop-wise and the mixture was stirred for 1 h. The reaction was quenched by the addition of 15 mL of methanol followed by 95 mL of ice-cold water. The mixture was then diluted with 300 mL of methylene chloride, stirred for 15 min and filtered through CELITE®. The organic phase was dried ($Na_2SO_4$), filtered and the solvent was removed in vacuo and the residue was purified by reverse phase chromatography (REVELERIS® C-18 column, eluting with a linear gradient of 10-60% acetonitrile in water) to provide 0.9 g (2.0 mmol, 97%) of 4-(((R)-tert-butylsulfinyl)amino)-N-(3-chloro-4-fluorophenyl)-2-methyl-2,4,5,6,7,8-hexahydrocyclohepta[c]pyrrole-1-carboxamide (XIf). LCMS: m/z found 440.4/442.1 $[M+H]^+$, RT=2.51, 2.61 min, diastereomeric ratio 10:1.

4-Amino-N-(3-chloro-4-fluorophenyl)-2-methyl-2,4,5,6,7,8-hexahydrocyclohepta[c]pyrrole-1-carboxamide (80, IXr)

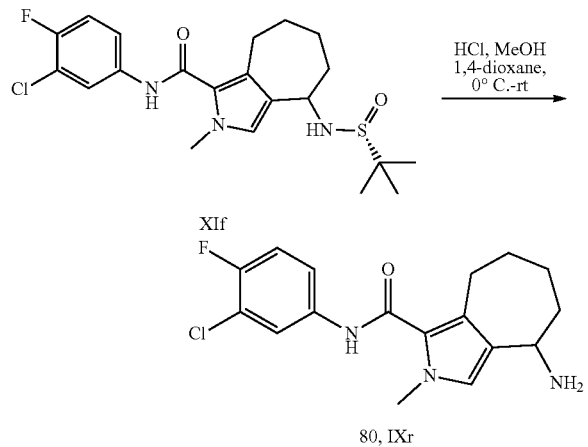

To a solution of 0.9 g (2.0 mmol, 1.0 eq.) of scalemic 4-(((R)-tert-butylsulfinyl)amino)-N-(3-chloro-4-fluorophenyl)-2-methyl-2,4,5,6,7,8-hexahydrocyclohepta[c]pyrrole-1-carboxamide (XIf) in 20 mL of methanol at 0° C. was added 1.5 mL (6.0 mmol, 3.0 eq.) of a 4 M solution of HCl in 1,4-dioxane. The mixture was allowed to warm to room temperature and stirred for 2 h. The solvent was removed in vacuo and the residue was resuspended in 20 mL of saturated sodium bicarbonate solution and stirred for a further 20 min. The precipitated solid was collected by filtration and dried under high vacuum to provide 0.45 g of 4-amino-N-(3-chloro-4-fluorophenyl)-2-methyl-2,4,5,6,7,8-hexahydrocyclohepta[c]pyrrole-1-carboxamide. A 41 mg portion of the product was subjected to chiral SFC purification. Method isocratic, Mobile phase MeOH:CO$_2$—30:70. Column: Chiralcel OX-H: (30×250 mm), 5 μm, flow rate: 60 g/min, isolating the major enantiomer.

(4-Amino-N-(3-chloro-4-fluorophenyl)-2-methyl-2,4,5,6,7,8-hexahydro cyclohepta[c]pyrrole-1-carboxamide Enantiomer I (80, IXr) LCMS: m/z found 319.3/321.3 [M-NH$_2$]$^+$; Chiral-SFC: RT=1.98 min (Chiralcel OD-3 (150 mm×4.6 mm, 3 μm); $^1$H NMR (400 MHz, DMSO-d$_6$): δ10.06 (s, 1H), 7.96-7.98 (m, 1H), 7.56-7.60 (m, 1H), 7.37 (t, 1H), 6.70 (s, 1H), 3.74-3.77 (m, 1H), 3.60 (s, 3H), 2.81-2.86 (m, 1H), 2.43-2.50 (m, 1H), 1.53-1.97 (m, 6H), 1.31-1.43 (m, 2H).

Example 83: Methyl (1-((3-chloro-4-fluorophenyl)carbamoyl)-2-methyl-2,4,5,6,7,8-hexahydro cyclohepta[c]pyrrol-4-yl)carbamate (79)

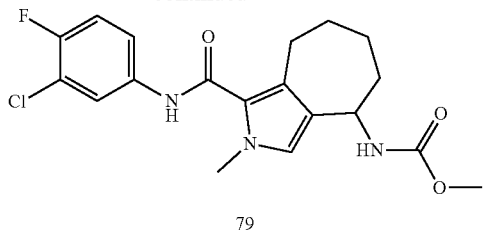

To a solution of 120 mg scalemic 4-amino-N-(3-chloro-4-fluorophenyl)-2-methyl-2,4,5,6,7,8-hexahydrocyclohepta[c]pyrrole-1-carboxamide (IXr, derived from (R)-2-methylpropane-2-sulfinamide) in 20 mL of THF at 0° C. under a nitrogen atmosphere was added 0.18 g (1.79 mmol, of triethylamine followed by 50 mg (0.54 mmol) of methyl chloroformate. The reaction was allowed to warm to room temperature and stirred for 16 h. The mixture was then diluted with 30 mL of water and 50 mL of ethyl acetate and stirred for 15 min. The organic phase was washed with 30 mL of water, 30 mL of brine, dried (Na$_2$SO$_4$), filtered and the solvent was removed in vacuo. The residue was purified by flash chromatography (SiO$_2$, eluting with a linear gradient of 20-35% ethyl acetate in petroleum ether) to provide 52 mg (0.13 mmol) of methyl (1-((3-chloro-4-fluorophenyl)carbamoyl)-2-methyl-2,4,5,6,7,8-hexahydrocyclohepta[c]pyrrol-4-yl)carbamate. The major enantiomer was isolated by chiral SFC purification. Method isocratic, Mobile phase MeOH:CO$_2$—20:80. Column: Chiralpak IG (30×250 mm, 5 μm), flow rate=70 g/min (4-Amino-N-(3-chloro-4-fluorophenyl)-2-methyl-2,4,5,6,7,8-hexahydro cyclohepta[c]pyrrole-1-carboxamide Enantiomer I (79) LCMS: m/z found 394.2/396.3 [M+H]$^+$; Chiral SFC: RT=1.79 min (Chiralcel OD-3 (150 mm×4.6 mm, 3 μm); $^1$H NMR (400 MHz, DMSO-d$_6$): δ10.12 (s, 1H), 7.96-7.98 (m, 1H), 7.56-7.60 (m, 1H), 7.35-7.45 (m, 2H), 6.59 (s, 1H), 4.49-4.53 (m, 1H), 3.59 (s, 3H), 3.54 (s, 3H), 2.80-2.87 (m, 1H), 2.49-2.53 (m, 1H), 1.9-1.98 (m, 1H), 1.56-1.75 (m, 4H), 1.29-1.36 (m, 1H).

Example 84: (1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate (86)

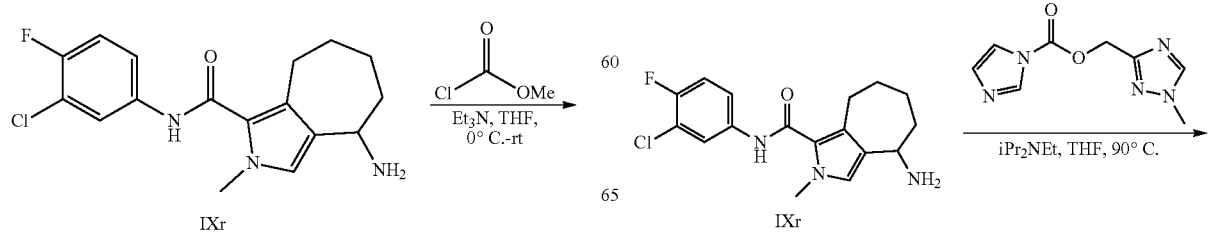

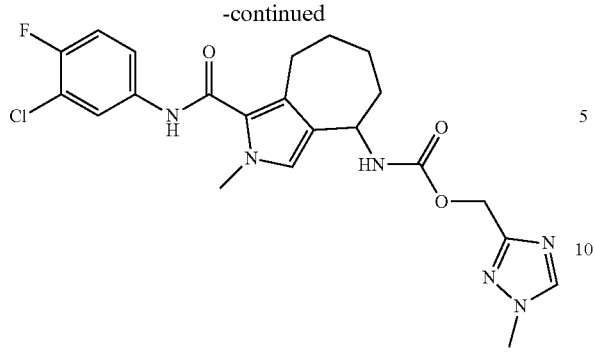

86

(1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate was synthesized in a similar manner as described above from 4-amino-N-(3-chloro-4-fluorophenyl)-2-methyl-2,4,5,6,7,8-hexahydrocyclohepta[c]pyrrole-1-carboxamide (IXr, derived from (R)-2-methylpropane-2-sulfinamide) and (1-methyl-1H-1,2,4-triazol-3-yl)methyl 1H-imidazole-1-carboxylate. (1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate—Enantiomer II (86) LCMS: m/z found 475.1/477.1 [M+H]$^+$; Chiral SFC: RT=7.88 min (Chiralpak IG (150 mm×4.6 mm, 3 μm); $^1$H NMR (400 MHz, DMSO-d$_6$): δ10.08 (s, 1H), 8.43 (s, 1H), 7.95-7.98 (m, 1H), 7.56-7.60 (m, 2H), 7.37 (t, 1H), 6.61 (s, 1H), 4.99 (s, 2H), 4.49-4.53 (m, 1H), 3.85 (s, 3H), 3.59 (s, 3H), 2.80-2.87 (m, 1H), 2.49-2.57 (m, 1H), 1.94-1.98 (m, 1H), 1.56-1.76 (m, 4H), 1.29-1.36 (m, 1H).

Example 85: 4-Amino-N-(3-chloro-4-fluorophenyl)-2-methyl-2,4,5,6,7,8-hexahydrocyclohepta [c]pyrrole-1-carboxamide (87)

4-(((S)-tert-Butylsulfinyl)amino)-N-(3-chloro-4-fluorophenyl)-2-methyl-2,4,5,6,7,8-hexahydro cyclohepta[c]pyrrole-1-carboxamide (XIf)

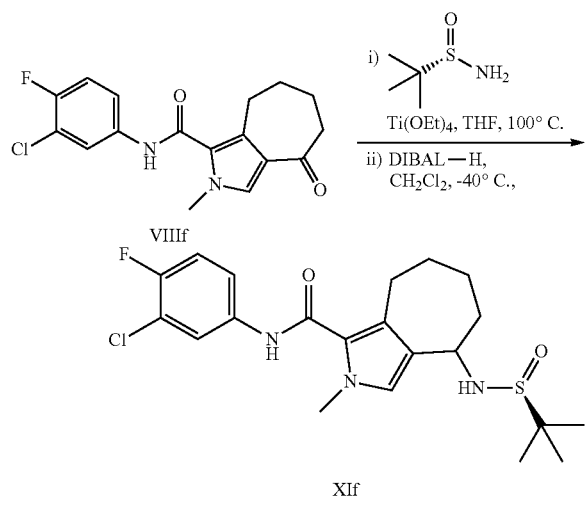

4-(((S)-tert-Butylsulfinyl)amino)-N-(3-chloro-4-fluorophenyl)-2-methyl-2,4,5,6,7,8-hexahydro cyclohepta[c]pyrrole-1-carboxamide (XIf) was synthesized in an identical manner as described above from N-(3-chloro-4-fluorophenyl)-2-methyl-4-oxo-2,4,5,6,7,8-hexahydrocyclohepta[c]pyrrole-1-carboxamide (VIIIe) and (S)-2-methylpropane-2-sulfinamide. LCMS: m/z found 440.4/442.1 [M+H]$^+$, RT=2.51, 2.61 min, diastereomeric ratio ~1:6.

4-Amino-N-(3-chloro-4-fluorophenyl)-2-methyl-2,4,5,6,7,8-hexahydrocyclohepta [c]pyrrole-1-carboxamide (87, IXr)

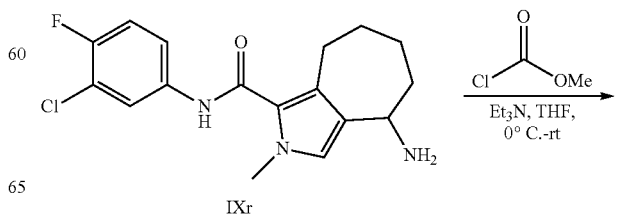

4-Amino-N-(3-chloro-4-fluorophenyl)-2-methyl-2,4,5,6,7,8-hexahydrocyclohepta[c]pyrrole-1-carboxamide was synthesized in an identical manner as described above from 4-(((S)-tert-butylsulfinyl)amino)-N-(3-chloro-4-fluorophenyl)-2-methyl-2,4,5,6,7,8-hexahydro cyclohepta[c]pyrrole-1-carboxamide (XIf).

4-Amino-N-(3-chloro-4-fluorophenyl)-2-methyl-2,4,5,6,7,8-hexahydro cyclohepta[c]pyrrole-1-carboxamide Enantiomer II (87). LCMS: m/z found 319.3/321.3 [M-NH$_2$]$^+$; Chiral-SFC: RT=3.98 min, Chiralcel OX-H (150 mm×4.6 mm, 3 μm); $^1$H NMR (400 MHz, DMSO-d$_6$): δ10.06 (s, 1H), 7.96-7.98 (m, 1H), 7.56-7.60 (m, 1H), 7.37 (t, 1H), 6.70 (s, 1H), 3.74-3.77 (m, 1H), 3.60 (s, 3H), 2.81-2.86 (m, 1H), 2.43-2.50 (m, 1H), 1.53-1.97 (m, 6H), 1.31-1.43 (m, 2H).

Example 86: Methyl (1-((3-chloro-4-fluorophenyl)carbamoyl)-2-methyl-2,4,5,6,7,8-hexahydro cyclohepta[c]pyrrol-4-yl)carbamate (85)

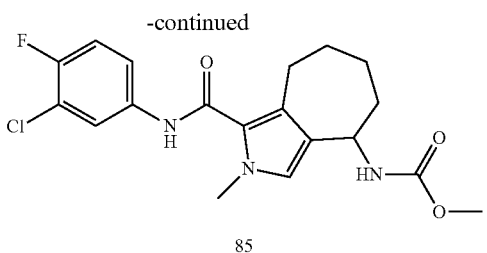

85

Methyl (1-((3-chloro-4-fluorophenyl)carbamoyl)-2-methyl-2,4,5,6,7,8-hexahydro cyclohepta[c]pyrrol-4-yl)carbamate was synthesized in an identical manner as described above from 4-amino-N-(3-chloro-4-fluorophenyl)-2-methyl-2,4,5,6,7,8-hexahydrocyclohepta[c]pyrrole-1-carboxamide (IXr, derived from (S)-2-methylpropane-2-sulfinamide) and methyl chloroformate (4-Amino-N-(3-chloro-4-fluorophenyl)-2-methyl-2,4,5,6,7,8-hexahydro cyclohepta[c]pyrrole-1-carboxamide Enantiomer II (85) LCMS: m/z found 394.2/396.3 [M+H]$^+$; Chiral SFC: RT=6.62 min (Chiralpak IG (150 mm×4.6 mm, 3 μm); $^1$H NMR (400 MHz, DMSO-d$_6$): δ10.12 (s, 1H), 7.96-7.98 (m, 1H), 7.56-7.60 (m, 1H), 7.35-7.45 (m, 2H), 6.59 (s, 1H), 4.49-4.53 (m, 1H), 3.59 (s, 3H), 3.54 (s, 3H), 2.80-2.87 (m, 1H), 2.49-2.53 (m, 1H), 1.9-1.98 (m, 1H), 1.56-1.75 (m, 4H), 1.29-1.36 (m, 1H).

Example 87: (1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate (89)

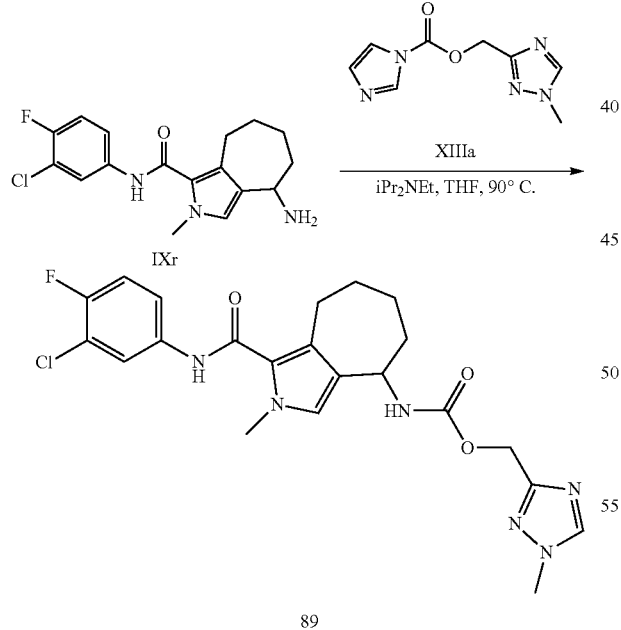

89

(1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate was synthesized in a similar manner as described above from 4-amino-N-(3-chloro-4-fluorophenyl)-2-methyl-2,4,5,6,7,8-hexahydrocyclohepta[c]pyrrole-1-carboxamide (IXr, derived from (S)-2-methylpropane-2-sulfinamide) and (1-methyl-1H-1,2,4-triazol-3-yl)methyl 1H-imidazole-1-carboxylate. (1-Methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate—Enantiomer I (89) LCMS: m/z found 475.1/477.1 [M+H]$^+$; Chiral SFC: RT=6.89 min (Chiralpak IG (150 mm×4.6 mm, 3 μm); $^1$H NMR (400 MHz, DMSO-d$_6$): δ10.08 (s, 1H), 8.43 (s, 1H), 7.95-7.98 (m, 1H), 7.56-7.60 (m, 2H), 7.37 (t, 1H), 6.61 (s, 1H), 4.99 (s, 2H), 4.49-4.53 (m, 1H), 3.85 (s, 3H), 3.59 (s, 3H), 2.80-2.87 (m, 1H), 2.49-2.57 (m, 1H), 1.94-1.98 (m, 1H), 1.56-1.76 (m, 4H), 1.29-1.36 (m, 1H).

Compounds of formula XXVII can be synthesized according to Scheme 5. Generation of intermediates of formula XXII can be achieved according to procedures outlined in *Synthesis* 2012, 44, 2798-2804. Palladium catalysed carbonylation of XXII in the presence of carbon monoxide gas and an alcohol, for example ethanol, provides ester XXIII. Reductive amination utilizing XXIII can be performed with an ammonia equivalent. Additionally, use of a sulfinamine to generate a sulfinimine allows for reduction to intermediates of type XXIV. In cases where the sulfinamine is enantioenriched or enantiopure, intermediates of type XXIV can be generated with stereoenrichment. Amidation of XXIV with, for example a primary amine or primary aniline, can be performed to generate intermediated of type XXV, and subsequent liberation of the primary amine via acid mediated deprotection allows for N-functionalization of XXVI to provide compounds of formula XXVII.

Scheme 5.

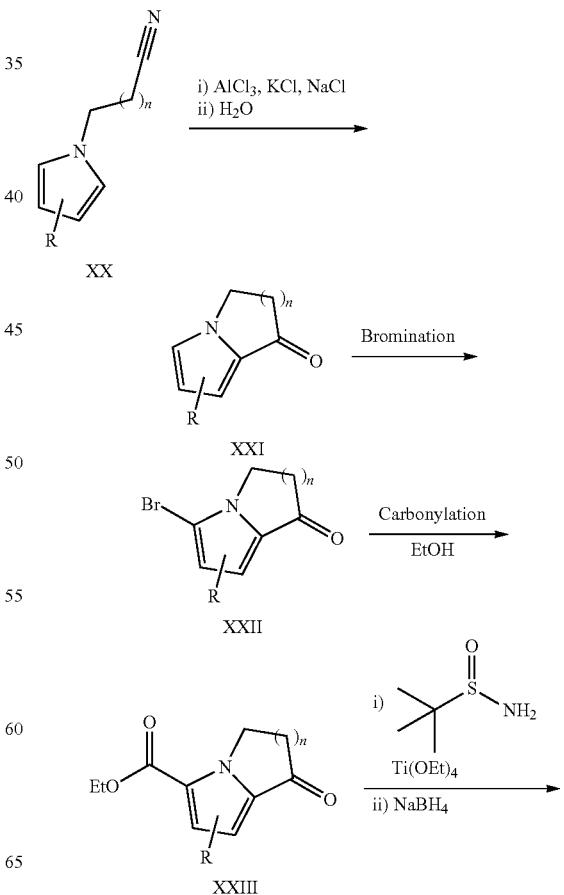

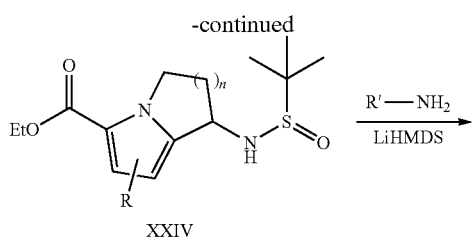

XXIV

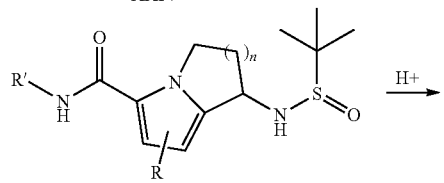

XXV

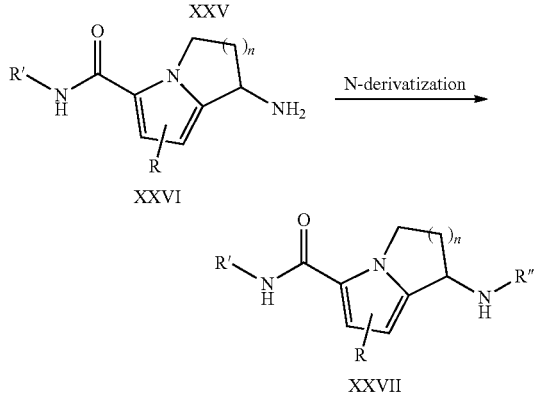

XXVII

Example 88: Methyl (5-((3-chloro-4-fluorophenyl)carbamoyl)-2,3-dihydro-1H-pyrrolizin-1-yl)carbamate (38, 39)

2,3-Dihydro-1H-pyrrolizin-1-one (XXIa) (*Synthesis* 2012, 44, 2798-2804)

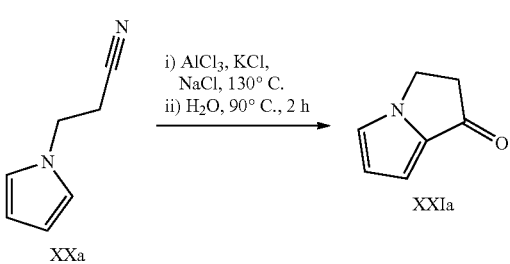

A mixture of 18.9 g (141.5 mmol, 3.4 eq.) of aluminium trichloride, 5.0 g (66.6 mmol, 1.6 eq.) of anhydrous potassium chloride and 4.6 g (79.1 mmol, 1.9 eq.) was heated at 130° C. until a brown oil was formed. To this preheated mixture was added 5.0 g (41.6 mmol 1.0 eq.) of 3-(1H-pyrrol-1-yl)propanenitrile (XXa) and the reaction was stirred vigorously at 130° C. for 10 min. The resulting hot solution was poured into 25 mL of ice-cold water and then heated at 90° C. for 2 h. The mixture was allowed to cool to room temperature and extracted with 3×30 mL of ethyl acetate. The combined organic extracts were dried (Na$_2$SO$_4$), filtered and the solvent was removed in vacuo. The above detailed reaction was performed in duplicate and the combined crude products purified by flash chromatography (SiO$_2$, eluting with a linear gradient of 40-50% ethyl acetate in methylene chloride) to provide 6.3 g (52.1 mmol, 62%) of 2,3-dihydro-1H-pyrrolizin-1-one (XXIa). LCMS: m/z found 121.8 [M+H]$^+$; $^1$H NMR (400 MHz, CDCl$_3$): δ 7.04 (d, 1H), 6.74 (d, 1H), 6.51-6.53 (m, 1H), 4.31 (t, 2H), 3.09 (t, 2H).

5-Bromo-2,3-dihydro-1H-pyrrolizin-1-one (XXIIa) (*Synthesis* 2012, 44, 2798-2804)

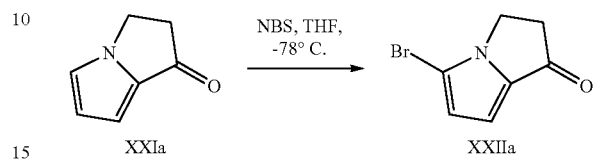

To a solution of 3.0 g (24.8 mmol, 1.0 eq.) of 2,3-dihydro-1H-pyrrolizin-1-one (XXIa) in 40 mL of THF at −78° C. under a nitrogen atmosphere was added a solution of 4.84 g (27.3 mmol, 1.0 eq.) of N-bromosuccinimide in 40 mL of THF drop-wise over approximately 15 min and the mixture was stirred at −78° C. for 2 h. The reaction was quenched with 50 mL of ice-cold water and extracted with 3×50 mL methylene chloride. The combined organic extracts were washed with 50 mL of brine, dried (Na$_2$SO$_4$), filtered and the solvent was removed in vacuo. The residue was purified by flash chromatography (SiO$_2$, eluting with a linear gradient of 15-20% ethyl acetate in petroleum ether) to provide 4.0 g (20.0 mmol, 72%) of 5-bromo-2,3-dihydro-1H-pyrrolizin-1-one (XXIIa). LCMS: m/z found 200.3/202.3 [M+H]$^+$; $^1$H NMR (400 MHz, CDCl$_3$): δ 6.71 (d, 1H), 6.47 (d, 1H), 4.18 (t, 2H), 3.10 (t, 2H).

Ethyl 1-oxo-2,3-dihydro-1H-pyrrolizine-5-carboxylate (XXIIa)

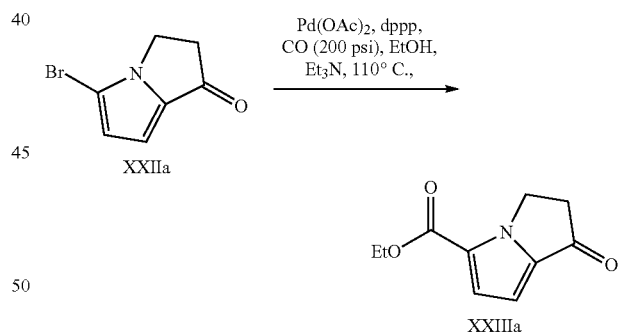

A steel pressure vessel was charged with 4.0 g (20.0 mmol, 1.0 eq.) of 5-bromo-2,3-dihydro-1H-pyrrolizin-1-one (XXIIa) and 40 mL of ethanol. The solution was purged with argon for 10 min and 8.4 mL (60.4 mmol, 3.0 eq.) of triethylamine was added. Purging was continued for a further 5 min and 0.45 g (2.0 mmol, 0.1 eq.) of palladium acetate and 1.23 g (3.0 mmol, 0.15 eq.) of 1,3-bis(diphenylphosphino)propane were added. The mixture was then heated at 110° C. under 200 psi of carbon monoxide for 16 h. The mixture was allowed to cool to room temperature and filtered through CELITE®. The pad was washed with 20 mL of methylene chloride and the filtrate was concentrated in vacuo. The residue was purified by flash chromatography (SiO$_2$, eluting with a linear gradient of 15-20% ethyl acetate in petroleum ether) to provide 2.6 g (13.5 mmol, 67%) of ethyl 1-oxo-2,3-dihydro-1H-pyrrolizine-5-carboxylate (XXIIIa). LCMS: m/z found 194.4 [M+H]⁺; ¹H NMR (400 MHz, CDCl₃): δ 7.07 (d, 1H), 6.68 (d, 1H), 4.58 (t, 2H), 4.36 (q, 2H), 3.10 (t, 2H), 1.39 (t, 3H).

Ethyl 1-((tert-butylsulfinyl)amino)-2,3-dihydro-1H-pyrrolizine-5-carboxylate (XXIVa)

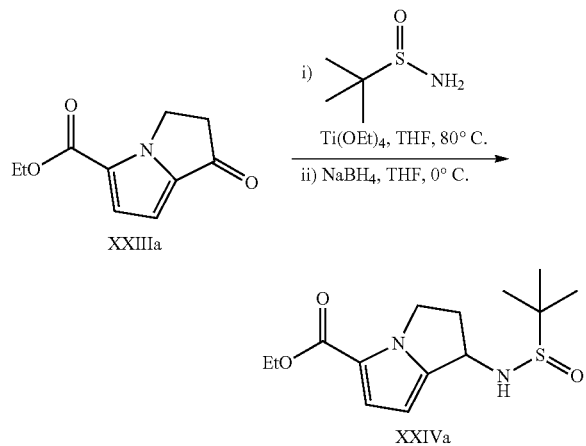

To a solution of 1.0 g (5.2 mmol, 1.0 eq.) of ethyl 1-oxo-2,3-dihydro-1H-pyrrolizine-5-carboxylate (XXIIIa) in 20 mL of THF was added 0.75 g (6.2 mmol, 1.2 eq.) of racemic 2-methylpropane-2-sulfinamide and 3.3 mL (15.5 mmol, 3.0 eq.) of titanium tetraethoxide and the mixture was heated at 80° C. for 16 h. The mixture was allowed to cool to room temperature, further cooled to 0° C. and 0.39 g (10.4 mmol, 2.0 eq.) of sodium borohydride was added. After stirring at 0° C. for 4 h, the reaction was diluted with 50 mL of ice-cold water and extracted with 3×70 mL of ethyl acetate. The combined organic extracts were washed with 2×50 mL of brine, dried (Na₂SO₄), filtered and the solvent was removed in vacuo. The residue was purified by flash chromatography (SiO₂, eluting with a linear gradient of 30-40% ethyl acetate in petroleum ether) to provide 1.6 g of ethyl 1-((tert-butylsulfinyl)amino)-2,3-dihydro-1H-pyrrolizine-5-carboxylate (XXIVa) as a ~2:1 mixture of racemic diastereoisomers. LCMS: m/z found 299.0 [M+14]⁺.

1-((tert-Butylsulfinyl)amino)-N-(3-chloro-4-fluorophenyl)-2,3-dihydro-1H-pyrrolizine-5-carboxamide (XXVa)

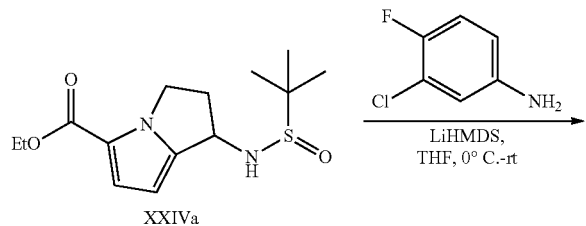

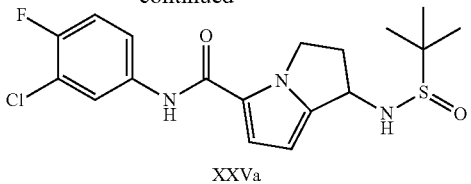

To a solution of 0.5 g (1.6 mmol, 1.0 eq.) of ethyl 1-((tert-butylsulfinyl)amino)-2,3-dihydro-1H-pyrrolizine-5-carboxylate (XXIVa) and 0.37 g (2.5 mmol, 1.5 eq) of 3-chloro-4-fluoroaniline in 5 mL of THF at 0° C. under an argon atmosphere was added 10.0 mL (10.0 mmol, 6 eq.) of a 1 M solution of lithium bis(trimethylsilyl)amide in THF. The mixture was allowed to warm to room temperature and stirred for 2 h. The reaction was quenched with 20 mL of saturated ice-cold water and extracted with 3×30 mL of ethyl acetate. The combined organic extracts were dried (Na₂SO₄), filtered and the solvent was removed in vacuo. The residue was purified by flash chromatography (SiO₂, eluting with a linear gradient of 40-60% ethyl acetate in petroleum ether) to provide 0.42 g (1.055 mmol, 63%) of 1-((tert-butylsulfinyl)amino)-N-(3-chloro-4-fluorophenyl)-2,3-dihydro-1H-pyrrolizine-5-carboxamide (XXVa) as a ~2:1 mixture of racemic diastereoisomers. LCMS: m/z found 398.1/400.1 [M+H⁺].

1-Amino-N-(3-chloro-4-fluorophenyl)-2,3-dihydro-1H-pyrrolizine-5-carboxamide (XXVIa)

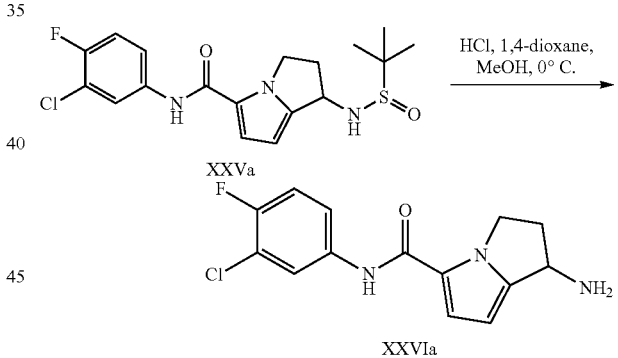

To a solution of 0.42 g (1.06 mmol, 1.0 eq.) of 1-((tert-butylsulfinyl)amino)-N-(3-chloro-4-fluorophenyl)-2,3-dihydro-1H-pyrrolizine-5-carboxamide (XXVa) in 8 mL of methanol at 0° C. was added 4 mL of a 4 M solution of HCl in 1,4-dioxane and the mixture was stirred at 0° C. for 1 h. The solvent was removed in vacuo and the residue was triturated with 10 mL of diethyl ether. The solids were dissolved in 40 mL of 10% methanol in methylene chloride and washed with 3×30 mL of saturated sodium bicarbonate solution. The organic phase was dried (Na₂SO₄), filtered and the solvent was removed in vacuo to provide 0.3 g (1.02 mmol, 97%) of 1-amino-N-(3-chloro-4-fluorophenyl)-2,3-dihydro-1H-pyrrolizine-5-carboxamide (XXVIa). ¹H NMR (300 MHz, DMSO-d₆): δ 9.79 (s, 1H), 8.01-8.05 (m, 1H), 7.61-7.66 (m, 1H), 7.36 (t, 1H), 7.09 (d, 1H), 5.95 (d, 1H), 4.31-4.39 (m, 1H), 4.22-4.27 (m, 1H), 4.03-4.12 (m, 1H), 2.63-2.73 (m, 1H), 2.01-2.13 (m, 3H).

Methyl (5-((3-chloro-4-fluorophenyl)carbamoyl)-2,3-dihydro-1H-pyrrolizin-1-yl)carbamate (38, 39)

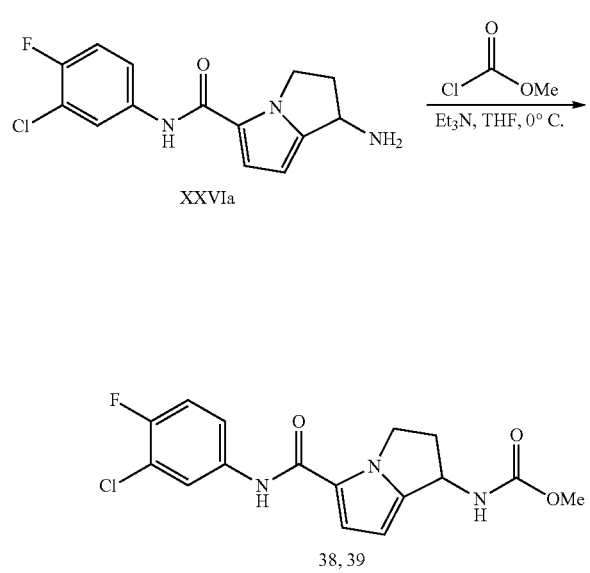

XXVIa 38, 39

To a solution of 0.3 g (1.0 mmol, 1.0 eq.) of 1-amino-N-(3-chloro-4-fluorophenyl)-2,3-dihydro-1H-pyrrolizine-5-carboxamide (XXVIa) in 6 mL of THF at 0° C. under a nitrogen atmosphere was added 0.43 mL (3.07 mmol, 3.0 eq.) of triethylamine followed by 0.16 mL (2.0 mmol, 2 eq.) of methyl chloroformate and the mixture was stirred at room temperature for 2 h. The reaction was quenched with 10 mL of ice-cold water and extracted with 3×30 mL of ethyl acetate. The combined organic extracts were washed with 30 mL of brine (30 mL), dried ($Na_2SO_4$), filtered and the solvent was removed in vacuo. The residue was purified by flash chromatography ($SiO_2$, eluting with a linear gradient of 30-35% ethyl acetate in petroleum ether) to provide 0.22 g (0.63 mmol, 61%) of methyl (5-((3-chloro-4-fluorophenyl)carbamoyl)-2,3-dihydro-1H-pyrrolizin-1-yl)carbamate. The enantiomers were subsequently separated by preparative SFC. Method: isocratic, Mobile phase MeOH:$CO_2$ 50:50. Column: Chiralpak IG (30×250 mm), 5 µm, flow rate: 100 g/min.

Methyl (5-((3-chloro-4-fluorophenyl)carbamoyl)-2,3-dihydro-1H-pyrrolizin-1-yl)carbamate Enantiomer I (38) LCMS: m/z found 352.2/354.21 [M+H]$^+$, RT=5.73 min (Method A); HPLC: RT=7.75 min (Method B); Chiral SFC: RT=4.95 min, Column: Chiralpak IG (4.6×250 mm, 3 µm); $^1$H NMR (400 MHz, DMSO-$d_6$): δ 9.82 (bs, 1H), 8.03 (dd, 1H), 7.61-7.70 (m, 2H), 7.37 (t, 1H), 7.11 (d, 1H), 5.96 (d, 1H), 4.94-5.02 (m, 1H), 4.30-4.39 (m, 1H), 4.11-4.20 (m, 1H), 3.56 (s, 3H), 2.73-2.85 (m, 1H), 2.19-2.31 (m, 1H).

Methyl (5-((3-chloro-4-fluorophenyl)carbamoyl)-2,3-dihydro-1H-pyrrolizin-1-yl)carbamate Enantiomer II (39) LCMS: m/z found 352.2/354.21 [M+H]$^+$, RT=5.70 min (Method A); HPLC: RT=7.72 min (Method B); Chiral SFC: RT=9.98 min, Column: Chiralpak IG (4.6×250 mm, 3 µm); $^1$H NMR (400 MHz, DMSO-$d_6$): δ 9.82 (bs, 1H), 8.03 (dd, 1H), 7.61-7.70 (m, 2H), 7.37 (t, 1H), 7.11 (d, 1H), 5.96 (d, 1H), 4.94-5.02 (m, 1H), 4.30-4.39 (m, 1H), 4.11-4.20 (m, 1H), 3.56 (s, 3H), 2.73-2.85 (m, 1H), 2.19-2.31 (m, 1H).

Example 89: Pyridin-2-ylmethyl (5-((3-chloro-4-fluorophenyl)carbamoyl)-2,3-dihydro-1H-pyrrolizin-1-yl)carbamate (42, 43)

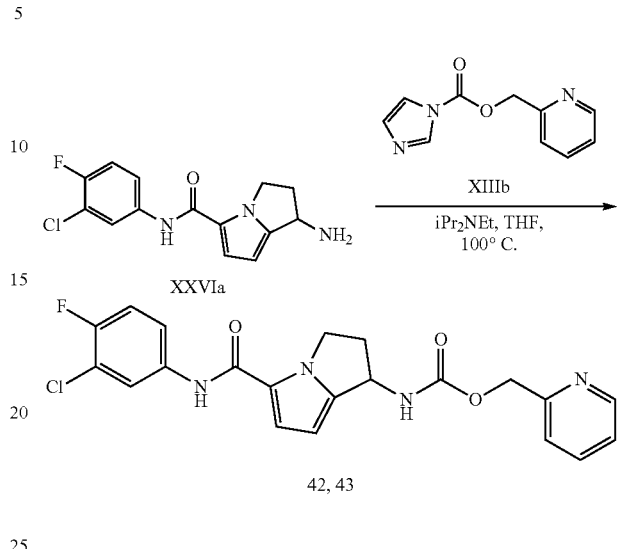

XXVIa 42, 43

To a solution of 0.4 g (1.4 mmol, 1.0 eq.) of 1-amino-N-(3-chloro-4-fluorophenyl)-2,3-dihydro-1H-pyrrolizine-5-carboxamide (XXVIa) and 0.42 g (2.0 mmol, 1.5 eq.) of pyridin-2-ylmethyl 1H-imidazole-1-carboxylate in 5 mL of THF under a nitrogen atmosphere was added 0.53 g (4.1 mmol, 3.0 eq.) of N,N-diisoproplethylamine and the mixture was heated at 100° C. for 16 h. The mixture was allowed to cool to room temperature, diluted with 10 mL of ice-cold water and extracted with 3×30 mL of ethyl acetate. The combined organic extracts were dried ($Na_2SO_4$), filtered and the solvent was removed in vacuo. The residue was purified by flash chromatography ($SiO_2$, eluting with a linear gradient of 0-2% methanol/methylene chloride) to provide 0.35 g (0.83 mmol, 60%) of pyridin-2-ylmethyl (5-((3-chloro-4-fluorophenyl)carbamoyl)-2,3-dihydro-1H-pyrrolizin-1-yl) carbamate The enantiomers were subsequently separated by SFC (Waters SFC investigator). Method isocratic, Mobile phase MeOH:$CO_2$—50:50. Column: Chiralpak IG (30×250 mm), 5 µm, flow rate: 90 g/min. Pyridin-2-ylmethyl (5-((3-chloro-4-fluorophenyl)carbamoyl)-2,3-dihydro-1H-pyrrolizin-1-yl)carbamate—Enantiomer I (42) LCMS: m/z found 429.2/431.2 [M+H]$^+$, RT=5.14 min (Method A); HPLC: RT=6.77 min (Method B); Chiral SFC: RT=10.45 min, Chiralpak IG (4.6×250 mm, 5 µm); $^1$H NMR (400 MHz, DMSO-$d_6$) δ 9.86 (bs, 1H), 8.54 (d, 1H), 8.02-8.05 (m, 1H), 7.95 (d, 1H), 7.80-7.86 (m, 1H), 7.61-7.67 (m, 1H), 7.31-7.40 (m, 3H), 7.12 (d, 1H), 5.98 (d, 1H), 5.12 (s, 2H), 4.99-5.06 (m, 1H), 4.31-4.40 (m, 1H), 4.16-4.22 (m, 1H), 2.78-2.86 (m, 1H), 2.27-2.34 (m, 1H).

Pyridin-2-ylmethyl (5-((3-chloro-4-fluorophenyl)carbamoyl)-2,3-dihydro-1H-pyrrolizin-1-yl)carbamate—Enantiomer II (43) LCMS: m/z found 429.2/431.2 [M+H]$^+$, RT=5.14 min (Method A); HPLC: RT=6.78 min (Method B); Chiral SFC: RT=16.12 min, Chiralpak IG (4.6×250 mm, 5 µm); $^1$H NMR (400 MHz, DMSO-$d_6$) δ 9.86 (bs, 1H), 8.54 (d, 1H), 8.02-8.05 (m, 1H), 7.95 (d, 1H), 7.80-7.86 (m, 1H), 7.61-7.67 (m, 1H), 7.31-7.40 (m, 3H), 7.12 (d, 1H), 5.98 (d, 1H), 5.12 (s, 2H), 4.99-5.06 (m, 1H), 4.31-4.40 (m, 1H), 4.16-4.22 (m, 1H), 2.78-2.86 (m, 1H), 2.27-2.34 (m, 1H).

Example 90: (1-Methyl-1H-1,2,4-triazol-3-yl)methyl (5-((3-chloro-4-fluorophenyl)carbamoyl)-2,3-dihydro-1H-pyrrolizin-1-yl)carbamate (40, 41)

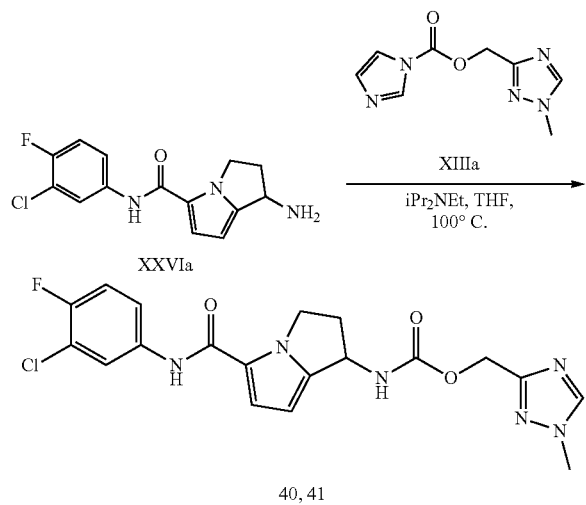

(1-Methyl-1H-1,2,4-triazol-3-yl)methyl (5-((3-chloro-4-fluorophenyl)carbamoyl)-2,3-dihydro-1H-pyrrolizin-1-yl)carbamate was synthesized in a similar manner as described above from 1-amino-N-(3-chloro-4-fluorophenyl)-2,3-dihydro-1H-pyrrolizine-5-carboxamide (XXVIa) and (1-methyl-1H-1,2,4-triazol-3-yl)methyl 1H-imidazole-1-carboxylate. The enantiomers were subsequently separated by SFC. Method isocratic, Mobile phase MeOH:$CO_2$—25:75. Column: Chiralpak IA (21×250 mm), 5 μm, flow rate: 100 g/min.

(1-Methyl-1H-1,2,4-triazol-3-yl)methyl (5-((3-chloro-4-fluorophenyl)carbamoyl)-2,3-dihydro-1H-pyrrolizin-1-yl)carbamate—Enantiomer I (40) LCMS: m/z found 433.0/435.0 [M+H]$^+$; Chiral SFC: RT=5.18 min Chiralpak IA (4.6×250 mm, 5 μm); $^1$H NMR (400 MHz, DMSO-$d_6$) δ 9.86 (bs, 1H), 8.43 (s, 1H), 8.01-8.05 (m, 1H), 7.83 (d, 1H), 7.61-7.68 (m, 1H), 7.36 (t, 1H), 7.11 (d, 1H), 5.97 (d, 1H), 4.94-5.03 (m, 3H), 4.30-4.39 (m, 1H), 4.11-4.21 (m, 1H), 3.84 (s, 3H), 2.78-2.85 (m, 1H), 2.23-2.29 (m, 1H).

(1-Methyl-1H-1,2,4-triazol-3-yl)methyl (5-((3-chloro-4-fluorophenyl)carbamoyl)-2,3-dihydro-1H-pyrrolizin-1-yl)carbamate—Enantiomer II (41) LCMS: m/z found 433.0/435.0 [M+H]$^+$; Chiral SFC: RT=7.86 min Chiralpak IA (4.6×250 mm, 5 μm); $^1$H NMR (400 MHz, DMSO-$d_6$) δ 9.86 (bs, 1H), 8.43 (s, 1H), 8.01-8.05 (m, 1H), 7.83 (d, 1H), 7.61-7.68 (m, 1H), 7.36 (t, 1H), 7.11 (d, 1H), 5.97 (d, 1H), 4.94-5.03 (m, 3H), 4.30-4.39 (m, 1H), 4.11-4.21 (m, 1H), 3.84 (s, 3H), 2.78-2.85 (m, 1H), 2.23-2.29 (m, 1H).

Example 91: Biological Results

Representative compounds of the invention were tested for their abilities to inhibit formation of relaxed circular DNA (rcDNA) in a HepDE19 assay, as described elsewhere herein. Results are illustrated in Table 1.

TABLE 1

| No. | Nomenclature | DE-19 bDNA $EC_{50}$ (μM) |
|---|---|---|
| 1 | methyl (1-((3-chloro-4-fluorophenyl)carbamoyl)-2-methyl-2,4,5,6-tetrahydrocyclopenta[c]pyrrol-4-yl)carbamate | 0.09 |
| 2 | pyridin-2-ylmethyl (1-((3-chloro-4-fluorophenyl)carbamoyl)-2-methyl-2,4,5,6-tetrahydrocyclopenta[c]pyrrol-4-yl)carbamate | 0.26 |
| 3 | N-(3-chloro-4-fluorophenyl)-2-methyl-4-(3-methylureido)-2,4,5,6-tetrahydrocyclopenta[c]pyrrole-l-carboxamide | 0.94 |
| 4 | methyl (1-((3-chloro-4-fluorophenyl)carbamoyl)-2-methyl-2,4,5,6-tetrahydrocyclopenta[c]pyrrol-4-yl)carbamate, enantiomer I | 0.05 |
| 5 | methyl (1-((3-chloro-4-fluorophenyl)carbamoyl)-2-methyl-2,4,5,6-tetrahydrocyclopenta[c]pyrrol-4-yl)carbamate, enantiomer II | 0.99 |
| 6 | pyridin-2-ylmethyl ((3-chloro-4-fluorophenyl)carbamoyl)-2-methyl-2,4,5,6-tetrahydrocyclopenta[c]pyrrol-4-yl)carbamate, enantiomer I | 0.14 |
| 7 | pyridin-2-ylmethyl(1-((3-chloro-4-fluorophenyl)carbamoyl)-2-methyl-2,4,5,6-tetrahydrocyclopenta[c]pyrrol-4-yl)carbamate, enantiomer II | 1.4 |
| 8 | N-(3-chloro-4-fluorophenyl)-4-(3-methylureido)-2,4,5,6-tetrahydrocyclopenta[c]pyrrole-l-carboxamide | 18 |
| 9 | methyl (1-((3-chloro-4-fluorophenyl)carbamoyl)-2,4,5,6-tetrahydrocyclopenta[c]pyrrol-4-yl)carbamate | 3.0 |
| 10 | N-(3-chloro-4-fluorophenyl)-4-(3-methylureido)-2,4,5,6-tetrahydrocyclopenta[c]pyrrole-l-carboxamide, enantiomer I | 16 |
| 11 | N-(3-chloro-4-fluorophenyl)-4-(3-methylureido)-2,4,5,6-tetrahydrocyclopenta[c]pyrrole-l-carboxamide, enantiomer II | 2.4 |
| 12 | N-(3-chloro-4-fluorophenyl)-4-(cyclopropanesulfonamido)-2-ethyl-2,4,5,6-tetrahydrocyclopenta[c]pyrrole-l-carboxamide | 0.26 |
| 13 | N-(3-chloro-4-fluorophenyl)-4-(cyclopropanesulfonamido)-2-methyl-2,4,5,6-tetrahydrocyclopenta[c]pyrrole-l-carboxamide, enantiomer I | 6.8 |
| 14 | N-(3-chloro-4-fluorophenyl)-4-(cyclopropanesulfonamido)-2-methyl-2,4,5,6-tetrahydrocyclopenta[c]pyrrole-l-carboxamide, enantiomer II | 0.07 |
| 15 | N-(3-chloro-4-fluorophenyl)-4-(cyclopropanesulfonamido)-2-ethyl-2,4,5,6-tetrahydrocyclopenta[c]pyrrole-l-carboxamide, enantiomer I | 25 |
| 16 | N-(3-chloro-4-fluorophenyl)-4-(cyclopropanesulfonamido)-2-ethyl-2,4,5,6-tetrahydrocyclopenta[c]pyrrole-l-carboxamide, enantiomer II | 0.13 |
| 17 | N-(3-chloro-4-fluorophenyl)-4-(cyclopropanecarboxamido)-2-ethyl-2,4,5,6-tetrahydrocyclopenta[c]pyrrole-l-carboxamide, enantiomer I | 4.9 |
| 18 | N-(3-chloro-4-fluorophenyl)-4-(cyclopropanecarboxamido)-2-ethyl-2,4,5,6-tetrahydrocyclopenta[c]pyrrole-l-carboxamide, enantiomer II | 0.35 |

TABLE 1-continued

| No. | Nomenclature | DE-19 bDNA EC$_{50}$ (μM) |
|---|---|---|
| 19 | (1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate, enantiomer I | 2.1 |
| 20 | (1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate, enantiomer II | 0.18 |
| 21 | (1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate, enantiomer I | 0.04 |
| 22 | (1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate, enantiomer II | 0.78 |
| 23 | N-(3-chloro-4-fluorophenyl)-4-(cyclopropanecarboxamido)-2-methyl-2,4,5,6-tetrahydrocyclopenta[c]pyrrole-1-carboxamide, enantiomer I | 0.12 |
| 24 | N-(3-chloro-4-fluorophenyl)-4-(cyclopropanecarboxamido)-2-methyl-2,4,5,6-tetrahydrocyclopenta[c]pyrrole-1-carboxamide, enantiomer II | 1.6 |
| 25 | (1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate, enantiomer I | 3.5 |
| 26 | (1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate, enantiomer II | 0.05 |
| 27 | (1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate, enantiomer I | 1.5 |
| 28 | (1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate, enantiomer II | 0.23 |
| 29 | methyl (1-((3-chloro-4-fluorophenyl)carbamoyl)-2-methyl-4,5,6,7-tetrahydro-2H-isoindol-4-yl)carbamate, enantiomer I | 0.47 |
| 30 | N-(3-chloro-4-fluorophenyl)-4-(cyclopropanesulfonamido)-2-methyl-4,5,6,7-tetrahydro-2H-isoindole-1-carboxamide, enantiomer II | 2.1 |
| 31 | (1-methyl-1H-pyrazol-3-yl)methyl (1-((3-chloro-4-fluorophenyl)carbamoyl)-2-methyl-4,5,6,7-tetrahydro-2H-isoindol-4-yl)carbamate, enantiomer I | 0.50 |
| 32 | (1-((3-chloro-4-fluorophenyl)carbamoyl)-2-methyl-4,5,6,7-tetrahydro-2H-isoindol-4-yl)carbamate, | |
| 33 | (1-methyl-1H-1,2,4-triazol-3-yl)methyl (1-((3-chloro-4-fluorophenyl)carbamoyl)-enantiomer II | 0.03 |
| 34 | oxazol-2-ylmethyl (1-((3-chloro-4-fluorophenyl)carbamoyl)-2-methyl-2,4,5,6-tetrahydrocyclopenta[c]pyrrol-4-yl)carbamate, enantiomer I | 0.08 |
| 35 | oxazol-2-ylmethyl (1-((3-chloro-4-fluorophenyl)carbamoyl)-2-methyl-2,4,5,6-tetrahydrocyclopenta[c]pyrrol-4-yl)carbamate, enantiomer II | 1.8 |
| 36 | oxazol-5-ylmethyl (1-((3-chloro-4-fluorophenyl)carbamoyl)-2-methyl-2,4,5,6-tetrahydrocyclopenta[c]pyrrol-4-yl)carbamate, enantiomer I | 0.02 |
| 37 | oxazol-5-ylmethyl (1-((3-chloro-4-fluorophenyl)carbamoyl)-2-methyl-2,4,5,6-tetrahydrocyclopenta[c]pyrrol-4-yl)carbamate, enantiomer II | 2.6 |
| 38 | methyl (5-((3-chloro-4-fluorophenyl)carbamoyl)-2,3-dihydro-1H-pyrrolizin-1-yl)carbamate, enantiomer I | 4.7 |
| 39 | methyl (5-((3-chloro-4-fluorophenyl)carbamoyl)-2,3-dihydro-1H-pyrrolizin-1-yl)carbamate, enantiomer II | 15 |
| 40 | (1-methyl-1H-1,2,4-triazol-3-yl)methyl (5-((3-chloro-4-fluorophenyl)carbamoyl)-2,3-dihydro-1H-pyrrolizin-1-yl)carbamate, enantiomer I | 6.6 |
| 41 | (1-methyl-1H-1,2,4-triazol-3-yl)methyl (5-((3-chloro-4-fluorophenyl)carbamoyl)-2,3-dihydro-1H-pyrrolizin-1-yl)carbamate, enantiomer II | 25 |
| 44 | N-(3-chloro-4-fluorophenyl)-2-methyl-4-oxo-2,4,5,6-19 tetrahydrocyclopenta[c]pyrrole-1-carboxamide | |
| 45 | N-(3-chloro-4-fluorophenyl)-2-methyl-4-oxo-4,5,6,7-tetrahydro-2H-isoindole-1-carboxamide | 0.07 |
| 46 | isopropyl 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate | 2.3 |
| 47 | (1-methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate, enantiomer I | 3.1 |
| 48 | (1-methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate, enantiomer II | 0.01 |
| 49 | 2-cyanoethyl (1-((3-chloro-4-fluorophenyl)carbamoyl)-2-methyl-2,4,5,6-tetrahydrocyclopenta[c]pyrrol-4-yl)carbamate, enantiomer I | 0.06 |
| 50 | 2-cyanoethyl (1-((3-chloro-4-fluorophenyl)carbamoyl)-2-methyl-2,4,5,6-tetrahydrocyclopenta[c]pyrrol-4-yl)carbamate, enantiomer II | 3.0 |
| 51 | (1-methyl-1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate, enantiomer I | 0.01 |
| 52 | (1-methyl-1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate, enantiomer II | 0.31 |
| 53 | 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid | 2.7 |
| 54 | (1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate | 0.06 |

TABLE 1-continued

| No. | Nomenclature | DE-19 bDNA EC$_{50}$ (μM) |
|---|---|---|
| 55 | (1-carbamoyl-3,3-difluorocyclobutypmethyl (1-((3-chloro-4-fluorophenyl)carbamoyl)-2-methyl-2,4,5,6-tetrahydrocyclopenta[c]pyrrol-4-yl)carbamate, enantiomer I | 4.4 |
| 56 | (1-carbamoyl-3,3-difluorocyclobutypmethyl (1-((3-chloro-4-fluorophenyl)carbamoyl)-2-methyl-2,4,5,6-tetrahydrocyclopenta[c]pyrrol-4-yl)carbamate, enantiomer II | 0.60 |
| 57 | (1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate, enantiomer I | 0.05 |
| 58 | (1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate, enantiomer II | 0.97 |
| 59 | (1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer II | 4.2 |
| 60 | (1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer I | 0.06 |
| 61 | (1-methyl-1H-1,2,4-triazol-3-yl)methyl 2,4,5,6-tetrahydrocyclopenta[c]pyrrol-4-yl)carbamate, enantiomer II | |
| 62 | (1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-2,3-dimethyl-2,4,5,6-tetrahydrocyclopenta[c]pyrrol-4-yl)carbamate | 0.09 |
| 63 | (1-(tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate | 0.14 |
| 64 | (1-methyl-1H-1,2,4-triazol-3-yl)methyl (1((3,4-difluorophenyl)carbamoyl)-2-methyl-2,4,5,6-tetrahydrocyclopenta[c]pyrrol-4-yl)carbamate, enantiomer I | 0.41 |
| 65 | (1-methy1-1H-1,2,4-triazol-3-yl)methyl (1((4-fluorophenyl)carbamoyl)-2-methyl-2,4,5,6-tetrahydrocyclopenta[c]pyrrol-4-yl)carbamate, enantiomer II | 0.81 |
| 66 | (1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate, enantiomer II | 0.90 |
| 67 | (1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate, enantiomer II | 0.06 |
| 68 | (1-methyl-1H-1,2,4-triazol-3-yl)methyl (1((2-chloropyridin-4-yl)carbamoyl)-2-methyl-2,4,5,6-tetrahydrocyclopenta[c]pyrrol-4-yl)carbamate, enantiomer II | 0.66 |
| 69 | (1-methyl-1H-1,2,4-triazol-3-yl)methyl (1-((3-(trifluoromethyl)-4-fluorophenyl)carbamoyl)-2-methyl-2,4,5,6-tetrahydrocyclopenta[c]pyrrol-4-yl)carbamate, enantiomer II | 0.28 |
| 70 | (1-methyl-1H-1,2,4-triazol-3-yl)methyl (1-((3-(difluoromethyl)-4-fluorophenyl)carbamoyl)-2-methyl-2,4,5,6-tetrahydrocyclopenta[c]pyrrol-4-yl)carbamate, enantiomer II | 0.07 |
| 71 | (1-methyl-1H-1,2,4-triazol-3-yl)methyl (2-methy1-1-((3,4,5-trifluorophenyl)carbamoyl)-2,4,5,6-tetrahydrocyclopenta[c]pyrrol-4-yl)carbamate, enantiomer II | 0.18 |
| 72 | N-(3-chloro-4-fluorophenyl)-2-methyl-4-oxo-2,4,5,6,7,8-hexahydrocyclohepta[c]pyrrole-l-carboxamide | 0.05 |
| 73 | (1-methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate, enantiomer I | 0.54 |
| 74 | methyl (1-((3-chloro-4-fluorophenyl)carbamoyl)-2-methyl-2,4,5,6-tetrahydrocyclopenta[c]pyrrol-4-yl)carbamate, enantiomer II | 0.61 |
| 75 | 4-amino-N-(3-chloro-4-fluorophenyl)-2-methy1-4,5,6,7-tetrahydro-2H-isoindole-1-carboxamide, enantiomer I | 2.1 |
| 76 | N-(3-chloro-4-fluorophenyl)-4-(cyclopropanecarboxamido)-2-methy1-4,5,6,7-tetrahydro-2H-isoindole-1-carboxamide, enantiomer II | 1.0 |
| 77 | (1-methyl-1H-pyrazol-3-yl)methyl (1-((3-chloro-4-fluorophenyl)carbamoyl)-2-methy1-2,4,5,6-tetrahydrocyclopenta[c]pyrrol-4-yl)carbamate, enantiomer II | 0.07 |
| 78 | N-(3-chloro-4-fluorophenyl)-4-(cyclopropanesulfonamido)-2-methy1-4,5,6,7-tetrahydro-2H-isoindole-1-carboxamide, enantiomer I | 3.96 |
| 79 | methyl (1-((3-chloro-4-fluorophenyl)carbamoyl)-2-methyl-2,4,5,6,7,8-hexahydrocyclohepta[c]pyrrol-4-yl)carbamate, enantiomer I | 0.73 |
| 80 | 4-amino-N-(3-chloro-4-fluorophenyl)-2-methyl-2,4,5,6,7,8-hexahydrocyclohepta[c]pyrrole-l-carboxamide, enantiomer I | 1.85 |
| 81 | (1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate, enantiomer II | 0.60 |
| 82 | (1-methyl-1H-1,2,4-triazol-3-yl)methyl (1-((3-chloro-4-fluorophenyl)carbamoyl)-2,3-dimethy1-2,4,5,6-tetrahydrocyclopenta[c]pyrrol-4-yl)carbamate, enantiomer I | 0.11 |
| 83 | (1-methyl-1H-1,2,4-triazol-3-yl)methyl (1-((3-chloro-4-fluorophenyl)carbamoyl)-2,3-dimethy1-2,4,5,6-tetrahydrocyclopenta[c]pyrrol-4-yl)carbamate, enantiomer II | 3.3 |
| 84 | N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide, enantiomer II | 0.34 |
| 85 | methyl 1-((3-chloro-4-fluorophenyl)carbamoyl)-2-methyl-2,4,5,6,7,8-hexahydrocyclohepta[c]pyrrol-4-yl)carbamate, enantiomer II | 1.5 |
| 86 | (1-methyl-1H-1,2,4-triazol-3-yl)methyl (1-((3-chloro-4-fluorophenyl)carbamoyl)-2-methy1-2,4,5,6,7,8-hexahydrocyclohepta[c]pyrrol-4-yl)carbamate, enantiomer II | 0.16 |
| 87 | 4-amino-N-(3-chloro-4-fluorophenyl)-2-methyl-2,4,5,6,7,8-hexahydrocyclohepta[c]pyrrole-l-carboxamide, enantiomer II | 1.6 |

TABLE 1-continued

| No. | Nomenclature | DE-19 bDNA EC$_{50}$ (μM) |
|---|---|---|
| 88 | (1H-1,2,4-triazol-3-yl)methyl (1-((3-chloro-4-fluorophenyl)carbamoy1)-2-methyl-4,5,6,7-tetrahydro-2H-isoindol-4-yl)carbamate, enantiomer II | 0.51 |
| 89 | (1-methyl-1H-1,2,4-triazol-3-yl)methyl (1-((3-chloro-4-fluorophenyl)carbamoy1)-2-methy1-2,4,5,6,7,8-hexahydrocyclohepta[c]pyrrol-4-yl)carbamate, enantiomer I | 2.9 |
| 90 | (1-methyl-1H-1,2,4-triazol-3-yl)methyl (1-((3-chloro-4-fluorophenyl)carbamoy1)-3-cyclopropy1-2-methy1-2,4,5,6-tetrahydrocyclopenta[c]pyrrol-4-yl)carbamate, enantiomer I | 0.42 |
| 91 | (1-methyl-1H-1,2,4-triazol-3-yl)methyl (1-((3-chloro-4-fluorophenyl)carbamoy1)-3-cyclopropy1-2-methy1-2,4,5,6-tetrahydrocyclopenta[c]pyrrol-4-yl)carbamate, enantiomer II | 22 |
| 92 | (1-methyl-1H-1,2,4-triazol-3-yl)methyl (1-((3-chloro-4-fluorophenyl)carbamoy1)-2,3-dimethy1-4,5,6,7-tetrahydro-2H-isoindol-4-ypcarbamate, enantiomer I | 0.53 |
| 93 | (1-methyl-1H-1,2,4-triazol-3-yl)methyl (1-((3-chloro-4-fluorophenyl)carbamoy1)-2,3-dimethy1-4,5,6,7-tetrahydro-2H-isoindol-4-ypcarbamate, enantiomer II | 0.95 |
| 94 | (1-methyl-1H-1,2,4-triazol-3-yl)methyl (3-chloro-1-((3-chloro-4-fluorophenyl)carbamoy1)-2-methyl-4,5,6,7-tetrahydro-2H-isoindol-4-yl)carbamate, enantiomer II | 0.44 |
| 95 | (1H-1,2,4-triazol-3-yl)methyl (1-((3-chloro-4-fluorophenyl)carbamoy1)-3-cyclopropy1-2-methyl-2,4,5,6-tetrahydrocyclopenta[c]pyrrol-4-yl)carbamate | 15 |
| 96 | (1-methyl-1H-1,2,4-triazol-3-yl)methyl (1-((3-chloro-4-fluorophenyl)carbamoy1)-3-cyclobuty1-2-methy1-2,4,5,6-tetrahydrocyclopenta[c]pyrrol-4-yl)carbamate, enantiomer I | 0.42 |
| 97 | (1-methyl-1H-1,2,4-triazol-3-yl)methyl (1-((3-chloro-4-fluorophenyl)carbamoy1)-3-cyclobuty1-2-methy1-2,4,5,6-tetrahydrocyclopenta[c]pyrrol-4-yl)carbamate, enantiomer II | 25 |
| 98 | (1H-1,2,4-triazol-3-yl)methyl (1-((3-chloro-4-fluorophenyl)carbamoy1)-3-cyclopropy1-2-methyl-2,4,5,6-tetrahydrocyclopenta[c]pyrrol-4-yl)carbamate, enantiomer II | 15 |
| 99 | (1H-1,2,4-triazol-3-yl)methyl (1-((3-chloro-4-fluorophenyl)carbamoy1)-3-cyclopropy1-2-methyl-2,4,5,6-tetrahydrocyclopenta[c]pyrrol-4-yl)carbamate, enantiomer I | 0.33 |
| 100 | 4-amino-N-(3-chloro-4-fluorophenyl)-2-methyl-2,4,5,6-tetrahydrocyclopenta[c]pyrrole-l-carboxamide | 3.8 |
| 101 | prop-2-yn-1-y1 (1-((3-chloro-4-fluorophenyl)carbamoy1)-2-methyl-2,4,5,6-tetrahydrocyclopenta[c]pyrrol-4-yl)carbamate, enantiomer I | 1.6 |
| 102 | prop-2-yn-1-y1 (1-((3-chloro-4-fluorophenyl)carbamoy1)-2-methyl-2,4,5,6-tetrahydrocyclopenta[c]pyrrol-4-yl)carbamate, enantiomer II | 0.02 |
| 103 | (1H-1,2,4-triazol-3-yl)methyl (3-chloro-1-((3-chloro-4-fluorophenyl)carbamoy1)-2-methyl-2,4,5,6-tetrahydrocyclopenta[c]pyrrol-4-fluorophenyl)carbamate | 0.02 |
| 104 | (1H-1,2,4-triazol-3-yl)methyl (3-chloro-1-((3-chloro-4-fluorophenyl)carbamoy1)-2-methyl-2,4,5,6-tetrahydrocyclopenta[c]pyrrol-4-yl)carbamate, enantiomer I | 1.9 |
| 105 | (1H-1,2,4-triazol-3-yl)methyl (3-chloro-1-((3-chloro-4-fluorophenyl)carbamoy1)-2-methyl-2,4,5,6-tetrahydrocyclopenta[c]pyrrol-4-yl)carbamate, enantiomer II | 0.01 |
| 106 | (2H-1,2,3-triazol-4-yl)methyl (3-chloro-1-((3-chloro-4-fluorophenyl)carbamoy1)-2-methyl-2,4,5,6-tetrahydrocyclopenta[c]pyrrol-4-yl)carbamate, enantiomer I | 1.4 |
| 107 | (2H-1,2,3-triazol-4-yl)methyl (3-chloro-1-((3-chloro-4-fluorophenyl)carbamoy1)-2-methyl-2,4,5,6-tetrahydrocyclopenta[c]pyrrol-4-yl)carbamate, enantiomer II | 0.01 |
| 108 | (2-methy1-2H-1,2,3-triazol-4-yl)methyl (1-((3-chloro-4-fluorophenyl)carbamoy1)-2-methyl-3-pheny1-2,4,5,6-tetrahydrocyclopenta[c]pyrrol-4-yl)carbamate, enantiomer I | 5.2 |
| 109 | (2-methy1-2H-1,2,3-triazol-4-yl)methyl (1-((3-chloro-4-fluorophenyl)carbamoy1)-2-methyl-3-pheny1-2,4,5,6-tetrahydrocyclopenta[c]pyrrol-4-yl)carbamate, enantiomer II | 24 |
| 110 | but-2-yn-l-y1 (1-((3-chloro-4-fluorophenyl)carbamoy1)-2-methy1-2,4,5,6-tetrahydrocyclopenta[c]pyrrol-4-yl)carbamate, enantiomer I | 1.5 |
| 111 | but-2-yn-l-y1 (1-((3-chloro-4-fluorophenyl)carbamoy1)-2-methy1-2,4,5,6-tetrahydrocyclopenta[c]pyrrol-4-yl)carbamate, enantiomer II | 0.06 |
| 112 | pent-2-yn-l-y1 (1-((3-chloro-4-fluorophenyl)carbamoy1)-2-methy1-2,4,5,6-tetrahydrocyclopenta[c]pyrrol-4-yl)carbamate, enantiomer I | 5.7 |
| 113 | pent-2-yn-l-y1 (1-((3-chloro-4-fluorophenyl)carbamoy1)-2-methy1-2,4,5,6-tetrahydrocyclopenta[c]pyrrol-4-yl)carbamate, enantiomer II | 0.12 |
| 114 | 3-cyclopropylprop-2-yn-l-y1 (1-((3-chloro-4-fluorophenyl)carbamoy1)-2-methyl-2,4,5,6-tetrahydrocyclopenta[c]pyrrol-4-yl)carbamate, enantiomer I | 0.47 |
| 115 | 3-cyclopropylprop-2-yn-l-y1 (1-((3-chloro-4-fluorophenyl)carbamoy1)-2-methyl-2,4,5,6-tetrahydrocyclopenta[c]pyrrol-4-yl)carbamate, enantiomer II | 5.4 |
| 116 | (1-methyl-1H-1,2,3-triazol-4-yl)methyl (1-((3-chloro-4-fluorophenyl)carbamoy1)-2-methyl-2,4,5,6-tetrahydrocyclopenta[c]pyrrol-4-yl)carbamate, enantiomer I | 0.05 |
| 117 | (1-methyl-1H-1,2,3-triazol-4-yl)methyl (1-((3-chloro-4-fluorophenyl)carbamoy1)-2-methyl-2,4,5,6-tetrahydrocyclopenta[c]pyrrol-4-yl)carbamate, enantiomer II | 6.1 |
| 118 | (S)-5-oxopyrrolidin-2-yl)methyl (1-((3-chloro-4-fluorophenyl)carbamoy1)-2-methyl-2,4,5,6-tetrahydrocyclopenta[c]pyrrol-4-yl)carbamate, diastereoisomer I | 0.16 |
| 119 | ((S)-5-oxopyrrolidin-2-yl)methyl (1-((3-chloro-4-fluorophenyl)carbamoy1)-2-methyl-2,4,5,6-tetrahydrocyclopenta[c]pyrrol-4-yl)carbamate, diastereoisomer II | 1.9 |
| 120 | ((R)-5-oxopyrrolidin-2-yl)methyl (1-((3-chloro-4-fluorophenyl)carbamoy1)-2-methyl-2,4,5,6-tetrahydrocyclopenta[c]pyrrol-4-yl)carbamate, diastereoisomer I | 0.21 |

TABLE 1-continued

| No. | Nomenclature | DE-19 bDNA EC$_{50}$ (μM) |
|---|---|---|
| 121 | ((S)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate, diastereoisomer II | 4.0 |
| 122 | (1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer I | 0.45 |
| 123 | (1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer II | 8.0 |
| 124 | (1H-1,2,4-triazol-3-yl)methyl(3-bromo-1-((3-chloro-4-fluorophenyl)carbamoyl)-2-methyl-2,4,5,6-tetrahydrocyclopenta[c]pyrrol-4-yl)carbamate, enantiomer I | |
| 125 | (1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate, enantiomer II | 0.04 |
| 126 | (1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer I | 8.7 |
| 127 | (1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer II | 0.44 |
| 128 | (2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer I | 1.7 |
| 129 | (2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer II | 0.04 |
| 130 | (2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate, enantiomer I | 9.0 |
| 131 | (2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate, enantiomer I | 1.7 |
| 132 | (2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer II | 13 |
| 133 | (2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate, enantiomer II | 0.43 |
| 134 | (1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate, enantiomer I | 1.9 |
| 135 | (1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate, enantiomer II | 0.18 |
| 136 | (2H-1,2,3-triazol-4-yl)methyl (3-chloro-1-((3-chloro-4-fluorophenyl)carbamoyl)-2-methyl-4,5,6,7-tetrahydro-2H-isoindol-4-yl)carbamate, enantiomer I | 1.2 |
| 137 | (2H-1,2,3-triazol-4-yl)methyl (3-chloro-1-((3-chloro-4-fluorophenyl)carbamoyl)-2-methyl-4,5,6,7-tetrahydro-2H-isoindol-4-yl)carbamate, enantiomer II | 0.16 |
| 138 | (5-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer I | 0.86 |
| 139 | (5-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer II | 3.6 |
| 140 | (5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer I | 12 |
| 141 | (5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer II | 1.2 |
| 142 | 1-(2-methyl-2H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer I | 3.2 |
| 143 | (2-methyl-2H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer II | 0.07 |
| 144 | (1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer I | 0.06 |
| 145 | (1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer II | 2.7 |
| 146 | (5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer I | 9.3 |
| 147 | (5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate, enantiomer II | 3.6 |
| 148 | (1H-tetrazol-5-yl)methyl (1-((3-chloro-4-fluorophenyl)carbamoyl)-2-methyl-2,4,5,6-tetrahydrocyclopenta[c]pyrrol-4-yl)carbamate | 1.9 |
| 149 | (1H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer I | 1.1 |
| 150 | (1H-tetrazol-5-yl)methyl (1-((3-chloro-4-fluorophenyl)carbamoyl)-2-methyl-2,4,5,6-tetrahydrocyclopenta[c]pyrrol-4-yl)carbamate, enantiomer II | 6.8 |

Enumerated Embodiments

The following exemplary embodiments are provided, the numbering of which is not to be construed as designating levels of importance.

Embodiment 1 provides a compound of formula (I) or (II), or a salt, solvate, prodrug, stereoisomer, tautomer, or isotopically labeled derivative thereof, or any mixtures thereof:

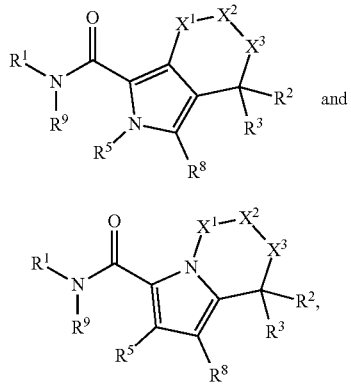

wherein independently in (I) or (II): —$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH(CH_3)CH(CH_3)$—*, —$C(CH_3)_2CH(CH_3)$—*, and —$CH(CH_3)C(CH_3)_2$—*, wherein the single bond marked as "*" is formed with $X^3$; —$X^3$— is selected from the group consisting of a bond, —$CH_2$—, —$CH(CH_3)$—, —$C(CH_3)_2$—, —$CH_2CH_2$—, *—$CH_2CH(CH_3)$—, *—$CH_2C(CH_3)_2$—, *—$CH(CH_3)CH_2$—, *—$C(CH_3)_2CH_2$—, —$CH(CH_3)CH(CH_3)$—, *—$C(CH_3)_2CH(CH_3)$—, and *—$CH(CH_3)C(CH_3)_2$—, wherein the single bond marked as "*" is formed with $X^1$—$X^2$—; $R^1$ is selected from the group consisting of optionally substituted phenyl, optionally substituted benzyl, optionally substituted heteroaryl, and —($CH_2$)(optionally substituted heteroaryl); $R^2$ is selected from the group consisting of H, —OH, —$OR^6$, —$NH_2$, —$NHR^6$, —$NR^6R^{6a}$, —OC(=O)$OR^6$, —OC(=O)N($R^4$)$R^6$, —N($R^3$)C(=O)$OR^6$, —$NR^7$C(=O)N($R^6$)($R^7$), —N($R^4$)C(=O)$R^6$, and —$NR^4$S(=O)$_{1-2}R^6$; $R^3$ is H or $C_1$-$C_6$ alkyl; or $R^2$ and $R^3$ combine to form =O; each occurrence of $R^4$ is independently selected from the group consisting of H and $C_1$-$C_6$ alkyl; $R^5$ is selected from the group consisting of H and $C_1$-$C_6$ alkyl; each occurrence of $R^6$ is independently selected from the group consisting of optionally substituted $C_1$-$C_6$ alkyl, optionally substituted $C_1$-$C_6$ alkenyl, optionally substituted $C_1$-$C_6$ alkynyl, optionally substituted $C_3$-$C_8$ cycloalkyl, optionally substituted phenyl, and optionally substituted hetereoaryl; each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl; each occurrence of $R^7$ is independently selected from the group consisting of H and optionally substituted $C_1$-$C_6$ alkyl; or, if $R^6$ and $R^7$ are bound to the same N atom, $R^6$ and $R^7$ optionally combine with the N atom to which both are bound to form an optionally substituted 3-7 membered heterocycle; $R^8$ is selected from the group consisting of H, halo, $C_1$-$C_6$ alkyl, $C_1$-$C_6$ haloalkyl, $C_3$-$C_8$ cycloalkyl, and optionally substituted phenyl; and $R^9$ is selected from the group consisting of H and $C_1$-$C_6$ alkyl.

Embodiment 2 provides the compound of Embodiment 1, wherein each occurrence of $R^6$ or $R^{6a}$ is independently selected from the group consisting of —($CH_2$)$_{1-3}$-(optionally substituted heteroaryl), —($CH_2$)$_{1-3}$-(optionally substituted heterocyclyl), and —($CH_2$)$_{1-3}$-(optionally substituted aryl).

Embodiment 3 provides the compound of Embodiment 1 or 2, wherein each occurrence of optionally substituted alkyl, optionally substituted alkenyl, optionally substituted alkynyl, optionally substituted heterocyclyl, or optionally substituted cycloalkyl is independently optionally substituted with at least one substituent selected from the group consisting of $C_1$-$C_6$ alkyl, $C_2$-$C_8$ alkenyl, $C_2$-$C_8$ alkynyl, $C_3$-$C_8$ cycloalkyl, halo, cyano, —$OR^a$, optionally substituted phenyl, optionally substituted heteroaryl, optionally substituted heterocyclyl, —N($R^a$)C(=O)$R^a$, —C(=O)OH, —C(=O)$OR^a$, —C(=O)$NR^aR^a$, and —N($R^a$)($R^a$), wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

Embodiment 4 provides the compound of any one of Embodiments 1-3, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, heterocyclyl, halo, —CN, —$OR^b$, —N($R^b$)($R^b$), —$NO_2$, —S(=O)$_2$N($R^b$)($R^b$), acyl, and $C_1$-$C_6$ alkoxycarbonyl, wherein each occurrence of $R^b$ is independently H, $C_1$-$C_6$ alkyl or $C_3$-$C_8$ cycloalkyl.

Embodiment 5 provides the compound of any one of Embodiments 1-4, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —N($R^c$)($R^c$), and $C_1$-$C_6$ alkoxycarbonyl, wherein each occurrence of $R^c$ is independently H, $C_1$-$C_6$ alkyl, or $C_3$-$C_8$ cycloalkyl.

Embodiment 6 provides the compound of any one of Embodiments 1-5, wherein $R^1$ is selected from the group consisting of optionally substituted phenyl, optionally substituted benzyl, and —($CH_2$)(optionally substituted heteroaryl), wherein the phenyl, benzyl, or heteroaryl is optionally substituted with at least one selected from the group consisting of $C_1$-$C_6$ alkyl, halo, $C_1$-$C_3$ haloalkyl, and —CN.

Embodiment 7 provides the compound of any one of Embodiments 1-6, wherein $R^1$ is selected from the group consisting of phenyl, 3-chlorophenyl, 4-chlorophenyl, 3-fluorophenyl, 4-fluorophenyl, 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, 2-chloro-4-pyridyl, 2-fluoro-4-pyridyl, 2-fluoromethyl-4- pyridyl, 2-difluromethyl-4-pyridyl, 2-trifluoromethyl-4-pyridyl, and 6-methyl-4-pyridyl.

Embodiment 8 provides the compound of any one of Embodiments 1-7, wherein $R^2$ is selected from the group consisting of: —NHS(=O)$_2$(C$_1$-C$_6$ alkyl); —NHS(=O)$_2$ (C$_3$-C$_6$ cycloalkyl); —NHC(=O)(C$_1$-C$_6$ alkyl); —NHC(=O)(C$_3$-C$_8$ cycloalkyl); —NHC(=O)O(C$_1$-C$_6$ alkyl); —NHC(=O)O(C$_3$-C$_8$ cycloalkyl); —NHC(=O)O(C$_1$-C$_6$ haloalkyl); —NHC(=O)O(CH$_2$)$_{1-3}$(pyridinyl); —NHC(=O)O(CH$_2$)$_{1-3}$ (pyrazinyl); —NHC(=O)O(CH$_2$)$_{1-3}$ (pyrimidinyl); —NHC(=O)O(CH$_2$)$_{1-3}$ (isoxazolyl); —NHC(=O)O(CH$_2$)$_{1-3}$ (oxazolyl); —NHC(=O)O(CH$_2$)$_{1-3}$ (oxadiazolyl); —NHC(=O)O(CH$_2$)$_{1-3}$ (triazolyl); —NHC(=O)O(CH$_2$)$_{1-3}$ (thiazolyl); —NHC(=O)O(CH$_2$)$_{1-3}$ (imidazolyl); —NHC(=O)O(CH$_2$)$_{1-3}$ (pyrazolyl); —NHC(=O)NH(C$_1$-C$_6$ alkyl); —NHC(=O)NH(C$_3$-C$_8$ cycloalkyl); —NHC(=O)NH(C$_1$-C$_6$ haloalkyl); —NHC(=O)NH(CH$_2$)$_{1-3}$ (pyridinyl); —NHC(=O)NH(CH$_2$)$_{1-3}$ (pyrazinyl); —NHC(=O)NH(CH$_2$)$_{1-3}$(pyrimidinyl); —NHC(=O)NH(CH$_2$)$_{1-3}$ (isoxazolyl); —NHC(=O)NH(CH$_2$)$_{1-3}$ (oxazolyl); —NHC(=O)NH(CH$_2$)$_{1-3}$ (oxadiazolyl); —NHC(=O)NH(CH$_2$)$_{1-3}$ (triazolyl); —NHC(=O)NH(CH$_2$)$_{1-3}$(thiazolyl); —NHC(=O)NH(CH$_2$)$_{1-3}$ (imidazolyl); and —NHC(=O)NH(CH$_2$)$_{1-3}$ (pyrazolyl).

Embodiment 9 provides the compound of any one of Embodiments 1-8, wherein $R^3$ is H or CH$_3$.

Embodiment 10 provides the compound of any one of Embodiments 1-9, wherein each occurrence of $R^4$ is independently selected from the group consisting of H and methyl.

Embodiment 11 provides the compound of any one of Embodiments 1-10, which is selected from the group consisting of:

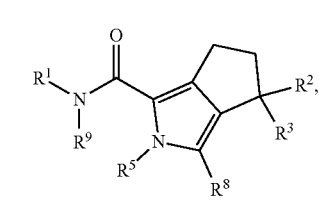
(I-1)

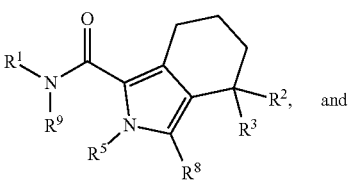
(I-2)

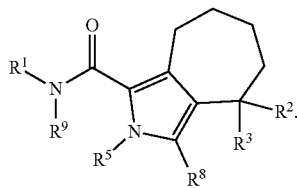
(I-3)

Embodiment 12 provides the compound of any one of Embodiments 1-11, which is selected from the group consisting of:

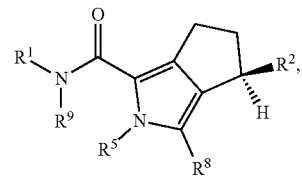
(I-22)

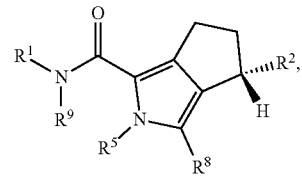
(I-23)

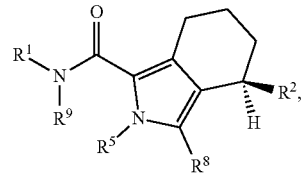
(I-10)

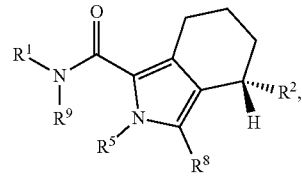
(I-11)

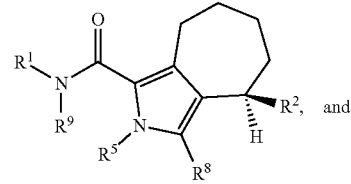
(I-14)

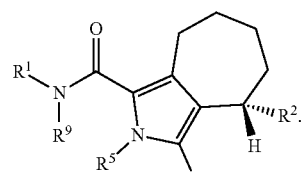
(I-15)

Embodiment 13 provides the compound of any one of Embodiments 1-12, which is at least one selected from the group consisting of: methyl (1-((3-chloro-4-fluorophenyl)carbamoyl)-2-methyl-2,4,5,6-tetrahydrocyclopenta[c]pyrrol-4-yl)carbamate; pyridin-2-ylmethyl (1,4-difluorophenyl)carbamoyl)-2-methyl-2,4,5,6-tetrahydrocyclopenta[c]pyrrol-4-yl)carbamate; N-(3-chloro-4-fluorophenyl)-2-methyl-4-(3-methylureido)-2,4,5,6-tetrahydrocyclopenta[c]pyrrole-1-carboxamide; N-(3-chloro-4-fluorophenyl)-4-(3-methylureido)-2,4,5,6-tetrahydrocyclopenta[c]pyrrole-1-carboxamide; methyl (1-((3-chloro-4-fluorophenyl)carbamoyl)-2,4,5,6-tetrahydrocyclopenta[c]pyrrol-4-yl) carbamate; N-(3-chloro-4-fluorophenyl)-4-(cyclopropanesulfonamido)-2-ethyl-2,4,5,6-tetrahydrocyclopenta[c]pyrrole-1-carboxamide; N-(3-chloro-4-fluorophenyl)-4-(cyclopropanesulfonamido)-2-methyl-2,4,5,6-tetrahydrocyclopenta[c]pyrrole-1-carboxamide; N-(3-chloro-4-fluorophenyl)-4-(cyclopropanecarboxamido)-2-ethyl-2,4,5,6- tetrahydrocyclopenta[c]pyrrole-1-carboxamide; (1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate; (1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate; N-(3-chloro-4-fluorophenyl)-4-(cyclopropanecarboxamido)-2-methyl-2,4,5,6-tetrahydrocyclopenta[c]pyrrole-1-carboxamide; (1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate; (1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate; methyl (1-((3-chloro-4-fluorophenyl)carbamoyl)-2-methyl-4,5,6,7-tetrahydro-2H-isoindol-4-yl)carbamate; N-(3-chloro-4-fluorophenyl)-4-(cyclopropanesulfonamido)-2-methyl-4,5,6,7-tetrahydro-2H-isoindole-1-carboxamide; (1-methyl-1H-pyrazol-3-yl)methyl (1-((3-chloro-4-fluorophenyl)carbamoyl)-2-methyl-4,5,6,7-tetrahydro-2H-isoindol-4-yl)carbamate; (1-methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate; oxazol-2-ylmethyl (1-((3-chloro-4-fluorophenyl)carbamoyl)-2-methyl-2,4,5,6-tetrahydrocyclopenta[c]pyrrol-4-yl)carbamate; oxazol-5-ylmethyl (1-((3-chloro-4-fluorophenyl)carbamoyl)-2-methyl-2,4,5,6-tetrahydrocyclopenta[c]pyrrol-4-yl)carbamate; methyl (5-((3-chloro-4-fluorophenyl)carbamoyl)-2,3-dihydro-1H-pyrrolizin-1-yl)carbamate; (1-methyl-1H-1,2,4-triazol-3-yl)methyl (5-((3-chloro-4-fluorophenyl)carbamoyl)-2,3-dihydro-1H-pyrrolizin-1-yl)carbamate; pyridin-2-ylmethyl (5-((3-chloro-4-fluorophenyl)carbamoyl)-2,3-dihydro-1H-pyrrolizin-1-yl)carbamate; N-(3-chloro-4-fluorophenyl)-2-methyl-4-oxo-2,4,5,6-tetrahydrocyclopenta[c]pyrrole-1-carboxamide; N-(3-chloro-4-fluorophenyl)-2-methyl-4-oxo-4,5,6,7-tetrahydro-2H-isoindole-1-carboxamide; isopropyl 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate; (1-methyl-1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate; 2-cyanoethyl (1-((3-chloro-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate; 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid; (1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate; (1-carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate; (1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate; (1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate; (1-(tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3,4-difluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate; (1-methyl-1H-1,2,4-triazol-3-yl)methyl (1-((3-(trifluoromethyl)-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3-(difluoromethyl)-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl(2-methyl-1-((3,4,5-trifluorophenyl)carbamoyl)-2,4,5,6-tetrahydrocyclopenta[c]pyrrol-4-yl)carbamate; N-(3-chloro-4-fluorophenyl)-2-methyl-4-oxo-2,4,5,6,7,8-hexahydrocyclohepta[c]pyrrole-1-carboxamide; (1-methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate; 4-amino-N-(3-chloro-4-fluorophenyl)-2-methyl-4,5,6,7-tetrahydro-2H-isoindole-1-carboxamide; N-(3-chloro-4-fluorophenyl)-4-(cyclopropanecarboxamido)-2-methyl-4,5,6,7-tetrahydro-2H-isoindole-1-carboxamide; methyl (1-((3-chloro-4-fluorophenyl)carbamoyl)-2-methyl-2,4,5,6,7,8-hexahydrocyclohepta[c]pyrrol-4-yl)carbamate; 4-amino-N-(3-chloro-4-fluorophenyl)-2-methyl-2,4,5,6,7,8-hexahydrocyclohepta[c]pyrrole-1-carboxamide; (1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate; N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide; (1-methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate; (1H-1,2,4-triazol-3-yl)methyl (1-((3-chloro-4-fluorophenyl)carbamoyl)-2-methyl-4,5,6,7-tetrahydro-2H-isoindol-4-yl)carbamate; (1-methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate; (1-methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate; (1-methyl-1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate; (1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate; (1-methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate; 4-amino-N-(3-chloro-4-fluorophenyl)-2-methyl-2,4,5,6-tetrahydrocyclopenta[c]pyrrole-1-carboxamide; prop-2-yn-1-yl (1-((3-chloro-4-fluorophenyl)carbamoyl)-2-methyl-2,4,5,6-tetrahydrocyclopenta[c]pyrrol-4-yl)carbamate; (1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate; (2H-1,2,3-triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate; (2-methyl-2H-1,2,3-triazol-4-yl)

methyl (1-((3-chloro-4-fluorophenyl)carbamoyl)-2-methyl-3-phenyl-2,4,5,6-tetrahydrocyclopenta[c]pyrrol-4-yl)carbamate; but-2-yn-1-yl (1-((3-chloro-4-fluorophenyl)carbamoyl)-2-methyl-2,4,5,6-tetrahydrocyclopenta[c]pyrrol-4-yl)carbamate; pent-2-yn-1-yl (1-((3-chloro-4-fluorophenyl)carbamoyl)-2-methyl-2,4,5,6-tetrahydrocyclopenta[c]pyrrol-4-yl)carbamate; 3-cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate; (1-methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; ((S)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate; ((R)-5-oxopyrrolidin-2-yl)methyl(1-((3-chloro-4-fluorophenyl)carbamoyl)-2-methyl-2,4,5,6-tetrahydrocyclopenta[c]pyrrol-4-yl)carbamate; (1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate; (1H-1,2,4-triazol-3-yl)methyl(3-bromo-1-((3-chloro-4-fluorophenyl)carbamoyl)-2-methyl-2,4,5,6-tetrahydrocyclopenta[c]pyrrol-4-yl)carbamate; (1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate; (2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; (2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate; (2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate; (1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate; (2H-1,2,3-triazol-4-yl)methyl (3-chloro-1-((3-chloro-4-fluorophenyl)carbamoyl)-2-methyl-4,5,6,7-tetrahydro-2H-isoindol-4-yl) carbamate; (5-methyl-2H-1,2,3-triazol-4-yl)methyl(1-((3-chloro-4-fluorophenyl)carbamoyl)-2-methyl-2,4,5,6-tetrahydrocyclopenta[c]pyrrol-4-yl)carbamate; (5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; (2-methyl-2H-tetrazol-5-yl)methyl (1-((3-chloro-4-fluorophenyl)carbamoyl)-2-methyl-2,4,5,6-tetrahydrocyclopenta[c]pyrrol-4-yl)carbamate; (1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate; (5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; (1H-tetrazol-5-yl)methyl (1-((3-chloro-4-fluorophenyl)carbamoyl)-2-methyl-2,4,5,6-tetrahydrocyclopenta[c]pyrrol-4-yl) carbamate; or a salt, solvate, prodrug, isotopically labeled derivative, stereoisomer, or tautomer thereof, or any mixtures thereof.

Embodiment 14 provides the compound of any of Embodiments 1-13, wherein the configuration is (R) at the $C(R^2)(R^3)$ center.

Embodiment 15 provides the compound of any of Embodiments 1-13, wherein the configuration is (S) at the $C(R^2)(R^3)$ center.

Embodiment 16 provides a pharmaceutical composition comprising at least one compound of any of Embodiments 1-15 and a pharmaceutically acceptable carrier.

Embodiment 17 provides the pharmaceutical composition of Embodiment 16, further comprising at least one additional agent useful for treating hepatitis infection.

Embodiment 18 provides the pharmaceutical composition of Embodiment 17, wherein the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript.

Embodiment 19 provides a method of treating or preventing hepatitis B virus (HBV) infection in a subject, the method comprising administering to the subject in need thereof a therapeutically effective amount of at least one compound of any of Embodiments 1-15.

Embodiment 20 provides the method of Embodiment 19, wherein the at least one compound is administered to the subject in a pharmaceutically acceptable composition.

Embodiment 21 provides the method of any of Embodiments 19-20, wherein the subject further suffers from, or may develop, hepatitis D.

Embodiment 22 provides the method of any of Embodiments 19-21, wherein the subject is further administered at least one additional agent useful for treating the hepatitis B and/or D infection.

Embodiment 23 provides the method of Embodiment 21, wherein the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript.

Embodiment 24 provides the method of any of Embodiments 21-23, wherein the subject is co-administered the at least one compound and the at least one additional agent.

Embodiment 25 provides the method of any of Embodiments 21-24, wherein the at least one compound and the at least one additional agent are coformulated.

Embodiment 26 provides a method of inhibiting expression and/or function of a viral capsid protein directly or indirectly in a HBV-infected subject, the method comprising administering to the subject in need thereof a therapeutically effective amount of at least one compound of any of Embodiments 1-15.

Embodiment 27 provides the method of Embodiment 26, wherein the at least one compound is administered to the subject in a pharmaceutically acceptable composition.

Embodiment 28 provides the method of any of Embodiments 26-27, wherein the subject further suffers from, or may develop, hepatitis D.

Embodiment 29 provides the method of any of Embodiments 26-28, wherein the subject is further administered at least one additional agent useful for treating the HBV and/or HDV infection.

Embodiment 30 provides the method of Embodiment 29, wherein the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript.

Embodiment 31 provides the method of any of Embodiments 29-30, wherein the subject is co-administered the at least one compound and the at least one additional agent.

Embodiment 32 provides the method of any of Embodiments 29-31, wherein the at least one compound and the at least one additional agent are coformulated.

Embodiment 33 provides the method of any of Embodiments 19-32, wherein the subject is a mammal.

Embodiment 34 provides the method of Embodiment 33, wherein the mammal is a human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I) or (II), or a salt, solvate, prodrug, stereoisomer, tautomer, or isotopically labeled derivative thereof, or any mixtures thereof:

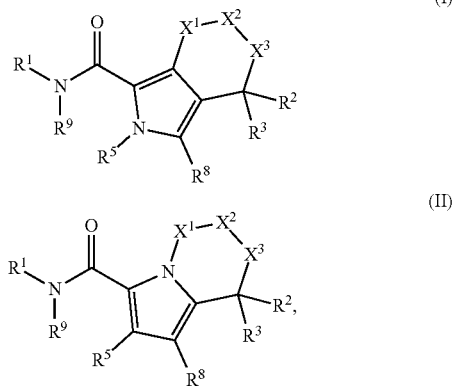

wherein independently in (I) or (II):

—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH(CH_3)CH(CH_3)$—*, —$C(CH_3)_2CH(CH_3)$—*, and —$CH(CH_3)C(CH_3)_2$—*, wherein the single bond marked as "*" is formed with $X^3$;

—$X^3$— is selected from the group consisting of a bond, —$CH_2$—, —$CH(CH_3)$—, —$C(CH_3)_2$—, —$CH_2CH_2$—, *—$CH_2CH(CH_3)$—, *—$CH_2C(CH_3)_2$—, *—$CH(CH_3)CH_2$—, *—$C(CH_3)_2CH_2$—, —$CH(CH_3)CH(CH_3)$—, *—$C(CH_3)_2CH(CH_3)$—*, and *—$CH(CH_3)C(CH_3)_2$—, wherein the single bond marked as "*" is formed with $X^1$—$X^2$—;

$R^1$ is selected from the group consisting of optionally substituted phenyl, optionally substituted benzyl, optionally substituted heteroaryl, and —$(CH_2)$(optionally substituted heteroaryl);

$R^2$ is selected from the group consisting of —OH, —$OR^6$, —$NH_2$, —$NHR^6$, —$NR^6R^{6a}$, —OC(=O)$OR^6$, —OC(=O)N($R^4$)$R^6$, —N($R^3$)C(=O)$OR^6$, —$NR^7$C(=O)N($R^6$)($R^7$), —N($R^4$)C(=O)$R^6$, and —$NR^4$S(=O)$_{1-2}R^6$;

$R^3$ is H or $C_1$-$C_6$ alkyl;
or $R^2$ and $R^3$ combine to form =O;

each occurrence of $R^4$ is independently selected from the group consisting of H and $C_1$-$C_6$ alkyl;

$R^5$ is selected from the group consisting of H and $C_1$-$C_6$ alkyl;

each occurrence of $R^6$ is independently selected from the group consisting of optionally substituted $C_1$-$C_6$ alkyl, optionally substituted $C_1$-$C_6$ alkenyl, optionally substituted $C_1$-$C_6$ alkynyl, optionally substituted $C_3$-$C_8$ cycloalkyl, optionally substituted phenyl, and optionally substituted heteroaryl;

each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl;

each occurrence of $R^7$ is independently selected from the group consisting of H and optionally substituted $C_1$-$C_6$ alkyl;
or, if $R^6$ and $R^7$ are bound to the same N atom, $R^6$ and $R^7$ optionally combine with the N atom to which both are bound to form an optionally substituted 3-7 membered heterocycle;

$R^8$ is selected from the group consisting of H, halogen, $C_1$-$C_6$ alkyl, $C_1$-$C_6$ haloalkyl, $C_3$-$C_8$ cycloalkyl, and optionally substituted phenyl; and $R^9$ is selected from the group consisting of H and $C_1$-$C_6$ alkyl.

2. The compound of claim 1, wherein each occurrence of $R^6$ or $R^{6a}$ is independently selected from the group consisting of —$(CH_2)_{1-3}$-(optionally substituted heteroaryl), —$(CH_2)_{1-3}$-(optionally substituted heterocyclyl), and —$(CH_2)_{1-3}$-(optionally substituted aryl).

3. The compound of claim 1, wherein each occurrence of optionally substituted alkyl, optionally substituted alkenyl, optionally substituted alkynyl, optionally substituted heterocyclyl, or optionally substituted cycloalkyl is independently optionally substituted with at least one substituent selected from the group consisting of $C_1$-$C_6$ alkyl, $C_2$-$C_8$ alkenyl, $C_2$-$C_8$ alkynyl, $C_3$-$C_8$ cycloalkyl, halogen, cyano, —OR', optionally substituted phenyl, optionally substituted heteroaryl, optionally substituted heterocyclyl, —N($R^a$)C(=O)$R^a$, —C(=O)OH, —C(=O)$OR^a$, —C(=O)N$R^aR^a$, and —N($R^a$)($R^a$), wherein each occurrence of $R^a$ is independently H, optionally substituted $C_1$-$C_6$ alkyl, optionally substituted $C_3$-$C_8$ cycloalkyl, optionally substituted aryl, or optionally substituted heteroaryl, or two $R^a$ groups combine with the N to which they are bound to form a heterocycle.

4. The compound of claim 1, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, heterocyclyl, halogen, —CN, —$OR^b$, —N($R^b$)($R^b$), —$NO_2$, —S(=O)$_2$N($R^b$)($R^b$), acyl, and $C_1$-$C_6$ alkoxycarbonyl, wherein each occurrence of $R^b$ is independently H, $C_1$-$C_6$ alkyl or $C_3$-$C_8$ cycloalkyl.

5. The compound of claim 1, wherein each occurrence of optionally substituted aryl or optionally substituted heteroaryl is independently optionally substituted with at least one substituent selected from the group consisting of $C_1$-$C_6$ alkyl, $C_1$-$C_6$ haloalkyl, $C_1$-$C_6$ haloalkoxy, halogen, —CN, —OR', —N($R^c$)($R^c$), and $C_1$-$C_6$ alkoxycarbonyl, wherein each occurrence of $R^c$ is independently H, $C_1$-$C_6$ alkyl, or $C_3$-$C_8$ cycloalkyl.

6. The compound of claim 1, wherein $R^1$ is selected from the group consisting of optionally substituted phenyl, optionally substituted benzyl, and —(CH$_2$)(optionally substituted heteroaryl), wherein the phenyl, benzyl, or heteroaryl is optionally substituted with at least one selected from the group consisting of $C_1$-$C_6$ alkyl, halogen, $C_1$-$C_3$ haloalkyl, and —CN.

7. The compound of claim 1, wherein $R^1$ is selected from the group consisting of phenyl, 3-chlorophenyl, 4-chlorophenyl, 3-fluorophenyl, 4-fluorophenyl, 3,4-difluorophenyl, 3,5-difluorophenyl, 2,4,5-trifluorophenyl, 3,4,5-trifluorophenyl, 3,4-dichlorophenyl, 3-chloro-4-fluorophenyl, 4-chloro-3-fluorophenyl, 4-chloro-3-methylphenyl, 3-chloro-4-methylphenyl, 4-fluoro-3-methylphenyl, 3-fluoro-4-methylphenyl, 4-chloro-3-methoxyphenyl, 3-chloro-4-methoxyphenyl, 4-fluoro-3-methoxyphenyl, 3-fluoro-4-methoxyphenyl, 3-trifluoromethylphenyl, 4-trifluoromethylphenyl, 3-trifluoromethyl-4-fluorophenyl, 4-trifluoromethyl-3-fluorophenyl, 3-cyanophenyl, 4-cyanophenyl, 3-cyano-4-fluorophenyl, 4-cyano-3-fluorophenyl, 3-difluoromethyl-4-fluorophenyl, 4-difluoromethyl-3-fluorophenyl, benzo[d][1,3]dioxol-5-yl, 2,3-dihydrobenzo[b][1,4]dioxin-6-yl, benzyl, 3-fluorobenzyl, 4-fluorobenzyl, 3-chlorobenzyl, 4-chlorobenzyl, 2-pyridyl, 4-methyl-2-pyridyl, 5-methyl-2-pyridyl, 6-methyl-2-pyridyl, 3-pyridyl, 2-methyl-3-pyridyl, 3-methyl-3-pyridyl, 4-pyridyl, 2-methyl-4-pyridyl, 2-chloro-4-pyridyl, 2-fluoro-4-pyridyl, 2-fluoromethyl-4-pyridyl, 2-difluromethyl-4-pyridyl, 2-trifluoromethyl-4-pyridyl, and 6-methyl-4-pyridyl.

8. The compound of claim 1, wherein $R^2$ is selected from the group consisting of: —NHS(=O)$_2$(C$_1$-C$_6$ alkyl); —NHS(=O)$_2$(C$_3$-C$_6$ cycloalkyl); —NHC(=O)(C$_1$-C$_6$ alkyl); —NHC(=O)(C$_3$-C$_8$ cycloalkyl); —NHC(=O)O(C$_1$-C$_6$ alkyl); —NHC(=O)O(C$_3$-C$_8$ cycloalkyl); —NHC(=O)O(C$_1$-C$_6$ haloalkyl); —NHC(=O)O(CH$_2$)$_{1-3}$ (pyridinyl); —NHC(=O)O(CH$_2$)$_{1-3}$ (pyrazinyl); —NHC(=O)O(CH$_2$)$_{1-3}$ (pyrimidinyl); —NHC(=O)O(CH$_2$)$_{1-3}$ (isoxazolyl); —NHC(=O)O(CH$_2$)$_{1-3}$(oxazolyl); —NHC(=O)O(CH$_2$)$_{1-3}$ (oxadiazolyl); —NHC(=O)O(CH$_2$)$_{1-3}$ (triazolyl); —NHC(=O)O(CH$_2$)$_{1-3}$ (thiazolyl); —NHC(=O)O(CH$_2$)$_{1-3}$ (imidazolyl); —NHC(=O)O(CH$_2$)$_{1-3}$(pyrazolyl); —NHC(=O)NH(C$_1$-C$_6$ alkyl); —NHC(=O)NH(C$_3$-C$_8$ cycloalkyl); —NHC(=O)NH(C$_1$-C$_6$ haloalkyl); —NHC(=O)NH(CH$_2$)$_{1-3}$ (pyridinyl); —NHC(=O)NH(CH$_2$)$_{1-3}$ (pyrazinyl); —NHC(=O)NH(CH$_2$)$_{1-3}$ (pyrimidinyl); —NHC(=O)NH(CH$_2$)$_{1-3}$ (isoxazolyl); —NHC(=O)NH(CH$_2$)$_{1-3}$(oxazolyl); —NHC(=O)NH(CH$_2$)$_{1-3}$ (oxadiazolyl); —NHC(=O)NH(CH$_2$)$_{1-3}$ (triazolyl); —NHC(=O)NH(CH$_2$)$_{1-3}$ (thiazolyl); —NHC(=O)NH(CH$_2$)$_{1-3}$ (imidazolyl); and —NHC(=O)NH(CH$_2$)$_{1-3}$(pyrazolyl).

9. The compound of claim 1, wherein $R^3$ is H or CH$_3$.

10. The compound of claim 1, wherein each occurrence of $R^4$ is independently selected from the group consisting of H and methyl.

11. The compound of claim 1, which is selected from the group consisting of:

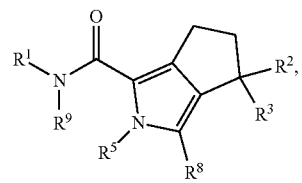
(I-1)

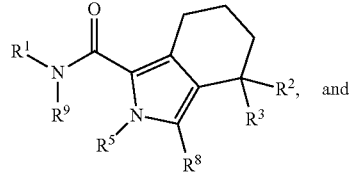
(I-2)

and

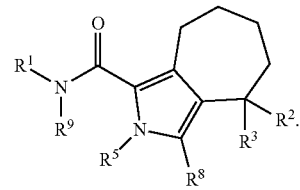
(I-3)

12. The compound of claim 1, which is selected from the group consisting of:

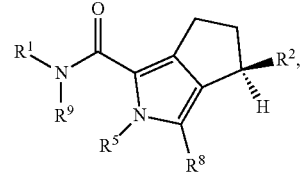
(I-22)

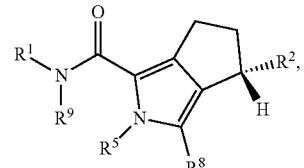
(I-23)

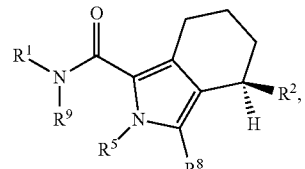
(I-10)

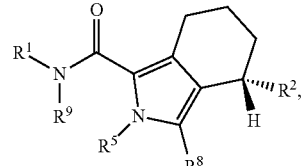
(I-11)

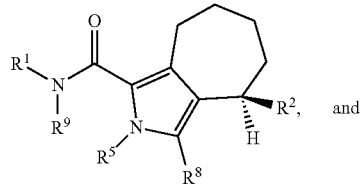
(I-14)

and

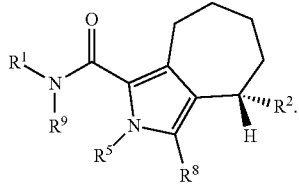

(I-15)

13. A compound selected from the group consisting of:
methyl (1-((3-chloro-4-fluorophenyl)carbamoyl)-2-methyl-2,4,5,6-tetrahydrocyclopenta[c]pyrrol-4-yl)carbamate;
pyridin-2-ylmethyl (1-((3,4-difluorophenyl)carbamoyl)-2-methyl-2,4,5,6-tetrahydrocyclopenta[c]pyrrol-4-yl)carbamate;
N-(3-chloro-4-fluorophenyl)-2-methyl-4-(3-methylureido)-2,4,5,6-tetrahydrocyclopenta[c]pyrrole-1-carboxamide;
N-(3-chloro-4-fluorophenyl)-4-(3-methylureido)-2,4,5,6-tetrahydrocyclopenta[c]pyrrole-1-carboxamide;
methyl (1-((3-chloro-4-fluorophenyl)carbamoyl)-2,4,5,6-tetrahydrocyclopenta[c]pyrrol-4-yl)carbamate;
N-(3-chloro-4-fluorophenyl)-4-(cyclopropanesulfonamido)-2-ethyl-2,4,5,6-tetrahydrocyclopenta[c]pyrrole-1-carboxamide;
N-(3-chloro-4-fluorophenyl)-4-(cyclopropanesulfonamido)-2-methyl-2,4,5,6-tetrahydrocyclopenta[c]pyrrole-1-carboxamide;
N-(3-chloro-4-fluorophenyl)-4-(cyclopropanecarboxamido)-2-ethyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
N-(3-chloro-4-fluorophenyl)-4-(cyclopropanecarboxamido)-2-methyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate;
methyl (1-((3-chloro-4-fluorophenyl)carbamoyl)-2-methyl-4,5,6,7-tetrahydro-2H-isoindol-4-yl)carbamate;
N-(3-chloro-4-fluorophenyl)-4-(cyclopropanesulfonamido)-2-methyl-4,5,6,7-tetrahydro-2H-isoindole-1-carboxamide;
(1-methyl-1H-pyrazol-3-yl)methyl (1-((3-chloro-4-fluorophenyl)carbamoyl)-2-methyl-4,5,6,7-tetrahydro-2H-isoindol-4-yl)carbamate;
(1-methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate;
oxazol-2-ylmethyl (1-((3-chloro-4-fluorophenyl)carbamoyl)-2-methyl-2,4,5,6-tetrahydrocyclopenta[c]pyrrol-4-yl)carbamate;
oxazol-5-ylmethyl (1-((3-chloro-4-fluorophenyl)carbamoyl)-2-methyl-2,4,5,6-tetrahydrocyclopenta[c]pyrrol-4-yl)carbamate;
methyl (5-((3-chloro-4-fluorophenyl)carbamoyl)-2,3-dihydro-1H-pyrrolizin-1-yl)carbamate;
(1-methyl-1H-1,2,4-triazol-3-yl)methyl (5-((3-chloro-4-fluorophenyl)carbamoyl)-2,3-dihydro-1H-pyrrolizin-1-yl)carbamate;
pyridin-2-ylmethyl (5-((3-chloro-4-fluorophenyl)carbamoyl)-2,3-dihydro-1H-pyrrolizin-1-yl)carbamate;
N-(3-chloro-4-fluorophenyl)-2-methyl-4-oxo-2,4,5,6-tetrahydrocyclopenta[c]pyrrole-1-carboxamide;
N-(3-chloro-4-fluorophenyl)-2-methyl-4-oxo-4,5,6,7-tetrahydro-2H-isoindole-1-carboxamide;
isopropyl 1-(((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate;
(1-methyl-1H-1,2,4-triazol-3-yl)methyl (3-bromo-1-(3-chloro-4-fluorophenyl)carbamoyl)-2-methyl-2,4,5,6-tetrahydrocyclopenta[c]pyrrol-4-yl)carbamate;
2-cyanoethyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (3-chloro-1-(3-chloro-4-fluorophenyl)carbamoyl)-2-methyl-2,4,5,6-tetrahydrocyclopenta[c]pyrrol-4-yl)carbamate;
1-(((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid;
(1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate;
(1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate;
(1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate;
(1-(tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3,4-difluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(trifluoromethyl)-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(difluoromethyl)-4-fluorophenyl)carbamoyl)-2-methyl-2,4,5,6-tetrahydrocyclopenta[c]pyrrol-4-yl)carbamate;

(1-methyl-1H-1,2,4-triazol-3-yl)methyl (2-methyl-1-((3, 4,5-trifluorophenyl)carbamoyl)-2,4,5,6-tetrahydrocyclopenta[c]pyrrol-4-yl)carbamate;

N-(3-chloro-4-fluorophenyl)-2-methyl-4-oxo-2,4,5,6,7,8-hexahydrocyclohepta[c]pyrrole-1-carboxamide;

(1-methyl-1H-1,2,4-triazol-3-yl)methyl (2-methyl-14(2-(trifluoromethyl)pyridin-4-yl)carbamoyl)-2,4,5,6-tetrahydrocyclopenta[c]pyrrol-4-yl)carbamate;

4-amino-N-(3-chloro-4-fluorophenyl)-2-methyl-4,5,6,7-tetrahydro-2H-isoindole-1-carboxamide;

N-(3-chloro-4-fluorophenyl)-4-(cyclopropanecarboxamido)-2-methyl-4,5,6,7-tetrahydro-2H-isoindole-1-carboxamide;

methyl (1-((3-chloro-4-fluorophenyl)carbamoyl)-2-methyl-2,4,5,6,7,8-hexahydrocyclohepta[c]pyrrol-4-yl)carbamate;

4-amino-N-(3-chloro-4-fluorophenyl)-2-methyl-2,4,5,6,7,8-hexahydrocyclohepta[c]pyrrole-1-carboxamide;

(1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate;

N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide;

(1-methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate;

(1H-1,2,4-triazol-3-yl)methyl (1-((3-chloro-4-fluorophenyl)carbamoyl)-2-methyl-4,5,6,7-tetrahydro-2H-isoindol-4-yl)carbamate;

(1-methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;

(1-methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate;

(1-methyl-1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate;

(1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;

(1-methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate;

4-amino-N-(3-chloro-4-fluorophenyl)-2-methyl-2,4,5,6-tetrahydrocyclopenta[c]pyrrole-1-carboxamide;

prop-2-yn-1-yl (1-((3-chloro-4-fluorophenyl)carbamoyl)-2-methyl-2,4,5,6-tetrahydrocyclopenta[c]pyrrol-4-yl)carbamate;

(1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate;

(2H-1,2,3-triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate;

(2-methyl-2H-1,2,3-triazol-4-yl)methyl (1-((3-chloro-4-fluorophenyl)carbamoyl)-2-methyl-3-phenyl-2,4,5,6-tetrahydrocyclopenta[c]pyrrol-4-yl)carbamate;

but-2-yn-1-yl (1-((3-chloro-4-fluorophenyl)carbamoyl)-2-methyl-2,4, 5,6-tetrahydrocyclopenta[c]pyrrol-4-yl)carbamate;

pent-2-yn-1-yl (1-((3-chloro-4-fluorophenyl)carbamoyl)-2-methyl-2,4, 5,6-tetrahydrocyclopenta[c]pyrrol-4-yl)carbamate;

3-cyclopropylprop-2-yn-1-yl (1-((3-chloro-4-fluorophenyl)carbamoyl)-2-methyl-2,4, 5,6-tetrahydrocyclopenta[c]pyrrol-4-yl)carbamate;

(1-methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

((S)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;

((R)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;

(1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate;

(1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate;

(2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate;

(2H-1,2,3-triazol-4-yl)methyl (3-chloro-1-((3-chloro-4-fluorophenyl)carbamoyl)-2-methyl-4,5,6,7-tetrahydro-2H-isoindol-4-yl)carbamate;

(5-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(2-methyl-2H-tetrazol-5-yl)methyl (1-((3-chloro-4-fluorophenyl)carbamoyl)-2-methyl-2,4,5,6-tetrahydrocyclopenta[c]pyrrol-4-yl)carbamate;

(1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;

(5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; and (1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;

or a salt, solvate, prodrug, isotopically labeled derivative, stereoisomer, or tautomer thereof, or any mixtures thereof.

14. The compound of claim 1, wherein the configuration is (R) or (S) at the $C(R^2)(R^3)$ center.

15. A pharmaceutical composition comprising at least one compound of claim 1 and a pharmaceutically acceptable carrier.

16. The pharmaceutical composition of claim 15, further comprising at least one additional agent useful for treating hepatitis B virus (HBV) infection, wherein the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript.

17. A method of treating or ameliorating hepatitis B virus (HBV) infection in a subject, the method comprising administering to the subject in need thereof a therapeutically effective amount of at least one compound of formula (I) or (II), or a salt, solvate, prodrug, stereoisomer, tautomer, or isotopically labeled derivative thereof, or any mixtures thereof:

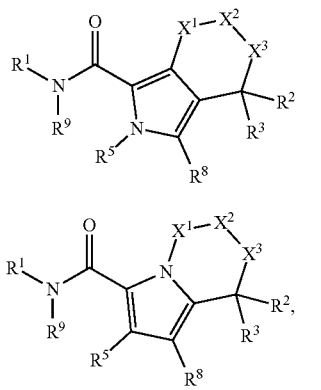

wherein independently in (I) or (II):
—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH(CH_3)CH(CH_3)$—*, —$C(CH_3)_2CH(CH_3)$—*, and —$CH(CH)C(CH_3)_2$—*, wherein the single bond marked as "*" is formed with $X^3$,
—$X^3$— is selected from the group consisting of a bond, —$CH_2$—, —$CH(CH_3)$—, —$C(CH_3)_2$—, —$CH_2CH_2$—, *—$CH_2CH(CH_3)$—, *—$CH_2C(CH_3)_2$—, *—$CH(CH_3)CH_2$—, *—$C(CH_3)_2CH_2$—, —$CH(CH_3)CH(CH_3)$—, *—$C(CH_3)_2CH(CH_3)$—*, and *—$CH(CH_3)C(CH_3)_2$—, wherein the single bond marked as "*" is formed with $X^1$—$X^2$—,
$R^1$ is selected from the group consisting of optionally substituted phenyl, optionally substituted benzyl, optionally substituted heteroaryl, and —($CH_2$)(optionally substituted heteroaryl);
$R^2$ is selected from the group consisting of —OH, —$OR^6$, —$NH_2$, —$NHR^6$, —$NR^6R^{6a}$, —OC(=O)$OR^6$, —OC(=O)N($R^4$)$R^6$, —N($R^3$)C(=O)$OR^6$, —$NR^7$C(=O)N($R^6$)($R^7$), —N($R^4$)C(=O)$R^6$, and —$NR^4$S(=O)$_{1-2}R^6$;
$R^3$ is H or $C_1$-$C_6$ alkyl;
or $R^2$ and $R^3$ combine to form =O;
each occurrence of $R^4$ is independently selected from the group consisting of H and $C_1$-$C_6$ alkyl;
$R^5$ is selected from the group consisting of H and $C_1$-$C_6$ alkyl;
each occurrence of $R^6$ is independently selected from the group consisting of optionally substituted $C_1$-$C_6$ alkyl, optionally substituted $C_1$-$C_6$ alkenyl, optionally substituted $C_1$-$C_6$ alkynyl, optionally substituted $C_3$-$C_8$ cycloalkyl, optionally substituted phenyl, and optionally substituted heteroaryl;

each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted hetereoaryl;
each occurrence of $R^7$ is independently selected from the group consisting of H and optionally substituted $C_1$-$C_6$ alkyl;
or, if $R^6$ and $R^7$ are bound to the same N atom, $R^6$ and $R^7$ optionally combine with the N atom to which both are bound to form an optionally substituted 3-7 membered heterocycle;
$R^8$ is selected from the group consisting of H, halogen, $C_1$-$C_6$ alkyl, $C_1$-$C_6$ haloalkyl, $C_3$-$C_8$ cycloalkyl, and optionally substituted phenyl; and
$R^9$ is selected from the group consisting of H and $C_1$-$C_6$ alkyl.

18. The method of claim 17, wherein the at least one compound is administered to the subject in a pharmaceutically acceptable composition.

19. The method of claim 17, wherein the subject further suffers from, or may develop, hepatitis D virus (HDV) infection.

20. The method of claim 19, wherein the subject is further administered at least one additional agent useful for treating the HBV infection or HDV infection.

21. The method of claim 20, wherein the at least one additional agent comprises at least one selected from the group consisting of reverse transcriptase inhibitor, capsid inhibitor, cccDNA formation inhibitor, RNA destabilizer, oligomeric nucleotide targeted against the hepatitis B virus (HBV) genome, immunostimulator, and GalNAc-siRNA conjugate targeted against an HBV gene transcript.

22. The method of claim 20, wherein the subject is co-administered the at least one compound and the at least one additional agent.

23. The method of claim 20, wherein the at least one compound and the at least one additional agent are coformulated.

24. A method of inhibiting expression or function of a viral capsid protein directly or indirectly in a hepatitis B virus (HBV)-infected subject, the method comprising administering to the subject in need thereof a therapeutically effective amount of at least one compound of formula (I) or (II), or a salt, solvate, prodrug, stereoisomer, tautomer, or isotopically labeled derivative thereof, or any mixtures thereof:

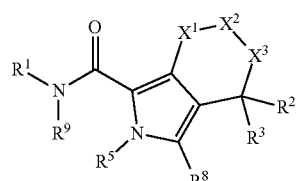

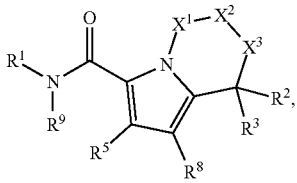

wherein independently in (I) or (II):
—$X^1$—$X^2$— is selected from the group consisting of —$CH_2CH_2$—*, —$CH_2CH(CH_3)$—*, —$CH_2C(CH_3)_2$—*, —$CH(CH_3)CH_2$—*, —$C(CH_3)_2CH_2$—*, —$CH(CH_3)CH(CH_3)$—*, —$C(CH_3)_2CH(CH_3)$—*, and —$CH(CH_3)C(CH_3)_2$—*, wherein the single bond marked as "*" is formed with $X^3$;
—$X^3$— is selected from the group consisting of a bond, —$CH_2$—, —$CH(CH_3)$—, —$C(CH_3)_2$—, —$CH_2CH_2$—, *—$CH_2CH(CH_3)$—, *—$CH_2C(CH_3)_2$—, *—$CH(CH_3)CH_2$—, *—$C(CH_3)_2CH_2$—, —$CH(CH_3)CH(CH_3)$—, *—$C(CH_3)_2CH(CH_3)$—*, and *—$CH(CH_3)C(CH_3)_2$—, wherein the single bond marked as "*" is formed with $X^1$—$X^2$—;
$R^1$ is selected from the group consisting of optionally substituted phenyl, optionally substituted benzyl, optionally substituted heteroaryl, and —($CH_2$)(optionally substituted heteroaryl);
$R^2$ is selected from the group consisting of —OH, —$OR^6$, —$NH_2$, —$NHR^6$, —$NR^6R^{6a}$, —OC(=O)$OR^6$, —OC(=O)N($R^4$)$R^6$, —N($R^3$)C(=O)$OR^6$, —$NR^7$C(=O)N($R^6$)($R^7$), —N($R^4$)C(=O)$R^6$, and —$NR^4$S(=O)$_{1-2}R^6$;
$R^3$ is H or $C_1$-$C_6$ alkyl;
or $R^2$ and $R^3$ combine to form =O;
each occurrence of $R^4$ is independently selected from the group consisting of H and $C_1$-$C_6$ alkyl;
$R^5$ is selected from the group consisting of H and $C_1$-$C_6$ alkyl;
each occurrence of $R^6$ is independently selected from the group consisting of optionally substituted $C_1$-$C_6$ alkyl, optionally substituted $C_1$-$C_6$ alkenyl, optionally substituted $C_1$-$C_6$ alkynyl, optionally substituted $C_3$-$C_8$ cycloalkyl, optionally substituted phenyl, and optionally substituted heteroaryl;
each occurrence of $R^{6a}$ is independently selected from the group consisting of H, optionally substituted $C_1$-$C_6$ alkyl, optionally substituted $C_3$-$C_8$ cycloalkyl, optionally substituted phenyl, and optionally substituted heteroaryl;
each occurrence of $R^7$ is independently selected from the group consisting of H and optionally substituted $C_1$-$C_6$ alkyl;
or, if $R^6$ and $R^7$ are bound to the same N atom, $R^6$ and $R^7$ optionally combine with the N atom to which both are bound to form an optionally substituted 3-7 membered heterocycle;
$R^8$ is selected from the group consisting of H, halogen, $C_1$-$C_6$ alkyl, $C_1$-$C_6$ haloalkyl, $C_3$-$C_8$ cycloalkyl, and optionally substituted phenyl; and
$R^9$ is selected from the group consisting of H and $C_1$-$C_6$ alkyl.

25. The method of claim 24, wherein the at least one compound is administered to the subject in a pharmaceutically acceptable composition.

26. The method of claim 24, wherein the subject further suffers from, or may develop, hepatitis D virus (HDV) infection.

27. The method of claim 24, wherein the subject is further administered at least one additional agent useful for treating the HBV or HDV infection.

28. The method of claim 27, wherein the at least one additional agent comprises at least one selected from the group consisting of reverse transcriptase inhibitor, capsid inhibitor, cccDNA formation inhibitor, RNA destabilizer, oligomeric nucleotide targeted against the HBV genome, immunostimulator, and GalNAc-siRNA conjugate targeted against an HBV gene transcript.

29. The method of claim 27, wherein the subject is co-administered the at least one compound and the at least one additional agent.

30. The method of claim 27, wherein the at least one compound and the at least one additional agent are coformulated.

31. The method of claim 17, wherein the subject is a mammal.

32. The method of claim 31, wherein the mammal is a human.

33. A method of treating or ameliorating hepatitis B virus (HBV) infection in a subject, the method comprising administering to the subject in need thereof a therapeutically effective amount of at least one compound selected from the group consisting of:
methyl (1-((3-chloro-4-fluorophenyl)carbamoyl)-2-methyl-2,4,5,6-tetrahydrocyclopenta[c]pyrrol-4-yl)carbamate;
pyridin-2-ylmethyl (1-((3,4-difluorophenyl)carbamoyl)-2-methyl-2,4,5,6-tetrahydrocyclopenta[c]pyrrol-4-yl)carbamate;
N-(3-chloro-4-fluorophenyl)-2-methyl-4-(3-methylureido)-2,4,5,6-tetrahydrocyclopenta[c]pyrrole-1-carboxamide;
N-(3-chloro-4-fluorophenyl)-4-(3-methylureido)-2,4,5,6-tetrahydrocyclopenta[c]pyrrole-1-carboxamide;
methyl (1-((3-chloro-4-fluorophenyl)carbamoyl)-2,4,5,6-tetrahydrocyclopenta[c]pyrrol-4-yl)carbamate;
N-(3-chloro-4-fluorophenyl)-4-(cyclopropanesulfonamido)-2-ethyl-2,4,5,6-tetrahydrocyclopenta[c]pyrrole-1-carboxamide;
N-(3-chloro-4-fluorophenyl)-4-(cyclopropanesulfonamido)-2-methyl-2,4,5,6-tetrahydrocyclopenta[c]pyrrole-1-carboxamide;
N-(3-chloro-4-fluorophenyl)-4-(cyclopropanecarboxamido)-2-ethyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
N-(3-chloro-4-fluorophenyl)-4-(cyclopropanecarboxamido)-2-methyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate;
methyl (1-((3-chloro-4-fluorophenyl)carbamoyl)-2-methyl-4,5,6,7-tetrahydro-2H-isoindol-4-yl)carbamate;
N-(3-chloro-4-fluorophenyl)-4-(cyclopropanesulfonamido)-2-methyl-4,5,6,7-tetrahydro-2H-isoindole-1-carboxamide;
(1-methyl-1H-pyrazol-3-yl)methyl (1-((3-chloro-4-fluorophenyl)carbamoyl)-2-methyl-4,5,6,7-tetrahydro-2H-isoindol-4-yl)carbamate;
(1-methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate;

oxazol-2-ylmethyl (1-((3-chloro-4-fluorophenyl)carbamoyl)-2-methyl-2,4,5,6-tetrahydrocyclopenta[c]pyrrol-4-yl)carbamate;
oxazol-5-ylmethyl (1-((3-chloro-4-fluorophenyl)carbamoyl)-2-methyl-2,4,5,6-tetrahydrocyclopenta[c]pyrrol-4-yl)carbamate;
methyl (5-((3-chloro-4-fluorophenyl)carbamoyl)-2,3-dihydro-1H-pyrrolizin-1-yl)carbamate;
(1-methyl-1H-1,2,4-triazol-3-yl)methyl (5-((3-chloro-4-fluorophenyl)carbamoyl)-2,3-dihydro-1H-pyrrolizin-1-yl)carbamate;
pyridin-2-ylmethyl (5-((3-chloro-4-fluorophenyl)carbamoyl)-2,3-dihydro-1H-pyrrolizin-1-yl)carbamate;
N-(3-chloro-4-fluorophenyl)-2-methyl-4-oxo-2,4,5,6-tetrahydrocyclopenta[c]pyrrole-1-carboxamide;
N-(3-chloro-4-fluorophenyl)-2-methyl-4-oxo-4,5,6,7-tetrahydro-2H-isoindole-1-carboxamide;
isopropyl 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate;
(1-methyl-1H-1,2,4-triazol-3-yl)methyl (3-bromo-1-(3-chloro-4-fluorophenyl)carbamoyl)-2-methyl-2,4,5,6-tetrahydrocyclopenta[c]pyrrol-4-yl)carbamate;
2-cyanoethyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (3-chloro-1-(3-chloro-4-fluorophenyl)carbamoyl)-2-methyl-2,4,5,6-tetrahydrocyclopenta[c]pyrrol-4-yl)carbamate;
1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid;
(1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate;
(1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate;
(1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate;
(1-(tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3,4-difluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(trifluoromethyl)-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(difluoromethyl)-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (2-methyl-1-((3,4,5-trifluorophenyl)carbamoyl)-2,4,5,6-tetrahydrocyclopenta[c]pyrrol-4-yl)carbamate;
N-(3-chloro-4-fluorophenyl)-2-methyl-4-oxo-2,4,5,6,7,8-hexahydrocyclohepta[c]pyrrole-1-carboxamide;
(1-methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate;
4-amino-N-(3-chloro-4-fluorophenyl)-2-methyl-4,5,6,7-tetrahydro-2H-isoindole-1-carboxamide;
N-(3-chloro-4-fluorophenyl)-4-(cyclopropanecarboxamido)-2-methyl-4,5,6,7-tetrahydro-2H-isoindole-1-carboxamide;
methyl (1-((3-chloro-4-fluorophenyl)carbamoyl)-2-methyl-2,4,5,6,7,8-hexahydrocyclohepta[c]pyrrol-4-yl)carbamate;
4-amino-N-(3-chloro-4-fluorophenyl)-2-methyl-2,4,5,6,7,8-hexahydrocyclohepta[c]pyrrole-1-carboxamide;
(1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate;
N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide;
(1-methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate;
(1H-1,2,4-triazol-3-yl)methyl (1-((3-chloro-4-fluorophenyl)carbamoyl)-2-methyl-4,5,6,7-tetrahydro-2H-isoindol-4-yl)carbamate;
(1-methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate;
(1-methyl-1H-1,2,4-triazol-3-yl)methyl (3-chloro-1-(3-chloro-4-fluorophenyl)carbamoyl)-2-methyl-4,5,6,7-tetrahydro-2H-isoindol-4-yl)carbamate;
(1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate;
4-amino-N-(3-chloro-4-fluorophenyl)-2-methyl-2,4,5,6-tetrahydrocyclopenta[c]pyrrole-1-carboxamide;
prop-2-yn-1-yl (1-((3-chloro-4-fluorophenyl)carbamoyl)-2-methyl-2,4,5,6-tetrahydrocyclopenta[c]pyrrol-4-yl)carbamate;
(1H-1,2,4-triazol-3-yl)methyl (3-chloro-1-(3-chloro-4-fluorophenyl)carbamoyl)-2-methyl-2,4,5,6-tetrahydrocyclopenta[c]pyrrol-4-yl)carbamate;
(2H-1,2,3-triazol-4-yl)methyl (3-chloro-1-(3-chloro-4-fluorophenyl)carbamoyl)-2-methyl-2,4,5,6-tetrahydrocyclopenta[c]pyrrol-4-yl)carbamate;
(2-methyl-2H-1,2,3-triazol-4-yl)methyl (1-((3-chloro-4-fluorophenyl)carbamoyl)-2-methyl-3-phenyl-2,4,5,6-tetrahydrocyclopenta[c]pyrrol-4-yl)carbamate;

but-2-yn-1-yl (1-((3-chloro-4-fluorophenyl)carbamoyl)-2-methyl-2,4,5,6-tetrahydrocyclopenta[c]pyrrol-4-yl)carbamate;
pent-2-yn-1-yl (1-((3-chloro-4-fluorophenyl)carbamoyl)-2-methyl-2,4, 5,6-tetrahydrocyclopenta[c]pyrrol-4-yl)carbamate;
3-cyclopropylprop-2-yn-1-yl (1-((3-chloro-4-fluorophenyl)carbamoyl)-2-methyl-2,4, 5,6-tetrahydrocyclopenta[c]pyrrol-4-yl)carbamate;
(1-methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
((S)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;
((R)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;
(1H-1,2,4-triazol-3-yl)methyl (3-bromo-1-((3-chloro-4-fluorophenyl)carbamoyl)-2-methyl-2,4,5,6-tetrahydrocyclopenta[c]pyrrol-4-yl)carbamate;
(1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;
(2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate;
(2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;
(1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate;
(2H-1,2,3-triazol-4-yl)methyl (3-chloro-1-((3-chloro-4-fluorophenyl)carbamoyl)-2-methyl-4,5,6,7-tetrahydro-2H-isoindol-4-yl)carbamate;
(5-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(2-methyl-2H-tetrazol-5-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;
(5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; and
(1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;
or a salt, solvate, prodrug, isotopically labeled derivative, stereoisomer, or tautomer thereof, or any mixtures thereof.

34. The method of claim 33, wherein the at least one compound is administered to the subject in a pharmaceutically acceptable composition.

35. The method of claim 33, wherein the subject further suffers from, or may develop, hepatitis D virus (HDV) infection.

36. The method of claim 35, wherein the subject is further administered at least one additional agent useful for treating the HBV infection or HDV infection.

37. The method of claim 36, wherein the at least one additional agent comprises at least one selected from the group consisting of reverse transcriptase inhibitor, capsid inhibitor, cccDNA formation inhibitor, RNA destabilizer, oligomeric nucleotide targeted against the hepatitis B virus (HBV) genome, immunostimulator, and GalNAc-siRNA conjugate targeted against an HBV gene transcript.

38. The method of claim 36, wherein the subject is co-administered the at least one compound and the at least one additional agent.

39. The method of claim 36, wherein the at least one compound and the at least one additional agent are coformulated.

40. The method of claim 33, wherein the subject is a mammal.

41. The method of claim 40, wherein the mammal is a human.

42. A method of inhibiting expression or function of a viral capsid protein directly or indirectly in a hepatitis B virus (HBV)-infected subject, the method comprising administering to the subject in need thereof a therapeutically effective amount of at least one compound of
methyl (1-((3-chloro-4-fluorophenyl)carbamoyl)-2-methyl-2,4,5,6-tetrahydrocyclopenta[c]pyrrol-4-yl)carbamate;
pyridin-2-ylmethyl (1-((3,4-difluorophenyl)carbamoyl)-2-methyl-2,4,5,6-tetrahydrocyclopenta[c]pyrrol-4-yl)carbamate;
N-(3-chloro-4-fluorophenyl)-2-methyl-4-(3-methylureido)-2,4,5,6-tetrahydrocyclopenta[c]pyrrole-1-carboxamide;
N-(3-chloro-4-fluorophenyl)-4-(3-methylureido)-2,4,5,6-tetrahydrocyclopenta[c]pyrrole-1-carboxamide;
methyl (1-((3-chloro-4-fluorophenyl)carbamoyl)-2,4,5,6-tetrahydrocyclopenta[c]pyrrol-4-yl)carbamate;
N-(3-chloro-4-fluorophenyl)-4-(cyclopropanesulfonamido)-2-ethyl-2,4,5,6-tetrahydrocyclopenta[c]pyrrole-1-carboxamide;
N-(3-chloro-4-fluorophenyl)-4-(cyclopropanesulfonamido)-2-methyl-2,4,5,6-tetrahydrocyclopenta[c]pyrrole-1-carboxamide;
N-(3-chloro-4-fluorophenyl)-4-(cyclopropanecarboxamido)-2-ethyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-ethyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
N-(3-chloro-4-fluorophenyl)-4-(cyclopropanecarboxamido)-2-methyl-2,4,5,6-tetrahydrocyclopenta[c]pyrrole-1-carboxamide;
(1-methyl-1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-pyrazol-3-yl)methyl (1-((3-chloro-4-fluorophenyl)carbamoyl)-2-ethyl-2,4,5,6-tetrahydrocyclopenta[c]pyrrol-4-yl)carbamate;

methyl (1-((3-chloro-4-fluorophenyl)carbamoyl)-2-methyl-4,5,6,7-tetrahydro-2H-isoindol-4-yl)carbamate;
N-(3-chloro-4-fluorophenyl)-4-(cyclopropanesulfonamido)-2-methyl-4,5,6,7-tetrahydro-2H-isoindole-1-carboxamide;
(1-methyl-1H-pyrazol-3-yl)methyl (1-((3-chloro-4-fluorophenyl)carbamoyl)-2-methyl-4,5,6,7-tetrahydro-2H-isoindol-4-yl)carbamate;
(1-methyl-1H-1,2,4-triazol-3-yl)methyl (1-((3-chloro-4-fluorophenyl)carbamoyl)-2-methyl-4,5,6,7-tetrahydro-2H-isoindol-4-yl)carbamate;
oxazol-2-ylmethyl (1-((3-chloro-4-fluorophenyl)carbamoyl)-2-methyl-2,4,5,6-tetrahydrocyclopenta[c]pyrrol-4-yl)carbamate;
oxazol-5-ylmethyl (1-((3-chloro-4-fluorophenyl)carbamoyl)-2-methyl-2,4,5,6-tetrahydrocyclopenta[c]pyrrol-4-yl)carbamate;
methyl (5-((3-chloro-4-fluorophenyl)carbamoyl)-2,3-dihydro-1H-pyrrolizin-1-yl)carbamate;
(1-methyl-1H-1,2,4-triazol-3-yl)methyl (5-((3-chloro-4-fluorophenyl)carbamoyl)-2,3-dihydro-1H-pyrrolizin-1-yl)carbamate;
pyridin-2-ylmethyl (5-((3-chloro-4-fluorophenyl)carbamoyl)-2,3-dihydro-1H-pyrrolizin-1-yl)carbamate;
N-(3-chloro-4-fluorophenyl)-2-methyl-4-oxo-2,4,5,6-tetrahydrocyclopenta[c]pyrrole-1-carboxamide;
N-(3-chloro-4-fluorophenyl)-2-methyl-4-oxo-4,5,6,7-tetrahydro-2H-isoindole-1-carboxamide;
isopropyl 1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylate;
(1-methyl-1H-1,2,4-triazol-3-yl)methyl (3-bromo-1-(3-chloro-4-fluorophenyl)carbamoyl)-2-methyl-2,4,5,6-tetrahydrocyclopenta[c]pyrrol-4-yl)carbamate;
2-cyanoethyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (3-chloro-1-(3-chloro-4-fluorophenyl)carbamoyl)-2-methyl-2,4,5,6-tetrahydrocyclopenta[c]pyrrol-4-yl)carbamate;
1-((((1-((3-chloro-4-fluorophenyl)carbamoyl)-2-methyl-2,4,5,6-tetrahydrocyclopenta[c]pyrrol-4-yl)carbamoyl)oxy)methyl)-3,3-difluorocyclobutane-1-carboxylic acid;
(1H-1,2,4-triazol-3-yl)methyl (1-((3-chloro-4-fluorophenyl)carbamoyl)-2-methyl-2,4,5,6-tetrahydrocyclopenta[c]pyrrol-4-yl)carbamate;
(1-carbamoyl-3,3-difluorocyclobutyl)methyl (1-((3-chloro-4-fluorophenyl)carbamoyl)-2-methyl-2,4,5,6-tetrahydrocyclopenta[c]pyrrol-4-yl)carbamate;
(1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2,3-dimethyl-2,4,5,6-tetrahydrocyclopenta[c]pyrrol-4-yl)carbamate;
(1-methyl-1H-1,2,4-triazol-3-yl)methyl (1-((4-fluoro-3-methylphenyl)carbamoyl)-2-methyl-2,4,5,6-tetrahydrocyclopenta[c]pyrrol-4-yl)carbamate;
(1-(tetrahydro-2H-pyran-2-yl)-1H-pyrazol-3-yl)methyl (1-((3-chloro-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3,4-difluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-cyano-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((2-chloropyridin-4-yl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(trifluoromethyl)-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (1-((3-(difluoromethyl)-4-fluorophenyl)carbamoyl)-2-methyl-2,4,5,6-tetrahydrocyclopenta[c]pyrrol-4-yl)carbamate;
(1-methyl-1H-1,2,4-triazol-3-yl)methyl (2-methyl-1-((3,4,5-trifluorophenyl)carbamoyl)-2,4,5,6-tetrahydrocyclopenta[c]pyrrol-4-yl)carbamate;
N-(3-chloro-4-fluorophenyl)-2-methyl-4-oxo-2,4,5,6,7,8-hexahydrocyclohepta[c]pyrrole-1-carboxamide;
(1-methyl-1H-1,2,4-triazol-3-yl)methyl (2-methyl-1-((2-(trifluoromethyl)pyridin-4-yl)carbamoyl)-2,4,5,6-tetrahydrocyclopenta[c]pyrrol-4-yl)carbamate;
4-amino-N-(3-chloro-4-fluorophenyl)-2-methyl-4,5,6,7-tetrahydro-2H-isoindole-1-carboxamide;
N-(3-chloro-4-fluorophenyl)-4-(cyclopropanecarboxamido)-2-methyl-4,5,6,7-tetrahydro-2H-isoindole-1-carboxamide;
methyl (1-((3-chloro-4-fluorophenyl)carbamoyl)-2-methyl-2,4,5,6,7,8-hexahydrocyclohepta[c]pyrrol-4-yl)carbamate;
4-amino-N-(3-chloro-4-fluorophenyl)-2-methyl-2,4,5,6,7,8-hexahydrocyclohepta[c]pyrrole-1-carboxamide;
(1-methyl-1H-1,2,4-triazol-3-yl)methyl (1-((2-(difluoromethyl)pyridin-4-yl)carbamoyl)-2-methyl-2,4,5,6-tetrahydrocyclopenta[c]pyrrol-4-yl)carbamate;
N-(3-chloro-4-fluorophenyl)-2-methyl-4-(3-((1-methyl-1H-1,2,4-triazol-3-yl)methyl)ureido)-4,5,6,7-tetrahydro-2H-isoindole-1-carboxamide;
(1-methyl-1H-1,2,4-triazol-3-yl)methyl (1-((3-chloro-4-fluorophenyl)carbamoyl)-2-methyl-2,4,5,6,7,8-hexahydrocyclohepta[c]pyrrol-4-yl)carbamate;
(1H-1,2,4-triazol-3-yl)methyl (1-((3-chloro-4-fluorophenyl)carbamoyl)-2-methyl-4,5,6,7-tetrahydro-2H-isoindol-4-yl)carbamate;
(1-methyl-1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-2,3-dimethyl-4,5,6,7-tetrahydro-2H-isoindol-4-yl)carbamate;
(1-methyl-1H-1,2,4-triazol-3-yl)methyl (3-chloro-1-(3-chloro-4-fluorophenyl)carbamoyl)-2-methyl-4,5,6,7-tetrahydro-2H-isoindol-4-yl)carbamate;
(1H-1,2,4-triazol-3-yl)methyl (1-((3-chloro-4-fluorophenyl)carbamoyl)-3-cyclopropyl-2-methyl-2,4,5,6-tetrahydrocyclopenta[c]pyrrol-4-yl)carbamate;
(1-methyl-1H-1,2,4-triazol-3-yl)methyl (1-((3-chloro-4-fluorophenyl)carbamoyl)-3-cyclobutyl-2-methyl-2,4,5,6-tetrahydrocyclopenta[c]pyrrol-4-yl)carbamate;
4-amino-N-(3-chloro-4-fluorophenyl)-2-methyl-2,4,5,6-tetrahydrocyclopenta[c]pyrrole-1-carboxamide;

prop-2-yn-1-yl (1-((3-chloro-4-fluorophenyl)carbamoyl)-2-methyl-2,4,5,6-tetrahydrocyclopenta[c]pyrrol-4-yl)carbamate;

(1H-1,2,4-triazol-3-yl)methyl (3-chloro-1-((3-chloro-4-fluorophenyl)carbamoyl)-2-methyl-2,4,5,6-tetrahydrocyclopenta[c]pyrrol-4-yl)carbamate;

(2H-1,2,3-triazol-4-yl)methyl (3-chloro-1-((3-chloro-4-fluorophenyl)carbamoyl)-2-methyl-2,4,5,6-tetrahydrocyclopenta[c]pyrrol-4-yl)carbamate;

(2-methyl-2H-1,2,3-triazol-4-yl)methyl (1-((3-chloro-4-fluorophenyl)carbamoyl)-2-methyl-3-phenyl-2,4,5,6-tetrahydrocyclopenta[c]pyrrol-4-yl)carbamate;

but-2-yn-1-yl (1-((3-chloro-4-fluorophenyl)carbamoyl)-2-methyl-2,4,5,6-tetrahydrocyclopenta[c]pyrrol-4-yl)carbamate;

pent-2-yn-1-yl (1-((3-chloro-4-fluorophenyl)carbamoyl)-2-methyl-2,4,5,6-tetrahydrocyclopenta[c]pyrrol-4-yl)carbamate;

3-cyclopropylprop-2-yn-1-yl (1-((3-chloro-4-fluorophenyl)carbamoyl)-2-methyl-2,4,5,6-tetrahydrocyclopenta[c]pyrrol-4-yl)carbamate;

(1-methyl-1H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

((S)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;

((R)-5-oxopyrrolidin-2-yl)methyl (1-((3-chloro-4-fluorophenyl)carbamoyl)-2-methyl-2,4,5,6-tetrahydrocyclopenta[c]pyrrol-4-yl)carbamate;

(1-methyl-1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(1H-1,2,4-triazol-3-yl)methyl (3-bromo-14(3-chloro-4-fluorophenyl)carbamoyl)-2-methyl-2,4,5,6-tetrahydrocyclopenta[c]pyrrol-4-yl)carbamate;

(1H-1,2,4-triazol-3-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(2-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(2H-1,2,3-triazol-4-yl)methyl (1-((3-chloro-4-fluorophenyl)carbamoyl)-2,3-dimethyl-2,4,5,6-tetrahydrocyclopenta[c]pyrrol-4-yl)carbamate;

(2H-1,2,3-triazol-4-yl)methyl (1-((3-chloro-4-fluorophenyl)carbamoyl)-2-methyl-3-(trifluoromethyl)-2,4,5,6-tetrahydrocyclopenta[c]pyrrol-4-yl)carbamate;

(1H-1,2,4-triazol-3-yl)methyl (3-chloro-1-((3-chloro-4-fluorophenyl)carbamoyl)-2-methyl-4,5,6,7-tetrahydro-2H-isoindol-4-yl)carbamate;

(2H-1,2,3-triazol-4-yl)methyl (3-chloro-1-((3-chloro-4-fluorophenyl)carbamoyl)-2-methyl-4,5,6,7-tetrahydro-2H-isoindol-4-yl)carbamate;

(5-methyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(5-ethyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate;

(2-methyl-2H-1,2,3-tetrazol-5-yl)methyl (1-((3-chloro-4-fluorophenyl)carbamoyl)-2-methyl-2,4,5,6-tetrahydrocyclopenta[c]pyrrol-4-yl)carbamate;

(1-methyl-1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;

(5-cyclopropyl-2H-1,2,3-triazol-4-yl)methyl (1-((3-chloro-4-fluorophenyl)carbamoyl)-2-methyl-2,4,5,6-tetrahydrocyclopenta[c]pyrrol-4-yl)carbamate; and (1H-tetrazol-5-yl)methyl (1-((3-chloro-4-fluorophenyl)carbamoyl)-2-methyl-2,4,5,6-tetrahydrocyclopenta[c]pyrrol-4-yl)carbamate;

or a salt, solvate, prodrug, isotopically labeled derivative, stereoisomer, or tautomer thereof, or any mixtures thereof.

43. The method of claim 42, wherein the at least one compound is administered to the subject in a pharmaceutically acceptable composition.

44. The method of claim 42, wherein the subject further suffers from, or may develop, hepatitis D virus (HDV) infection.

45. The method of claim 44, wherein the subject is further administered at least one additional agent useful for treating the HBV infection or HDV infection.

46. The method of claim 45, wherein the at least one additional agent comprises at least one selected from the group consisting of reverse transcriptase inhibitor, capsid inhibitor, cccDNA formation inhibitor, RNA destabilizer, oligomeric nucleotide targeted against the hepatitis B virus (HBV) genome, immunostimulator, and GalNAc-siRNA conjugate targeted against an HBV gene transcript.

47. The method of claim 45, wherein the subject is co-administered the at least one compound and the at least one additional agent.

48. The method of claim 45, wherein the at least one compound and the at least one additional agent are coformulated.

49. The method of claim 42, wherein the subject is a mammal.

50. The method of claim 49, wherein the mammal is a human.

* * * * *